United States Patent
Morita et al.

(10) Patent No.: US 9,505,740 B2
(45) Date of Patent: Nov. 29, 2016

(54) CYCLIC AMINE DERIVATIVE AND PHARMACEUTICAL USE THEREOF

(71) Applicant: Toray Industries, Inc., Tokyo (JP)

(72) Inventors: Yasuhiro Morita, Kamakura (JP);
Naoki Izumimoto, Kamakura (JP);
Katsuhiko Iseki, Kamakura (JP);
Shunsuke Iwano, Kamakura (JP);
Shuji Udagawa, Kamakura (JP);
Tomoya Miyoshi, Kamakura (JP); Yuji Osada, Iyo-gun (JP); Tetsuro Koreeda, Kamakura (JP); Masanori Murakami, Kamakura (JP); Motohiro Shiraki, Kamakura (JP); Kei Takahashi, Kamakura (JP); Keiyu Oshida, Kamakura (JP)

(73) Assignee: Toray Industries, Inc.

( * ) Notice: Subject to any disclaimer, the term of this patent is extended or adjusted under 35 U.S.C. 154(b) by 0 days.

(21) Appl. No.: 15/024,185

(22) PCT Filed: Sep. 26, 2014

(86) PCT No.: PCT/JP2014/075569
§ 371 (c)(1),
(2) Date: Mar. 23, 2016

(87) PCT Pub. No.: WO2015/046403
PCT Pub. Date: Apr. 2, 2015

(65) Prior Publication Data
US 2016/0194302 A1      Jul. 7, 2016

(30) Foreign Application Priority Data

Sep. 26, 2013  (JP) .................................. 2013-199853

(51) Int. Cl.
C07D 401/06    (2006.01)
C07D 405/14    (2006.01)
C07D 403/06    (2006.01)
A61K 31/454    (2006.01)

(52) U.S. Cl.
CPC .......... C07D 401/06 (2013.01); A61K 31/454 (2013.01); C07D 403/06 (2013.01); C07D 405/14 (2013.01)

(58) Field of Classification Search
None
See application file for complete search history.

(56) References Cited

FOREIGN PATENT DOCUMENTS

| FR | 2 567 885 A1 | 1/1986 |
| GB | 2 163 150 A | 2/1986 |
| JP | 2006-008664 A | 1/2006 |
| WO | 03/031432 A1 | 4/2003 |
| WO | 2004/074283 A1 | 9/2004 |
| WO | 2008/077089 A1 | 6/2008 |
| WO | 2009/158587 A1 | 12/2009 |
| WO | 2013/147160 A1 | 10/2013 |

OTHER PUBLICATIONS

Jill M. Recla, "New and emerging therapeutic agents for the treatment of fibromyalgia: an update," Journal of Pain Research, vol. 3, 2010, pp. 89-103.

*Primary Examiner* — Brian J Davis
(74) *Attorney, Agent, or Firm* — DLA Piper LLP (US)

(57) ABSTRACT

A compound exerts a strong analgesic effect against pain, in particular, neuropathic pain and/or fibromyalgia syndrome. The cyclic amine derivative is represented by formula, a prodrug thereof or a pharmacologically acceptable salt thereof:

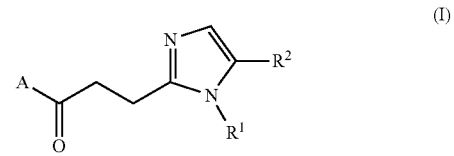

(I)

wherein A represents a group represented by Formula (IIa), (IIb) or (IIc):

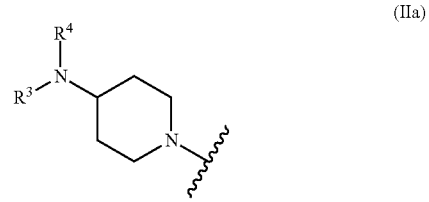

(IIa)

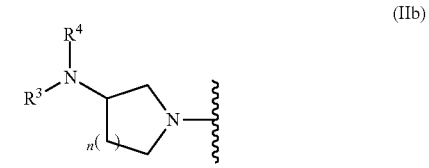

(IIb)

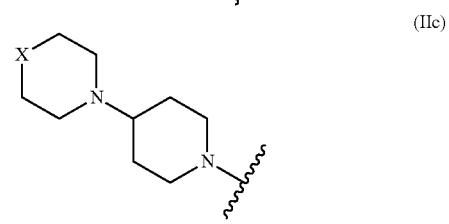

(IIc)

wherein
$R^3$ represents a hydrogen atom or an alkyl group having 1 to 6 carbon atoms, $R^4$ represents a hydrogen atom or an alkylcarbonyl group having 2 to 6 carbon atoms or an alkyl group having 1 to 6 carbon atoms and optionally substituted with an alkylcarbonylamino group having 2 to 6 carbon atoms and n represents 1 or 2, in which when $R^3$ and $R^4$ each independently represent an alkyl group having 1 to 6 carbon atoms, $R^1$ represents an alkyl group having 1 to 6 carbon atoms and substituted with a hydroxyl group, an amino group or a carboxyl group.

14 Claims, 24 Drawing Sheets

CYCLIC AMINE DERIVATIVE AND PHARMACEUTICAL USE THEREOF

TECHNICAL FIELD

This disclosure relates to a cyclic amine derivative and pharmaceutical use thereof.

BACKGROUND

Pain is an unpleasant sensory and emotional experience associated with actual or potential tissue damage. Pain is classified according to cause into nociceptive pain, neuropathic pain and psychogenic pain. As pain caused by an unknown cause, fibromyalgia syndrome is known.

The neuropathic pain is pathological pain caused by peripheral or central nervous system dysfunction, more specifically, pain caused by, e.g., direct damage and oppression of the nerve tissue despite of no nociceptive stimulus to a nociceptor. As a therapeutic agent for neuropathic pain, an anticonvulsant, an antidepressant, an anxiolytic drug or an antiepileptic drug such as gabapentin or pregabalin is used.

Fibromyalgia syndrome is a disorder in which systemic pain is a leading symptom and neuropsychiatric and neurovegetative symptoms are secondary symptoms. As therapeutic agents for fibromyalgia syndrome, pregabalin, which has been approved in the United States and Japan, duloxetine and milnacipran, which have been approved in the United States, are principally used. Also, drugs not approved as a therapeutic agent for fibromyalgia syndrome, i.e., a nonsteroidal anti-inflammatory agent, an opioid compound, an antidepressant, an anticonvulsant and an antiepileptic drug are used. However, nonsteroidal anti-inflammatory agents and opioid compounds are generally said to have a low therapeutic effect (Recla, Journal of Pain Research, Vol. 3, pp 89-103, 2010).

Other than these, French Patent 2 567 885 discloses that substituted piperidines have a cardiotonic activity; JP Patent Publication (Kokai) No. 2006-008664 discloses that imidazole derivatives have an FXa inhibitory effect; and International Publication WO 2003/031432 suggests that substituted piperidines have a potential drug efficacy against overweight or obesity.

However, therapy with a conventional therapeutic agent for neuropathic pain is highly frequently associated with central nervous system adverse drug reactions such as dizziness, nausea or vomiting. Because of this, it is difficult to administer a conventional therapeutic agent for a long-term. In the context, development of a novel therapeutic agent for neuropathic pain has been desired.

Even pregabalin, duloxetine and milnacipran, which have been approved as therapeutic agents for fibromyalgia syndrome, fail to provide clinically satisfactory therapeutic effect against fibromyalgia syndrome and their drug efficacy significantly varies among patients. In that context, it has been strongly desired to develop a novel therapeutic agent for fibromyalgia syndrome exerting a sufficient therapeutic effect.

Note that, FR '885 suggests that the substituted piperidines described therein have efficacy for migraine. However, it does not suggest the relevancy of analgesic action to a chemical structure. JP '664 which describes imidazole derivatives and WO '432 which describes substituted piperidines neither disclose nor suggest potentiality of analgesic action of those compounds.

It could therefore be helpful to provide a compound having a strong analgesic action for pain, in particular, neuropathic pain and/or fibromyalgia syndrome.

SUMMARY

We found a cyclic amine derivative having a strong analgesic effect against pain, in particular, neuropathic pain and/or fibromyalgia syndrome.

More specifically, we provide a cyclic amine derivative represented by Formula (I) or a pharmacologically acceptable salt thereof:

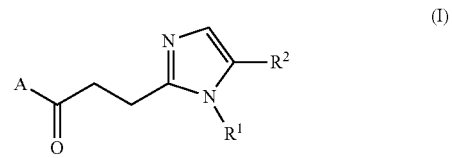

wherein A represents a group represented by Formula (IIa), (IIb) or (IIc):

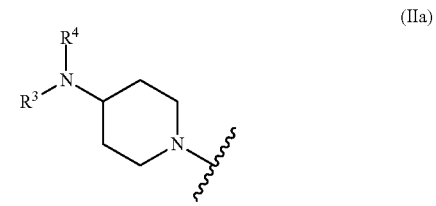

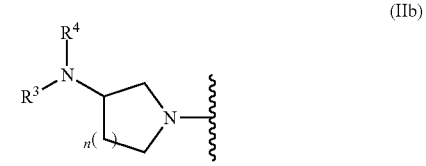

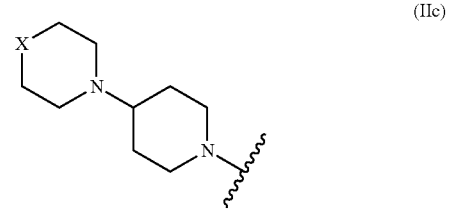

wherein when A represents a group represented by Formula (IIa) or (IIb), $R^1$ represents an alkyl group having 1 to 6 carbon atoms and optionally substituted with a halogen atom, a hydroxyl group, an amino group or a carboxyl group, $R^2$ represents a hydrogen atom or a halogen atom, $R^3$ represents a hydrogen atom or an alkyl group having 1 to 6 carbon atoms, $R^4$ represents a hydrogen atom or an alkylcarbonyl group having 2 to 6 carbon atoms or an alkyl group having 1 to 6 carbon atoms and optionally substituted with an alkylcarbonylamino group having 2 to 6 carbon atoms and n represents 1 or 2, in which when $R^3$ and $R^4$ each independently represent an alkyl group having 1 to 6 carbon atoms, $R^1$ represents an alkyl group having 1 to 6 carbon atoms and substituted with a hydroxyl group, an amino group or a carboxyl group; and when A represents a group represented by Formula (IIc), $R^1$ represents an alkyl group having 1 to 6 carbon atoms and substituted with a carboxyl group, $R^2$ represents a hydrogen atom or a halogen atom, X represents $CH_2$, O or $-NR^5$ and $R^5$ represents an alkyl group having 1 to 6 carbon atoms.

In the aforementioned cyclic amine derivative, it is preferable that A is Formula (IIa) or (IIb), in which $R^3$ is more preferably a hydrogen atom, a methyl group or an ethyl group; and it is further preferable that $R^2$ is a hydrogen atom or a chlorine atom, $R^3$ is a hydrogen atom or a methyl group and $R^4$ is a hydrogen atom, a methylcarbonyl group, or an alkyl group having 1 to 6 carbon atoms and optionally substituted with a methylcarbonylamino group.

More specifically, for example, a cyclic amine derivative represented by Formula (Ia) or (Ib) or a pharmacologically acceptable salt thereof is preferable. It is particularly preferable that $R^2$ is a hydrogen atom or a chlorine atom, $R^3$ is a hydrogen atom or a methyl group, $R^4$ is a hydrogen atom, a methylcarbonyl group, or an alkyl group having 1 to 6 carbon atoms and optionally substituted with a methylcarbonylamino group, in which when $R^3$ and $R^4$ are both methyl groups, $1e$ is an alkyl group having 1 to 6 carbon atoms and substituted with a hydroxyl group, an amino group or a carboxyl group.

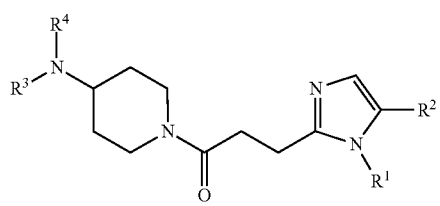

(Ia)

wherein $R^1$ represents an alkyl group having 1 to 6 carbon atoms and optionally substituted with a halogen atom, a hydroxyl group, an amino group or a carboxyl group, $R^2$ represents a hydrogen atom or a halogen atom, $R^3$ represents a hydrogen atom or an alkyl group having 1 to 6 carbon atoms, $R^4$ represents a hydrogen atom or an alkylcarbonyl group having 2 to 6 carbon atoms or an alkyl group having 1 to 6 carbon atoms and optionally substituted with an alkylcarbonylamino group having 2 to 6 carbon atoms, in which when $R^3$ and $R^4$ each independently represent an alkyl group having 1 to 6 carbon atoms, $R^1$ represents an alkyl group having 1 to 6 carbon atoms and substituted with a hydroxyl group, an amino group or a carboxyl group.

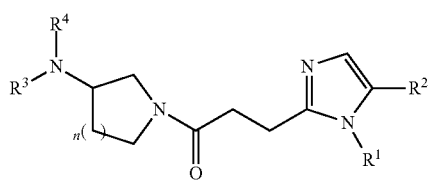

(Ib)

wherein $R^1$ represents an alkyl group having 1 to 6 carbon atoms and optionally substituted with a halogen atom, a hydroxyl group, an amino group or a carboxyl group, $R^2$ represents a hydrogen atom or a halogen atom, $R^3$ represents a hydrogen atom or an alkyl group having 1 to 6 carbon atoms, $R^4$ represents a hydrogen atom or an alkylcarbonyl group having 2 to 6 carbon atoms or an alkyl group having 1 to 6 carbon atoms and optionally substituted with an alkylcarbonylamino group having 2 to 6 carbon atoms, in which when $R^3$ and $R^4$ each independently represent an alkyl group having 1 to 6 carbon atoms, $R^1$ represents an alkyl group having 1 to 6 carbon atoms and substituted with a hydroxyl group, an amino group or a carboxyl group.

Analgesic action can be enhanced by defining as mentioned above.

In the above cyclic amine derivative, it is preferable that A is Formula (IIc), and more preferable that $R^2$ is a hydrogen atom or a chlorine atom and $R^5$ is a methyl group.

More specifically, for example, a cyclic amine derivative represented by Formula (Ic) or a pharmacologically acceptable salt thereof is preferable. It is more preferable that $R^2$ is a hydrogen atom or a chlorine atom and $R^5$ is a methyl group.

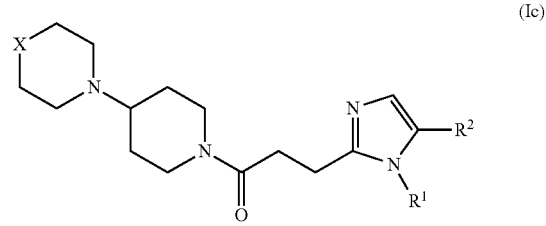

(Ic)

wherein $R^1$ represents an alkyl group having 1 to 6 carbon atoms and substituted with a carboxyl group, $R^2$ represents a hydrogen atom or a halogen atom, X represents $CH_2$, O or $-NR^5$ and $R^5$ represents an alkyl group having 1 to 6 carbon atoms.

Analgesic action can be enhanced by defining as mentioned above.

We provides a prodrug of the aforementioned cyclic amine derivative or a pharmacologically acceptable salt thereof. The prodrug is preferably a prodrug obtained by esterifying the carboxyl group of the aforementioned cyclic amine derivative.

Excellent pharmacokinetics can be expected in rats by oral administration by defining as mentioned above.

We also provide a medicine containing a cyclic amine derivative represented by Formula (I), a prodrug of the cyclic amine derivative or a pharmacologically acceptable salt thereof as an active ingredient.

The medicine is preferably an analgesic agent, and particularly preferably a therapeutic agent for neuropathic pain or a therapeutic agent for fibromyalgia syndrome.

The cyclic amine derivative or a prodrug thereof or a pharmacologically acceptable salt thereof has a strong analgesic effect against pain, in particular, neuropathic pain and fibromyalgia syndrome, and can be used as an analgesic agent, particularly a therapeutic agent for neuropathic pain or fibromyalgia syndrome, which can expectedly reduce a central nervous system side effects and be available for long-term administration.

DETAILED DESCRIPTION

Figure 1:
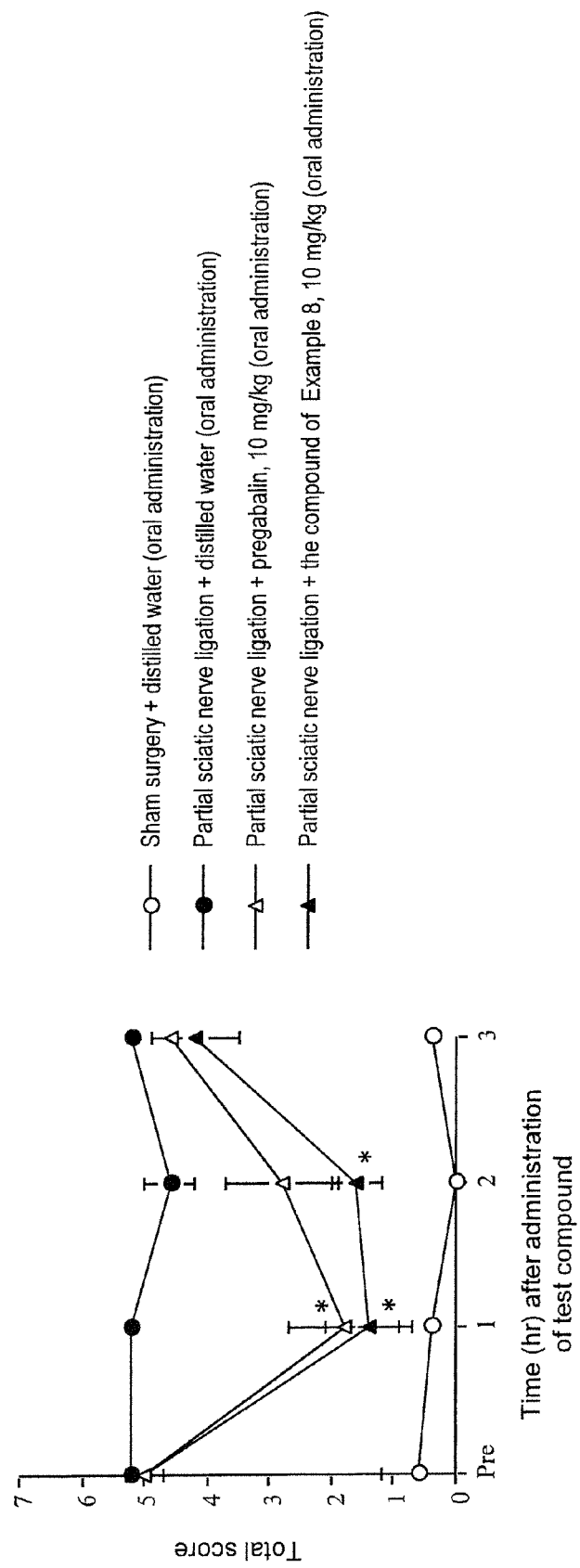
FIG. 1 is a graph showing the effect of the compound of Example 8 on mouse partial sciatic nerve ligation models (oral administration).

The following terms used in the specification are, unless otherwise specified, defined as follows.

It is characterized in that the cyclic amine derivative is represented by Formula (I):

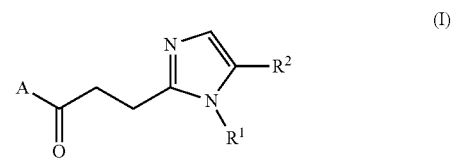

(I)

wherein A represents a group represented by Formula (IIa), (IIb) or (IIc),

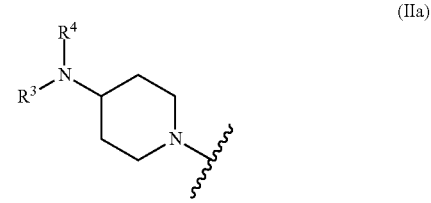

(IIa)

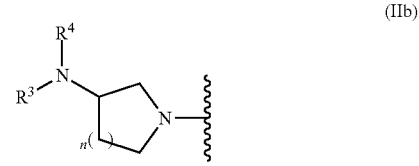

(IIb)

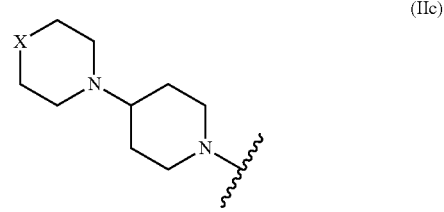

(IIc)

wherein when A represents a group represented by Formula (IIa) or (IIb), $R^1$ represents an alkyl group having 1 to 6 carbon atoms and optionally substituted with a halogen atom, a hydroxyl group, an amino group or a carboxyl group, $R^2$ represents a hydrogen atom or a halogen atom, $R^3$ represents a hydrogen atom or an alkyl group having 1 to 6 carbon atoms, $R^4$ represents a hydrogen atom or an alkylcarbonyl group having 2 to 6 carbon atoms or an alkyl group having 1 to 6 carbon atoms and optionally substituted with an alkylcarbonylamino group having 2 to 6 carbon atoms and n represents 1 or 2, in which when $R^3$ and $R^4$ each independently represent an alkyl group having 1 to 6 carbon atoms, $R^1$ represents an alkyl group having 1 to 6 carbon atoms and substituted with a hydroxyl group, an amino group or a carboxyl group; and when A represents a group represented by Formula (IIc), $R^1$ represents an alkyl group having 1 to 6 carbon atoms and substituted with a carboxyl group, $R^2$ represents a hydrogen atom or a halogen atom, X represents $CH_2$, O or $-NR^5$ and $R^5$ represents an alkyl group having 1 to 6 carbon atoms.

In the cyclic amine derivative, it is preferable that A is Formula (IIa) or (IIb) and $R^3$ is a hydrogen atom, a methyl group or an ethyl group; and more preferable that $R^2$ is a hydrogen atom or a chlorine atom, $R^3$ is a hydrogen atom or a methyl group and $R^4$ is a hydrogen atom or a methylcarbonyl group, or an alkyl group having 1 to 6 carbon atoms and optionally substituted with a methylcarbonylamino group.

In the cyclic amine derivative, it is preferable that A is Formula (IIc), $R^2$ is a hydrogen atom or a chlorine atom and $R^5$ is a methyl group.

The "halogen atom" refers to a fluorine atom, a chlorine atom, a bromine atom or an iodine atom.

The "alkyl group having 1 to 6 carbon atoms" refers to a linear, branched or cyclic saturated hydrocarbon group having 1 to 6 carbon atoms. For example, a methyl group, an ethyl group, a n-propyl group, an isopropyl group, a cyclopropyl group, a cyclopropylmethyl group, a n-butyl group, a sec-butyl group, a tert-butyl group, a n-pentyl group, an isopentyl group, a n-hexyl group, an isohexyl group or a cyclohexyl group can be mentioned.

The "alkyl group having 1 to 6 carbon atoms and optionally substituted with a halogen atom, a hydroxyl group, an amino group or a carboxyl group" refers to an alkyl group having 1 to 6 carbon atoms, in which the hydrogen atoms are each independently and optionally replaced with the aforementioned halogen atom or a hydroxyl group, an amino group or a carboxyl group, and is, for example, a methyl group, an ethyl group, a n-propyl group, an isopropyl group, a cyclopropyl group, a cyclopropylmethyl group, a n-butyl group, a sec-butyl group, a tert-butyl group, a n-pentyl group, an isopentyl group, a n-hexyl group, an isohexyl group or a cyclohexyl group, or a 2-chloroethyl group, a 2,2-difluoroethyl group, a 2,2,2-trifluoroethyl group, a 2-hydroxyethyl group, a 3-hydroxypropyl group, a 2-aminoethyl group, a 3-aminopropyl group, a 1-carboxymethyl group or a 2-carboxyethyl group.

The "alkylcarbonyl group having 2 to 6 carbon atoms" refers to a group obtained by binding a linear, branched or cyclic saturated hydrocarbon group having 1 to 5 carbon atoms to a carbonyl group. For example, an acetyl group, a n-propionyl group, a n-butyryl group or an isobutyryl group can be mentioned.

The "alkylcarbonylamino group having 2 to 6 carbon atoms" refers to a group obtained by binding the aforementioned alkylcarbonyl group having 2 to 6 carbon atoms to an amino group. For example, a methylcarbonylamino group, an ethylcarbonylamino group, a n-propylcarbonylamino group or an isopropylcarbonylamino group can be mentioned.

The "alkyl group having 1 to 6 carbon atoms and optionally substituted with an alkylcarbonylamino group having 2 to 6 carbon atoms" refers to the aforementioned alkyl group having 1 to 6 carbon atoms and optionally substituted with the aforementioned alkylcarbonylamino group having 2 to 6 carbon atoms. For example, a methyl group, an ethyl group, a n-propyl group, an isopropyl group, a cyclopropyl group, a cyclopropylmethyl group, a n-butyl group, a sec-butyl group, a tert-butyl group, a n-pentyl group, an isopentyl group, a n-hexyl group, an isohexyl or a cyclohexyl group or a 2-(methylcarbonylamino)ethyl group, a 2-(ethylcarbonylamino)ethyl group, a 2-(n-propylcarbonylamino)ethyl group, a 2-(isopropylcarbonylamino)ethyl group, a 3-(methylcarbonylamino)propyl group or a 4-(methylcarbonylamino)butyl group.

Specific examples of a preferable compound as a cyclic amine derivative represented by Formula (I) (hereinafter referred to as a cyclic amine derivative (I)) will be shown in Table 1-1 to Table 1-3. However, this disclosure is not limited to these.

TABLE 1-1

| Structural formula |
|---|
| 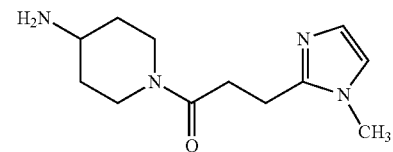 [SMILES: Cn1ccnc1CCC(=O)N1CCC(N)CC1] |
| 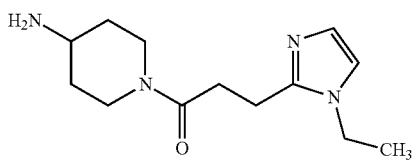 |
| 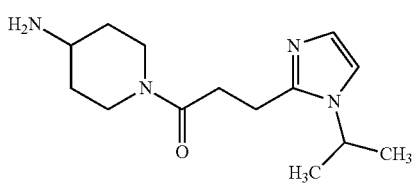 [SMILES: CC(C)n1ccnc1CCC(=O)N1CCC(N)CC1] |
| 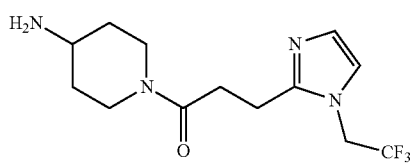 |
| 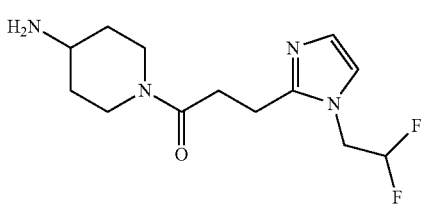 [SMILES: NC1CCN(C(=O)CCc2nccn2CC(F)F)CC1] |
| 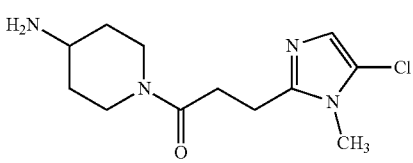 [SMILES: Cn1c(Cl)cnc1CCC(=O)N1CCC(N)CC1] |
| 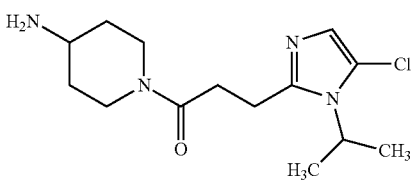 [SMILES: CC(C)n1c(Cl)cnc1CCC(=O)N1CCC(N)CC1] |
| 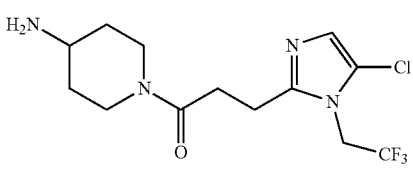 [SMILES: NC1CCN(C(=O)CCc2ncc(Cl)n2CC(F)(F)F)CC1] |
| 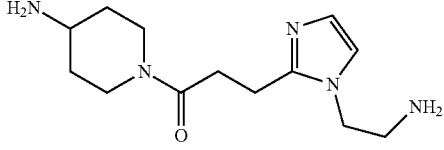 [SMILES: NCCn1ccnc1CCC(=O)N1CCC(N)CC1] |

TABLE 1-1-continued
Structural formula
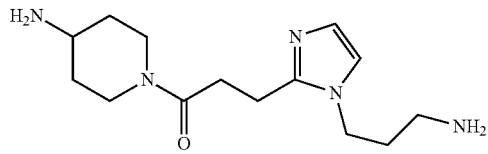 [SMILES: NCCCn1ccnc1CCC(=O)N1CCC(N)CC1]
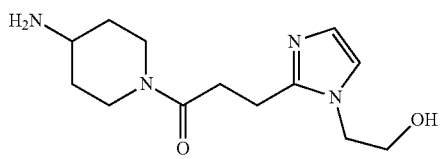 [SMILES: NC1CCN(C(=O)CCc2nccn2CCO)CC1]
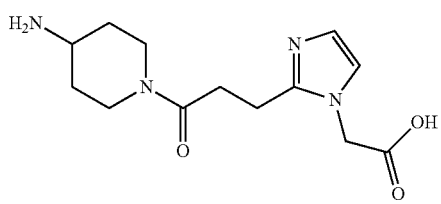 [SMILES: NC1CCN(C(=O)CCc2nccn2CC(=O)O)CC1]
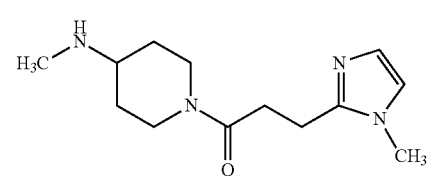 [SMILES: CNC1CCN(C(=O)CCc2nccn2C)CC1]
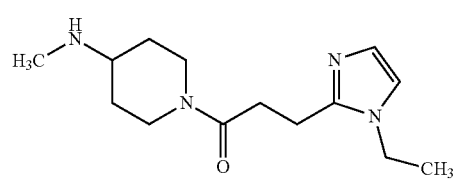
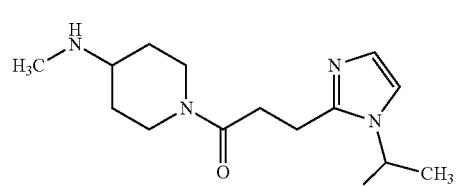 [SMILES: CCn1ccnc1CCC(=O)N1CCC(NC)CC1]
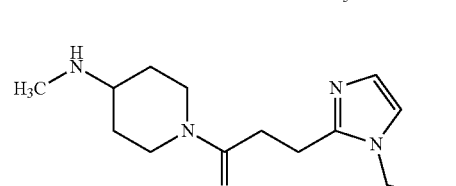
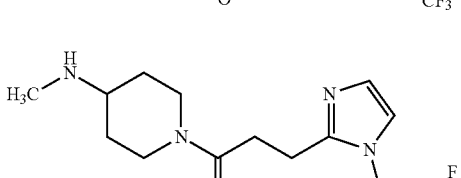
TABLE 1-1-continued
Structural formula
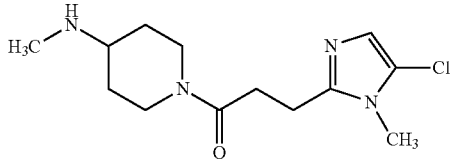 [SMILES: CNC1CCN(C(=O)CCc2ncc(Cl)n2C)CC1]
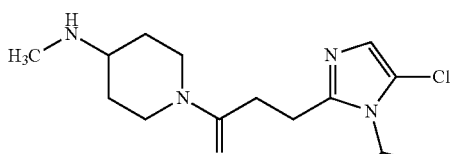
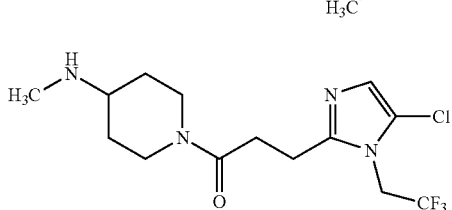
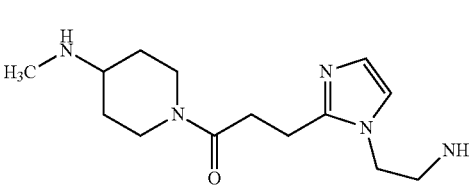
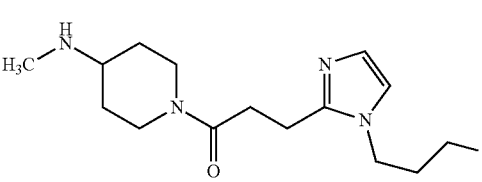
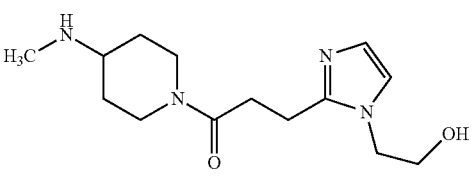 [SMILES: CNC1CCN(C(=O)CCc2nccn2CCO)CC1]
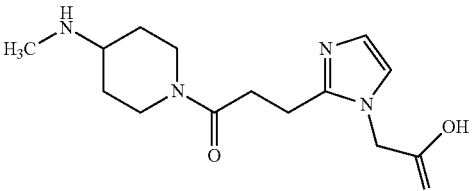
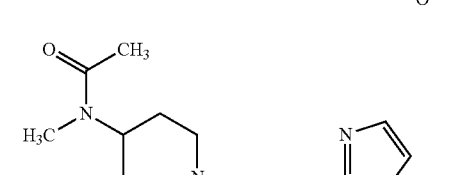

TABLE 1-1-continued

Structural formula

[Chemical structures shown]

TABLE 1-2

Structural formula

[Chemical structures shown]

TABLE 1-2-continued

Structural formula

[Chemical structures shown]

TABLE 1-2-continued

Structural formula

TABLE 1-2-continued
Structural formula
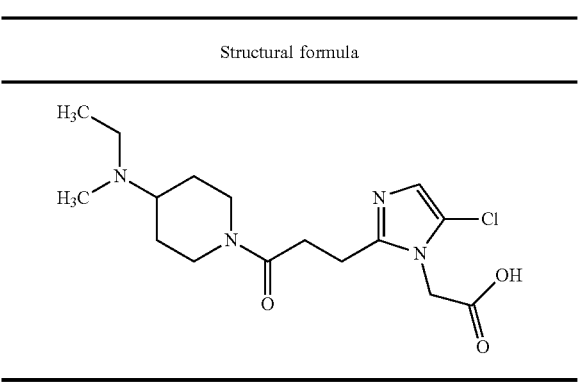
TABLE 1-3
Structural formula
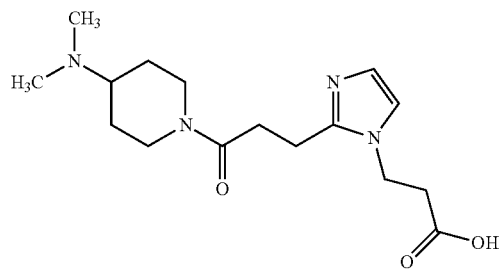
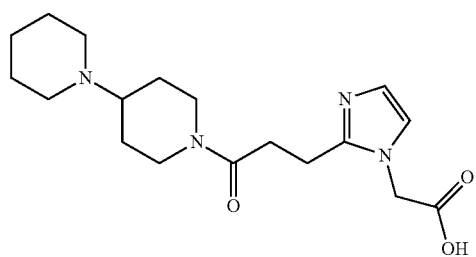 [SMILES: O=C(O)Cn1ccnc1CCC(=O)N1CCC(N2CCCCC2)CC1]
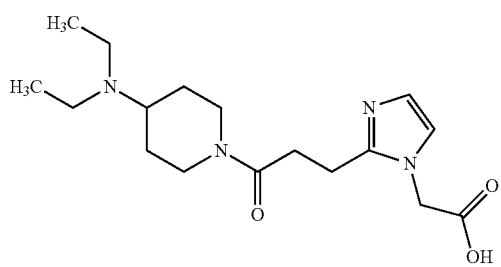 [SMILES: CCN(CC)C1CCN(C(=O)CCc2nccn2CC(=O)O)CC1]
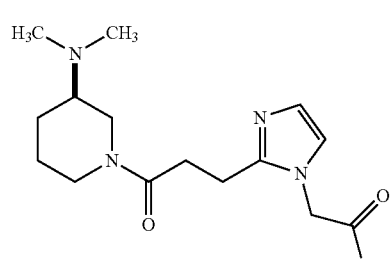
TABLE 1-3-continued
Structural formula
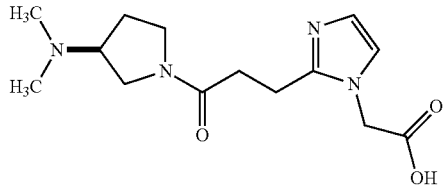 [SMILES: CN(C)[C@H]1CCN(C(=O)CCc2nccn2CC(=O)O)C1]
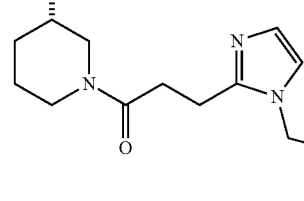
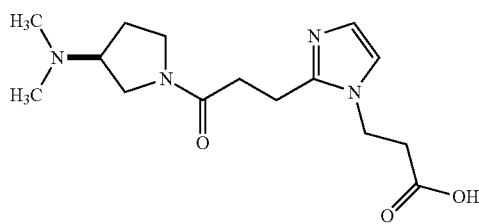 [SMILES: CN(C)[C@H]1CCN(C(=O)CCc2nccn2CCC(=O)O)C1]
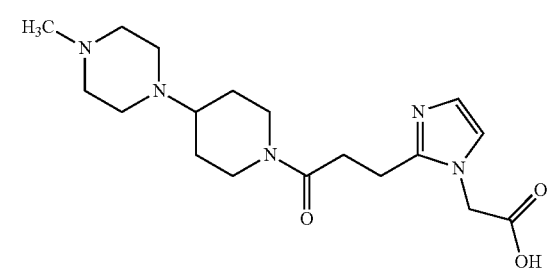 [SMILES: CN1CCN(C2CCN(C(=O)CCc3nccn3CC(=O)O)CC2)CC1]
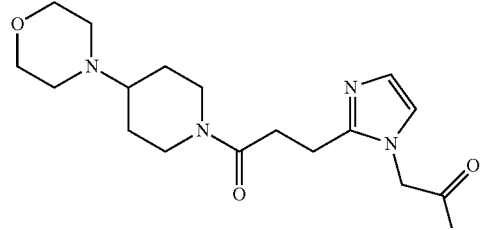
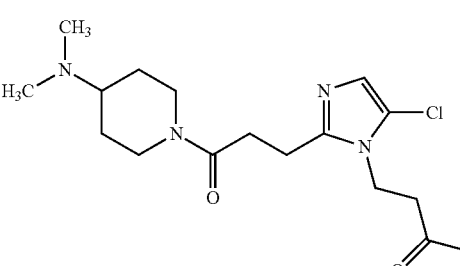

TABLE 1-3-continued

Structural formula

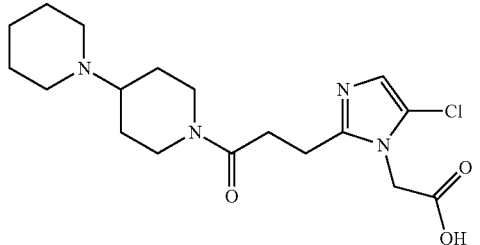 [SMILES: O=C(O)Cn1c(Cl)cnc1CCC(=O)N1CCC(N2CCCCC2)CC1]

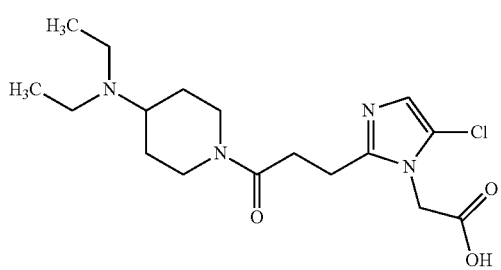

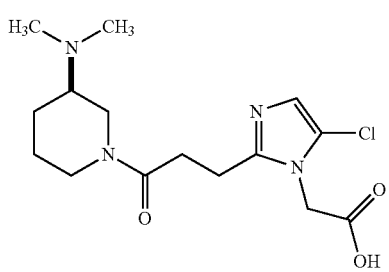 [SMILES: CN(C)[C@@H]1CCCN(C(=O)CCc2ncc(Cl)n2CC(=O)O)C1]

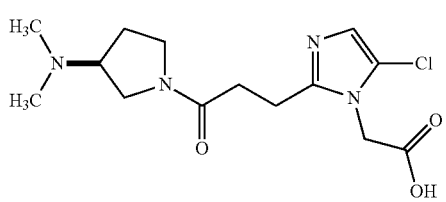 [SMILES: CN(C)[C@H]1CCN(C(=O)CCc2ncc(Cl)n2CC(=O)O)C1]

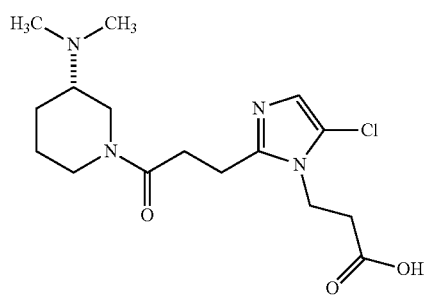 [SMILES: CN(C)[C@H]1CCCN(C(=O)CCc2ncc(Cl)n2CCC(=O)O)C1]

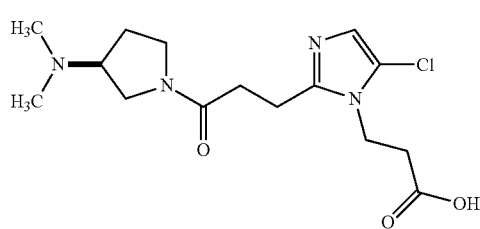 [SMILES: CN(C)[C@H]1CCN(C(=O)CCc2ncc(Cl)n2CCC(=O)O)C1]

TABLE 1-3-continued

Structural formula

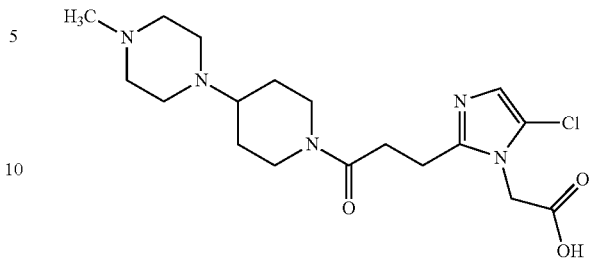

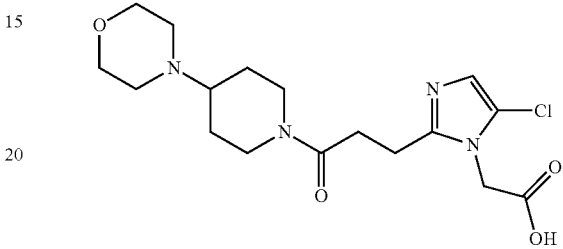

Note that, when an asymmetric carbon is present in a cyclic amine derivative (I), all enantiomers and mixtures of these are included. When a stereoisomer is present, all stereoisomers and mixtures of these are included.

A prodrug of a cyclic amine derivative (I) or a pharmacologically acceptable salt thereof is also included. The prodrug of a cyclic amine derivative (I) refers to a compound, which is enzymatically or chemically converted to the cyclic amine derivative (I) in vivo. The active form of a prodrug of a cyclic amine derivative (I) is the cyclic amine derivative (I); however a prodrug of the cyclic amine derivative (I) itself may have activity.

As the prodrug of a cyclic amine derivative (I), for example, a compound obtained by acylation, alkylation, phosphorylation or boration of a hydroxyl group or amino group of the cyclic amine derivative (I) or a compound obtained by esterification or amidation of a carboxyl group of the cyclic amine derivative (I) can be mentioned; however, a compound obtained by esterification of a carboxyl group is preferable. These compounds can be each synthesized from a cyclic amine derivative (I) in accordance with a known method.

As the compound obtained by esterification of a carboxyl group of a cyclic amine derivative (I), a methyl esterified, ethyl esterified, n-propyl esterified, isopropyl esterified, cyclopropyl esterified, n-butyl esterified, isobutyl esterified, sec-butyl esterified, tert-butyl esterified, cyclopropylmethyl esterified, n-pentyl esterified, isopentyl esterified, cyclopentyl esterified, n-hexyl esterified, isohexyl esterified, cyclohexyl esterified, n-heptyl esterified, n-octyl esterified, (5-methyl-2-oxo-1,3-dioxolen-4-yl)methyl esterified, acetyloxymethyl esterified, 1-acetyloxyethyl esterified, propionyloxymethyl esterified, 1-propionyloxyethyl esterified, valeryloxymethyl esterified, 1-valeryloxyethyl esterified, isobutyryloxymethyl esterified, 1-isobutylyloxyethyl esterified, pivaloyloxymethyl esterified, 1-pivaloyloxyethyl esterified, ethoxycarbonyl oxymethyl esterified, 1-((ethoxycarbonyl)oxy)ethyl esterified, 1-((ethoxycarbonyl)oxy) isobutyl esterified, cyclohexyloxycarbonylmethyl esterified, 1-((cyclohexyl)carbonyl)oxyethyl esterified, 2-(dimethylamino)-2-oxoethyl esterified, phthalidyl esterified or indanyl esterified compound can be mentioned; however, a methyl esterified, ethyl esterified, n-propyl esterified, isopropyl esterified, cyclopropyl esterified, n-butyl esterified, isobutyl esterified, sec-butyl esterified, tert-butyl esterified, cyclopropylmethyl esterified, n-octyl esterified, (5-methyl-2-oxo-1,3-dioxolen-4-yl)methyl esterified, pivaloyloxymethyl esterified, 2-(dimethylamino)-2-oxoethyl esterified, phthalidyl esterified or indanyl esterified compound is preferable.

Specific examples of a preferable compound as a prodrug of a cyclic amine derivative (I) will be shown in Tables 2-1 and 2-2. However, this disclosure is not limited to these.

TABLE 2-1

| Structural formula |
|---|

TABLE 2-1-continued

| Structural formula |
|---|

TABLE 2-1-continued

Structural formula

TABLE 2-2
| Structural formula |
|---|
| 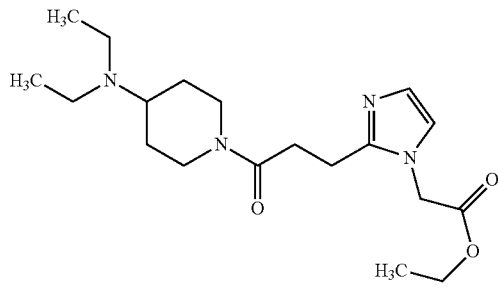 [SMILES: CCOC(=O)Cn1ccnc1CCC(=O)N1CCC(N(CC)CC)CC1] |
| 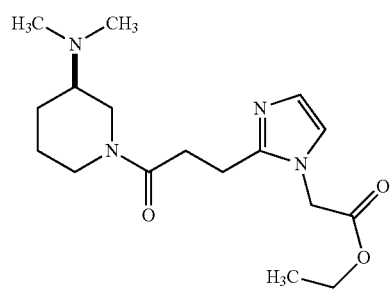 |
| 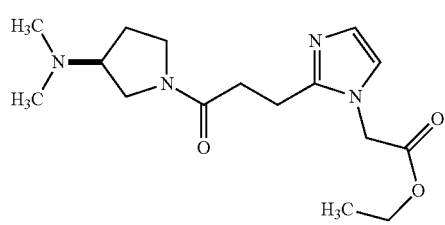 [SMILES: CCOC(=O)Cn1ccnc1CCC(=O)N1CC[C@H](N(C)C)C1] |
| 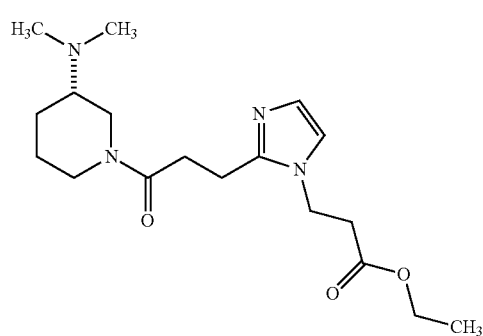 [SMILES: CCOC(=O)CCn1ccnc1CCC(=O)N1CCC[C@H](N(C)C)C1] |
| 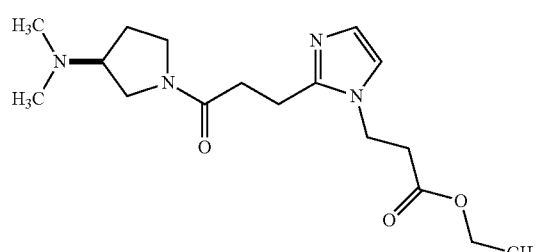 |
TABLE 2-2-continued
| Structural formula |
|---|
| 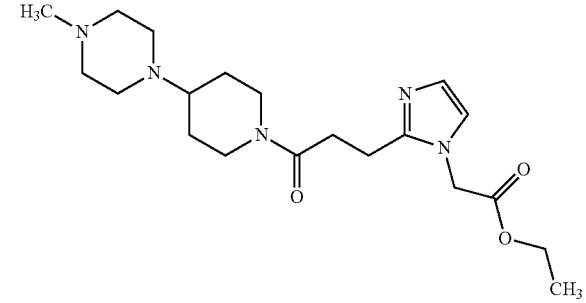 [SMILES: CCOC(=O)Cn1ccnc1CCC(=O)N1CCC(N2CCN(C)CC2)CC1] |
| 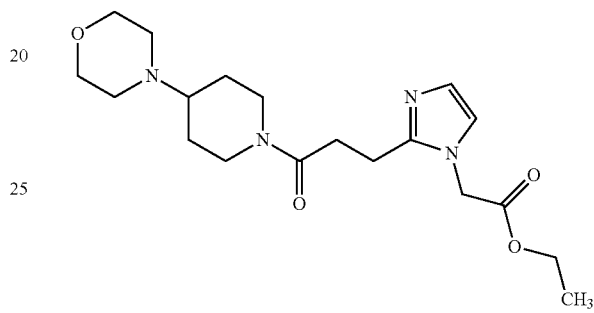 |
| 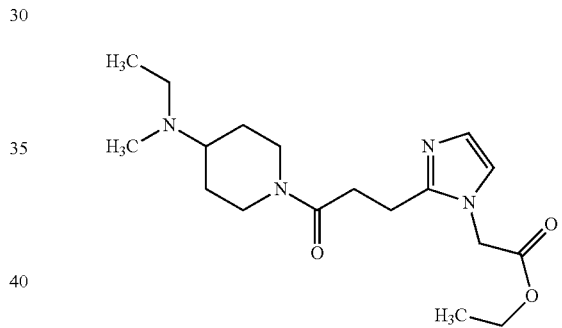 |
| 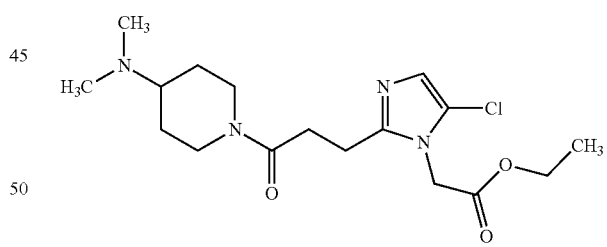 |
| 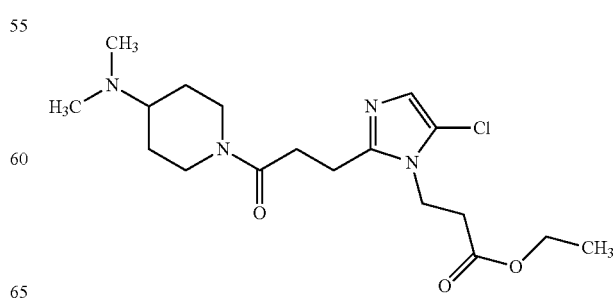 |

TABLE 2-2-continued

Structural formula

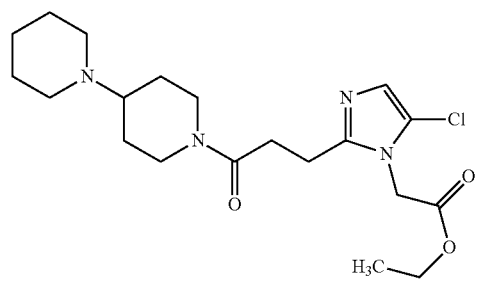 [SMILES: CCOC(=O)Cn1c(Cl)cnc1CCC(=O)N1CCC(N2CCCCC2)CC1]

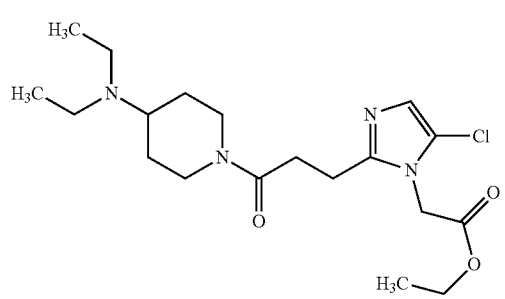 [SMILES: CCOC(=O)Cn1c(Cl)cnc1CCC(=O)N1CCC(N(CC)CC)CC1]

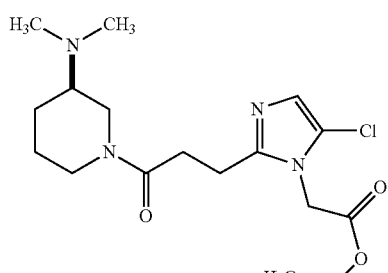

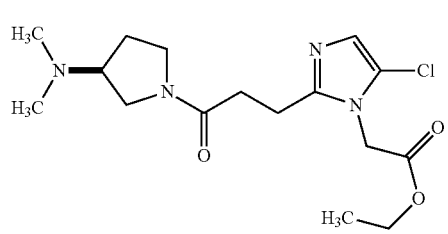 [SMILES: CCOC(=O)Cn1c(Cl)cnc1CCC(=O)N1CC[C@H](N(C)C)C1]

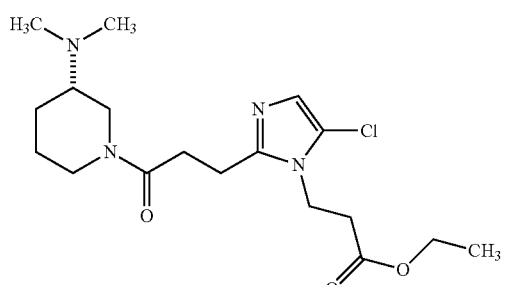

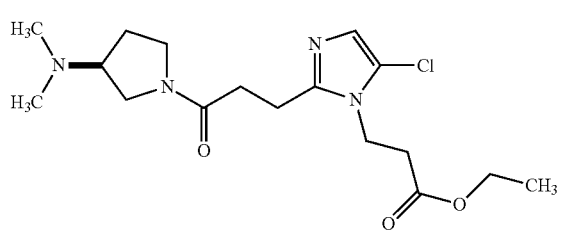 [SMILES: CCOC(=O)CCn1c(Cl)cnc1CCC(=O)N1CC[C@H](N(C)C)C1]

TABLE 2-2-continued

Structural formula

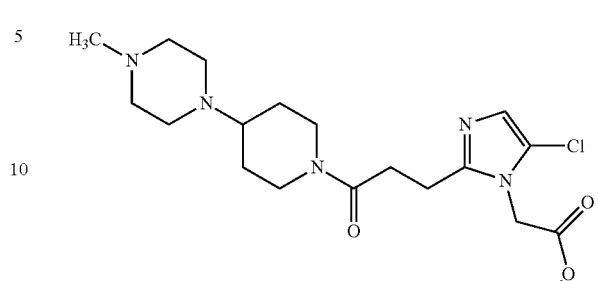

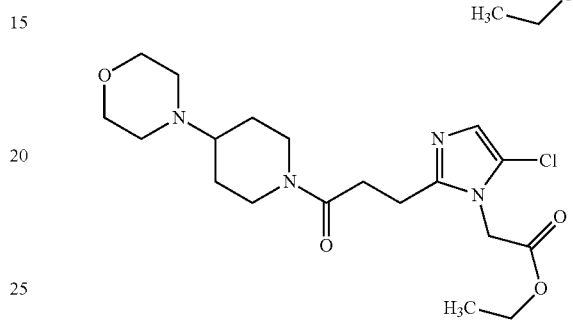

A prodrug of a cyclic amine derivative (I) may be converted into the cyclic amine derivative (I) in physiological conditions described in known literatures ("Development of pharmaceutical products," Hirokawa-Shoten Ltd., vol. 7, p. 163 to 198, 1990, and Prog. Med. 5, p. 2157 to 2161, 1985).

A cyclic amine derivative (I) or a prodrug thereof may be labeled with a radioisotope. Examples of the radioisotope for use in labeling include $^{3}H$, $^{14}C$ and/or $^{125}I$.

A cyclic amine derivative (I) or a prodrug thereof may be deuterated.

As the pharmacologically acceptable salt of a cyclic amine derivative (I), for example, an inorganic salt such as a hydrochloride, a sulfate, a phosphate or a hydrobromide; or an organic salt such as an oxalate, a malonate, a citrate, a fumarate, a lactate, a malate, a succinate, a tartrate, an acetate, a trifluoroacetate, a maleate, a gluconate, a benzoate, a salicylate, a xinafoate, a pamoate, an ascorbate, an adipate, a methanesulfonate, a p-toluenesulfonate or a cinnamate. These salts may be present in the form of a hydrate, a solvate or a crystalline polymorph.

A cyclic amine derivative (I) or a prodrug thereof can be synthesized by the production methods that will be described below. Note that, the cyclic amine derivatives (I) or prodrugs thereof obtained by the following production methods each can be isolated/purified by a known means such as solvent extraction, recrystallization and/or chromatography and converted into desired salts by known methods or a similar method thereto. When a cyclic amine derivative (I) or a prodrug thereof is obtained in the form of a salt, it can be converted into a cyclic amine derivative (I) or a prodrug thereof or another desired salt by a known method or a similar method thereto.

In individual reactions of the production methods that will be described below, when a starting compound has a hydroxyl group, an amino group or a carboxyl group, a protective group may be introduced in these groups. A desired compound can be obtained by removing the protective group if necessary after the reaction.

In individual reactions of the production methods that will be described below, when a starting compound has a hydroxyl group, an amino group or a carboxyl group, a prodrug of a cyclic amine derivative (I) can be obtained without removing the protective group introduced in these groups.

As the protective group of a hydroxyl group, for example, a trityl group, an aralkyl group having 7 to 10 carbon atoms (e.g., benzyl group) or a substituted silyl group (e.g., trimethylsilyl group, triethylsilyl group or tert-butyldimethylsilyl group) can be mentioned.

As the protective group of an amino group, for example, an alkylcarbonyl group having 2 to 6 carbon atoms (for example, acetyl group), a benzoyl group, an alkyloxycarbonyl group having 1 to 6 carbon atoms (for example, tert-butoxycarbonyl group or benzyloxycarbonyl group), an aralkyl group having 7 to 10 carbon atoms (for example, benzyl group) or a phthaloyl group can be mentioned.

As the protective group of a carboxyl group, for example, an alkyl group having 1 to 6 carbon atoms (e.g., methyl group, ethyl group or tert-butyl group) or an aralkyl group having 7 to 10 carbon atoms (for example, benzyl group) can be mentioned.

Removal of a protective group, which varies depending upon the type of protective group, can be performed in accordance with a known method (for example, Greene, T. W., "Greene's Protective Groups in Organic Synthesis," Wiley-Interscience) or a similar method thereto.

1. A compound (Ia) can be synthesized in accordance with the production method that will be described below.

1-1. Production Method for Compound (Ia-a):

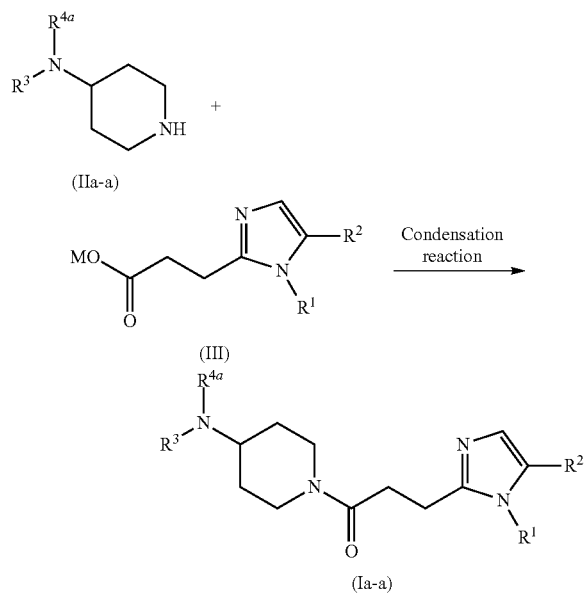

wherein M represents a hydrogen atom or an alkali metal such as lithium or sodium, $R^{4a}$ represents an alkyl group having 1 to 6 carbon atoms and optionally substituted with an alkylcarbonylamino group having 2 to 6 carbon atoms, and other reference symbols are the same as defined above.

A compound (Ia-a), which is a cyclic amine derivative (I) wherein A represents a group represented by the general formula (IIa) and $R^4$ represents an alkyl group having 1 to 6 carbon atoms and optionally substituted with an alkylcarbonylamino group having 2 to 6 carbon atoms, can be obtained, for example, by a condensation reaction of a compound (IIa-a) and a compound (III) using a condensing agent in the presence or absence of a base.

In the condensation reaction, a compound (IIa-a) and a salt thereof can be used. As the salt herein, for example, the same salt as a pharmacologically acceptable salt as mentioned above can be mentioned.

As the compound (IIa-a) and compound (III) to be used in the condensation reaction, commercially available compounds can be directly used. However, they can be synthesized, for example, in accordance with the production methods that will be described below.

As the base to be used in the condensation reaction, for example, an aromatic amine such as pyridine or lutidine, or a tertiary amine such as triethylamine, triisopropylamine, tributylamine, cyclohexyldimethylamine, 4-dimethylaminopyridine, N,N-dimethylaniline, N-methylpiperidine, N-methylpyrrolidine, N-methylmorpholine or diisopropylethylamine (DIEA) can be mentioned.

The amount of the base to be used in the condensation reaction is preferably 0.5 to 10 moles relative to 1 mol of a compound (IIa-a) and more preferably 0.8 to 5.0 moles.

As the condensing agent to be used in the condensation reaction, for example, 0-(benzotriazol-1-yl)-N,N,N',N'-tetramethyluronium hexafluorophosphate (HBTU), cyclohexylcarbodiimide (DCC), N-(3-dimethylaminopropyl)-N'-ethyl carbodiimide (EDC) or a hydrochloride thereof, 2-ethoxy-1-ethoxycarbonyl-1,2-dihydroxyquinoline (EEDQ), carbonyldiimidazole (CDI), diethylphosphoryl cyanide, benzotriazol-1-yloxytrispyrrolidinophosphonium hexafluorophosphate (PyBOP), diphenylphosphorylazide (DPPA), 4-(4,6-dimethoxy-1,3,5-triazin-2-yl)-4-methylmorpholinium chloride (DMTMM), isobutyl chloroformate, diethyl acetyl chloride or trimethylacetyl chloride can be mentioned. These condensing agents are used alone or in combination with an additive such as N-hydroxysuccinimide (HONSu), hydroxybenzotriazole (HOBT), 3-hydroxy-4-oxo-3,4-dihydro-1,2,3-benzotriazine (HOOBT) or 4-dimethylaminopyridine (DMAP).

The amount of the condensing agent to be used in the condensation reaction is preferably 0.5 to 10 moles relative to 1 mole of a compound (IIa-a) and more preferably 0.8 to 5.0 moles.

The amount of the compound (III) to be used in the condensation reaction is preferably 0.5 to 3 moles relative to 1 mole of a compound (IIa-a) and more preferably 0.8 to 1.5 moles.

The condensation reaction is generally performed in a solvent and a solvent which does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; an amide such as N,N-dimethylformamide or N-methylpyrrolidone; an alcohol such as methanol, ethanol or 2-propanol; or an aliphatic nitrile such as acetonitrile or propionitrile can be mentioned. A mixed solvent of these may be used. When an aromatic amine such as pyridine is selected as the solvent, a condensation reaction can be performed in the absence of a base.

In the condensation reaction, the reaction temperature is preferably −20° C. to 150° C. and more preferably 0 to 100° C.

In the condensation reaction, the reaction time, which varies depending upon the reaction conditions, is preferably 5 minutes to 72 hours, and more preferably 30 minutes to 48 hours.

1-2. Production Method for Compound (Ia-b), (Ia-c) and (Ia-d):

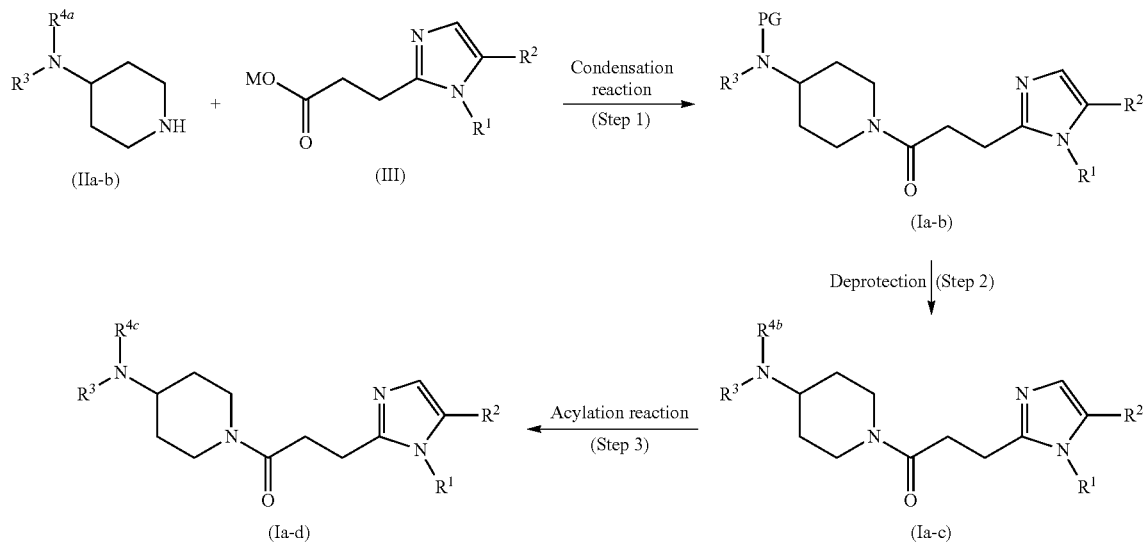

wherein PG represents a protective group, $R^{4b}$ represents a hydrogen atom, $R^{4c}$ represents an alkylcarbonyl group having 2 to 6 carbon atoms, and other reference symbols are the same as defined above.

Step 1

A compound (Ia-b) can be obtained, for example, by the condensation reaction of a compound (IIa-b) and a compound (III) with a condensing agent in the presence or absence of a base.

In the condensation reaction, the compound (IIa-b) and a salt thereof can be used. As the salt herein, for example, the same salt as a pharmacologically acceptable salt as mentioned above can be mentioned.

As the compound (IIa-b) and compound (III) to be used in the condensation reaction, commercially available compounds can be directly used; however, they can be synthesized, for example, in accordance with the production methods that will be described below.

As the base to be used in the condensation reaction, for example, an aromatic amine such as pyridine or lutidine, or a tertiary amine such as triethylamine, triisopropylamine, tributylamine, cyclohexyldimethylamine, 4-dimethylaminopyridine, N,N-dimethylaniline, N-methylpiperidine, N-methylpyrrolidine, N-methylmorpholine or diisopropylethylamine (DIEA) can be mentioned.

The amount of the base to be used in the condensation reaction is preferably 0.5 to 10 moles relative to 1 mole of a compound (IIa-b) and more preferably 0.8 to 5.0 moles.

As the condensing agent to be used in the condensation reaction, for example, 0-(benzotriazol-1-yl)-N,N,N',N'-tetramethyluronium hexafluorophosphate (HBTU), cyclohexylcarbodiimide (DCC), N-(3-dimethylaminopropyl)-N'-ethyl carbodiimide (EDC) or a hydrochloride thereof, 2-ethoxy-1-ethoxycarbonyl-1,2-dihydroxyquinoline (EEDQ), carbonyldiimidazole (CDI), diethylphosphoryl cyanide, benzotriazol-1-yloxytrispyrrolidinophosphonium hexafluorophosphate (PyBOP), diphenylphosphorylazide (DPPA), 4-(4,6-dimethoxy-1,3,5-triazin-2-yl)-4-methylmorpholinium chloride (DMTMM), isobutyl chloroformate, diethyl acetyl chloride or trimethylacetyl chloride can be mentioned. These condensing agents are used alone or in combination with an additive such as N-hydroxysuccinimide (HONSu), hydroxybenzotriazole (HOBT), 3-hydroxy-4-oxo-3,4-dihydro-1,2,3-benzotriazine (HOOBT) or 4-dimethylaminopyridine (DMAP).

The amount of the condensing agent to be used in the condensation reaction is preferably 0.5 to 10 moles relative to 1 mole of a compound (IIa-b) and more preferably 0.8 to 5.0 moles.

The amount of the compound (III) to be used in the condensation reaction is preferably 0.5 to 3 moles relative to 1 mole of a compound (IIa-b) and more preferably 0.8 to 1.5 moles.

The condensation reaction is generally performed in a solvent and a solvent which does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; an amide such as N,N-dimethylformamide or N-methylpyrrolidone; an alcohol such as methanol, ethanol or 2-propanol; or an aliphatic nitrile such as acetonitrile or propionitrile can be mentioned. A mixed solvent of these may be used. When an aromatic amine such as pyridine is selected as the solvent, a condensation reaction can be performed in the absence of a base.

In the condensation reaction, the reaction temperature is preferably −20° C. to 150° C. and more preferably 0 to 100° C.

In the condensation reaction, the reaction time, which varies depending upon the reaction conditions, is preferably 5 minutes to 72 hours, and more preferably 30 minutes to 48 hours.

Step 2

A compound (Ia-c), which is a cyclic amine derivative (I) wherein A represents a group represented by the general formula (IIa) and R4 is a hydrogen atom, can be obtained by deprotection of a compound (Ia-b).

Removal of a protective group, which varies depending upon the type of protective group, can be performed in accordance with a known method (for example, Greene, T.

W., "Greene's Protective Groups in Organic Synthesis," Wiley-Interscience) or a similar method thereto.

Step 3

A compound (Ia-d), which is a cyclic amine derivative (I) wherein A represents a group represented by the general formula (IIa) and R4 is an alkylcarbonyl group having 2 to 6 carbon atoms, can be obtained by reacting a compound (Ia-c) and an acylating agent such as carboxylic halide having 2 to 6 carbon atoms or an acid anhydride, in the presence of a base.

In the acylation reaction, a compound (Ia-c) and a salt thereof can be used. As the salt herein, for example, the same salt as a pharmacologically acceptable salt as mentioned above can be mentioned.

As the base to be used in the acylation reaction, for example, pyridine, triethylamine, diisopropylethylamine or N,N-dimethylaminopyridine can be mentioned.

The amount of the base to be used in the acylation reaction is preferably 0.5 to 10 moles relative to 1 mole of a compound (Ia-c) and more preferably 0.8 to 5.0 moles.

The acylation reaction is generally performed in a solvent and a solvent which does not inhibit the reaction is appropriately selected. As the solvent, for example, an aromatic amine such as pyridine; a halogenated hydrocarbon such as dichloromethane, chloroform or 1,2-dichloroethane; an ether such as tetrahydrofuran or 1,4-dioxane; or an aliphatic nitrile such as acetonitrile or propionitrile can be mentioned. A mixed solvent of these may be used. When an aromatic amine such as pyridine is selected as the solvent, an acylation reaction can be performed in the absence of a base.

1-3. Salt Formation Steps of Compound (Ia-a), (Ia-b), (Ia-c) and (Ia-d):

Pharmacologically acceptable salts of a compound (Ia-a), (Ia-b), (Ia-c) and (Ia-d) can be obtained through a salt formation reaction performed by mixing, for example, the compound (Ia-a), (Ia-b), (Ia-c) or (Ia-d) and an acid.

As the acid to be used for a salt formation reaction, for example, an inorganic acid such as hydrochloric acid, sulfuric acid, phosphoric acid or hydrobromic acid; and an organic acid such as oxalic acid, malonic acid, citric acid, fumaric acid, lactic acid, malic acid, succinic acid, tartaric acid, acetic acid, trifluoroacetic acid, maleic acid, gluconic acid, benzoic acid, salicylic acid, 1-hydroxy-2-naphthoic acid, pamoic acid, ascorbic acid, adipic acid, methanesulfonic acid, p-toluenesulfonic acid or cinnamic acid can be mentioned.

A salt formation reaction is generally performed in a solvent and a solvent which does not inhibit the reaction is appropriately selected. As the solvent, for example, an aliphatic alcohol such as methanol, ethanol or isopropanol; an ether such as diethyl ether, tetrahydrofuran, 1,4-dioxane or ethylene glycol dimethyl ether; an amide such as N,N-dimethylformamide or N-methylpyrrolidone; a sulfoxide such as dimethyl sulfoxide; an aliphatic nitrile such as acetonitrile or propionitrile; a ketone such as acetone or 2-butanone; an ester such as ethyl acetate, methyl acetate or n-butyl acetate or water can be mentioned. A mixture of these solvents may be used. 2. A compound (IIa) can be synthesized in accordance with the production method that will be described below.

2-1. Production Method for Compound (IIa-a):

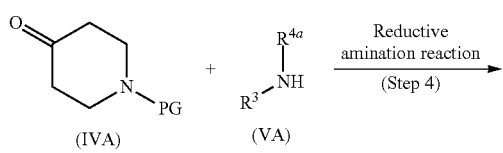

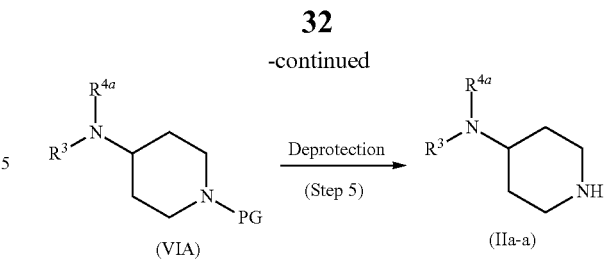

wherein individual reference symbols are the same as defined above.

Step 4

A compound (VIA) can be obtained by the reductive amination reaction between a compound (IVA) and a compound (VA).

As the compound (VA) to be used as the reductive amination reaction, a commercially available compound can be directly used.

The reductive amination reaction can be performed in accordance with a known method (for example, Journal of Organic Chemistry, vol. 68, p. 770-779, 2003) or a similar method thereto.

Step 5

A compound (IIa-a) can be obtained by deprotection of a compound (VIA).

Removal of a protective group, which varies depending upon the type of protective group, can be performed in accordance with a known method (for example, Greene, T. W., "Greene's Protective Groups in Organic Synthesis," Wiley-Interscience) or a similar method thereto.

2-2. Production Method for Compound (IIa-b):

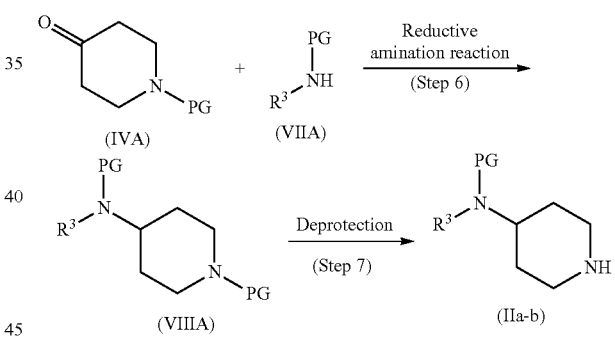

wherein individual reference symbols are the same as defined above.

Step 6

A compound (VIIIA) can be obtained by the reductive amination reaction between a compound (IVA) and a compound (VIIA).

As the compound (VIIA) to be used in the reductive amination reaction, a commercially available compound can be directly used.

The reductive amination reaction can be performed in accordance with a known method (for example, Journal of Organic Chemistry, vol. 68, p. 770-779, 2003) or a similar method thereto.

Step 7

A compound (IIa-b) can be obtained by deprotection of a compound (VIIIA).

Removal of a protective group, which varies depending upon the type of protective group, can be performed in accordance with a known method (for example, Greene, T. W., "Greene's Protective Groups in Organic Synthesis," Wiley-Interscience) or a similar method thereto.

3. Production Method for a Compound (IIIa):

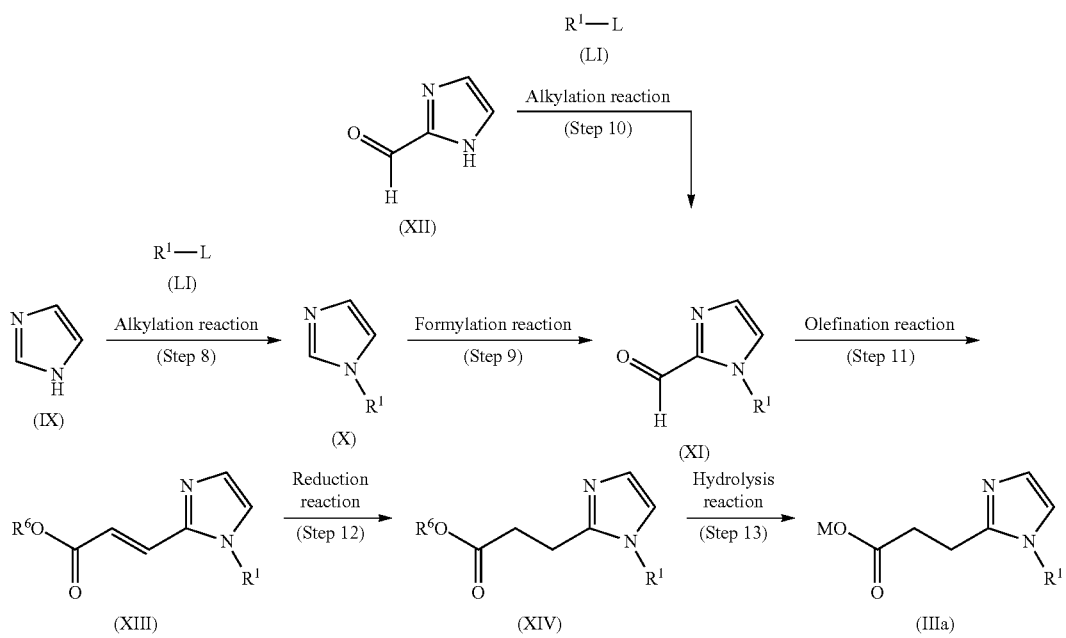

wherein L represents a leaving group such as a chlorine atom, a bromine atom or an iodine atom, R⁶ represents an alkyl group having 1 to 6 carbon atoms or an aralkyl group having 7 to 10 carbon atoms such as a methyl group, an ethyl group, a propyl group, a n-butyl group or a benzyl group, and other individual reference symbols are the same as defined above.

Step 8

A compound (X) can be obtained by deprotonation of a compound (IX) with a base, followed by an alkylation reaction with an alkylating reagent (LI).

As the compound (IX) to be used in the alkylation reaction, a commercially available compound can be used.

As the base to be used in the alkylation reaction, for example, an alkali metal hydride such as sodium hydride or potassium hydride or a butyllithium such as n-butyllithium, secbutyllithium or tert-butyllithium can be mentioned.

The amount of the base to be used in the alkylation reaction is preferably 0.5 to 3.0 moles relative to 1 mole of a compound (IX) and more preferably 0.8 to 2.0 moles.

As the alkylating reagent (LI) to be used in the alkylation reaction, a commercially available compound can be used.

The amount of the alkylating reagent (LI) to be used in the alkylation reaction is preferably 0.5 to 10.0 moles relative to 1 mole of a compound (IX) and more preferably 0.8 to 5.0 moles.

The alkylation reaction is generally performed in a solvent and a solvent which does not inhibit the reaction is appropriately selected. As the solvent, for example, an aliphatic hydrocarbon such as heptane or hexane, or an ether such as tetrahydrofuran, diethyl ether or 1,4-dioxane can be mentioned. A mixture of these solvents may be used.

In the alkylation reaction, the reaction temperature is preferably −20° C. to 150° C. and more preferably 0 to 100° C.

In the alkylation reaction, the reaction time, which varies depending upon the reaction conditions, is preferably 5 minutes to 72 hours, and more preferably 30 minutes to 48 hours.

Step 9

A compound (XI) can be obtained by deprotonation of a compound (X) with a base, followed by a formylation reaction with a formyl group introducing reagent.

As the base to be used in the formylation reaction, for example, n-butyllithium, secbutyllithium or tert-butyllithium can be mentioned.

The amount of base to be used in the formylation reaction is preferably 0.5 to 3.0 moles relative to 1 mole of a compound (X) and more preferably 0.8 to 2.0 moles.

As the formyl group introducing reagent to be used in the formylation reaction, for example, N,N-dimethylformamide can be mentioned. As the N,N-dimethylformamide, a commercially available compound can be used.

The amount of the formyl group introducing reagent to be used in the formylation reaction is preferably 0.5 to 3.0 moles relative to 1 mole of a compound (X) and more preferably 0.8 to 2.0 moles.

The formylation reaction is generally performed in a solvent and a solvent which does not inhibit the reaction is appropriately selected. As the solvent, for example, an aliphatic hydrocarbon such as heptane or hexane, or an ether such as tetrahydrofuran, diethyl ether or 1,4-dioxane can be mentioned. A mixture of these solvents may be used.

In the deprotonation of the formylation reaction, the reaction temperature is preferably −100 to 0° C. and more preferably −80 to −20° C. In the formylation of the formylation reaction, the reaction temperature is preferably −20° C. to 150° C. and more preferably 0 to 100° C.

In the formylation reaction, the reaction time, which varies depending upon the reaction conditions, is preferably 5 minutes to 72 hours, and more preferably 30 minutes to 48 hours.

Step 10

A compound (XI) can be obtained by deprotonation of a compound (XII) with a base, followed by an alkylation reaction with an alkylating reagent (LI).

As the compound (XII) to be used in the alkylation reaction, a commercially available compound can be used.

As the base to be used in the alkylation reaction, for example, a metal carbonate such as sodium carbonate, potassium carbonate or cesium carbonate, or an alkali metal hydroxide such as sodium hydroxide or potassium hydroxide can be mentioned.

The amount of the base to be used in the alkylation reaction is preferably 0.5 to 3.0 moles relative to 1 mole of a compound (XII) and more preferably 0.8 to 2.0 moles.

The amount of the alkylating reagent (LI) to be used in the alkylation reaction is preferably 0.5 to 3.0 moles relative to 1 mole of a compound (XII) and more preferably 0.8 to 2.0 moles.

The alkylation reaction is generally performed in a solvent and a solvent which does not inhibit the reaction is appropriately selected. As the solvent, for example, an ether such as tetrahydrofuran or 1,4-dioxane, an amide such as N,N-dimethylformamide or N-methylpyrrolidone or an aliphatic nitrile such as acetonitrile or propionitrile can be mentioned. A mixture of these solvents may be used.

In the alkylation reaction, the reaction temperature is preferably −20° C. to 150° C. and more preferably 0 to 100° C.

In the alkylation reaction, the reaction time, which varies depending upon the reaction conditions, is preferably 5 minutes to 72 hours, and more preferably 30 minutes to 48 hours.

Step 11

A compound (XIII) can be obtained by the olefination reaction of a compound (XI).

As the reagent to be used in the olefination reaction, for example, a Wittig reagent such as methyl 2-(triphenylphosphoranylidene)acetate or a Horner-Emmons reagent such as ethyl diethylphosphonoacetate can be mentioned. As the Wittig reagent or Horner-Emmons reagent, a commercially available compound can be directly used.

The amount of the Wittig reagent or Horner-Emmons reagent to be used in the olefination reaction is preferably 0.5 to 3.0 moles relative to 1 mole of a compound (XI) and more preferably 0.8 to 2.0 moles.

The olefination reaction is generally performed in a solvent and a solvent which does not inhibit the reaction is appropriately selected. As the solvent, for example, an aromatic hydrocarbon such as toluene, chlorobenzene or xylene, an ether such as tetrahydrofuran or 1,4-dioxane, an amide such as N,N-dimethylformamide or N-methylpyrrolidone or an aliphatic nitrile such as acetonitrile or propionitrile can be mentioned. A mixture of these solvents may be used.

In the olefination reaction, the reaction temperature is preferably −20° C. to 150° C. and more preferably 0 to 100° C.

In the olefination reaction, the reaction time, which varies depending upon the reaction conditions, is preferably 5 minutes to 72 hours, and more preferably 30 minutes to 48 hours.

Step 12

A compound (XIV) can be obtained by the reduction reaction of a compound (XIII) in the presence of a transition metal catalyst under a hydrogen atmosphere.

As the transition metal catalyst to be used in the reduction reaction, for example, palladium-carbon can be mentioned.

The amount of the transition metal catalyst to be used in the reduction reaction is preferably 0.1 to 100 wt % relative to a compound (XIII) and more preferably 1 to 50 wt %

The reduction reaction is generally performed in a solvent and a solvent which does not inhibit the reaction is appropriately selected. As the solvent, for example, an aliphatic hydrocarbon such as heptane or hexane or an aliphatic alcohol such as methanol, ethanol or propanol can be mentioned. A mixture of these solvents may be used.

In the reduction reaction, the reaction temperature is preferably 0 to 80° C. and more preferably 10 to 40° C.

In the reduction reaction, the reaction time, which varies depending upon the reaction conditions, is preferably 5 minutes to 72 hours, and more preferably 30 minutes to 48 hours.

Step 13

A compound (IIIa), which is a compound (III) wherein $R^2$ is a hydrogen atom, can be obtained by hydrolysis reaction of a compound (XIV).

As the base to be used in the hydrolysis reaction, for example, lithium hydroxide, potassium hydroxide or sodium hydroxide can be mentioned.

The amount of the base to be used in the hydrolysis reaction is preferably 0.5 to 3.0 moles relative to 1 mole of a compound (XIV) and more preferably 0.8 to 2.0 moles.

The hydrolysis reaction is generally performed in a solvent and a solvent which does not inhibit the reaction is appropriately selected. As the solvent, for example, an aliphatic alcohol such as methanol, ethanol or propanol, or water can be mentioned. A mixture of these solvents may be used.

In the hydrolysis reaction, the reaction temperature is preferably −20° C. to 150° C. and more preferably 0 to 100° C.

In the hydrolysis reaction, the reaction time, which varies depending upon the reaction conditions, is preferably 5 minutes to 72 hours, and more preferably 30 minutes to 48 hours. 4. Production method for compound (III):

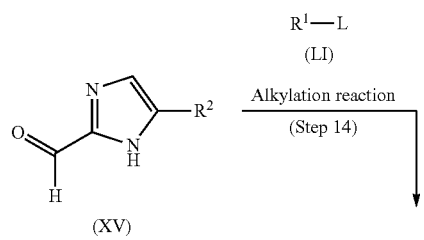

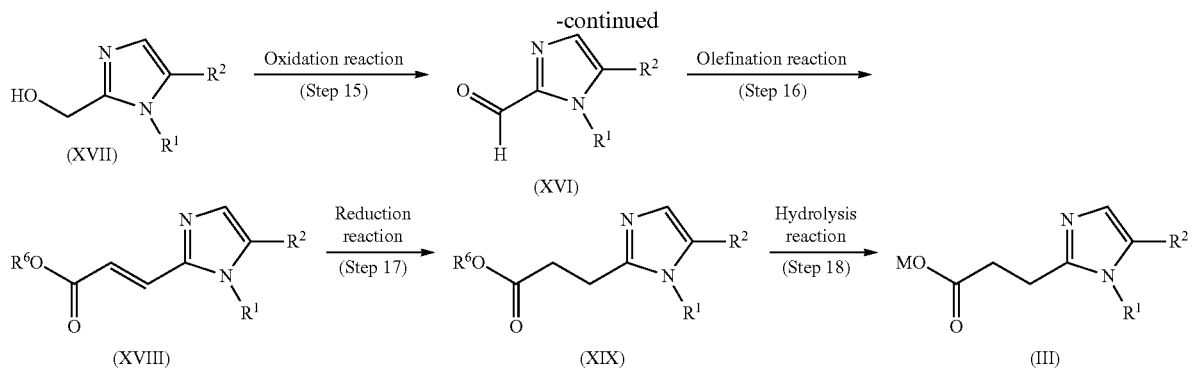

wherein individual reference symbols are the same as defined above.

Step 14

A compound (XVI) can be obtained by deprotonation of a compound (XV) with a base, followed by an alkylation reaction with an alkylating reagent (LI).

As the compound (XV) to be used in the alkylation reaction, a commercially available compound can be directly used.

As the base to be used in the alkylation reaction, for example, a metal carbonate such as sodium carbonate, potassium carbonate or cesium carbonate or an alkaline metal hydroxide such as sodium hydroxide or potassium hydroxide can be mentioned.

The amount of the base to be used in the alkylation reaction is preferably 0.5 to 3.0 moles relative to 1 mole of a compound (XV) and more preferably 0.8 to 2.0 moles.

The amount of the alkylating reagent (LI) to be used in the alkylation reaction is preferably 0.5 to 3.0 moles relative to 1 mole of a compound (XV) and more preferably 0.8 to 2.0 moles.

The alkylation reaction is generally performed in a solvent and a solvent which does not inhibit the reaction is appropriately selected. As the solvent, for example, an ether such as tetrahydrofuran or 1,4-dioxane, an amide such as N,N-dimethylformamide or N-methylpyrrolidone or an aliphatic nitrile such as acetonitrile or propionitrile can be mentioned. A mixture of these solvents may be used.

In the alkylation reaction, the reaction temperature is preferably −20° C. to 150° C. and more preferably 0 to 100° C.

In the alkylation reaction, the reaction time, which varies depending upon the reaction conditions, is preferably 5 minutes to 72 hours, and more preferably 30 minutes to 48 hours.

Step 15

A compound (XVI) can be obtained by the oxidation reaction of a compound (XVII).

As the compound (XVII) to be used in the oxidation reaction, a commercially available compound can be directly used; however, it can be also synthesized by a method known to those skilled in the art.

As the oxidant to be used in the oxidation reaction, for example, sulfur trioxidepyridine, activated dimethyl sulfoxide or a Dess-Martin reagent can be mentioned.

The amount of the oxidant to be used in the oxidation reaction is preferably 0.5 to 3.0 moles relative to 1 mole of a compound (XVII) and more preferably 0.8 to 2.0 moles.

The oxidation reaction is generally performed in a solvent and a solvent which does not inhibit the reaction is appropriately selected. As the solvent, for example, an aromatic amine such as pyridine, a halogenated hydrocarbon such as dichloromethane, chloroform or 1,2-dichloroethane, an ether such as tetrahydrofuran or 1,4-dioxane or an aliphatic nitrile such as acetonitrile or propionitrile can be mentioned. A mixture of these solvents may be used.

In the oxidation reaction, the reaction temperature is preferably −78° C. to 100° C. and more preferably −78° C. to 40° C.

In the oxidation reaction, the reaction time, which varies depending upon the reaction conditions, is preferably 5 minutes to 72 hours, and more preferably 30 minutes to 48 hours.

Step 16

A compound (XVIII) can be obtained by the olefination reaction of a compound (XVI).

As the reagent to be used in the olefination reaction, for example, a Wittig reagent such as methyl 2-(triphenylphosphoranylidene)acetate or a Horner-Emmons reagent such as ethyl diethylphosphonoacetate can be mentioned. As the Wittig reagent or Horner-Emmons reagent, a commercially available compound can be directly used.

The amount of the Wittig reagent or Horner-Emmons reagent to be used in the olefination reaction is preferably 0.5 to 3.0 moles relative to 1 mole of a compound (XVI) and more preferably 0.8 to 2.0 moles.

The olefination reaction is generally performed in a solvent and a solvent which does not inhibit the reaction is appropriately selected. As the solvent, for example, an aromatic hydrocarbon such as toluene, chlorobenzene or xylene, an ether such as tetrahydrofuran or 1,4-dioxane, an amide such as N,N-dimethylformamide or N-methylpyrrolidone or an aliphatic nitrile such as acetonitrile or propionitrile can be mentioned. A mixture of these solvents may be used.

In the olefination reaction, the reaction temperature is preferably −20° C. to 150° C. and more preferably 0 to 100° C.

In the olefination reaction, the reaction time, which varies depending upon the reaction conditions, is preferably 5 minutes to 72 hours, and more preferably 30 minutes to 48 hours.

Step 17

A compound (XIX) can be obtained by the reduction reaction of a compound (XVIII) in the presence of a transition metal catalyst under a hydrogen atmosphere.

As the transition metal catalyst to be used in the reduction reaction, for example, palladium-carbon can be mentioned.

The amount of the transition metal catalyst to be used in the reduction reaction is preferably 0.1 to 100 wt % relative to a compound (XVIII) and more preferably 1 to 50 wt %.

The reduction reaction is generally performed in a solvent and a solvent which does not inhibit the reaction is appropriately selected. As the solvent, for example, an aliphatic hydrocarbon such as heptane or hexane or an aliphatic alcohol such as methanol, ethanol or propanol can be mentioned. A mixture of these solvents may be used.

In the reduction reaction, the reaction temperature is preferably 0 to 80° C. and more preferably 10 to 40° C.

In the reduction reaction, the reaction time, which varies depending upon the reaction conditions, is preferably 5 minutes to 72 hours, and more preferably 30 minutes to 48 hours.

Step 18

A compound (III) can be obtained by the hydrolysis reaction of a compound (XIX).

As the base to be used in the hydrolysis reaction, for example, lithium hydroxide, potassium hydroxide or sodium hydroxide can be mentioned.

The amount of the base to be used in the hydrolysis reaction is preferably 0.5 to 3.0 moles relative to 1 mole of a compound (XIX) and more preferably 0.8 to 2.0 moles.

The hydrolysis reaction is generally performed in a solvent and a solvent which does not inhibit the reaction is appropriately selected. As the solvent, for example, an aliphatic alcohol such as methanol, ethanol or propanol or water can be mentioned. A mixture of these solvents may be used.

In the hydrolysis reaction, the reaction temperature is preferably, −20° C. to 150° C. and more preferably 0 to 100° C.

In the hydrolysis reaction, the reaction time, which varies depending upon the reaction conditions, is preferably 5 minutes to 72 hours, and more preferably 30 minutes to 48 hours.

5. Production Method for a Compound (XIII)

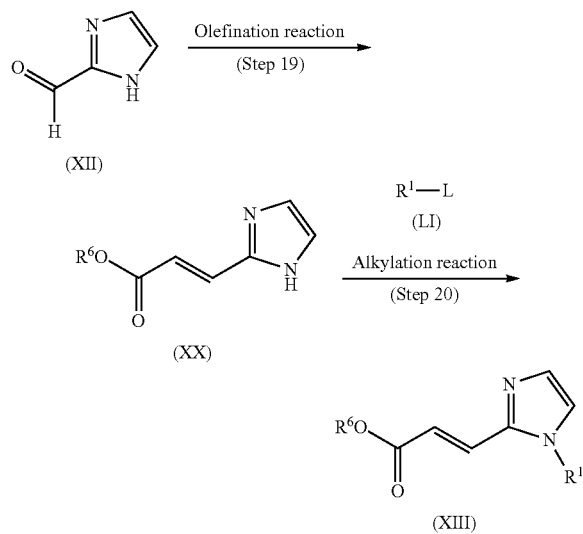

wherein individual reference symbols are the same as defined above.

Step 19

A compound (XX) can be obtained by the olefination reaction of a compound (XII).

As the reagent to be used in the olefination reaction, for example, a Wittig reagent such as methyl 2-(triphenylphosphoranylidene)acetate or a Horner-Emmons reagent such as ethyl diethylphosphonoacetate can be mentioned. As the Wittig reagent or Horner-Emmons reagent, a commercially available compound can be directly used.

The amount of the Wittig reagent or Horner-Emmons reagent to be used in the olefination reaction is preferably 0.5 to 3.0 moles relative to 1 mole of a compound (XII) and more preferably 0.8 to 2.0 moles.

The olefination reaction is generally performed in a solvent and a solvent which does not inhibit the reaction is appropriately selected. As the solvent, for example, an aromatic hydrocarbon such as toluene, chlorobenzene or xylene, an ether such as tetrahydrofuran or 1,4-dioxane, an amide such as N,N-dimethylformamide or N-methylpyrrolidone or an aliphatic nitrile such as acetonitrile or propionitrile can be mentioned. A mixture of these solvents may be used.

In the olefination reaction, the reaction temperature is preferably −20° C. to 150° C. and more preferably 0 to 100° C.

In the olefination reaction, the reaction time, which varies depending upon the reaction conditions, is preferably 5 minutes to 72 hours, and more preferably 30 minutes to 48 hours.

Step 20

A compound (XIII) can be obtained by deprotonation of a compound (XX) with a base, followed by an alkylation reaction with an alkylating reagent (LI).

As the base to be used in the alkylation reaction, for example, a metal carbonate such as sodium carbonate, potassium carbonate or cesium carbonate or an alkali metal hydroxide such as sodium hydroxide or potassium hydroxide can be mentioned.

The amount of the base to be used in the alkylation reaction is preferably 0.5 to 3.0 moles relative to 1 mole of a compound (XX) and more preferably 0.8 to 2.0 moles.

The amount of the alkylating reagent (LI) to be used in the alkylation reaction is preferably 0.5 to 3.0 moles relative to 1 mole of a compound (XX) and more preferably 0.8 to 2.0 moles.

The alkylation reaction is generally performed in a solvent and a solvent which does not inhibit the reaction is appropriately selected. As the solvent, for example, an ether such as tetrahydrofuran or 1,4-dioxane, an amide such as N,N-dimethylformamide or N-methylpyrrolidone or an aliphatic nitrile such as acetonitrile or propionitrile can be mentioned. A mixture of these solvents may be used.

In the alkylation reaction, the reaction temperature is preferably, −20° C. to 150° C. and more preferably 0 to 100° C.

In the alkylation reaction, the reaction time, which varies depending upon the reaction conditions, is preferably 5 minutes to 72 hours, and more preferably 30 minutes to 48 hours.

6. Production Method for a Compound (XVIII):

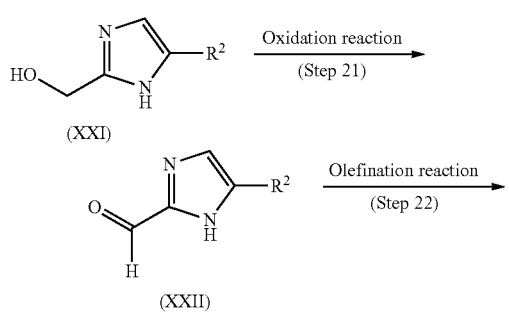

-continued (XXIII)

$R^1$—L
(LI)

Alkylation reaction
(Step 23)

(XVIII)

wherein individual reference symbols are the same as defined above.

Step 21

A compound (XXII) can be obtained by the oxidation reaction of a compound (XXI).

As the compound (XXI) to be used in the oxidation reaction, a commercially available compound can be directly used; however, it can be synthesized even by a known method.

As the oxidant to be used in the oxidation reaction, for example, sulfur trioxidepyridine, activated dimethyl sulfoxide or a Dess-Martin reagent can be mentioned.

The amount of the oxidant to be used in the oxidation reaction is preferably 0.5 to 3.0 moles relative to 1 mole of a compound (XXI) and more preferably 0.8 to 2.0 moles.

The oxidation reaction is generally performed in a solvent and a solvent which does not inhibit the reaction is appropriately selected. As the solvent, for example, an aromatic amine such as pyridine, a halogenated hydrocarbon such as dichloromethane, chloroform or 1,2-dichloroethane, an ether such as tetrahydrofuran or 1,4-dioxane or an aliphatic nitrile such as acetonitrile or propionitrile can be mentioned. A mixture of these solvents may be used.

In the oxidation reaction, the reaction temperature is preferably −78° C. to 100° C. and more preferably −78° C. to 40° C.

In the oxidation reaction, the reaction time, which varies depending upon the reaction conditions, is preferably 5 minutes to 72 hours, and more preferably 30 minutes to 48 hours.

Step 22

A compound (XXIII) can be obtained by the olefination reaction of a compound (XXII).

As the reagent to be used in the olefination reaction, for example, a Wittig reagent such as methyl 2-(triphenylphosphoranylidene)acetate or a Horner-Emmons reagent such as ethyl diethylphosphonoacetate can be mentioned. As the Wittig reagent or Horner-Emmons reagent, a commercially available compound can be directly used.

The amount of the Wittig reagent or Horner-Emmons reagent to be used in the olefination reaction is preferably 0.5 to 3.0 moles relative to 1 mole of a compound (XXII) and more preferably 0.8 to 2.0 moles.

The olefination reaction is generally performed in a solvent and a solvent which does not inhibit the reaction is appropriately selected. As the solvent, for example, an aromatic hydrocarbon such as toluene, chlorobenzene or xylene, an ether such as tetrahydrofuran or 1,4-dioxane, an amide such as N,N-dimethylformamide or N-methylpyrrolidone or an aliphatic nitrile such as acetonitrile or propionitrile can be mentioned. A mixture of these solvents may be used.

In the olefination reaction, the reaction temperature is preferably −20° C. to 150° C. and more preferably 0 to 100° C.

In the olefination reaction, the reaction time, which varies depending upon the reaction conditions, is preferably 5 minutes to 72 hours, and more preferably 30 minutes to 48 hours.

Step 23

A compound (XVIII) can be obtained by deprotonation of a compound (XXIII) with a base, followed by an alkylation reaction with an alkylating reagent (LI).

As the base to be used in the alkylation reaction, for example, a metal carbonate such as sodium carbonate, potassium carbonate or cesium carbonate or an alkali metal hydroxide such as sodium hydroxide or potassium hydroxide can be mentioned.

The amount of the base to be used in the alkylation reaction is preferably 0.5 to 3.0 moles relative to 1 mole of a compound (XXIII) and more preferably 0.8 to 2.0 moles.

The amount of the alkylating reagent (LI) to be used in the alkylation reaction is preferably 0.5 to 3.0 moles relative to 1 mole of a compound (XXIII) and more preferably 0.8 to 2.0 moles.

The alkylation reaction is generally performed in a solvent and a solvent which does not inhibit the reaction is appropriately selected. As the solvent, for example, an ether such as tetrahydrofuran or 1,4-dioxane, an amide such as N,N-dimethylformamide or N-methylpyrrolidone or an aliphatic nitrile such as acetonitrile or propionitrile can be mentioned. A mixture of these solvents may be used.

In the alkylation reaction, the reaction temperature is preferably −20° C. to 150° C. and more preferably 0 to 100° C.

In the alkylation reaction, the reaction time, which varies depending upon the reaction conditions, is preferably 5 minutes to 72 hours, and more preferably 30 minutes to 48 hours.

7. Compound (Ib) can be synthesized in accordance with the production method that will be described below.

7-1. Production Method for a Compound (Ib-a):

(IIb-a)

(III)

Condensation reaction (Ib-a)

wherein individual reference symbols are the same as defined above.

A compound (Ib-a), which is a cyclic amine derivative (I) wherein A represents a group represented by a general formula (IIb) and $R^4$ represents an alkyl group having 1 to 6 carbon atoms and optionally substituted with an alkylcarbonylamino group having 2 to 6 carbon atoms, can be obtained, for example, by a condensation reaction between a compound (IIb-a) and a compound (III) with a condensing agent, in the presence or absence of a base.

In the condensation reaction, a compound (IIb-a) and a salt thereof can be used. As the salt herein, for example, the same salt as a pharmacologically acceptable salt as mentioned above can be mentioned.

As the compound (IIb-a) and the compound (III) to be used in the condensation reaction, commercially available compounds can be directly used; however, for example, the compound (IIb-a) can be synthesized in accordance with the production method that will be described below and the compound (III) can be synthesized in accordance with the above production method.

As the base to be used in the condensation reaction, for example, an aromatic amine such as pyridine or lutidine or a tertiary amine such as triethylamine, triisopropylamine, tributylamine, cyclohexyldimethylamine, 4-dimethylaminopyridine, N,N-dimethylaniline, N-methylpiperidine, N-methylpyrrolidine, N-methylmorpholine or diisopropylethylamine (DIEA) can be mentioned.

The amount of the base to be used in the condensation reaction is preferably 0.5 to 10 moles relative to 1 mole of a compound (IIb-a) and more preferably 0.8 to 5.0 moles.

As the condensing agent to be used in the condensation reaction, for example, 0-(benzotriazol-1-yl)-N,N,N',N'-tetramethyluronium hexafluorophosphate (HBTU), cyclohexylcarbodiimide (DCC), N-(3-dimethylaminopropyl)-N'-ethyl carbodiimide (EDC) or a hydrochloride thereof, mentioned. These condensing agents may be used alone or in combination with an additive such as N-hydroxysuccinimide (HONSu), hydroxybenzotriazole (HOBT), 3-hydroxy-4-oxo-3,4-dihydro-1,2,3-benzotriazine (HOOBT) or 4-dimethylaminopyridine (DMAP).

The amount of the condensing agent to be used in the condensation reaction is preferably 0.5 to 10 moles relative to 1 mole of a compound (IIb-a) and more preferably 0.8 to 5.0 moles.

The amount of the compound (III) to be used in the condensation reaction is preferably 0.5 to 3 moles relative to 1 mole of a compound (IIb-a) and more preferably 0.8 to 1.5 moles.

The condensation reaction is generally performed in a solvent and a solvent which does not inhibit the reaction is appropriately selected. As the solvent, for example, an aromatic amine such as pyridine, a halogenated hydrocarbon such as dichloromethane, chloroform or 1,2-dichloroethane, an ether such as tetrahydrofuran or 1,4-dioxane, an amide such as N,N-dimethylformamide or N-methylpyrrolidone, an alcohol such as methanol, ethanol or 2-propanol or an aliphatic nitrile such as acetonitrile or propionitrile can be mentioned. A mixture of these solvents may be used. When an aromatic amine such as pyridine is selected as the solvent, the condensation reaction may be performed in the absence of a base.

In the condensation reaction, the reaction temperature is preferably −20° C. to 150° C. and more preferably 0 to 100° C.

In the condensation reaction, the reaction time, which varies depending upon the reaction conditions, is preferably 5 minutes to 72 hours, and more preferably 30 minutes to 48 hours.

7-2. Production Methods for Compounds (Ib-b), (Ib-c) and (Ib-d):

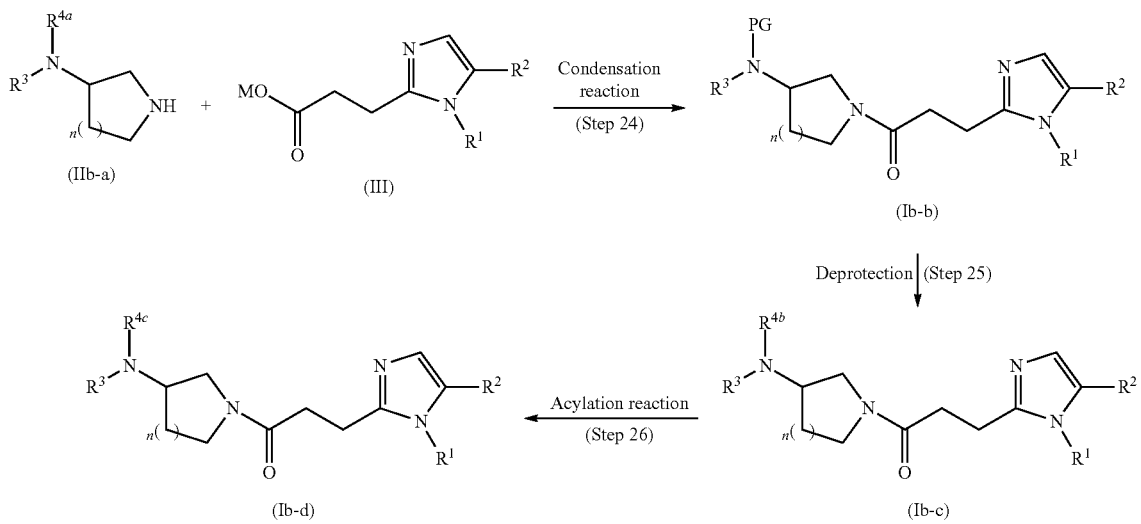

2-ethoxy-1-ethoxycarbonyl-1,2-dihydroxyquinoline (EEDQ), carbonyldiimidazole (CDI), diethylphosphoryl cyanide, benzotriazol-1-yloxytrispyrrolidinophosphonium hexafluorophosphate (PyBOP), diphenylphosphoryl azide (DPPA), 4-(4,6-dimethoxy-1,3,5-triazin-2-yl)-4-methylmorpholinium chloride (DMTMM), isobutyl chloroformate, diethylacetyl chloride or trimethylacetyl chloride can be wherein individual reference symbols are the same as defined above.

Step 24

A compound (Ib-b) can be obtained, for example, by a condensation reaction between a compound (IIb-b) and a compound (III) with a condensing agent, in the presence or absence of a base.

In the condensation reaction, a compound (IIb-b) and a salt thereof can be used. As the salt herein, for example, the same salt as a pharmacologically acceptable salt as mentioned above can be mentioned.

As the compound (IIb-b) and compound (III) to be used in the condensation reaction, commercially available compounds can be directly used; however, for example, the compound (IIb-b) can be synthesized in accordance with the production method that will be described below and the compound (III) can be synthesized in accordance with the above production method.

As the base to be used in the condensation reaction, for example, an aromatic amine such as pyridine or lutidine or a tertiary amine such as triethylamine, triisopropylamine, tributylamine, cyclohexyldimethylamine, 4-dimethylaminopyridine, N,N-dimethylaniline, N-methylpiperidine, N-methylpyrrolidine, N-methylmorpholine or diisopropylethylamine (DIEA) can be mentioned.

The amount of the base to be used in the condensation reaction is preferably 0.5 to 10 moles relative to 1 mole of a compound (IIb-b) and more preferably 0.8 to 5.0 moles.

As the condensing agent to be used in the condensation reaction, for example, 0-(benzotriazol-1-yl)-N,N,N',N'-tetramethyluronium hexafluorophosphate (HBTU), cyclohexylcarbodiimide (DCC), N-(3-dimethylaminopropyl)-N'-ethyl carbodiimide (EDC) or a hydrochloride thereof, 2-ethoxy-1-ethoxycarbonyl-1,2-dihydroxyquinoline (EEDQ), carbonyldiimidazole (CDI), diethylphosphoryl cyanide, benzotriazol-1-yloxytrispyrrolidinophosphonium hexafluorophosphate (PyBOP), diphenylphosphoryl azide (DPPA), 4-(4,6-dimethoxy-1,3,5-triazin-2-yl)-4-methylmorpholinium chloride (DMTMM), isobutyl chloroformate, diethylacetyl chloride or trimethylacetyl chloride can be mentioned. These condensing agents may be used alone or in combination with an additive such as N-hydroxysuccinimide (HONSu), hydroxybenzotriazole (HOBT), 3-hydroxy-4-oxo-3,4-dihydro-1,2,3-benzotriazine (HOOBT) or 4-dimethylaminopyridine (DMAP).

The amount of the condensing agent to be used in the condensation reaction is preferably 0.5 to 10 moles relative to 1 mole of a compound (IIb-b) and more preferably 0.8 to 5.0 moles.

The amount of the compound (III) to be used in the condensation reaction is preferably 0.5 to 3 moles relative to 1 mole of a compound (IIb-b) and more preferably 0.8 to 1.5 moles.

The condensation reaction is generally performed in a solvent and a solvent which does not inhibit the reaction is appropriately selected. As the solvent, for example, an aromatic amine such as pyridine, a halogenated hydrocarbon such as dichloromethane, chloroform or 1,2-dichloroethane, an ether such as tetrahydrofuran or 1,4-dioxane, an amide such as N,N-dimethylformamide or N-methylpyrrolidone, an alcohol such as methanol, ethanol or 2-propanol or an aliphatic nitrile such as acetonitrile or propionitrile can be mentioned. A mixture of these solvents may be used. When an aromatic amine such as pyridine is selected as the solvent, the condensation reaction may be performed in the absence of a base.

In the condensation reaction, the reaction temperature is preferably −20° C. to 150° C. and more preferably 0 to 100° C.

In the condensation reaction, the reaction time, which varies depending upon the reaction conditions, is preferably 5 minutes to 72 hours, and more preferably 30 minutes to 48 hours.

Step 25

A compound (Ib-c), which is a cyclic amine derivative (I) wherein A represents a group represented by a general formula (IIb) and $R^4$ is a hydrogen atom, can be obtained by deprotection of a compound (Ib-b).

Removal of a protective group, which varies depending upon the type of protective group, can be performed in accordance with a known method (for example, Greene, T. W., "Greene's Protective Groups in Organic Synthesis," Wiley-Interscience) or a similar method thereto.

Step 26

A compound (Ib-d), which is a cyclic amine derivative (I) wherein A represents a group represented by a general formula (IIb) and $R^4$ represents an alkylcarbonyl group having 2 to 6 carbon atoms can be obtained by, for example, reacting a compound (Ib-c) and an acylating agent such as carboxylic halide having 2 to 6 carbon atoms or an acid anhydride, in the presence of a base.

In the acylation reaction, a compound (Ib-c) and a salt thereof can be used. As the salt herein, for example, the same salt as a pharmacologically acceptable salt as mentioned above can be mentioned.

As the base to be used in the acylation reaction, for example, pyridine, triethylamine, diisopropylethylamine or N,N-dimethylaminopyridine can be mentioned.

The amount of the base to be used in the acylation reaction is preferably 0.5 to 10 moles relative to 1 mole of a compound (Ib-c) and more preferably 0.8 to 5.0 moles.

The acylation reaction is generally performed in a solvent and a solvent which does not inhibit the reaction is appropriately selected. As the solvent, for example, an aromatic amine such as pyridine, a halogenated hydrocarbon such as dichloromethane, chloroform or 1,2-dichloroethane, an ether such as tetrahydrofuran or 1,4-dioxane or an aliphatic nitrile such as acetonitrile or propionitrile can be mentioned. A mixture of these solvents may be used. When an aromatic amine such as pyridine is selected as a solvent, the acylation reaction can be performed in the absence of a base.

7-3. Salt Formation Steps of Compounds (Ib-a), (Ib-b), (Ib-c) and (Ib-d):

Pharmacologically acceptable salts of compounds (Ib-a), (Ib-b), (Ib-c) and (Ib-d) can be obtained, for example, by a salt formation reaction performed by mixing the compound (Ib-a), (Ib-b), (Ib-c) or (Ib-d) and an acid.

As the acid to be used in the salt formation reaction, for example, an inorganic acid such as hydrochloric acid, sulfuric acid, phosphoric acid or hydrobromic acid, or an organic acid such as oxalic acid, malonic acid, citric acid, fumaric acid, lactic acid, malic acid, succinic acid, tartaric acid, acetic acid, trifluoroacetic acid, maleic acid, gluconic acid, benzoic acid, salicylic acid, xinafoic acid, pamoic acid, ascorbic acid, adipic acid, methanesulfonic acid, p-toluenesulfonic acid or cinnamic acid can be mentioned.

The salt formation reaction is generally performed in a solvent and a solvent which does not inhibit the reaction is appropriately selected. As the solvent, for example, an aliphatic alcohol such as methanol, ethanol or isopropanol, an ether such as diethyl ether, tetrahydrofuran, 1,4-dioxane or ethylene glycol dimethyl ether, an amide such as N,N-dimethylformamide or N-methylpyrrolidone, a sulfoxide such as dimethyl sulfoxide, an aliphatic nitrile such as acetonitrile or propionitrile, a ketone such as acetone or 2-butanone, an ester such as ethyl acetate, methyl acetate or n-butyl acetate, or water can be mentioned. A mixture of these solvents may be used.

8. Compound (IIb) can be synthesized in accordance with the production method that will be described below.

8-1. Production Method for Compound (IIb-a):

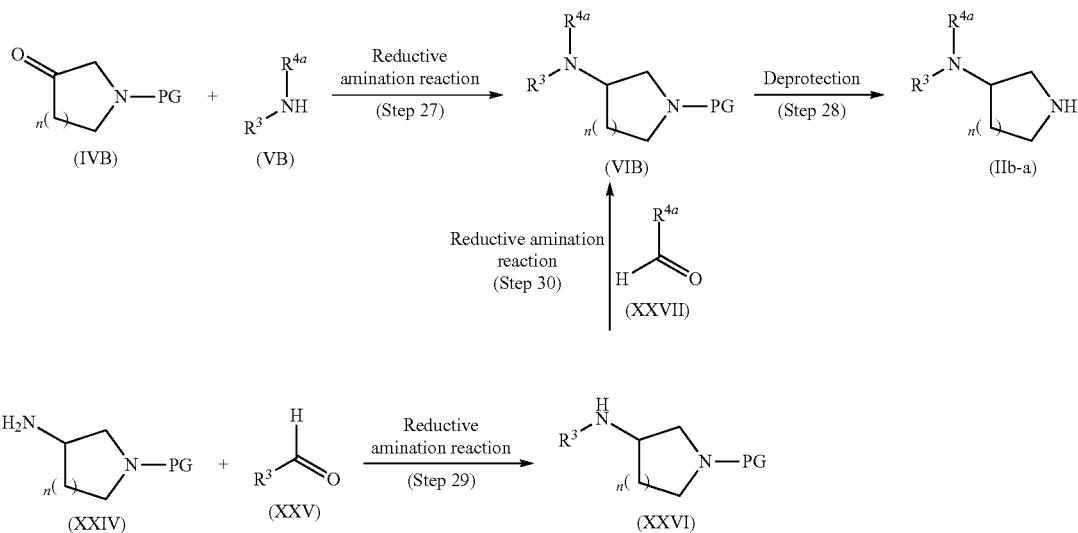

wherein individual reference symbols are the same as defined above.

Step 27

A compound (VIB) can be obtained by the reductive amination reaction between a compound (IVB) and a compound (VB).

As the compound (VB) to be used in the reductive amination reaction, a commercially available compound can be directly used.

The reductive amination reaction can be performed in accordance with a known method (for example, Journal of Organic Chemistry, vol. 68, p. 770-779, 2003) or a similar method thereto.

Step 28

A compound (IIb-a) can be obtained by the deprotection of a compound (VIB).

Removal of a protective group, which varies depending upon the type of protective group, can be performed in accordance with a known method (for example, Greene, T. W., "Greene's Protective Groups in Organic Synthesis," Wiley-Interscience) or a similar method thereto.

Step 29

A compound (XXVI) can be obtained by the reductive amination reaction between a compound (XXIV) and a compound (XXV).

As the compound (XXV) to be used in the reductive amination reaction, a commercially available compound can be directly used.

The reductive amination reaction can be performed in accordance with a known method (for example, Journal of Organic Chemistry, vol. 68, p. 770-779, 2003) or a similar method thereto.

Step 30

A compound (VIB) can be obtained by the reductive amination reaction between a compound (XXVI) and a compound (XXVII).

As the compound (XXVII) to be used in the reductive amination reaction, a commercially available compound can be directly used.

The reductive amination reaction can be performed in accordance with a known method (for example, Journal of Organic Chemistry, vol. 68, p. 770-779, 2003) or a similar method thereto.

8-2. Production Method for Compound (IIb-b):

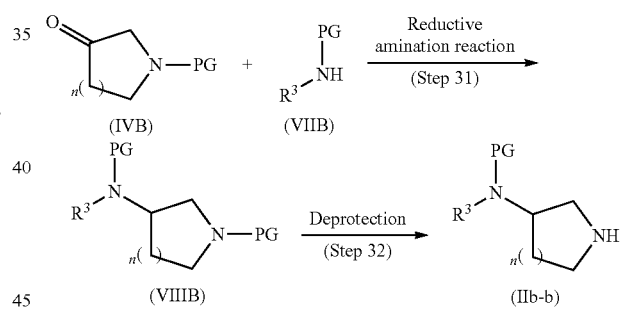

wherein individual reference symbols are the same as defined above.

Step 31

A compound (VIIIB) can be obtained by the reductive amination reaction between a compound (IVB) and a compound (VIIB).

As the compound (VIIB) to be used in the reductive amination reaction, a commercially available compound can be directly used.

The reductive amination reaction can be performed in accordance with a known method (for example, Journal of Organic Chemistry, vol. 68, p. 770-779, 2003) or a similar method thereto.

Step 32

The compound (IIb-b) can be obtained by the deprotection of a compound (VIIIB).

Removal of a protective group, which varies depending upon the type of protective group, can be performed in accordance with a known method (for example, Greene, T. W., "Greene's Protective Groups in Organic Synthesis," Wiley-Interscience) or a similar method thereto.

9. Compound (Ic) can be synthesized in accordance with the production method that will be described below.

9-1. Production Method for Compound (Ic):

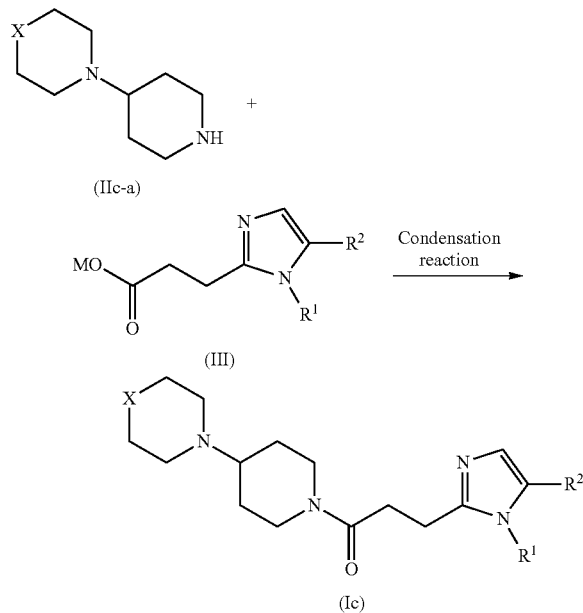

wherein individual reference symbols are the same as defined above.

A compound (Ic), which is a cyclic amine derivative (I) wherein A represents a group represented by Formula (IIc), can be obtained, for example, by the condensation reaction between a compound (IIc-a) and a compound (III) with a condensing agent in the presence or absence of a base.

In the condensation reaction, a compound (IIc-a) and a salt thereof can be used. As the salt herein, for example, the same salt as a pharmacologically acceptable salt as mentioned above can be mentioned.

As the compound (IIc-a) and compound (III) to be used in the condensation reaction, commercially available compounds can be directly used. However, for example, a compound (IIc-a) can be synthesized in accordance with the production method that will be described below and the compound (III) can be synthesized in accordance with the above production method.

As the base to be used in the condensation reaction, for example, an aromatic amine such as pyridine or lutidine or a tertiary amine such as triethylamine, triisopropylamine, tributylamine, cyclohexyldimethylamine, 4-dimethylaminopyridine, N,N-dimethylaniline, N-methylpiperidine, N-methylpyrrolidine, N-methylmorpholine or diisopropylethylamine (DIEA) can be mentioned.

The amount of the base to be used in the condensation reaction is preferably 0.5 to 10 moles relative to 1 mole of a compound (IIc-a) and more preferably 0.8 to 5.0 moles.

As the condensing agent to be used in the condensation reaction, for example, 0-(benzotriazol-1-yl)-N,N,N',N'-tetramethyluronium hexafluorophosphate (HBTU), cyclohexylcarbodiimide (DCC), N-(3-dimethylaminopropyl)-N'-ethyl carbodiimide (EDC) or a hydrochloride thereof, 2-ethoxy-1-ethoxycarbonyl-1,2-dihydroxyquinoline (EEDQ), carbonyldiimidazole (CDI), diethylphosphoryl cyanide, benzotriazol-1-yloxytrispyrrolidinophosphonium hexafluorophosphate (PyBOP), diphenylphosphoryl azide (DPPA), 4-(4,6-dimethoxy-1,3,5-triazin-2-yl)-4-methyl morpholinium chloride (DMTMM), isobutyl chloroformate, diethylacetyl chloride or trimethyl acetyl chloride can be mentioned. These condensing agents may be used alone or in combination with an additive such as N-hydroxysuccinimide (HONSu), hydroxybenzotriazole (HOBT), 3-hydroxy-4-oxo-3,4-dihydro-1,2,3-benzotriazine (HOOBT) or 4-dimethylaminopyridine (DMAP).

The amount of the condensing agent to be used in the condensation reaction is preferably 0.5 to 10 moles relative to 1 mole of a compound (IIc-a) and more preferably 0.8 to 5.0 moles.

The amount of the compound (III) to be used in the condensation reaction is preferably 0.5 to 3 moles relative to 1 mole of a compound (IIc-a) and more preferably 0.8 to 1.5 moles.

The condensation reaction is generally performed in a solvent and a solvent which does not inhibit the reaction is appropriately selected. As the solvent, for example, an aromatic amine such as pyridine, a halogenated hydrocarbon such as dichloromethane, chloroform or 1,2-dichloroethane, an ether such as tetrahydrofuran or 1,4-dioxane, an amide such as N,N-dimethylformamide or N-methylpyrrolidone, an alcohol such as methanol, ethanol or 2-propanol or an aliphatic nitrile such as acetonitrile or propionitrile can be mentioned. A mixture of these solvents may be used. When an aromatic amine such as pyridine is selected as the solvent, the condensation reaction may be performed in the absence of a base.

In the condensation reaction, the reaction temperature is preferably −20° C. to 150° C. and more preferably 0 to 100° C.

In the condensation reaction, the reaction time, which varies depending upon the reaction conditions, is preferably 5 minutes to 72 hours, and more preferably 30 minutes to 48 hours.

9-2. Salt Formation Steps of a Compound (Ic):

A pharmacologically acceptable salt of a compound (Ic) can be obtained, for example, by a salt formation reaction performed by mixing the compound (Ic) and an acid.

As the acid to be used in the salt formation reaction, for example, an inorganic acid such as hydrochloric acid, sulfuric acid, phosphoric acid or hydrobromic acid, or an organic acid such as oxalic acid, malonic acid, citric acid, fumaric acid, lactic acid, malic acid, succinic acid, tartaric acid, acetic acid, trifluoroacetic acid, maleic acid, gluconic acid, benzoic acid, salicylic acid, xinafoate, pamoic acid, ascorbic acid, adipic acid, methanesulfonic acid, p-toluenesulfonic acid or cinnamic acid.

The salt formation reaction is generally performed in a solvent and a solvent which does not inhibit the reaction is appropriately selected. As the solvent, for example, an aliphatic alcohol such as methanol, ethanol or isopropanol, an ether such as diethyl ether, tetrahydrofuran, 1,4-dioxane or ethylene glycol dimethyl ether, an amide such as N,N-dimethylformamide or N-methylpyrrolidone, a sulfoxide such as dimethyl sulfoxide, an aliphatic nitrile such as acetonitrile or propionitrile, a ketone such as acetone or 2-butanone, an ester such as ethyl acetate, methyl acetate or n-butyl acetate, or water can be mentioned. A mixture of these solvents may be used.

10. Production Method for a Compound (IIc-a):

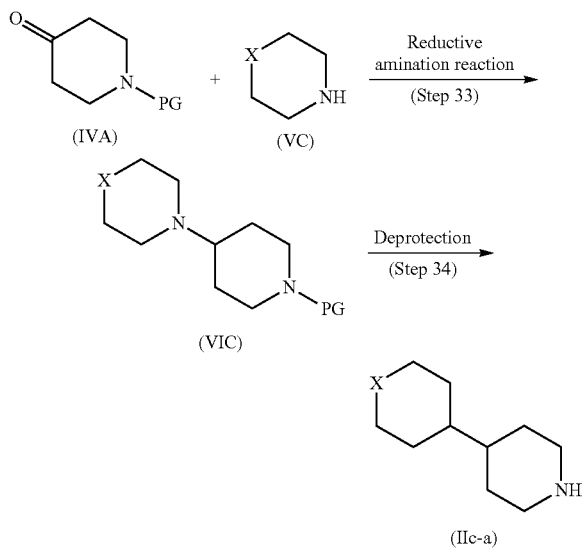

wherein individual reference symbols are the same as defined above.

Step 33

A compound (VIC) can be obtained by the reductive amination reaction between a compound (IVA) and a compound (VC).

As the compound (VC) to be used in the reductive amination reaction, a commercially available compound can be directly used.

The reductive amination reaction can be performed in accordance with a known method (for example, Journal of Organic Chemistry, vol. 68, p. 770-779, 2003) or a similar method thereto.

Step 34

A compound (IIc-a) can be obtained by the deprotection of a compound (VIC).

Removal of a protective group, which varies depending upon the type of protective group, can be performed in accordance with a known method (for example, Greene, T. W., "Greene's Protective Groups in Organic Synthesis," Wiley-Interscience) or a similar method thereto.

The analgesic action of a cyclic amine derivative (I) or a prodrug thereof or a pharmacologically acceptable salt thereof, particularly the therapeutic effect on neuropathic pain and fibromyalgia syndrome can be evaluated by use of an appropriate animal model. As the appropriate animal model for neuropathic pain, for example, a mouse or rat partial sciatic nerve ligation model (Malmberg et al., Pain, vol. 76, p. 215-222, 1998) or a mouse or rat spinal nerve ligation model (Kim et al., Pain, vol. 50, p. 355-363, 1992) can be mentioned. As the appropriate animal model for fibromyalgia syndrome, for example, rat fibromyalgia syndrome models (Sluka et al., Journal of Pharmacology and Experimental Therapeutics, vol. 302, p. 1146-50, 2002; Nagakura et al., Pain, vol. 146, p. 26-33, 2009; Sluka et al., Pain, vol. 146, p. 3-4, 2009) can be mentioned.

The cyclic amine derivative (I) or a prodrug thereof or a pharmacologically acceptable salt thereof, since it has an excellent analgesic action, particularly a therapeutic effect on neuropathic pain or fibromyalgia syndrome, can be used as a medicine, preferably used as an analgesic agent, and particularly preferably as a therapeutic agent for neuropathic pain or fibromyalgia syndrome. Note that, a prodrug of a cyclic amine derivative (I) exerts an excellent analgesic action when it is converted in vivo to a cyclic amine derivative (I); however, a prodrug of a cyclic amine derivative (I) in itself may have an analgesic action.

As the neuropathic pain herein, for example, cancer pain, shingles pain, postherpetic neuralgia, AIDS-related neuralgia, diabetic neuropathy pain or trigeminal neuralgia can be mentioned.

The "fibromyalgia syndrome" is a symptom diagnosed by a specialist physician as fibromyalgia syndrome. The diagnosis by a specialist physician is generally made with reference to the classification standard of the American College of Rheumatology.

The cyclic amine derivative (I) or a prodrug thereof or a pharmacologically acceptable salt thereof is useful for treating acute and chronic pain. The acute pain usually lasts for a short period, and, for example, postoperative pain, post-extraction pain or trigeminal neuralgia can be mentioned. The chronic pain is defined as pain usually lasting for 3 to 6 months and includes body neuropathic pain and psychogenic pain, and, for example, chronic rheumatoid arthritis, osteoarthritis or postherpetic neuralgia can be mentioned.

A medicine containing a cyclic amine derivative (I) or a prodrug thereof or a pharmacologically acceptable salt as an active ingredient, exerts an excellent analgesic action, particularly a therapeutic effect on neuropathic pain or fibromyalgia syndrome when it is administered to a mammal (for example, mouse, rat, hamster, rabbit, cat, dog, cow, sheep, monkey or human), especially to a human.

When a cyclic amine derivative (I) or a prodrug thereof or a pharmacologically acceptable salt thereof is used as a medicine, the cyclic amine derivative (I) or a prodrug thereof or a pharmacologically acceptable salt thereof directly or in combination with a pharmaceutically acceptable carrier can be orally or parenterally administered. When a prodrug or a pharmacologically acceptable salt thereof of a cyclic amine derivative (I) is used as a medicine, oral administration is preferable.

As the dosage form when a medicine containing a cyclic amine derivative (I) or a prodrug thereof or a pharmacologically acceptable salt thereof as an active ingredient is orally administered, for example, tablets (including sugar-coated and film-coated tablets), pills, granules, powders, capsules (including soft capsules and micro capsules), syrups, emulsions or suspensions can be mentioned. As the dosage form when a medicine containing a cyclic amine derivative (I) or a prodrug thereof or a pharmacologically acceptable salt thereof as an active ingredient is parenterally administered, for example, injections, infusions, drops, suppositories, endermic liniments or adhesive patches can be mentioned. It is further effective to prepare a sustained-release formulation by using an appropriate base (for example, a butyric acid polymer, a glycolic acid polymer, a butyric acid-glycolic acid copolymer, mixtures of a butyric acid polymer and a glycolic acid polymer, or a polyglycerol fatty acid ester) in combination.

Formulations having the aforementioned dosage forms can be prepared in accordance with production methods known in the field of drug formulation. In this case, if necessary, production can be made by adding an excipient, a binder, a lubricant, a disintegrating agent, a sweetening agent, a surfactant, a suspending agent or an emulsifying agent, which is generally used in the field of drug formulation.

Tablets can be prepared, for example, by adding an excipient, a binder, a disintegrating agent or a lubricant. Pills and granules can be prepared by adding, for example, an excipient, a binder or a disintegrating agent. Powders and capsules can be prepared by adding, for example, an excipient. Syrups can be prepared by adding, for example, a sweetening agent. Emulsions or suspensions can be prepared by adding, for example, a surfactant, a suspending agent or an emulsifier.

As the excipient, for example, lactose, glucose, starch, sucrose, microcrystalline cellulose, powdered *glycyrrhiza*, mannitol, sodium hydrogen carbonate, calcium phosphate or calcium sulfate can be mentioned.

As the binder, for example, a starch paste solution, a gum arabic solution, a gelatin solution, a tragacanth solution, a carboxymethylcellulose solution, a sodium alginate solution or glycerin can be mentioned.

As the disintegrating agent, for example, starch or calcium carbonate can be mentioned.

As the lubricant, for example, magnesium stearate, stearic acid, calcium stearate or purified talc can be mentioned.

As the sweetening agent, for example, glucose, fructose, invert sugar, sorbitol, xylitol, glycerin or simple syrup can be mentioned.

As the surfactant, for example, sodium lauryl sulfate, polysorbate 80, sorbitan monofatty acid ester or stearic acid polyoxyl 40 can be mentioned.

As the suspending agent, for example, Gum arabic, sodium alginate, sodium carboxymethylcellulose, methyl cellulose or bentonite can be mentioned.

As the emulsifier, for example, Gum arabic, tragacanth, gelatin or polysorbate 80 can be mentioned.

When a medicine containing a cyclic amine derivative (I) or a prodrug thereof or a pharmacologically acceptable salt thereof as an active ingredient is prepared in the aforementioned dosage forms, a coloring agent, a preserving agent, a fragrance, a flavoring agent, a stabilizer or a thickener generally used in the field of drug formulation can be added.

The dose per day of a medicine containing a cyclic amine derivative (I) or a prodrug thereof or a pharmacologically acceptable salt thereof as an active ingredient varies depending upon, e.g., the state or body weight of the patient or the type or administration route of a compound. For example, in oral administration to an adult (weight: about 60 kg), the amount of the cyclic amine derivative (I) or a prodrug thereof or a pharmacologically acceptable salt thereof serving as an active ingredient falls 1 to 1000 mg and administration is preferably made in 1 to 3 divided doses. In parenteral administration to an adult (weight: about 60 kg) by an injectable solution, the amount of the cyclic amine derivative (I) or a prodrug thereof or a pharmacologically acceptable salt thereof serving as an active ingredient in, e.g., an injection, falls within 0.01 to 100 mg per body weight (1 kg). The injectable solution is preferably intravenously administered.

A cyclic amine derivative (I) or a prodrug thereof or a pharmacologically acceptable salt thereof may be used in combination with other medicinal agents in an appropriate blending ratio to supplement or enhance a therapeutic or prophylactic effect or reduce the dose. In this case, as the other medicinal agents, for example, an antidepressant such as amitriptyline, milnacipran or duloxetine, an anxiolytic such as alprazolam, an anticonvulsant such as carbamazepine, a local anesthetic such as lidocaine, a sympathetic agonist such as adrenaline, an NMDA receptor antagonist such as ketamine, a GABA transaminase inhibitor such as sodium valproate, a calcium channel blocker such as pregabalin, a serotonin receptor antagonist such as risperidone, a GABA receptor function enhancer such as diazepam or an anti-inflammatory drug such as diclofenac can be mentioned.

EXAMPLES

Our derivatives and pharmaceuticals will be described in detail below with reference to Examples and Reference Examples. However, this disclosure is not limited to them.

In the following description, the names of the solvents shown in the NMR data represent the solvents used in the measurement. The 400 MHz NMR spectra were measured by using JNM-AL 400 series Nuclear Magnetic Resonance (NMR) spectorometer (JEOL, Ltd.). Chemical shifts are expressed by δ (unit: ppm) using tetramethylsilane as the reference, and the respective signals, respectively have the following meanings: s (singlet), d (doublet), t (triplet), q (quartet), quint (quintet), sept (septet), m (multiplet), br (broad), dd (double doublet), dt (double triplet), ddd (double double doublet), dq (double quantet), td (triple doublet), and tt (triple triplet). The ESI-MS spectra were measured by using Agilent Technologies 1200 Series, G6130A (from Agilent Technology). Commercially available products were used for all the solvents. For flash chromatography, YFLC W-prep2XY (from YAMAZEN) was used.

Raw materials and intermediates of cyclic amine derivatives (I) and prodrugs thereof were synthesized by the methods described in the following Reference Examples. Note that commercially-available products were used for the compounds used in synthesizing the compounds of Reference Examples for which synthesis methods are not described below.

Reference Example 1

Synthesis of benzyl 4-((2-((tert-butoxycarbonyl)amino)ethyl)(methyl)amino)piperidine-1-carboxylate

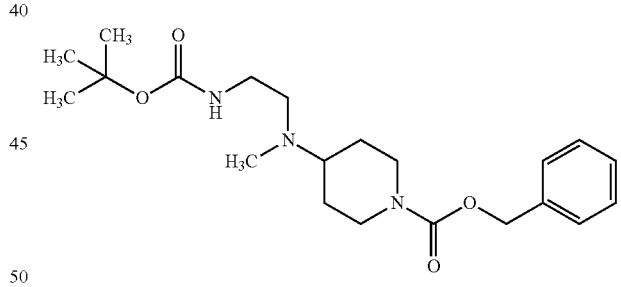

tert-Butyl (2-(methylamino)ethyl)carbamate hydrochloride (0.564 g, 2.68 mmol) and sodium triacetoxyborohydride (0.681 g, 3.22 mmol) were added to a solution of benzyl 4-oxopiperidine-1-carboxylate (0.500 g, 2.14 mmol) in dichloromethane (3.0 mL) at 0° C., and the resulting mixture was stirred at room temperature for 16 hours. The reaction liquid was cooled to 0° C. A saturated aqueous solution of sodium hydrogencarbonate was added to the reaction liquid, and the resulting mixture was extracted with chloroform. The organic layer was dried over anhydrous sodium sulfate and filtered, and the filtrate was concentrated under reduced pressure. The residue was purified by flash chromatography (silica gel, hexane/ethyl acetate) to obtain benzyl 4-((2-((tert-butoxycarbonyl)amino)ethyl)(methyl)amino)piperidine-1-carboxylate (0.590 g, 1.51 mmol, 70%) as a white solid.

$^{1}$H-NMR (400 MHz, CDCl$_{3}$) δ: 1.38-1.46 (11H, m), 1.67-1.76 (2H, m), 2.22 (3H, s), 2.47-2.55 (3H, m), 2.64-2.82 (2H, m), 3.12-3.21 (2H, m), 4.16-4.32 (2H, m), 4.90-5.00 (1H, m), 5.12 (2H, s), 7.30-7.37 (5H, m).
ESI-MS: m/z=392 (M+H)$^{+}$.

Reference Example 2

Synthesis of crude tert-butyl (2-(methyl(piperidin-4-yl)amino)ethyl)carbamate

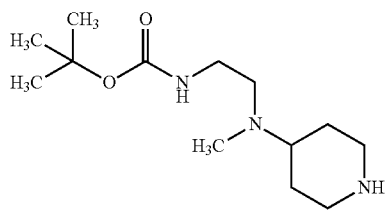 [SMILES: CN(CCNC(=O)OC(C)(C)C)C1CCNCC1]

Palladium/carbon (10% wet, 0.0815 g, 0.0766 mmol) was added to a solution of benzyl 4-((2-((tert-butoxycarbonyl)amino)ethyl)(methyl)amino)piperidine-1-carboxylate (0.300 g, 0.766 mmol) in methanol (4.0 mL) at room temperature, and the resulting mixture was stirred under hydrogen atmosphere for 16 hours. The reaction liquid was filtered through Celite, and the filtrate was concentrated under reduced pressure to obtain a crude product of tert-butyl (2-(methyl(piperidin-4-yl)amino)ethyl)carbamate.

Reference Example 3

Synthesis of tert-butyl 4-(N-benzyl-N-methylamino)piperidine-1-carboxylate

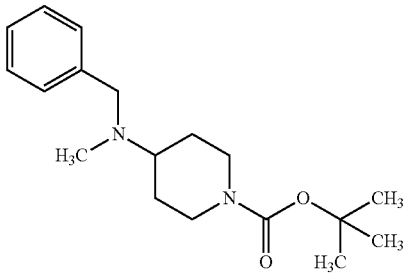 [SMILES: CN(Cc1ccccc1)C1CCN(C(=O)OC(C)(C)C)CC1]

N-benzyl-N-methylamine (2.43 mL, 18.8 mmol), acetic acid (0.0860 mL, 1.51 mmol), and sodium triacetoxyborohydride (1.20 g, 5.66 mmol) were added to a solution of tert-butyl 4-oxopiperidine-1-carboxylate (3.00 g, 15.1 mmol) in dichloromethane (20.0 mL) at 0° C. The reaction liquid was stirred at the same temperature for 30 minutes, and then sodium triacetoxyborohydride (1.20 g, 5.66 mmol) was added at 0° C. The reaction liquid was stirred at the same temperature for 30 minutes, and then sodium triacetoxyborohydride (2.40 g, 11.3 mmol) was added at 0° C., and the resulting mixture was stirred at room temperature for 16 hours. The reaction liquid was cooled to 0° C. A saturated aqueous solution of sodium hydrogencarbonate was added to the reaction liquid, and the resulting mixture was extracted with chloroform. The organic layer was dried over anhydrous sodium sulfate and filtered, and the filtrate was concentrated under reduced pressure. The residue was purified by flash chromatography (silica gel, hexane/ethyl acetate) to obtain tert-butyl 4-(N-benzyl-N-methylamino)piperidine-1-carboxylate (4.49 g, 14.7 mmol, 98%) as a white solid.

$^{1}$H-NMR (400 MHz, CDCl$_{3}$) δ: 1.46 (9H, s), 1.48-1.58 (2H, m), 1.76-1.84 (2H, m), 2.19 (3H, s), 2.54-2.75 (3H, m), 3.57 (2H, s), 4.05-4.25 (2H, m), 7.21-7.32 (5H, m).
ESI-MS: m/z=305 (M+H)$^{+}$.

Reference Example 4

Synthesis of N-benzyl-N-methylpiperidin-4-amine

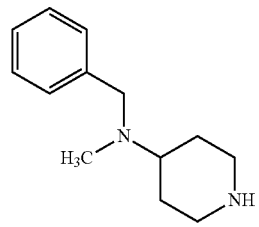

A solution of hydrogen chloride in 1,4-dioxane (4.0 N, 3.28 mL, 13.1 mmol) was added to a mixed solution of tert-butyl 4-(N-benzyl-N-methylamino)piperidine-1-carboxylate (1.00 g, 3.28 mmol) in 1,4-dioxane/methanol (1:1, 8.0 mL) at room temperature, and the reaction liquid was stirred at the same temperature for 6 hours. The reaction liquid was concentrated under reduced pressure, and a saturated aqueous solution of sodium hydrogencarbonate was added, and the resulting mixture was extracted with chloroform. The organic layer was dried over anhydrous sodium sulfate and filtered, and the filtrate was concentrated under reduced pressure. The residue was purified by flash chromatography (silica gel, chloroform/methanol) to obtain N-benzyl-N-methylpiperidin-4-amine (0.650 g, 0.318 mmol, 97%) as a colorless oil.

$^{1}$H-NMR (400 MHz, CDCl$_{3}$) δ: 1.44-1.56 (3H, m), 1.80-1.88 (2H, m), 2.21 (3H, s), 2.49-2.63 (3H, m), 3.12-3.19 (2H, m), 3.58 (2H, s), 7.22-7.32 (5H, m).
ESI-MS: m/z=205 (M+H)$^{+}$.

Reference Example 5

Synthesis of 1-(2-((tert-butyldimethylsilyl)oxy)ethyl)-1H-imidazole

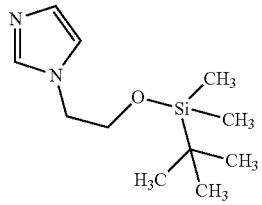

Diisopropylethylamine (3.55 mL, 20.33 mmol) and tert-butyldimethylchlorosilane (2.81 g, 18.64 mmol) were added to a solution of 2-(1H-imidazol-1-yl)ethanol (1.90 g, 16.94 mmol) in dichloromethane (56.5 mL) at 0° C., and the temperature of the resulting mixture was raised to room temperature and the resulting mixture was stirred for 1 hour. Water was added to the reaction liquid and the resulting mixture was extracted with chloroform. The organic layer was washed with a 10% aqueous solution of sodium chloride, and then dried over anhydrous sodium sulfate and filtered, and the filtrate was concentrated under reduced pressure. The residue was purified by flash chromatography (NH silica gel, n-hexane/ethyl acetate) to obtain 1-(2-((tert-butyldimethylsilyl)oxy)ethyl)-1H-imidazole (3.62 g, 15.99 mmol, 94%) as a colorless oil.

$^1$H-NMR (400 MHz, CDCl$_3$) δ: −0.03 (6H, s), 0.86 (9H, s), 3.84 (2H, t, J=5.1 Hz), 4.03 (2H, t, J=5.1 Hz), 6.95 (1H, s), 7.05 (1H, s), 7.51 (1H, s).

ESI-MS: m/z=227 (M+H)$^+$.

Reference Example 6

Synthesis of 1-(2-((tert-butyldimethylsilyl)oxy)ethyl)-1H-imidazole-2-carbaldehyde

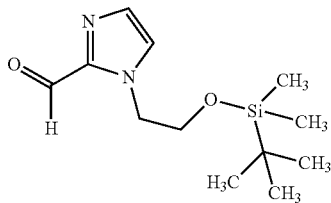 [SMILES: CC(C)(C)[Si](C)(C)OCCn1ccnc1C=O]

A solution of n-butyllithium in n-hexane (1.62 M, 10.80 mL, 17.49 mmol) was added dropwise to a solution of 1-(2-((tert-butyldimethylsilyl)oxy)ethyl)-1H-imidazole (3.60 g, 15.90 mmol) in tetrahydrofuran (31.8 mL) at −78° C., and the resulting mixture was stirred at the same temperature for 1 hour. DMF (1.46 mL, 19.08 mmol) was added to the reaction liquid at the same temperature, and the resulting mixture was stirred for 1 hour, and then the temperature of the reaction liquid was raised to room temperature. A saturated aqueous solution of ammonium chloride and ethyl acetate were added to the reaction liquid and then the resulting mixture was extracted with ethyl acetate. The organic layer was washed with a 10% aqueous solution of sodium chloride, and then dried over anhydrous sodium sulfate and filtered, and the filtrate was concentrated under reduced pressure. The residue was purified by column chromatography (silica gel, n-hexane/ethyl acetate) to obtain 1-(2-((tert-butyldimethylsilyl)oxy)ethyl)-1H-imidazole-2-carbaldehyde (3.96 g, 15.67 mmol, 98%) as a colorless oil.

$^1$H-NMR (400 MHz, CDCl$_3$) δ: −0.09 (6H, s), 0.83 (9H, s), 3.88 (2H, t, J=4.9 Hz), 4.51 (2H, t, J=4.9 Hz), 7.23 (1H, s), 7.27 (1H, s), 9.81 (1H, s).

ESI-MS: m/z=255 (M+H)$^+$.

Reference Example 7

Synthesis of tert-butyl 2-(2-formyl-1H-imidazol-1-yl)acetate

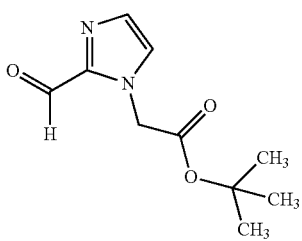

Potassium carbonate (1.73 g, 12.49 mmol) and tert-butyl 2-bromoacetate (1.83 mL, 12.49 mmol) were added to a solution of 1H-imidazole-2-carbaldehyde (1.00 g, 10.41 mmol) in N,N-dimethylformamide (52.0 mL) at room temperature, and the resulting mixture was stirred at the same temperature for 18 hours. Ethyl acetate and distilled water were added to the reaction liquid, and then the resulting mixture was extracted with ethyl acetate. The organic layer was washed with a 10% aqueous solution of sodium chloride, and then dried over anhydrous sodium sulfate and filtered, and the filtrate was concentrated under reduced pressure. The residue was purified by column chromatography (silica gel, n-hexane/ethyl acetate) to obtain tert-butyl 2-(2-formyl-1H-imidazol-1-yl)acetate (1.05 g, 0.733 mmol, 48%) as a yellow oil.

$^1$H-NMR (400 MHz, CDCl$_3$) δ: 1.48 (9H, s), 5.03 (2H, s), 7.13 (1H, s), 7.32 (1H, s), 9.80 (1H, s).

ESI-MS: m/z=211 (M+H)$^+$.

Reference Example 8

Synthesis of (E)-ethyl 3-(1-(2-((tert-butyldimethylsilyl)oxy)ethyl)-1H-imidazol-2-yl)acrylate

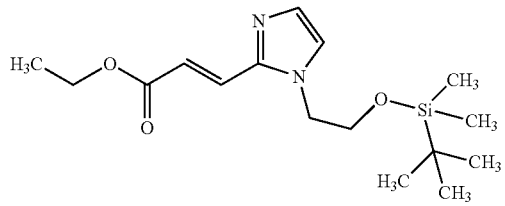 [SMILES: CCOC(=O)/C=C/c1nccn1CCO[Si](C)(C)C(C)(C)C]

Ethyl diethylphosphonoacetate (2.76 mL, 13.80 mmol) was added to a suspension of sodium hydride (0.702 g, 16.10 mmol, 55%) in tetrahydrofuran (40.0 mL) at 0° C. The resulting mixture was stirred at the same temperature for 1 hour, and then a solution of 1-(2-((tert-butyl-dimethylsilyl)oxy)ethyl)-1H-imidazole-2-carbaldehyde (3.90 g, 15.33 mmol) in tetrahydrofuran (36.7 mL) was added thereto, and the temperature of the resulting mixture was raised to room temperature, and then the reaction liquid was stirred for 1 hour. A saturated aqueous solution of ammonium chloride was added to the reaction liquid, and the resulting mixture was extracted with ethyl acetate. The organic layer was washed with a 10% aqueous solution of sodium chloride, and then dried over anhydrous sodium sulfate and filtered, and the filtrate was concentrated under reduced pressure. The residue was purified by column chromatography (NH silica gel, n-hexane/ethyl acetate) to obtain (E)-ethyl 3-(1-(2-((tert-butyldimethylsilyl)oxy)ethyl)-1H-imidazol-2-yl)acrylate (3.42 g, 10.54 mmol, 69%) as a colorless oil.

$^1$H-NMR (400 MHz, CDCl$_3$) δ: −0.08 (6H, s), 0.86 (9H, s), 1.32 (3H, t, J=7.1 Hz), 3.84 (2H, t, J=5.1 Hz), 4.15 (2H, t, J=5.1 Hz), 4.26 (3H, q, J=7.1 Hz), 6.84 (1H, d, J=15.4 Hz), 7.04 (1H, s), 7.16 (1H, s), 7.52 (1H, d, J=15.4 Hz).

ESI-MS: m/z=325 (M+H)$^+$.

Reference Example 9

Synthesis of (E)-benzyl 3-(1-(2-(tert-butoxy)-2-oxoethyl)-1H-imidazol-2-yl)acrylate

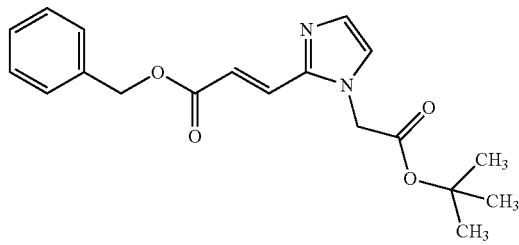 [SMILES: CC(C)(C)OC(=O)Cn1ccnc1/C=C/C(=O)OCc1ccccc1]

A solution of benzyl dimethylphosphonoacetate (0.700 g, 2.71 mmol) in tetrahydrofuran (3.0 mL) was added to a suspension of sodium hydride (0.125 g, 2.85 mmol, 55%) in tetrahydrofuran (3.5 mL) at 0° C. The resulting mixture was stirred at the same temperature for 30 minutes, and then a solution of tert-butyl 2-(2-formyl-1H-imidazol-1-yl)acetate (0.600 g, 2.85 mmol) in tetrahydrofuran (3.0 mL) was added, the temperature of the resulting mixture was raised to room temperature, and then the reaction liquid was stirred for 15 hours. A saturated aqueous solution of ammonium chloride was added to the reaction liquid, and then the resulting mixture was extracted with chloroform. The organic layer was washed with a 10% aqueous solution of sodium chloride, and then dried over anhydrous sodium sulfate and filtered, and the filtrate was concentrated under reduced pressure. The residue was purified by column chromatography (NH silica gel, n-hexane/ethyl acetate) to obtain (E)-benzyl 3-(1-(2-(tert-butoxy)-2-oxoethyl)-1H-imidazol-2-yl)acrylate (0.82 g, 2.39 mmol, 82%) as a yellow oil.

$^1$H-NMR (400 MHz, CDCl$_3$) δ: 1.45 (9H, s), 4.67 (2H, s), 5.25 (2H, s), 6.90 (1H, d, J=15.4 Hz), 7.01 (1H, s), 7.20 (1H, s), 7.31-7.44 (6H, s).

ESI-MS: m/z=343 (M+H)$^+$.

Reference Example 10

Synthesis of crude 3-(1-(2-((tert-butyldimethylsilyl)oxy)ethyl)-1H-imidazol-2-yl)propanoic acid

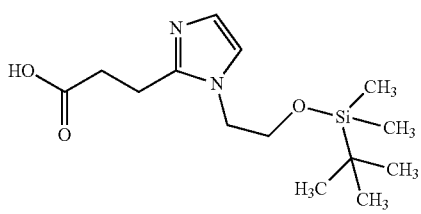 [SMILES: CC(C)(C)[Si](C)(C)OCCn1ccnc1CCC(=O)O]

Palladium-carbon (10% wet, 342 mg) was added to a solution of (E)-ethyl 3-(1-(2-((tert-butyldimethylsilyl)oxy)ethyl)-1H-imidazol-2-yl)acrylate (3.42 g, 10.54 mmol) in methanol (42.2 mL) at room temperature, and the resulting mixture was stirred under hydrogen atmosphere for 18 hours. The reaction liquid was filtered through Celite, and the filtrate was concentrated under reduced pressure. Methanol (21.0 mL) was added to the obtained residue at room temperature and the obtained residue was dissolved. The reaction solution was cooled to 0° C., and then an aqueous solution of sodium hydroxide (1.0 N, 11.59 mL, 11.59 mmol) was added to the reaction liquid at the same temperature, and the temperature of the resulting mixture was raised to room temperature, and the reaction liquid was stirred for 5 hours. An aqueous solution of sodium hydroxide (1.0 N, 5.80 mL, 5.80 mmol) was added to the reaction liquid at room temperature, and the resulting mixture was stirred for 1 hour. The reaction liquid was cooled to 0° C., and then hydrochloric acid (1.0 N, 17.4 mL) was added to the reaction liquid for neutralization, and then the reaction liquid was concentrated under reduced pressure. The residue was subjected to azeotropic distillation with toluene, and ethanol was added. The precipitate was filtered through Celite and the filtrate was concentrated under reduced pressure to obtain a crude product of 3-(1-(2-((tert-butyldimethylsilyl)oxy)ethyl)-1H-imidazol-2-yl)propanoic acid (3.30 g) as a colorless oil.

Reference Example 11

Synthesis of crude 3-(1-(2-(tert-butoxy)-2-oxoethyl)-1H-imidazol-2-yl)propanoic acid

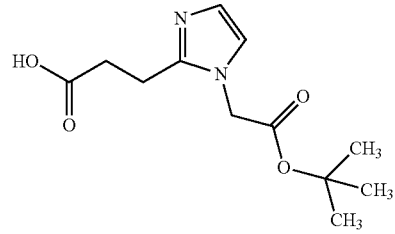

Palladium-carbon (10% wet, 81.8 mg) was added to a solution of (E)-benzyl 3-(1-(2-(tert-butoxy)-2-oxoethyl)-1H-imidazol-2-yl)acrylate (0.818 g, 2.39 mmol) in methanol (9.6 mL) at room temperature, and the resulting mixture was stirred under hydrogen atmosphere for 16 hours. The reaction liquid was filtered through Celite, and then the filtrate was concentrated under reduced pressure to obtain a crude product of 3-(1-(2-(tert-butoxy)-2-oxoethyl)-1H-imidazol-2-yl)propanoic acid (0.590 g).

Reference Example 12

Synthesis of 1-(4-benzyl(methyl)aminopiperidin-1-yl)-3-(1-methyl-1H-imidazol-2-yl)propan-1-one

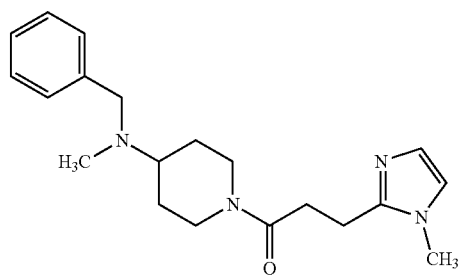 [SMILES: CN(Cc1ccccc1)C1CCN(C(=O)CCc2nccn2C)CC1]

Diisopropylethylamine (0.892 mL, 5.11 mmol), HBTU (0.969 g, 2.55 mmol), and N-benzyl-N-methylpiperidine-4-amine (0.348 g, 1.70 mmol) were added to a solution of 3-(1-methyl-1H-imidazol-2-yl)propanoic acid (0.300 g, 1.95 mmol) in chloroform (17.0 mL) at room temperature, and the reaction liquid was stirred at the same temperature for 60 hours. Methanol was added to the reaction liquid and the resulting mixture was concentrated under reduced pressure. The residue was purified by flash chromatography (NH silica gel, chloroform/methanol) to obtain 1-(4-benzyl (methyl)aminopiperidin-1-yl)-3-(1-methyl-1H-imidazol-2-yl)propan-1-one (0.204 g, 0.599 mmol, 35%) as a colorless oil.

¹H-NMR (400 MHz, CDCl₃) δ: 1.43-1.56 (2H, m), 1.80-1.88 (2H, m), 2.18 (3H, s), 2.51-2.70 (2H, m), 2.88-3.05 (5H, m), 3.56 (2H, s), 3.62 (3H, s), 4.00-4.07 (1H, m), 4.62-4.69 (1H, m), 6.79 (1H, d, J=1.2 Hz), 6.91 (1H, d, J=1.2 Hz), 7.22-7.34 (5H, m).

ESI-MS: m/z=341 (M+H)⁺.

Reference Example 13

Synthesis of 3-(1-(2-((tert-butyldimethylsilyl)oxy) ethyl)-1H-imidazol-2-yl)-1-(4-(dimethylamino)piperidin-1-yl)propan-1-one

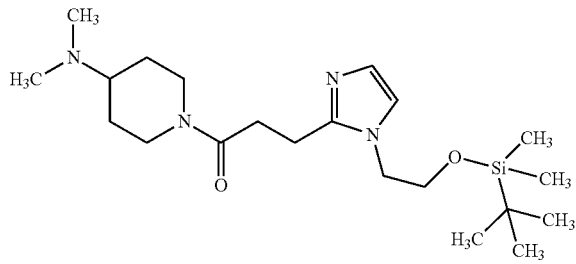 [SMILES: CN(C)C1CCN(C(=O)CCc2nccn2CCO[Si](C)(C)C(C)(C)C)CC1]

Diisopropylethylamine (2.76 mL, 15.81 mmol), HBTU (4.80 g, 12.65 mmol), and 4-(dimethylamino)piperidine (1.12 mL, 10.01 mmol) were added to a solution of a crude product of 3-(1-(2-((tert-butyldimethylsilyl)oxy)ethyl)-1H-imidazol-2-yl)propanoic acid (3.15 g) in chloroform (56.5 mL) at room temperature, and the reaction liquid was stirred at the same temperature for 12 hours. A saturated aqueous solution of potassium carbonate and a 10% aqueous solution of sodium chloride were added to the reaction liquid, and the resulting mixture was extracted with chloroform. The organic layer was dried over anhydrous sodium sulfate and then filtered, and the filtrate was concentrated under reduced pressure. The residue was purified by column chromatography (NH silica gel, chloroform/methanol) to obtain 3-(1-(2-((tert-butyldimethyl silyl)oxy)ethyl)-1H-imidazol-2-yl)-1-(4-(dimethylamino)piperidin-1-yl)propan-1-one (2.88 g, 7.05 mmol, 70%) as a white solid.

¹H-NMR (400 MHz, CDCl₃) δ: −0.05 (6H, s), 0.84 (9H, s), 1.30-1.42 (2H, m), 1.82-1.85 (2H, m), 2.27-2.36 (7H, m), 2.55-2.63 (1H, m), 2.90-3.03 (5H, m), 3.82 (2H, t, J=5.4 Hz), 4.01-4.05 (3H, m), 4.60-4.63 (1H, m), 6.88 (1H, d, J=1.2 Hz), 6.92 (1H, d, J=1.2 Hz).

ESI-MS: m/z=409 (M+H)⁺.

Reference Example 14

Synthesis of tert-butyl 2-(2-(3-(4-(dimethylamino) piperidin-1-yl)-3-oxopropyl)-1H-imidazol-1-yl)acetate

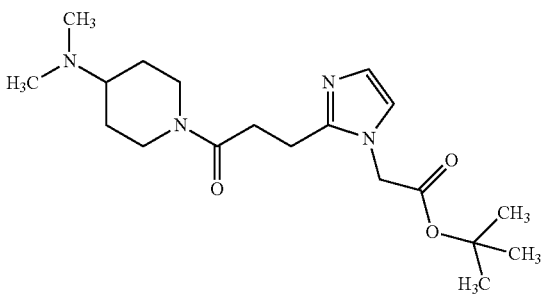 [SMILES: CN(C)C1CCN(C(=O)CCc2nccn2CC(=O)OC(C)(C)C)CC1]

Diisopropylethylamine (0.392 mL, 2.24 mmol), HBTU (0.680 g, 1.79 mmol), and 4-(dimethylamino)piperidine (0.167 mL, 1.42 mmol) were added to a solution of a crude product of 3-(1-(2-(tert-butoxy)-2-oxoethyl)-1H-imidazol-2-yl)propanoic acid (0.380 g) in chloroform (15.0 mL) at room temperature, and the reaction liquid was stirred at the same temperature for 12 hours. A saturated aqueous solution of potassium carbonate and a 10% aqueous solution of sodium chloride were added to the reaction liquid, and the resulting mixture was extracted with chloroform. The organic layer was dried over anhydrous sodium sulfate and then filtered, and the filtrate was concentrated under reduced pressure. The residue was purified by column chromatography (NH silica gel, chloroform/ethyl acetate) to obtain tert-butyl 2-(2-(3-(4-(dimethylamino)piperidin-1-yl)-3-oxopropyl)-1H-imidazol-1-yl)acetate (0.349 g, 0.957 mmol, 62%) as a colorless oil.

¹H-NMR (400 MHz, CDCl₃) δ: 1.29-1.42 (2H, m), 1.47 (9H, s), 1.81-1.83 (2H, m), 2.27-2.36 (7H, m), 2.55-2.62 (1H, m), 2.91 (4H, s), 2.96-3.03 (1H, m), 3.98-4.01 (1H, m), 4.57-4.60 (1H, m), 4.63 (2H, s), 6.81 (1H, d, J=1.2 Hz), 6.96 (1H, d, J=1.2 Hz).

Reference Example 15

Synthesis of tert-butyl (2-(methyl(1-(3-(1-methyl-1H-imidazol-2-yl)propanoyl)piperidin-4-yl)amino) ethyl)carbamate

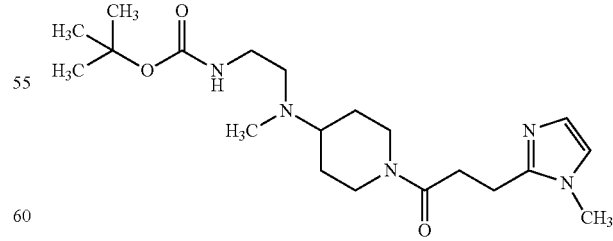

Diisopropylethylamine (0.401 mL, 2.30 mmol), HBTU (0.348 g, 0.919 mmol), and crude tert-butyl (2-(methyl (piperidin-4-yl)amino)ethyl)carbamate (0.197 g, 0.765 mmol) were added to a solution of 3-(1-methyl-1H-imidazol-2-yl)propanoic acid (0.118 g, 0.765 mmol) in chloroform (8.0 mL) at room temperature, and the reaction liquid was stirred at the same temperature for 16 hours. Methanol was added to the reaction liquid and the resulting mixture was concentrated under reduced pressure. The residue was purified by flash chromatography (NH silica gel, chloroform/methanol) to obtain tert-butyl (2-(methyl(1-(3-(1-methyl-1H-imidazol-2-yl)propanoyl)piperidin-4-yl)amino)ethyl)carbamate (0.260 g, 0.661 mmol, 86%) as a colorless oil.

$^1$H-NMR (400 MHz, CDCl$_3$) δ: 1.34-1.46 (11H, m), 1.71-1.80 (2H, m), 2.19-2.23 (3H, m), 2.47-2.60 (4H, m), 2.88-3.00 (5H, m), 3.12-3.20 (2H, m), 3.62 (3H, s), 4.00-4.08 (1H, m), 4.62-4.70 (1H, m), 4.91-4.98 (1H, m), 6.79 (1H, d, J=1.2 Hz), 6.91 (1H, d, J=1.2 Hz).

ESI-MS: m/z=394 (M+H)$^+$.

Reference Example 16

Synthesis of 1-(4-((2-aminoethyl)(methyl)amino)piperidin-1-yl)-3-(1-methyl-1H-imidazol-2-yl)propan-1-one

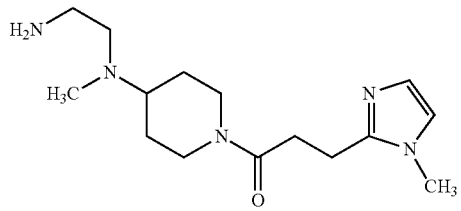 [SMILES: CN(CCN)C1CCN(C(=O)CCc2nccn2C)CC1]

A solution of hydrogen chloride in 1,4-dioxane (4.0 N, 0.762 mL, 3.05 mmol) was added to a solution of tert-butyl (2-(methyl(1-(3-(1-methyl-1H-imidazol-2-yl)propanoyl)piperidin-4-yl)amino)ethyl)carbamate (0.100 g, 0.254 mmol) in 1,4-dioxane (3.0 mL) at room temperature, and the resulting mixture was stirred at the same temperature for 16 hours. A saturated aqueous solution of sodium hydrogencarbonate was added to the reaction liquid, and the resulting mixture was extracted with ethyl acetate. The organic layer was washed with a 10% aqueous solution of sodium chloride, and then dried over anhydrous sodium sulfate and filtered, and the filtrate was concentrated under reduced pressure. The residue was purified by flash chromatography (NH silica gel, chloroform/methanol) to obtain 1-(4-((2-aminoethyl)(methyl)amino)piperidin-1-yl)-3-(1-methyl-1H-imidazol-2-yl)propan-1-one (0.0498 g, 0.170 mmol, 67%) as a colorless oil.

$^1$H-NMR (400 MHz, CDCl$_3$) δ: 1.31-1.46 (2H, m), 1.64-1.85 (2H, m), 2.20 (3H, m), 2.43-2.60 (4H, m), 2.68-2.74 (2H, m), 2.86-3.00 (5H, m), 3.60 (3H, s), 3.96-4.06 (1H, m), 4.60-4.68 (1H, m), 6.77 (1H, brs), 6.88 (1H, brs).

ESI-MS: m/z=294 (M+H)$^+$.

Reference Example 17

Synthesis of crude 4-ethylmethylaminopiperidine

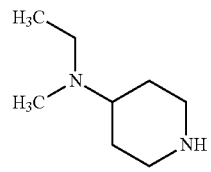

Ethylmethylamine (0.230 mL, 2.68 mmol), acetic acid (0.0120 mL, 0.214 mmol), and sodium triacetoxyborohydride (0.681 g, 3.22 mmol) were added to a solution of benzyl 4-oxopiperidine-1-carboxylate (0.500 g, 2.14 mmol) in dichloromethane (12.0 mL) at 0° C., and the reaction liquid was stirred at room temperature for 16 hours. The reaction liquid was cooled to 0° C. A saturated aqueous solution of sodium hydrogencarbonate was added to the reaction liquid, and the resulting mixture was extracted with chloroform. The organic layer was dried over anhydrous sodium sulfate and filtered, and the filtrate was concentrated under reduced pressure. The residue was purified by flash chromatography (silica gel, chloroform/methanol). The obtained crudely purified product was dissolved in methanol (8.0 mL), and palladium/carbon (10% wet, 0.185 g, 0.174 mmol) was added thereto at room temperature, and the resulting mixture was stirred under hydrogen atmosphere for 16 hours. The reaction liquid was filtered through Celite, and the filtrate was concentrated under reduced pressure to obtain a crude product of 4-ethylmethylaminopiperidine.

Reference Example 18

Synthesis of crude 4-diethylaminopiperidine

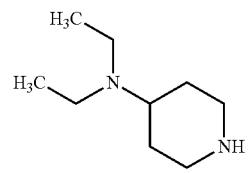

Diethylamine (0.276 mL, 2.68 mmol), acetic acid (0.0120 mL, 0.214 mmol), and sodium triacetoxyborohydride (0.681 g, 3.22 mmol) were added to a solution of benzyl 4-oxopiperidine-1-carboxylate (0.500 g, 2.14 mmol) in dichloromethane (12.0 mL) at 0° C., and the reaction liquid was stirred at room temperature for 16 hours. The reaction liquid was cooled to 0° C. A saturated aqueous solution of sodium hydrogencarbonate was added to the reaction liquid, and the resulting mixture was extracted with chloroform. The organic layer was dried over anhydrous sodium sulfate and filtered, and the filtrate was concentrated under reduced pressure. The residue was purified by flash chromatography (silica gel, chloroform/methanol). The obtained crudely purified product was dissolved in methanol (8.0 mL), and palladium/carbon (10% wet, 0.180 g, 0.169 mmol) was added thereto at room temperature, and the resulting mixture was stirred under hydrogen atmosphere for 16 hours. The reaction liquid was filtered through Celite, and the filtrate was concentrated under reduced pressure to obtain a crude product of 4-diethylaminopiperidine.

Reference Example 19

Synthesis of 4-(piperidin-1-yl)piperidine

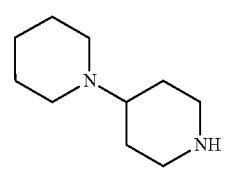 [SMILES: C1CCN(C2CCNCC2)CC1]

Piperidine (1.549 g, 18.19 mmol), sodium triacetoxyborohydride (3.85 g, 19.2 mmol), and acetic acid (0.0910 g, 1.52 mmol) were added to a solution of 1-tert-butoxycarbonyl-4-piperidinone (3.02 g, 15.2 mmol) in dichloromethane (25.0 mL) at 0° C., and the resulting mixture was stirred at room temperature for 16 hours. The reaction liquid was cooled to 0° C. A saturated aqueous solution of sodium hydrogencarbonate was added to the reaction liquid, and the resulting mixture was extracted with dichloromethane. The organic layer was dried over anhydrous sodium sulfate and filtered, and the filtrate was concentrated under reduced pressure. The residue was dissolved in hydrochloric acid (1.0 N), and the resulting mixture was extracted with ethyl acetate. A 48% aqueous solution of sodium hydroxide was added to the aqueous layer for basification, and then the resulting mixture was extracted with dichloromethane. The organic layer was dried over anhydrous sodium sulfate and filtered, and the filtrate was concentrated under reduced pressure. The residue was dissolved in methanol (25.0 mL), and concentrated hydrochloric acid (5.0 mL) was added, and then the resulting mixture was stirred at 40° C. for 12 hours. The reaction liquid was concentrated and exsiccated, and then the residue was dissolved in distilled water. A 48% aqueous solution of sodium hydroxide was added for basification, and then the resulting mixture was extracted with dichloromethane. The organic layer was dried over anhydrous sodium sulfate and filtered, and the filtrate was concentrated under reduced pressure. 4-(Piperidin-1-yl)piperidine (2.04 g, 12.1 mmol, 80%) was obtained as a white solid.

$^1$H-NMR (400 MHz, CDCl$_3$) δ: 1.35-1.50 (4H, m), 1.53-1.67 (4H, m), 1.82 (2H, d, J=12.4 Hz), 2.34 (1H, tt, J=11.2, 4.0 Hz), 2.45-2.65 (6H, m), 3.13 (2H, d, J=12.4 Hz).

ESI-MS: m/z=169 (M+H)$^+$.

Reference Example 20

Synthesis of 4-(morpholin-4-yl)piperidine

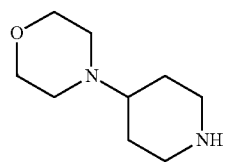 [SMILES: C1CC(N2CCOCC2)CCN1]

Morpholine (0.792 g, 9.09 mmol), sodium triacetoxyborohydride (1.93 g, 9.09 mmol), and acetic acid (0.0460 g, 0.758 mmol) were added to a solution of 1-tert-butoxycarbonyl-4-piperidinone (1.51 g, 7.58 mmol) in dichloromethane (25.0 mL) at 0° C., and the resulting mixture was stirred at room temperature for 16 hours. The reaction liquid was cooled to 0° C. A saturated aqueous solution of sodium hydrogencarbonate was added to the reaction liquid, and the resulting mixture was extracted with dichloromethane. The organic layer was dried over anhydrous sodium sulfate and filtered, and the filtrate was concentrated under reduced pressure. The residue was dissolved in hydrochloric acid (1.0 N), and the resulting mixture was extracted with ethyl acetate. A 48% aqueous solution of sodium hydroxide was added to the aqueous layer for basification, and then the resulting mixture was extracted with dichloromethane. The organic layer was dried over anhydrous sodium sulfate and filtered, and the filtrate was concentrated under reduced pressure. The residue was dissolved in methanol (25.0 mL), and concentrated hydrochloric acid (5.0 mL) was added, and then the resulting mixture was stirred at 40° C. for 12 hours. The reaction liquid was concentrated and exsiccated, and then the residue was dissolved in distilled water. A 48% aqueous solution of sodium hydroxide was added for basification, and then the resulting mixture was extracted with dichloromethane. The organic layer was dried over anhydrous sodium sulfate and filtered, and the filtrate was concentrated under reduced pressure. 4-(Morpholin-4-yl)piperidine (1.52 g, 5.63 mmol, 74%) was obtained as a yellow solid.

$^1$H-NMR (400 MHz, CDCl$_3$) δ: 1.34 (2H, dd, J=12.0, 4.0 Hz), 1.40 (2H, dd, J=12.0, 4.0 Hz), 1.85 (2H, d, J=12.4 Hz), 2.28 (1H, tt, J=11.2, 4.0 Hz), 3.53-3.63 (6H, m), 3.15 (2H, d, J=12.4 Hz), 3.73 (4H, t, J=4.4 Hz).

ESI-MS: m/z=171 (M+H)$^+$

Reference Example 21

Synthesis of 4-(1-methylpiperazin-4-yl)piperidine

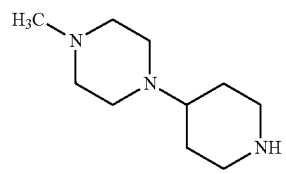

1-Methylpiperazine (0.905 g, 9.03 mmol), sodium triacetoxyborohydride (1.92 g, 9.03 mmol), and acetic acid (0.497 g, 8.28 mmol) were added to a solution of 1-tert-butoxycarbonyl-4-piperidinone (1.50 g, 7.53 mmol) in dichloromethane (25.0 mL) at 0° C., and the resulting mixture was stirred at room temperature for 16 hours. The reaction liquid was cooled to 0° C. A saturated aqueous solution of sodium hydrogencarbonate was added to the reaction liquid, and the resulting mixture was extracted with dichloromethane. The organic layer was dried over anhydrous sodium sulfate and filtered, and the filtrate was concentrated under reduced pressure. The residue was dissolved in hydrochloric acid (1.0 N), and the resulting mixture was extracted with ethyl acetate. A 48% aqueous solution of sodium hydroxide was added to the aqueous layer for basification, and then the resulting mixture was extracted with dichloromethane. The organic layer was dried over anhydrous sodium sulfate and filtered, and the filtrate was concentrated under reduced pressure. The residue was dissolved in methanol (25.0 mL), and concentrated hydrochloric acid (5.0 mL) was added, and then the resulting mixture was stirred at 40° C. for 12 hours. The reaction liquid was concentrated and exsiccated, and then the residue was dissolved in distilled water. A 48% aqueous solution of sodium hydroxide was added for basification, and then the resulting mixture was extracted with dichloromethane. The organic layer was dried over anhydrous sodium sulfate and filtered, and the filtrate was concentrated under reduced pressure. 4-(1-Methylpiperazin-4-yl)piperidine (0.826 g, 4.51 mmol, 60%) was obtained as a white solid.

$^1$H-NMR (400 MHz, CDCl$_3$) δ: 1.35 (2H, dd, J=12.0, 3.6 Hz), 1.41 (2H, dd, J=12.0, 3.6 Hz), 1.85 (2H, d, J=12.8 Hz), 1.96-2.06 (2H, br), 2.28 (3H, s), 2.32 (1H, tt, J=11.6, 3.6 Hz), 3.37-3.70 (8H, m), 3.14 (2H, d, J=12.8 Hz).

ESI-MS: m/z=169 (M+H)$^+$.

Reference Example 22

Synthesis of (R)-3-dimethylaminopiperidine

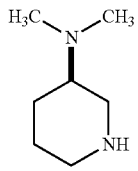

An aqueous solution of formalin (36-38 wt %, 2.08 g, 25.0 mmol), sodium triacetoxyborohydride (2.12 g, 9.99 mmol), and acetic acid (0.0300 g, 0.500 mmol) were added to a solution of (R)-3-amino-1-tert-butoxycarbonylpiperidine (1.00 g, 4.99 mmol) in dichloromethane (10.0 mL) at 0° C., and the resulting mixture was stirred at room temperature for 16 hours. The reaction liquid was cooled to 0° C. A saturated aqueous solution of sodium hydrogencarbonate was added to the reaction liquid, and the resulting mixture was extracted with dichloromethane. The organic layer was dried over anhydrous sodium sulfate and filtered, and the filtrate was concentrated under reduced pressure. The residue was dissolved in hydrochloric acid (1.0 N), and the resulting mixture was extracted with ethyl acetate. A 48% aqueous solution of sodium hydroxide was added to the aqueous layer for basification, and then the resulting mixture was extracted with dichloromethane. The organic layer was dried over anhydrous sodium sulfate and filtered, and the filtrate was concentrated under reduced pressure. The residue was dissolved in methanol (25.0 mL), and concentrated hydrochloric acid (5.0 mL) was added, and then the resulting mixture was stirred at 40° C. for 12 hours. The reaction liquid was concentrated and exsiccated, and then the residue was dissolved in distilled water. A 48% aqueous solution of sodium hydroxide was added for basification, and then the resulting mixture was extracted with dichloromethane. The organic layer was dried over anhydrous sodium sulfate and filtered, and the filtrate was concentrated under reduced pressure. (R)-3-Dimethylaminopiperidine (0.384 g, 3.00 mmol, 60%) was obtained as a colorless oil.

$^1$H-NMR (400 MHz, CDCl$_3$) δ: 1.22-1.50 (2H, m), 1.73-1.78 (1H, m), 1.93-2.01 (1H, m), 2.15 (1H, tt, J=10.0, 3.6 Hz), 2.29 (6H, s), 2.45-2.53 (2H, m), 2.92-2.96 (1H, m), 3.15-3.22 (1H, m).

ESI-MS: m/z=129 (M+H)$^+$.

Reference Example 23

Synthesis of (S)-3-dimethylaminopiperidine

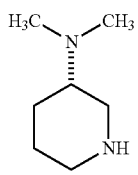

An aqueous solution of formalin (36-38 wt %, 2.10 g, 25.2 mmol), sodium triacetoxyborohydride (2.13 g, 10.0 mmol), and acetic acid (0.0300 g, 0.500 mmol) were added to a solution of (S)-3-amino-1-tert-butoxycarbonylpiperidine (1.00 g, 4.99 mmol) in dichloromethane (10.0 mL) at 0° C., and the resulting mixture was stirred at room temperature for 16 hours. The reaction liquid was cooled to 0° C. A saturated aqueous solution of sodium hydrogencarbonate was added to the reaction liquid, and the resulting mixture was extracted with dichloromethane. The organic layer was dried over anhydrous sodium sulfate and filtered, and the filtrate was concentrated under reduced pressure. The residue was dissolved in hydrochloric acid (1.0 N), and the resulting mixture was extracted with ethyl acetate. A 48% aqueous solution of sodium hydroxide was added to the aqueous layer for basification, and then the resulting mixture was extracted with dichloromethane. The organic layer was dried over anhydrous sodium sulfate and filtered, and the filtrate was concentrated under reduced pressure. The residue was dissolved in methanol (25.0 mL), and concentrated hydrochloric acid (5.0 mL) was added, and then the resulting mixture was stirred at 40° C. for 12 hours. The reaction liquid was concentrated and exsiccated, and then the residue was dissolved in distilled water. A 48% aqueous solution of sodium hydroxide was added for basification, and then the resulting mixture was extracted with dichloromethane. The organic layer was dried over anhydrous sodium sulfate and filtered, and the filtrate was concentrated under reduced pressure. (S)-3-Dimethylaminopiperidine (0.351 g, 2.74 mmol, 55%) was obtained as a colorless oil.

$^1$H-NMR (400 MHz, CDCl$_3$) δ: 1.22-1.50 (2H, m), 1.73-1.78 (1H, m), 1.93-2.01 (1H, m), 2.15 (1H, tt, J=10.0, 3.6 Hz), 2.29 (6H, s), 2.45-2.53 (2H, m), 2.92-2.96 (1H, m), 3.15-3.22 (1H, m).

ESI-MS: m/z=129 (M+H)$^+$.

Reference Example 24

Synthesis of Crude Cyclopropanol

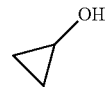

An aqueous solution of sodium hydroxide (10%, 1.29 mL, 3.49 mmol) and an aqueous solution of hydrogen peroxide (30%, 9.90 mL, 87.0 mmol) were added to cyclopropylboronic acid (0.300 g, 3.49 mmol) at 0° C., and the reaction liquid was stirred at the same temperature for 1 hour. A saturated aqueous solution of sodium thiosulfate was added to the reaction liquid, and the resulting mixture was extracted with diethyl ether. The organic layer was washed with a 10% aqueous solution of sodium chloride, and then dried over anhydrous sodium sulfate and filtered, and the filtrate was concentrated under reduced pressure to obtain a crude product of cyclopropanol.

Reference Example 25

Synthesis of crude 4-(hydroxymethyl)-5-methyl-1,3-dioxol-2-one

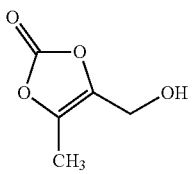

Formic acid (0.750 mL, 19.6 mmol) and triethylamine (2.62 mL, 18.8 mmol) were added to a solution of 4-(chloromethyl)-5-methyl-1,3-dioxol-2-one (1.00 g, 6.73 mmol) in acetonitrile (10.0 mL) at 0° C., the temperature of the reaction liquid was raised to 65° C., and the reaction liquid was stirred for 3 hours. The precipitate was filtered through Celite, and the filtrate was concentrated under reduced pressure. Distilled water was added to the residue, and the resulting mixture was extracted with ethyl acetate. The organic layer was washed with a 10% aqueous solution of sodium chloride, and then dried over anhydrous sodium sulfate and filtered, and the filtrate was concentrated under reduced pressure. Methanol (10.0 mL) was added to the obtained residue at room temperature and the obtained residue was dissolved. Distilled water (3.0 mL) and concentrated hydrochloric acid (0.120 mL, 3.95 mmol) were added to the reaction liquid at room temperature, and the resulting mixture was stirred at the same temperature for 3 hours. Distilled water was added to the reaction liquid, and the reaction liquid was concentrated under reduced pressure. Distilled water was added to the residue, and the resulting mixture was extracted with ethyl acetate. The organic layer was washed with a 10% aqueous solution of sodium chloride, and then dried over anhydrous sodium sulfate and filtered, and the filtrate was concentrated under reduced pressure to obtain a crude product of 4-(hydroxymethyl)-5-methyl-1,3-dioxol-2-one.

Reference Example 26

Synthesis of 2-hydroxy-N,N-dimethylacetamide

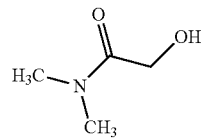

Diisopropylethylamine (2.10 mL, 12.0 mmol), HBTU (2.74 g, 7.22 mmol), and a solution of dimethylamine in THF (2.0 M, 3.61 mL, 7.22 mmol) were added to a solution of 2-(benzyloxy)acetic acid (1.00 g, 6.02 mmol) in chloroform (30.0 mL) at room temperature, and the reaction liquid was stirred at the same temperature for 16 hours. The reaction liquid was concentrated under reduced pressure. The residue was purified by flash chromatography (silica gel, chloroform/methanol). The obtained residue was dissolved in methanol (30.0 mL), and palladium-carbon (10% wet, 0.640 g, 0.602 mmol) was added at room temperature, and the resulting mixture was stirred under hydrogen atmosphere at the same temperature for 16 hours. The reaction liquid was filtered through Celite, and the filtrate was concentrated under reduced pressure. The residue was purified by flash chromatography (silica gel, chloroform/methanol) to obtain 2-hydroxy-N,N-dimethylacetamide (0.255 g, 2.47 mmol, 41%) as a colorless oil.

$^1$H-NMR (400 MHz, CDCl$_3$) δ: 2.88 (3H, s), 3.03 (3H, s), 4.14 (2H, brs).

Reference Example 27

Synthesis of ethyl 2-(2-formyl-1H-imidazol-1-yl)acetate

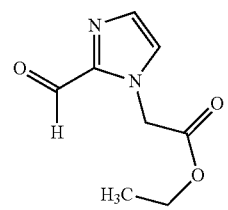

Potassium carbonate (1.44 g, 10.4 mmol), ethyl chloroacetate (0.585 mL, 5.46 mmol), and potassium iodide (0.864 g, 5.20 mmol) were added to a solution of 1H-imidazole-2-carbaldehyde (0.500 g, 5.20 mmol) in N,N-dimethylformamide (10.0 mL) at room temperature, the temperature of the reaction liquid was raised to 90° C., and the reaction liquid was stirred for 4 hours. Distilled water was added to the reaction liquid, and the resulting mixture was extracted with ethyl acetate. The organic layer was washed with a 10% aqueous solution of sodium chloride, and then dried over anhydrous sodium sulfate and filtered, and the filtrate was concentrated under reduced pressure. The residue was purified by flash chromatography (silica gel, chloroform/methanol) to obtain ethyl 2-(2-formyl-1H-imidazol-1-yl)acetate (0.269 g, 1.48 mmol, 28%) as a yellow oil.

$^1$H-NMR (400 MHz, CDCl$_3$) δ: 1.29 (3H, t, J=7.2 Hz), 4.25 (2H, q, J=7.2 Hz), 5.14 (2H, s), 7.15 (1H, brs), 7.33 (1H, s), 9.79-9.91 (1H, m).

ESI-MS: m/z=183 (M+H)$^+$.

Reference Example 28

Synthesis of (E)-benzyl 3-(1-(2-ethoxy-2-oxoethyl)-1H-imidazol-2-yl)acrylate

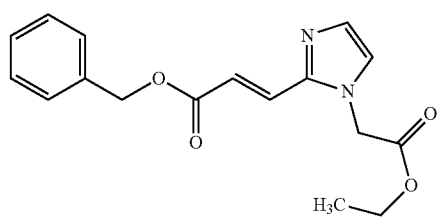 [SMILES: CCOC(=O)Cn1ccnc1/C=C/C(=O)OCc1ccccc1]

Benzyl dimethylphosphonoacetate (4.61 mL, 22.0 mmol) was added to a suspension of sodium hydride (55%, 0.958 g, 22.0 mmol) in tetrahydrofuran (30.0 mL) at 0° C., and the resulting mixture was stirred at the same temperature for 1 hour. Ethyl 2-(2-formyl-1H-imidazol-1-yl)acetate (4.00 g, 22.0 mmol) was added to the reaction liquid, and the reaction liquid was stirred at room temperature for 3 hours. A saturated aqueous solution of ammonium chloride was added to the reaction liquid, and the resulting mixture was extracted with ethyl acetate. The organic layer was washed with a 10% aqueous solution of sodium chloride, and then dried over anhydrous sodium sulfate and filtered, and the filtrate was concentrated under reduced pressure. The residue was purified by flash chromatography (silica gel, n-hexane/ethyl acetate) to obtain (E)-benzyl 3-(1-(2-ethoxy-2-oxoethyl)-1H-imidazol-2-yl)acrylate (4.31 g, 13.7 mmol, 62%) as a white solid.

$^1$H-NMR (400 MHz, CDCl$_3$) δ: 1.28 (3H, t, J=7.2 Hz), 4.24 (2H, q, J=7.2 Hz), 4.77 (2H, s), 5.25 (2H, s), 6.92 (1H, d, J=15.6 Hz), 7.02 (1H, brs), 7.21 (1H, brs), 7.28-7.45 (6H, m).

ESI-MS: m/z=315 (M+H)$^+$.

Reference Example 29

Synthesis of crude 3-(1-(2-ethoxy-2-oxoethyl)-1H-imidazol-2-yl)propanoic acid

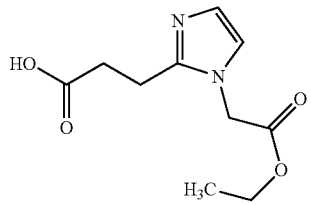 [SMILES: CCOC(=O)Cn1ccnc1CCC(=O)O]

Palladium-carbon (10% wet, 1.46 g, 1.37 mmol) was added to a solution of (E)-benzyl 3-(1-(2-ethoxy-2-oxoethyl)-1H-imidazol-2-yl)acrylate (4.31 g, 13.7 mmol) in ethanol (80.0 mL) at room temperature, and the reaction liquid was stirred under hydrogen atmosphere at the same temperature for 24 hours. The temperature of the reaction liquid was raised to 40° C., and the reaction liquid was stirred for 1 hour. The reaction liquid was filtered through Celite, and the filtrate was concentrated under reduced pressure to obtain a crude product of 3-(1-(2-ethoxy-2-oxoethyl)-1H-imidazol-2-yl)propanoic acid.

Reference Example 30

Synthesis of (E)-benzyl 3-(1H-imidazol-2-yl)acrylate

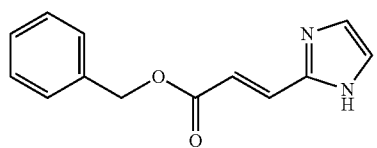 [SMILES: O=C(/C=C/c1ncc[nH]1)OCc1ccccc1]

Benzyl dimethylphosphonoacetate (5.12 mL, 24.4 mmol) was added to a suspension of sodium hydride (55%, 1.12 g, 25.6 mmol) in tetrahydrofuran (40.0 mL) at 0° C., and the reaction liquid was stirred at the same temperature for 1 hour. 1H-Imidazole-2-carbaldehyde (2.46 g, 25.6 mmol) was added to the reaction liquid at 0° C., and the reaction liquid was stirred at room temperature for 60 hours. A saturated aqueous solution of ammonium chloride was added to the reaction liquid, and the resulting mixture was extracted with ethyl acetate. The organic layer was washed with a 10% aqueous solution of sodium chloride, and then dried over anhydrous sodium sulfate and filtered, and the filtrate was concentrated under reduced pressure. The residue was purified by flash chromatography (silica gel, chloroform/methanol) to obtain (E)-benzyl 3-(1H-imidazol-2-yl)acrylate (0.380 g, 1.66 mmol, 7%) as a white solid.

$^1$H-NMR (400 MHz, CDCl$_3$) δ: 5.25 (2H, s), 6.62 (1H, d, J=15.6 Hz), 7.14-7.23 (2H, m), 7.28-7.43 (5H, m), 7.57 (1H, d, J=16.0 Hz).

ESI-MS: m/z=229 (M+H)$^+$.

Reference Example 31

Synthesis of (E)-benzyl 3-(1-(3-ethoxy-3-oxopropyl)-1H-imidazol-2-yl)acrylate

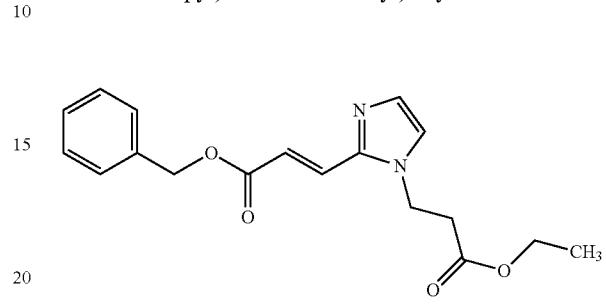

Potassium carbonate (0.606 g, 4.38 mmol), ethyl 3-bromopropanoate (0.419 mL, 3.29 mmol), and potassium iodide (0.364 g, 2.19 mmol) were added to a solution of (E)-benzyl 3-(1H-imidazol-2-yl)acrylate (0.500 g, 2.19 mmol) in DMF (7.3 mL) at room temperature, the temperature of the reaction liquid was raised to 90° C., and the reaction liquid was stirred for 4 hours. Distilled water was added to the reaction liquid, and the resulting mixture was extracted with ethyl acetate. The organic layer was washed with a 10% aqueous solution of sodium chloride, and then dried over anhydrous sodium sulfate and filtered, and the filtrate was concentrated under reduced pressure. The residue was purified by flash chromatography (silica gel, n-hexane/ethyl acetate) to obtain (E)-benzyl 3-(1-(3-ethoxy-3-oxopropyl)-1H-imidazol-2-yl)acrylate (0.520 g, 1.59 mmol, 72%) as a yellow oil.

$^1$H-NMR (400 MHz, CDCl$_3$) δ: 1.23 (3H, t, J=7.2 Hz), 2.76 (2H, t, J=7.2 Hz), 4.13 (2H, q, J=7.2 Hz), 4.35 (2H, t, J=7.2 Hz), 5.26 (2H, s), 6.91 (1H, d, J=15.6 Hz), 7.06 (1H, brs), 7.15 (1H, brs), 7.30-7.42 (5H, m), 7.55 (1H, d, J=15.6 Hz).

ESI-MS: m/z=329 (M+H)$^+$.

Reference Example 32

Synthesis of crude 3-(1-(3-ethoxy-3-oxopropyl)-1H-imidazol-2-yl)propanoic acid

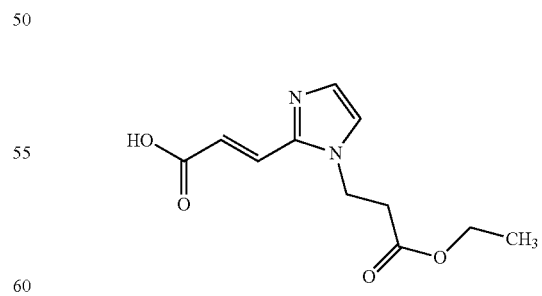

Palladium-carbon (10% wet, 0.169 g, 0.159 mmol) was added to a solution of (E)-benzyl 3-(1-(3-ethoxy-3-oxopropyl)-1H-imidazol-2-yl)acrylate (0.520 g, 1.59 mmol) in ethanol (9.0 mL) at room temperature, and the reaction liquid was stirred under hydrogen atmosphere at the same temperature for 16 hours. The reaction liquid was filtered through Celite, and the filtrate was concentrated under reduced pressure to obtain a crude product of 3-(1-(3-ethoxy-3-oxopropyl)-1H-imidazol-2-yl)propanoic acid.

Example 1

Synthesis of 3-(1-methyl-1H-imidazol-2-yl)-1-(4-(methylamino)piperidin-1-yl)propan-1-one

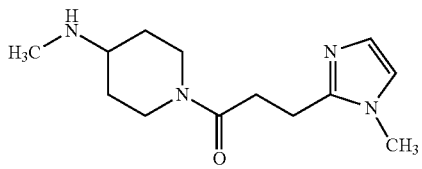

Palladium hydroxide on carbon (10% wet, 0.0820 g, 0.0587 mmol) was added to a solution of 1-(4-benzyl(methyl)aminopiperidin-1-yl)-3-(1-methyl-1H-imidazol-2-yl)propan-1-one (0.200 g, 0.587 mmol) in ethanol (2.0 mL) at room temperature, and the resulting mixture was stirred under hydrogen atmosphere for 3 hours. The reaction liquid was filtered through Celite, and the filtrate was concentrated under reduced pressure. The residue was purified by silica gel column chromatography (chloroform/methanol) to obtain 3-(1-methyl-1H-imidazol-2-yl)-1-(4-(methylamino)piperidin-1-yl)propan-1-one (0.131 g, 0.523 mmol, 89%) (hereinafter referred to as a "compound of Example 1") as a colorless oil.

$^1$H-NMR (400 MHz, CDCl$_3$) δ: 1.17-1.28 (2H, m), 1.85-1.94 (2H, m), 2.44 (3H, s), 2.54-2.62 (1H, m), 2.72-2.81 (1H, m), 2.88-3.00 (4H, m), 3.03-3.13 (1H, m), 3.62 (3H, s), 3.90-3.98 (1H, m), 4.41-4.49 (1H, m), 6.79 (1H, d, J=1.2 Hz), 6.91 (1H, d, J=1.2 Hz).

ESI-MS: m/z=251 (M+H)$^+$.

Example 2

Synthesis of 3-(1-methyl-1H-imidazol-2-yl)-1-(4-(methylamino)piperidin-1-yl)propan-1-one hydrochloride

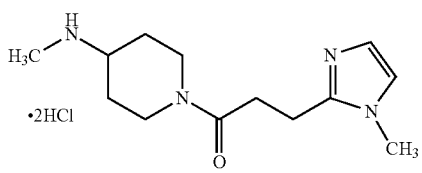 [SMILES: CNC1CCN(C(=O)CCc2nccn2C)CC1]

A solution of hydrogen chloride in diethyl ether (2.0 N, 0.675 mL, 1.35 mmol) was added to a solution of 3-(1-methyl-1H-imidazol-2-yl)-1-(4-methylaminopiperidin-1-yl)propan-1-one (0.131 g, 0.523 mmol) in diethyl ether (5.0 mL) at 0° C. The reaction liquid was stirred at the same temperature for 30 minutes. The precipitated white solid was filtered and collected, and washed with diethyl ether (19.5 mL), and dried at room temperature for 36 hours to obtain 3-(1-methyl-1H-imidazol-2-yl)-1-(4-(methylamino)piperidin-1-yl)propan-1-one hydrochloride (0.0635 g, 0.196 mmol, 38%) (hereinafter referred to as a "compound of Example 2") as a white solid.

$^1$H-NMR (400 MHz, D$_2$O) δ: 1.40-1.68 (2H, m), 2.13-2.26 (2H, m), 2.72-2.80 (4H, m), 3.01-3.08 (2H, m), 3.15-3.26 (3H, m), 3.33-3.43 (1H, m), 3.82 (3H, s), 4.01-4.13 (1H, m), 4.43-4.52 (1H, m), 7.28-7.34 (2H, m).

ESI-MS: as 3-(1-methyl-1H-imidazol-2-yl)-1-(4-(methylamino)piperidin-1-yl)propan-1-one: m/z=251 (M+H)$^+$.

Example 3

Synthesis of N-methyl-N-(1-(3-(1-methyl-1H-imidazol-2-yl)propanoyl)piperidin-4-yl)acetamide

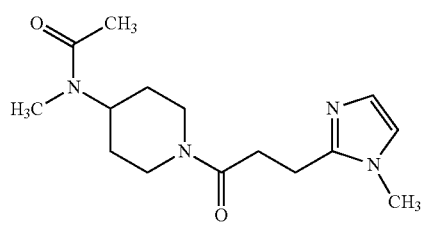 [SMILES: CC(=O)N(C)C1CCN(C(=O)CCc2nccn2C)CC1]

Triethylamine (0.0842 mL, 0.599 mmol) and acetic anhydride (0.0565 mL, 0.599 mmol) were added to a solution of 3-(1-methyl-1H-imidazol-2-yl)-1-(4-methylaminopiperidin-1-yl)propan-1-one (0.0500 g, 0.200 mmol) in dichloromethane (1.0 mL) at room temperature, and the reaction liquid was stirred at the same temperature for 16 hours. A saturated aqueous solution of sodium hydrogencarbonate was added to the reaction liquid and the resulting mixture was extracted with chloroform. The organic layer was washed with a 10% aqueous solution of sodium chloride, and then dried over anhydrous sodium sulfate and filtered, and the filtrate was concentrated under reduced pressure. The residue was purified by flash chromatography (NH silica gel, chloroform/methanol) to obtain N-methyl-N-(1-(3-(1-methyl-1H-imidazol-2-yl)propanoyl)piperidin-4-yl)acetamide (0.0499 g, 0.171 mmol, 85%) (hereinafter referred to as a "compound of Example 3") as a colorless oil.

$^1$H-NMR (400 MHz, CD$_3$OD) δ: 1.43-1.72 (4H, m), 2.01-2.12 (3H, m), 2.52-2.93 (8H, m), 3.00-3.14 (1H, m), 3.59-3.61 (3H, m), 3.96-4.05 (1H, m), 4.47-4.60 (2H, m), 6.74-6.78 (1H, m), 6.87-6.90 (1H, m).

ESI-MS: m/z=293 (M+H)$^+$.

Example 4

Synthesis of N-methyl-N-(1-(3-(1-methyl-1H-imidazol-2-yl)propanoyl)piperidin-4-yl)acetamide hydrochloride

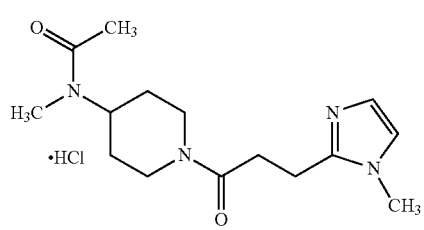 [SMILES: CC(=O)N(C)C1CCN(C(=O)CCc2nccn2C)CC1 ; Cl]

A solution of hydrogen chloride in diethyl ether (2.0 N, 0.111 mL, 0.222 mmol) was added to a solution of N-methyl-N-(1-(3-(1-methyl-1H-imidazol-2-yl)propanoyl)piperidin-4-yl)acetamide (0.0499 g, 0.171 mmol) in diethyl ether (2.0 mL) at 0° C. The reaction liquid was stirred at the same temperature for 1 hour, and then the reaction liquid was stirred at room temperature for 30 minutes. The precipitated white solid was filtered and collected, and washed with diethyl ether (6.0 mL), and dried at room temperature for 36 hours to obtain N-methyl-N-(1-(3-(1-methyl-1H-imidazol-2-yl)propanoyl)piperidin-4-yl)acetamide hydrochloride (0.0397 g, 0.121 mmol, 71%) (hereinafter referred to as a "compound of Example 4") as a white solid.

$^1$H-NMR (400 MHz, D$_2$O) δ: 1.55-1.85 (4H, m), 2.08-2.19 (3H, m), 2.66-2.89 (4H, m), 2.98-3.05 (2H, m), 3.13-3.25 (3H, m), 3.80 (3H, s), 3.95-4.05 (1H, m), 4.38-4.53 (2H, m), 7.27-7.30 (2H, m).

ESI-MS: as N-methyl-N-(1-(3-(1-methyl-1H-imidazol-2-yl)propanoyl)piperidin-4-yl)acetamide: m/z=293 (M+H)$^+$.

Example 5

Synthesis of N-(2-(methyl(1-(3-(1-methyl-1H-imidazol-2-yl)propanoyl)piperidin-4-yl)amino)ethyl)acetamide

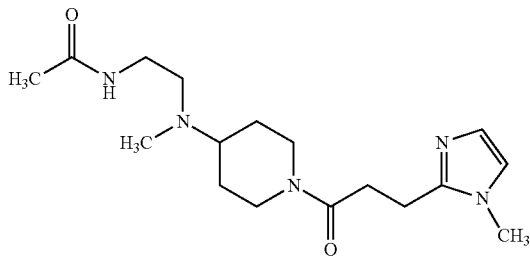 [SMILES: CC(=O)NCCN(C)C1CCN(C(=O)CCc2nccn2C)CC1]

Pyridine (0.0410 mL, 0.511 mmol) and acetic anhydride (0.0480 mL, 0.511 mmol) were added to a solution of 1-(4-((2-aminoethyl)(methyl)amino)piperidin-1-yl)-3-(1-methyl-1H-imidazol-2-yl)propan-1-one (0.0500 g, 0.170 mmol) in dichloromethane (2.0 mL) at room temperature, and the reaction liquid was stirred at the same temperature for 16 hours. The reaction liquid was concentrated under reduced pressure. The residue was purified by flash chromatography (NH silica gel, chloroform/methanol) to obtain N-(2-(methyl(1-(3-(1-methyl-1H-imidazol-2-yl)propanoyl)piperidin-4-yl)amino)ethyl)acetamide (0.0451 g, 0.134 mmol, 79%) (hereinafter referred to as a "compound of Example 5") as a colorless oil.

$^1$H-NMR (400 MHz, CDCl$_3$) δ: 1.30-1.42 (2H, m), 1.70-1.80 (2H, m), 1.97 (3H, s), 2.21 (3H, m), 2.46-2.62 (4H, m), 2.87-3.01 (5H, m), 3.25-3.32 (2H, m), 3.61 (3H, s), 4.00-4.08 (1H, m), 4.63-4.72 (1H, m), 5.97-6.05 (1H, m), 6.78 (1H, d, J=1.2 Hz), 6.90 (1H, d, J=1.2 Hz).

ESI-MS: m/z=336 (M+H)$^+$.

Example 6

Synthesis of N-(2-(methyl(1-(3-(1-methyl-1H-imidazol-2-yl)propanoyl)piperidin-4-yl)amino)ethyl)acetamide hydrochloride

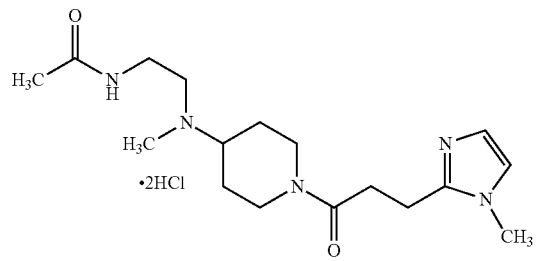 [SMILES: CC(=O)NCCN(C)C1CCN(C(=O)CCc2nccn2C)CC1]

A solution of hydrogen chloride in diethyl ether (2.0 N, 0.174 mL, 0.349 mmol) was added to a solution of N-(2-(methyl(1-(3-(1-methyl-1H-imidazol-2-yl)propanoyl)piperidin-4-yl)amino)ethyl)acetamide (0.0451 g, 0.134 mmol) in diethyl ether (2.0 mL) at 0° C., and the resulting mixture was stirred at the same temperature for 30 minutes. The precipitated white solid was filtered and collected, and washed with diethyl ether (6.0 mL), and dried at room temperature for 36 hours to obtain N-(2-(methyl(1-(3-(1-methyl-1H-imidazol-2-yl)propanoyl)piperidin-4-yl)amino)ethyl)acetamide hydrochloride (0.0211 g, 0.0517 mmol, 39%) (hereinafter referred to as a "compound of Example 6") as a white solid.

$^1$H-NMR (400 MHz, D$_2$O) δ: 1.60-1.85 (2H, m), 2.04 (3H, s), 2.07-2.20 (2H, m), 2.70-2.80 (1H, m), 2.88 (3H, s), 3.02-3.10 (2H, m), 3.18-3.30 (4H, m), 3.40-3.52 (1H, m), 3.60-3.75 (3H, m), 3.84 (3H, s), 4.10-4.18 (1H, m), 7.31-7.35 (2H, m), 7.52-7.60 (1H, m).

ESI-MS: as N-(2-(methyl(1-(3-(1-methyl-1H-imidazol-2-yl)propanoyl)piperidin-4-yl)amino)ethyl)acetamide: m/z=336 (M+H)$^+$.

Example 7

Synthesis of 1-(4-aminopiperidin-1-yl)-3-(1-methyl-1H-imidazol-2-yl)propan-1-one

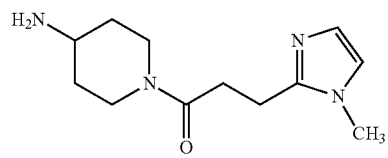 [SMILES: Cn1ccnc1CCC(=O)N1CCC(N)CC1]

Diisopropylethylamine (0.544 mL, 3.11 mmol), HBTU (0.472 g, 1.25 mmol), and tert-butyl piperidin-4-ylcarbamate (0.208 g, 1.04 mmol) were added to a solution of 3-(1-methyl-1H-imidazol-2-yl)propanoic acid (0.160 g, 1.04 mmol) in chloroform (6.0 mL) at room temperature, and the reaction liquid was stirred at the same temperature for 60 hours. Methanol was added to the reaction liquid and the resulting mixture was concentrated under reduced pressure. The residue was purified by flash chromatography (NH silica gel, chloroform/methanol). 1,4-Dioxane (11.0 mL) was added to the obtained residue at room temperature and the obtained residue was dissolved. A solution of hydrogen chloride in 1,4-dioxane (4.0 N, 3.11 mL, 12.5 mmol) was added to the reaction liquid at room temperature, and the resulting mixture was stirred at the same temperature for 16 hours. A 1.0 N aqueous solution of sodium hydroxide was added to the reaction liquid and the resulting mixture was concentrated under reduced pressure. The residue was purified by flash chromatography (NH silica gel, chloroform/methanol) to obtain 1-(4-aminopiperidin-1-yl)-3-(1-methyl-1H-imidazol-2-yl)propan-1-one (0.231 g, 0.978 mmol, 94%) (hereinafter referred to as a "compound of Example 7") as a colorless oil.

$^1$H-NMR (400 MHz, CDCl$_3$) δ: 1.16-1.28 (2H, m), 1.79-1.89 (2H, m), 2.65-2.75 (1H, m), 2.85-3.10 (6H, m), 3.62 (3H, s), 3.90-3.98 (1H, m), 4.45-4.54 (1H, m), 6.79 (1H, d, J=1.2 Hz), 6.91 (1H, d, J=1.2 Hz).

ESI-MS: m/z=237 (M+H)$^+$.

Example 8

Synthesis of 1-(4-aminopiperidin-1-yl)-3-(1-methyl-1H-imidazol-2-yl)propan-1-one hydrochloride

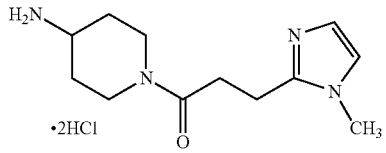 [SMILES: Cn1ccnc1CCC(=O)N1CCC(N)CC1]

A solution of hydrogen chloride in diethyl ether (2.0 N, 0.227 mL, 0.455 mmol) was added to a solution of 1-(4-aminopiperidin-1-yl)-3-(1-methyl-1H-imidazol-2-yl)propan-1-one (0.0430 g, 0.182 mmol) in diethyl ether (2.0 mL) at 0° C. The reaction liquid was stirred at the same temperature for 30 minutes, and then the reaction liquid was stirred at room temperature for 1 hour. The precipitated white solid was filtered and collected, and washed with diethyl ether, and dried at room temperature to obtain 1-(4-aminopiperidin-1-yl)-3-(1-methyl-1H-imidazol-2-yl)propan-1-one hydrochloride (0.0420 g, 0.136 mmol, 75%) (hereinafter referred to as a "compound of Example 8") as a white solid.

$^1$H-NMR (400 MHz, D$_2$O) δ: 1.46-1.69 (2H, m), 2.09-2.16 (2H, m), 2.76-2.83 (1H, m), 3.04-3.07 (2H, m), 3.20-3.25 (3H, m), 3.48-3.53 (1H, m), 3.84 (3H, s), 4.02-4.06 (1H, m), 4.43-4.46 (2H, m), 7.26 (2H, s).

ESI-MS: as 1-(4-aminopiperidin-1-yl)-3-(1-methyl-1H-imidazol-2-yl)propan-1-one: m/z=237 (M+H)$^+$.

Example 9

Synthesis of N-(1-(3-(1-methyl-1H-imidazol-2-yl)propanoyl)piperidin-4-yl)acetamide

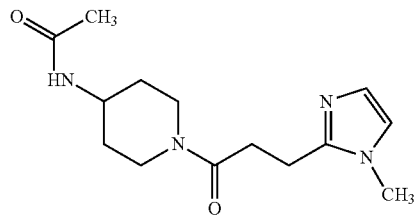 [SMILES: CC(=O)NC1CCN(C(=O)CCc2nccn2C)CC1]

Pyridine (0.0510 mL, 0.635 mmol) and acetic anhydride (0.0600 mL, 0.635 mmol) was added to a solution of 1-(4-aminopiperidin-1-yl)-3-(1-methyl-1H-imidazol-2-yl)propan-1-one (0.0500 g, 0.212 mmol) in dichloromethane (2.0 mL) at room temperature, and the reaction liquid was stirred at the same temperature for 3 hours. The reaction liquid was concentrated under reduced pressure. The residue was purified by flash chromatography (NH silica gel, chloroform/methanol) to obtain N-(1-(3-(1-methyl-1H-imidazol-2-yl)propanoyl)piperidin-4-yl)acetamide (0.0510 g, 0.183 mmol, 86%) (hereinafter referred to as a "compound of Example 9") as a colorless oil.

$^1$H-NMR (400 MHz, CDCl$_3$) δ: 1.19-1.34 (2H, m), 1.88-2.02 (4H, m), 2.07-2.20 (1H, m), 2.65-2.75 (1H, m), 2.82-3.02 (4H, m), 3.05-3.15 (1H, m), 3.60 (3H, s), 3.88-4.02 (2H, m), 4.45-4.55 (1H, m), 5.68-5.82 (1H, m), 6.77 (1H, d, J=1.2 Hz), 6.87 (1H, d, J=1.2 Hz).

Example 10

Synthesis of N-(1-(3-(1-methyl-1H-imidazol-2-yl)propanoyl)piperidin-4-yl)acetamide hydrochloride

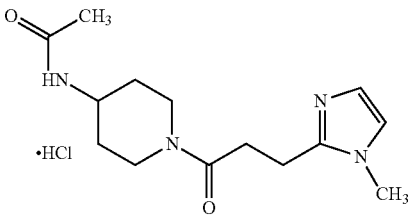 [SMILES: CC(=O)NC1CCN(C(=O)CCc2nccn2C)CC1 ; Cl]

A solution of hydrogen chloride in diethyl ether (2.0 N, 0.119 mL, 0.238 mmol) was added to a solution of N-(1-(3-(1-methyl-1H-imidazol-2-yl)propanoyl)piperidin-4-yl)acetamide (0.0510 g, 0.183 mmol) in diethyl ether (2.0 mL) at 0° C. The reaction liquid was stirred at the same temperature for 30 minutes. The precipitated white solid was filtered and collected, and washed with diethyl ether (6.0 mL), and dried at room temperature for 36 hours to obtain N-(1-(3-(1-methyl-1H-imidazol-2-yl)propanoyl)piperidin-4-yl)acetamide hydrochloride (0.0344 g, 0.109 mmol, 60%) (hereinafter referred to as a "compound of Example 10") as a white solid.

$^1$H-NMR (400 MHz, D$_2$O) δ: 1.30-1.50 (2H, m), 1.85-1.99 (5H, m), 2.83-2.94 (1H, m), 2.97-3.06 (2H, m), 3.17-3.30 (3H, m), 3.79-3.93 (5H, m), 4.17-4.27 (1H, m), 7.27-7.33 (2H, m).

ESI-MS: as N-(1-(3-(1-methyl-1H-imidazol-2-yl)propanoyl)piperidin-4-yl)acetamide: m/z=279 (M+H)$^+$.

Example 11

Synthesis of 1-(4-(dimethylamino)piperidin-1-yl)-3-(1-(2-hydroxyethyl)-1H-imidazol-2-yl)propan-1-one

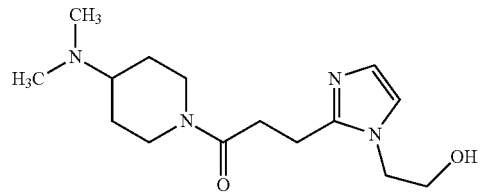 [SMILES: CN(C)C1CCN(C(=O)CCc2nccn2CCO)CC1]

A solution of tetrabutylammonium fluoride in tetrahydrofuran (1.0 M, 3.06 mL, 3.06 mmol) was added to a solution of 3-(1-(2-((tert-butyldimethylsilyl)oxy)ethyl)-1H-imidazol-2-yl)-1-(4-(dimethylamino)piperidin-1-yl)propan-1-one (1.00 g, 2.45 mmol) in tetrahydrofuran (12.2 mL) at 0° C., and the temperature of the resulting mixture was raised to room temperature, and the resulting mixture was stirred for 2 hours. The reaction liquid was concentrated under reduced pressure, and then the residue was purified by column chromatography (NH silica gel, chloroform/methanol) to obtain 1-(4-(dimethylamino)piperidin-1-yl)-3-(1-(2-hydroxyethyl)-1H-imidazol-2-yl)propan-1-one (0.605 g, 2.06 mmol, 84%) (hereinafter referred to as a "compound of Example 11") as a colorless oil.

$^1$H-NMR (400 MHz, CDCl$_3$) δ: 1.26-1.41 (2H, m), 1.78-1.86 (2H, m), 2.26-2.36 (7H, m), 2.52-2.59 (1H, m), 2.95-3.03 (5H, m), 3.88 (2H, t, J=4.9 Hz), 3.96-4.00 (1H, m), 4.09 (2H, t, J=4.9 Hz), 4.51-4.55 (1H, m), 6.85 (1H, s), 6.90 (1H, s).

ESI-MS: m/z=295 (M+H)$^+$.

Example 12

Synthesis of 1-(4-(dimethylamino)piperidin-1-yl)-3-(1-(2-hydroxyethyl)-1H-imidazol-2-yl)propan-1-one hydrochloride

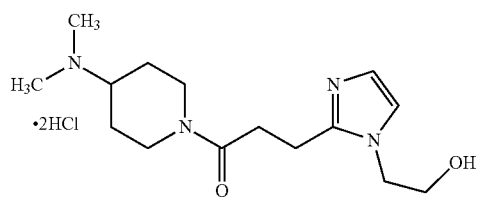 [SMILES: CN(C)C1CCN(C(=O)CCc2nccn2CCO)CC1]

A solution of hydrogen chloride in diethyl ether (2.0 N, 0.16 mL, 0.32 mmol) was added to a solution of 1-(4-(dimethylamino)piperidin-1-yl)-3-(1-(2-hydroxyethyl)-1H-imidazol-2-yl)propan-1-one (37.7 mg, 0.128 mmol) in diethyl ether (2.5 mL)-dichloromethane at 0° C. The reaction liquid was stirred at the same temperature for 1 hour, and the temperature of the reaction liquid was raised to room temperature, and the reaction liquid was stirred for 1 hour. The precipitated white solid was filtered and collected, and washed with diethyl ether, and dried at room temperature to obtain 1-(4-(dimethylamino)piperidin-1-yl)-3-(1-(2-hydroxyethyl)-1H-imidazol-2-yl)propan-1-one hydrochloride (43.1 mg, 0.117 mmol, 92%) (hereinafter referred to as a "compound of Example 12") as a white solid.

$^1$H-NMR (400 MHz, D$_2$O) δ: 1.54-1.76 (2H, m), 2.13-2.20 (2H, m), 2.70-2.78 (1H, m), 2.87 (6H, s), 3.05-3.08 (2H, m), 3.16-3.30 (3H, m), 3.52 (2H, tt, J=12.0, 4.0 Hz), 3.96 (2H, t, J=5.0 Hz), 4.09-4.12 (1H, m), 4.33 (2H, t, J=5.0 Hz), 4.53-4.57 (1H, m), 7.37-7.44 (2H, m).

ESI-MS: as 1-(4-(dimethylamino)piperidin-1-yl)-3-(1-(2-hydroxyethyl)-1H-imidazol-2-yl)propan-1-one: m/z=295 (M+H)$^+$.

Example 13

Synthesis of 2-(2-(3-(4-(dimethylamino)piperidin-1-yl)-3-oxopropyl)-1H-imidazol-1-yl)acetic acid hydrochloride

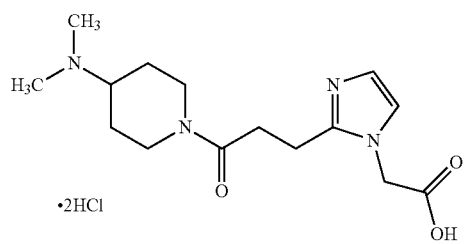 [SMILES: CN(C)C1CCN(C(=O)CCc2nccn2CC(=O)O)CC1 ; "·2HCl"]

A solution of hydrogen chloride in 1,4-dioxane (4.0 N, 0.861 mL, 3.45 mmol) was added to a solution of tert-butyl 2-(2-(3-(4-(dimethylamino)piperidin-1-yl)-3-oxopropyl)-1H-imidazol-1-yl)acetate (0.104 g, 0.287 mmol) in 1,4-dioxane (1.0 mL) at 0° C. The reaction liquid was stirred at the same temperature for 30 minutes. The precipitated white solid was filtered and collected to obtain 2-(2-(3-(4-(dimethylamino)piperidin-1-yl)-3-oxopropyl)-1H-imidazol-1-yl)acetic acid hydrochloride (quant.) (hereinafter referred to as a "compound of Example 13") as a white solid.

$^1$H-NMR (400 MHz, D$_2$O) δ: 1.54-1.76 (2H, m), 2.13-2.19 (2H, m), 2.70-2.76 (1H, m), 2.87 (6H, s), 2.99-3.02 (2H, m), 3.15-3.24 (3H, m), 3.47-3.55 (1H, m), 4.06-4.10 (1H, m), 4.53-4.56 (1H, m), 5.02 (2H, s), 7.39 (2H, s).

ESI-MS: as 2-(2-(3-(4-(dimethylamino)piperidin-1-yl)-3-oxopropyl)-1H-imidazol-1-yl)acetic acid: m/z=307 (M−H)$^−$.

Example 14

Synthesis of 3-(1-(2-aminoethyl)-1H-imidazol-2-yl)-1-(4-(dimethylamino)piperidin-1-yl)propan-1-one

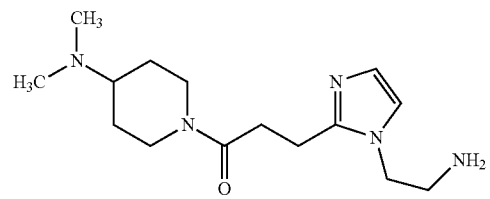 [SMILES: CN(C)C1CCN(C(=O)CCc2nccn2CCN)CC1]

Triethylamine (0.342 mL, 2.47 mmol) and methanesulfonyl chloride (0.191 mL, 2.47 mmol) were added to a solution of 1-(4-(dimethylamino)piperidin-1-yl)-3-(1-(2-hydroxyethyl)-1H-imidazol-2-yl)propan-1-one (0.660 g, 2.24 mmol) in dichloromethane (11.0 mL) at 0° C., and the temperature of the resulting mixture was raised to room temperature, and the resulting mixture was stirred for 1 hour. A saturated aqueous solution of potassium carbonate was added to the reaction liquid, and the resulting mixture was extracted with dichloromethane. The organic layer was dried over anhydrous sodium sulfate and then filtered, and the filtrate was concentrated under reduced pressure. Acetonitrile (10.8 mL) was added to the obtained residue, and the obtained residue was dissolved. Phthalimide potassium (0.452 g, 2.44 mmol) was added thereto at room temperature, and the resulting mixture was heated under reflux for 3 hours. The reaction liquid was concentrated under reduced pressure, and then dichloromethane and a saturated aqueous solution of potassium carbonate were added to the residue, and the resulting mixture was extracted with dichloromethane. The organic layer was dried over anhydrous sodium sulfate and then filtered, and the filtrate was concentrated under reduced pressure. Methanol (10.8 mL) was added to the obtained residue, and the obtained residue was dissolved. Hydrazine hydrate (0.158 mL, 3.25 mmol) was added thereto at room temperature, and the resulting mixture was heated under reflux for 1 hour. The temperature of the reaction liquid was cooled to room temperature, and the reaction liquid was filtered, and then the filtrate was concentrated under reduced pressure. Dichloromethane and an aqueous solution of hydrochloric acid (1.0 N, 8.0 mL) were added to the residue, and then the aqueous layer was washed with dichloromethane. An aqueous solution of sodium hydroxide (1 N, 8.0 mL) was added to the aqueous layer, and the resulting mixture was concentrated under reduced pressure. The residue was purified by column chromatography (NH silica gel, chloroform/methanol) to obtain 3-(1-(2-aminoethyl)-1H-imidazol-2-yl)-1-(4-(dimethylamino)piperidin-1-yl)propan-1-one (0.338 g, 1.15 mmol, 51%) (hereinafter referred to as a "compound of Example 14") as a colorless oil.

$^1$H-NMR (400 MHz, CDCl$_3$) δ: 1.30-1.43 (2H, m), 1.81-1.87 (2H, m), 2.27 (6H, s), 2.34 (1H, tt, J=11.0, 3.8 Hz) 2.56-2.63 (1H, m), 2.92-3.05 (7H, m), 3.98-4.04 (3H, m), 4.59-4.62 (1H, m), 6.88 (1H, t, J=1.2 Hz), 6.96 (1H, t, J=1.2 Hz).

ESI-MS: m/z=294 (M+H)$^+$.

Example 15

Synthesis of 3-(1-(2-aminoethyl)-1H-imidazol-2-yl)-1-(4-(dimethylamino)piperidin-1-yl)propan-1-one hydrochloride

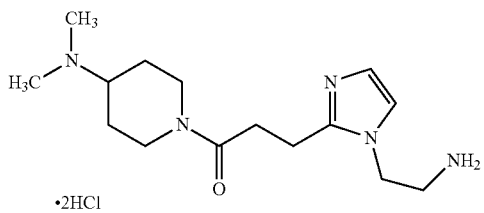 [SMILES: CN(C)C1CCN(C(=O)CCc2nccn2CCN)CC1 ; "·2HCl"]

A solution of hydrogen chloride in diethyl ether (2.0 N, 0.245 mL, 0.491 mmol) was added to a solution of 3-(1-(2-aminoethyl)-1H-imidazol-2-yl)-1-(4-(dimethylamino)piperidin-1-yl)propan-1-one (0.0576 g, 0.196 mmol) in diethyl ether (3.9 mL) at 0° C. The reaction liquid was stirred at the same temperature for 1 hour, and the temperature of the reaction liquid was raised to room temperature, and then the reaction liquid was stirred for 1 hour. The precipitated white solid was filtered and collected, and washed with diethyl ether, and dried at room temperature to obtain 3-(1-(2-aminoethyl)-1H-imidazol-2-yl)-1-(4-(dimethylamino)piperidin-1-yl)propan-1-one hydrochloride (0.0633 g, 0.173 mmol, 88%) (hereinafter referred to as a "compound of Example 15") as a white solid.

$^1$H-NMR (400 MHz, D$_2$O) δ: 1.55-1.81 (2H, m), 2.14-2.22 (2H, m), 2.71-2.77 (1H, m), 2.88 (6H, s), 3.06-3.31 (5H, m), 3.50-3.60 (3H, m), 4.12-4.15 (1H, m), 4.52-4.55 (1H, m), 4.61 (2H, t, J=6.6 Hz), 7.44-7.51 (2H, m).

ESI-MS: as 3-(1-(2-(aminoethyl)-1H-imidazol-2-yl)-1-(4-(dimethylamino)piperidin-1-yl)propan-1-one: m/z=294 (M+H)$^+$.

Example 16

Synthesis of ethyl 2-(2-(3-(4-(ethylmethylamino) piperidin-1-yl)-3-oxopropyl)-1H-imidazol-1-yl)acetate

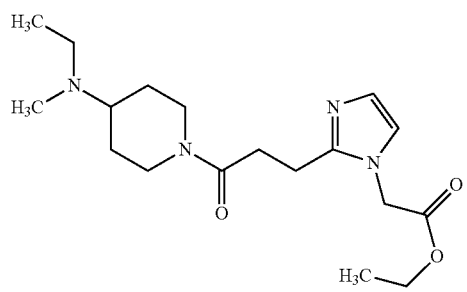 [SMILES: CCOC(=O)Cn1ccnc1CCC(=O)N1CCC(N(C)CC)CC1]

Diisopropylethylamine (0.116 mL, 0.663 mmol), HBTU (0.126 g, 0.332 mmol), and crude 4-ethylmethylaminopiperidine (0.0310 g, 0.221 mmol) were added to a solution of crude 3-(1-(2-ethoxy-2-oxoethyl)-1H-imidazol-2-yl)propanoic acid (0.0500 g, 0.221 mmol) in chloroform (2.0 mL) at room temperature, and the reaction liquid was stirred at the same temperature for 16 hours. The reaction liquid was concentrated under reduced pressure. The residue was purified by flash chromatography (NH silica gel, chloroform/methanol) to obtain ethyl 2-(2-(3-(4-(ethylmethylamino)piperidin-1-yl)-3-oxopropyl)-1H-imidazol-1-yl)acetate (0.0250 g, 0.0713 mmol, 32%) (hereinafter referred to as a "compound of Example 16") as a colorless oil.

$^1$H-NMR (400 MHz, CDCl$_3$) δ: 1.06 (3H, t, J=7.2 Hz), 1.25-1.45 (5H, m), 1.73-1.83 (2H, m), 2.23 (3H, s), 2.48-2.63 (4H, m), 2.88-3.03 (5H, m), 3.97-4.05 (1H, m), 4.19-4.26 (2H, m), 4.58-4.65 (1H, m), 4.75 (2H, s), 6.80-6.82 (1H, m), 6.95-6.97 (1H, m).

ESI-MS: m/z=351 (M+H)$^+$.

Example 17

Synthesis of 2-(2-(3-(4-(ethylmethylamino)piperidin-1-yl)-3-oxopropyl)-1H-imidazol-1-yl)acetic acid

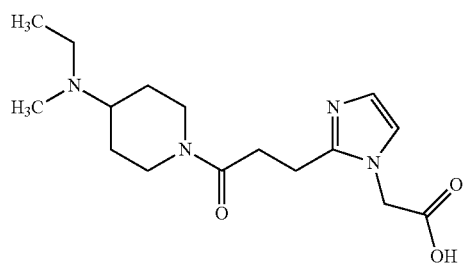 [SMILES: CCN(C)C1CCN(C(=O)CCc2nccn2CC(=O)O)CC1]

An aqueous solution of sodium hydroxide (1.0 N, 0.565 mL, 0.565 mmol) was added to a solution of ethyl 2-(2-(3-(4-(ethylmethylamino)piperidin-1-yl)-3-oxopropyl)-1H-imidazol-1-yl)acetate (0.180 g, 0.514 mmol) in ethanol (3.0 mL) at room temperature, and the reaction liquid was stirred at the same temperature for 4 hours. The reaction liquid was cooled to 0° C., and then hydrochloric acid (1.0 N) was added to the reaction liquid for neutralization, and then the reaction liquid was concentrated under reduced pressure. The residue was subjected to azeotropic distillation with toluene, and ethanol was added. The precipitate was filtered through Celite, and the filtrate was concentrated under reduced pressure to obtain 2-(2-(3-(4-(ethylmethylamino)piperidin-1-yl)-3-oxopropyl)-1H-imidazol-1-yl)acetic acid (0.161 g, 0.499 mmol, 97%) (hereinafter referred to as a "compound of Example 17") as a white solid.

$^1$H-NMR (400 MHz, DMSO-$d_6$) δ: 1.15-1.24 (3H, m), 1.33-1.65 (2H, m), 1.86-1.97 (2H, m), 2.25-2.70 (6H, m), 2.72-2.80 (3H, m), 2.95-3.12 (3H, m), 3.95-4.05 (1H, m), 4.44-4.54 (1H, m), 4.76-4.83 (2H, m), 6.74-6.85 (1H, m), 7.00-7.09 (1H, m).

ESI-MS: m/z=323 (M+H)$^+$.

Example 18

Synthesis of 2-(2-(3-(4-(ethylmethylamino)piperidin-1-yl)-3-oxopropyl)-1H-imidazol-1-yl)acetic acid hydrochloride

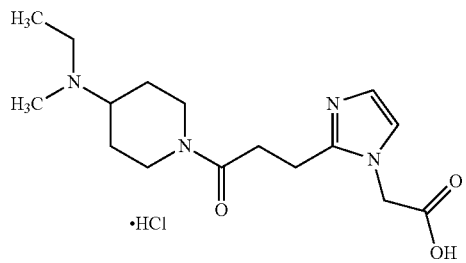 [SMILES: CCN(C)C1CCN(C(=O)CCc2nccn2CC(=O)O)CC1 ; Cl]

Hydrochloric acid (1.0 N, 0.354 mL, 0.354 mmol) was added to a solution of 2-(2-(3-(4-(ethylmethylamino)piperidin-1-yl)-3-oxopropyl)-1H-imidazol-1-yl)acetic acid (0.161 g, 0.499 mmol) in water (1.0 mL) at 0° C., and the reaction liquid was stirred at the same temperature for 2 hours. The reaction liquid was concentrated under reduced pressure, and the precipitated white solid was filtered and collected to obtain 2-(2-(3-(4-(ethylmethylamino)piperidin-1-yl)-3-oxopropyl)-1H-imidazol-1-yl)acetic acid hydrochloride (0.160 g, 0.446 mmol, 89%) (hereinafter referred to as a "compound of Example 18") as a white solid.

$^1$H-NMR (400 MHz, D$_2$O) δ: 1.28-1.35 (3H, m), 1.54-1.82 (2H, m), 2.05-2.16 (2H, m), 2.68-2.81 (4H, m), 2.96-3.04 (2H, m), 3.12-3.24 (4H, m), 3.28-3.38 (1H, m), 3.54-3.64 (1H, m), 4.02-4.10 (1H, m), 4.48-4.58 (1H, m), 4.98 (2H, s), 7.35-7.38 (2H, m).

ESI-MS: as 2-(2-(3-(4-(ethylmethylamino)piperidin-1-yl)-3-oxopropyl)-1H-imidazol-1-yl)acetic acid: m/z=323 (M+H)$^+$.

Example 19

Synthesis of ethyl 2-(2-(3-(4-(diethylamino)piperidin-1-yl)-3-oxopropyl)-1H-imidazol-1-yl)acetate

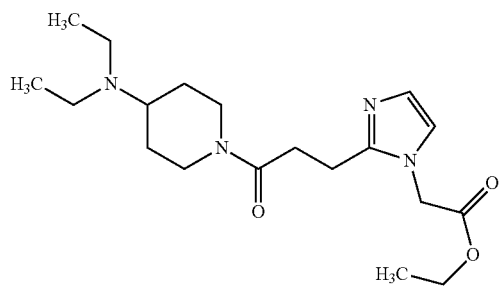 [SMILES: CCOC(=O)Cn1ccnc1CCC(=O)N1CCC(N(CC)CC)CC1]

Diisopropylethylamine (0.116 mL, 0.663 mmol), HBTU (0.126 g, 0.332 mmol), and crude 4-diethylaminopiperidine (0.0350 g, 0.221 mmol) were added to a solution of crude 3-(1-(2-ethoxy-2-oxoethyl)-1H-imidazol-2-yl)propanoic acid (0.0500 g, 0.221 mmol) in chloroform (2.0 mL) at room temperature, and the reaction liquid was stirred at the same temperature for 16 hours. The reaction liquid was concentrated under reduced pressure. The residue was purified by flash chromatography (NH silica gel, chloroform/methanol) to obtain ethyl 2-(2-(3-(4-(diethylamino)piperidin-1-yl)-3-oxopropyl)-1H-imidazol-1-yl)acetate (0.0700 g, 0.192 mmol, 87%) (hereinafter referred to as a "compound of Example 19") as a colorless oil.

$^1$H-NMR (400 MHz, CDCl$_3$) δ: 1.03 (6H, t, J=7.2 Hz), 1.25-1.43 (5H, m), 1.72-1.82 (2H, m), 2.47-2.58 (4H, m), 2.65-2.77 (1H, m), 2.88-3.00 (6H, m), 3.95-4.04 (1H, m), 4.23 (2H, q, J=6.8 Hz), 4.58-4.65 (1H, m), 4.75 (2H, s), 6.80-6.83 (1H, m), 6.95-6.97 (1H, m).

ESI-MS: m/z=365 (M+H)$^+$.

Example 20

Synthesis of ethyl 2-(2-(3-(4-(diethylamino)piperidin-1-yl)-3-oxopropyl)-1H-imidazol-1-yl)acetate hydrochloride

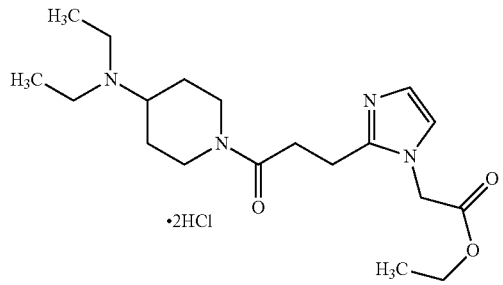 [SMILES: CCOC(=O)Cn1ccnc1CCC(=O)N1CCC(N(CC)CC)CC1 ; "·2HCl"]

A solution of hydrogen chloride in diethyl ether (2.0 N, 0.106 mL, 0.211 mmol) was added to a solution of ethyl 2-(2-(3-(4-(diethylamino)piperidin-1-yl)-3-oxopropyl)-1H-imidazol-1-yl)acetate (0.0350 g, 0.0960 mmol) in diethyl ether (1.0 mL) at 0° C., and the reaction liquid was stirred at the same temperature for 30 minutes. The precipitated white solid was filtered and collected, and washed with diethyl ether (4.0 mL), and dried at room temperature for 36 hours to obtain ethyl 2-(2-(3-(4-(di ethyl amino)piperidin-1-yl)-3-oxopropyl)-1H-imidazol-1-yl)acetate hydrochloride (0.0217 g, 0.0496 mmol, 24%) (hereinafter referred to as a "compound of Example 20") as a white solid.

$^1$H-NMR (400 MHz, D$_2$O) δ: 1.25-1.36 (9H, m), 1.55-1.78 (2H, m), 2.08-2.18 (2H, m), 2.68-2.77 (1H, m), 2.95-3.05 (2H, m), 3.13-3.35 (7H, m), 3.60-3.70 (1H, m), 4.02-4.08 (1H, m), 4.29 (2H, q, J=7.6 Hz), 4.48-4.55 (1H, m), 5.17 (2H, m), 7.34-7.40 (2H, m).

ESI-MS: as ethyl 2-(2-(3-(4-(diethylamino)piperidin-1-yl)-3-oxopropyl)-1H-imidazol-1-yl)acetate: m/z=365 (M+H)$^+$ Example 21

Synthesis of 2-(2-(3-(4-(diethylamino)piperidin-1-yl)-3-oxopropyl)-1H-imidazol-1-yl)acetic acid

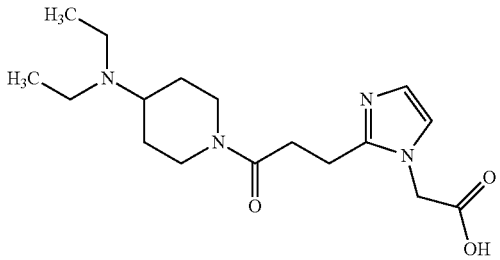

An aqueous solution of sodium hydroxide (1.0 N, 0.452 mL, 0.452 mmol) was added to a solution of ethyl 2-(2-(3-(4-(diethylamino)piperidin-1-yl)-3-oxopropyl)-1H-imidazol-1-yl)acetate (0.150 g, 0.412 mmol) in ethanol (2.0 mL) at room temperature, and the reaction liquid was stirred at the same temperature for 4 hours. The reaction liquid was cooled to 0° C., hydrochloric acid (1.0 N) was added to the reaction liquid for neutralization, and then the reaction liquid was concentrated under reduced pressure. The residue was subjected to azeotropic distillation with toluene, and ethanol was added. The precipitate was filtered through Celite, and the filtrate was concentrated under reduced pressure to obtain 2-(2-(3-(4-(diethylamino)piperidin-1-yl)-3-oxopropyl)-1H-imidazol-1-yl)acetic acid (0.124 g, 0.369 mmol, 89%) (hereinafter referred to as a "compound of Example 21") as a white solid.

$^1$H-NMR (400 MHz, CD$_3$OD) δ: 1.36 (3H, t, J=7.6 Hz), 1.56-1.86 (2H, m), 2.03-2.13 (2H, m), 2.64-2.75 (1H, m), 2.87-3.06 (2H, m), 3.12-3.28 (10H, m), 3.58-3.66 (1H, m), 4.02-4.10 (1H, m), 4.62-4.70 (1H, m), 5.05 (2H, s), 7.42-7.47 (2H, m).

ESI-MS: m/z=337 (M+H)$^+$.

Example 22

Synthesis of 2-(2-(3-(4-(diethylamino)piperidin-1-yl)-3-oxopropyl)-1H-imidazol-1-yl)acetic acid hydrochloride

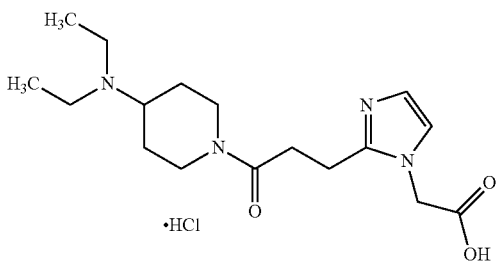 [SMILES: CCN(CC)C1CCN(C(=O)CCc2nccn2CC(=O)O)CC1 ; Cl]

Hydrochloric acid (1.0 N, 0.785 mL, 0.785 mmol) was added to a solution of 2-(2-(3-(4-(diethylamino)piperidin-1-yl)-3-oxopropyl)-1H-imidazol-1-yl)acetic acid (0.124 g, 0.369 mmol) in water (1.0 mL) at 0° C., and the reaction liquid was stirred at the same temperature for 2 hours. The reaction liquid was concentrated under reduced pressure, and the precipitated white solid was filtered and collected to obtain 2-(2-(3-(4-(diethylamino)piperidin-1-yl)-3-oxopropyl)-1H-imidazol-1-yl)acetic acid hydrochloride (0.104 g, 0.278 mmol, 75%) (hereinafter referred to as a "compound of Example 22") as a white solid.

$^1$H-NMR (400 MHz, D$_2$O) δ: 1.27-1.34 (6H, m), 1.55-1.80 (2H, m), 2.06-2.17 (2H, m), 2.68-2.76 (1H, m), 2.95-3.02 (2H, m), 3.13-3.35 (7H, m), 3.59-3.69 (1H, m), 4.01-4.08 (1H, m), 4.48-4.56 (1H, m), 4.95 (2H, s), 7.33-7.36 (2H, m).

ESI-MS: as 2-(2-(3-(4-(diethylamino)piperidin-1-yl)-3-oxopropyl)-1H-imidazol-1-yl)acetic acid: m/z=337 (M+H)$^+$.

Example 23

Synthesis of ethyl 2-(2-(3-(4-(piperidin-1-yl)piperidin-1-yl)-3-oxopropyl)-1H-imidazol-1-yl)acetate

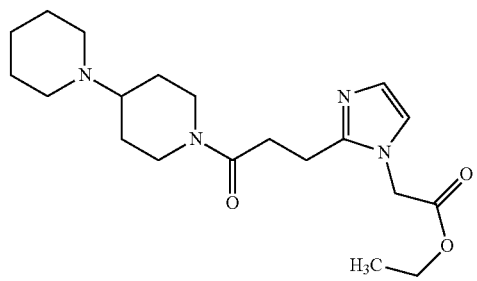 [SMILES: CCOC(=O)Cn1ccnc1CCC(=O)N1CCC(N2CCCCC2)CC1]

Diisopropylethylamine (0.171 g, 1.33 mmol), HBTU (0.402 g, 1.06 mmol), and 4-(piperidin-1-yl)piperidine (0.149 g, 0.884 mmol) were added to a solution of crude 3-(1-(2-ethoxy-2-oxoethyl)-1H-imidazol-2-yl)propanoic acid (0.200 g, 0.884 mmol) in dichloromethane (10.0 mL) at room temperature, and the reaction liquid was stirred at the same temperature for 12 hours. The reaction liquid was concentrated under reduced pressure. The residue was purified by flash chromatography (NH silica gel, hexane/ethyl acetate and chloroform/methanol) to obtain ethyl 2-(2-(3-(4-(piperidin-1-yl)piperidin-1-yl)-3-oxopropyl)-1H-imidazol-1-yl)acetate (0.266 g, 0.708 mmol, 80%) (hereinafter referred to as a "compound of Example 23") as a reddish brown oil.

$^1$H-NMR (400 MHz, CDCl$_3$) δ: 1.29 (3H, t, J=7.2 Hz), 1.36-1.48 (4H, m), 1.54-1.63 (4H, m), 1.7-1.86 (2H, m), 2.40-2.58 (6H, m), 2.85-3.00 (1H, m), 2.91 (4H, s), 3.96-4.03 (1H, m), 4.23 (2H, t, J=7.2 Hz), 4.57-4.65 (1H, m), 4.75 (2H, q, J=7.2 Hz), 6.82 (1H, d, J=1.2 Hz), 6.97 (1H, d, J=1.2 Hz).

ESI-MS: m/z=377 (M+H)$^+$.

Example 24

Synthesis of 2-(2-(3-(4-(piperidin-1-yl)piperidin-1-yl)-3-oxopropyl)-1H-imidazol-1-yl)acetic acid

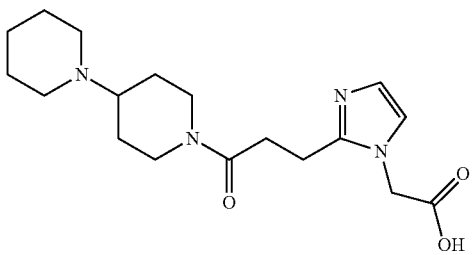 [SMILES: O=C(O)Cn1ccnc1CCC(=O)N1CCC(N2CCCCC2)CC1]

A solution of ethyl 2-(2-(3-(4-(piperidin-1-yl)piperidin-1-yl)-3-oxopropyl)-1H-imidazol-1-yl)acetate (0.0550 g, 0.146 mmol) in water (5.0 mL) was heated to 40° C., and the reaction liquid was stirred at the same temperature for 12 hours. The reaction liquid was concentrated and exsiccated, and then the obtained residue was dried under reduced pressure to obtain 2-(2-(3-(4-(piperidin-1-yl)piperidin-1-yl)-3-oxopropyl)-1H-imidazol-1-yl)acetic acid (0.0510 g, 0.146 mmol, 100%) (hereinafter referred to as a "compound of Example 24") as a reddish brown solid.

$^1$H-NMR (400 MHz, D$_2$O) δ: 1.35-1.90 (8H, m), 1.93-2.03 (2H, m), 2.55 (1H, t, J=12.0 Hz), 3.30 (1H, tt, J=12.0, 3.6 Hz), 3.88-4.00 (1H, m), 4.36-4.45 (1H, m), 4.48 (1H, s), 6.84 (1H, d, J=1.2 Hz), 6.92 (1H, d, J=1.2 Hz).

ESI-MS: m/z=349 (M+H)$^+$.

Example 25

Synthesis of 2-(2-(3-(4-(piperidin-1-yl)piperidin-1-yl)-3-oxopropyl)-1H-imidazol-1-yl)acetic acid hydrochloride

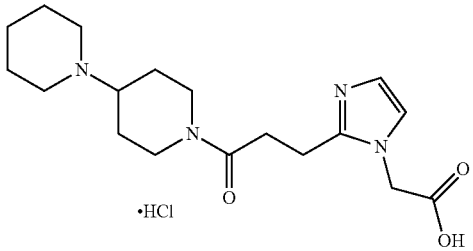 [SMILES: O=C(O)Cn1ccnc1CCC(=O)N1CCC(N2CCCCC2)CC1 ; Cl]

An aqueous solution of sodium hydroxide (1.0 N, 0.345 mL, 0.345 mmol) was added to a solution of ethyl 2-(2-(3-(4-(piperidin-1-yl)piperidin-1-yl)-3-oxopropyl)-1H-imidazol-1-yl)acetate (0.0650 g, 0.173 mmol) in water (5.0 mL) at 0° C. The reaction liquid was stirred at the same temperature for 1 hour. Hydrochloric acid (1.0 N, 0.518 mL, 0.518 mmol) was added thereto, and then the resulting mixture was concentrated and exsiccated. The obtained solid was washed with ethanol and filtered, and then the filtrate was concentrated and exsiccated. Again, the obtained solid was washed with ethanol and filtered, and then the filtrate was concentrated and exsiccated. The obtained residue was dried under reduced pressure to obtain 2-(2-(3-(4-(piperidin-1-yl)piperidin-1-yl)-3-oxopropyl)-1H-imidazol-1-yl)acetic acid hydrochloride (0.0510 g, 0.133 mmol, 77%) (hereinafter referred to as a "compound of Example 25") as a white solid.

$^1$H-NMR (400 MHz, D$_2$O) δ: 1.26-1.72 (6H, m), 1.83 (2H, d, J=14.4 Hz), 2.02 (2H, t, J=12.8 Hz), 2.57 (1H, t, J=12.8 Hz), 2.83-2.95 (4H, m), 2.97-3.14 (3H, m), 3.27-3.43 (3H, m), 3.88-3.98 (1H, m), 4.33-4.43 (1H, m), 4.99 (2H, s), 7.27 (2H, s).

ESI-MS: as 2-(2-(3-(4-(piperidin-1-yl)piperidin-1-yl)-3-oxopropyl)-1H-imidazol-1-yl)acetic acid: 349 (M+H)$^+$.

Example 26

Synthesis of ethyl 2-(2-(3-(4-(morpholin-1-yl)piperidin-1-yl)-3-oxopropyl)-1H-imidazol-1-yl)acetate

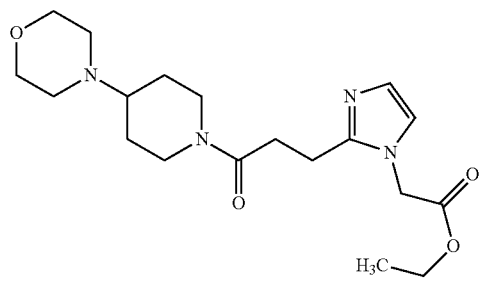 [SMILES: CCOC(=O)Cn1ccnc1CCC(=O)N1CCC(N2CCOCC2)CC1]

Diisopropylethylamine (0.171 g, 1.33 mmol), HBTU (0.402 g, 1.06 mmol), and 4-(morpholin-4-yl)piperidine (0.151 g, 0.884 mmol) were added to a solution of crude 3-(1-(2-ethoxy-2-oxoethyl)-1H-imidazol-2-yl)propanoic acid (0.200 g, 0.884 mmol) in dichloromethane (10.0 mL) at room temperature, and the reaction liquid was stirred at the same temperature for 12 hours. The reaction liquid was concentrated under reduced pressure. The residue was purified by flash chromatography (NH silica gel, hexane/ethyl acetate and chloroform/methanol) to obtain ethyl 2-(2-(3-(4-(morpholin-1-yl)piperidin-1-yl)-3-oxopropyl)-1H-imidazol-1-yl)acetate (0.265 g, 0.700 mmol, 79%) (hereinafter referred to as a "compound of Example 26") as a white solid.

$^1$H-NMR (400 MHz, CDCl$_3$) δ: 1.29 (3H, t, J=7.2 Hz), 1.30-1.45 (2H, m), 1.81-1.92 (2H, m), 2.39 (1H, tt, J=10.8, 3.6 Hz), 2.53 (4H, t, J=4.8 Hz), 2.59 (1H, td, J=13.2, 2.8 Hz), 2.91 (4H, s), 3.01 (1H, td, J=13.2, 2.8 Hz), 3.71 (4H, t, J=4.8 Hz), 3.97-4.04 (1H, m), 4.23 (2H, q, J=7.2 Hz), 4.54-4.62 (1H, m), 4.75 (2H, s), 6.82 (1H, d, J=1.6 Hz), 6.96 (1H, d, J=1.6 Hz).

ESI-MS: m/z=379 (M+H)$^+$.

Example 27

Synthesis of 2-(2-(3-(4-(morpholin-4-yl)piperidin-1-yl)-3-oxopropyl)-1H-imidazol-1-yl)acetic acid hydrochloride

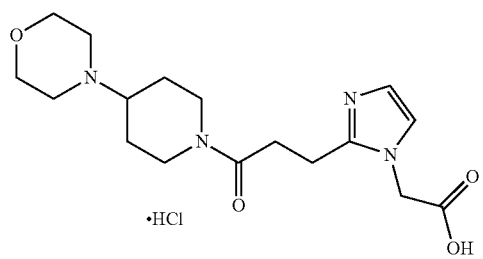 [SMILES: O=C(O)Cn1ccnc1CCC(=O)N1CCC(N2CCOCC2)CC1 ; Cl]

An aqueous solution of sodium hydroxide (1.0 N, 0.423 mL, 0.423 mmol) was added to a solution of ethyl 2-(2-(3-(4-(morpholin-4-yl)piperidin-1-yl)-3-oxopropyl)-1H-imidazol-1-yl)acetate (0.080 g, 0.211 mmol) in water (5.0 mL) at 0° C. The reaction liquid was stirred at the same temperature for 1 hour. Hydrochloric acid (1.0 N, 0.634 mL, 0.634 mmol) was added thereto, and then the resulting mixture was concentrated and exsiccated. The obtained solid was washed with ethanol and filtered, and then the filtrate was concentrated and exsiccated. Again, the obtained solid was washed with ethanol and filtered, and then the filtrate was concentrated and exsiccated. The obtained residue was dried under reduced pressure to obtain 2-(2-(3-(4-(morpholin-4-yl)piperidin-1-yl)-3-oxopropyl)-1H-imidazol-1-yl)acetic acid hydrochloride (0.0580 g, 0.150 mmol, 71%) (hereinafter referred to as a "compound of Example 27") as a white solid.

$^1$H-NMR (400 MHz, D$_2$O) δ: 1.44 (1H, ddd, J=25.4, 12.4, 4.4 Hz), 1.57 (1H, ddd, J=25.4, 12.4, 4.4 Hz), 2.11 (2H, t, J=12.8 Hz), 2.58 (1H, t, J=13.2 Hz), 2.98-3.17 (5H, m), 3.35-3.47 (3H, m), 3.68 (2H, t, J=12.4 Hz), 3.89-3.96 (1H, m), 3.97-4.06 (2H, m), 4.38-4.45 (1H, m), 4.68 (2H, s), 7.20 (1H, d, J=1.6 Hz), 7.21 (1H, d, 1.6 Hz).

ESI-MS: as 2-(2-(3-(4-(morpholin-4-yl)piperidin-1-yl)-3-oxopropyl)-1H-imidazol-1-yl)acetic acid: 351 (M+H)$^+$.

Example 28

Synthesis of ethyl 2-(2-(3-(4-(1-methylpiperazin-4-yl)piperidin-1-yl)-3-oxopropyl)-1H-imidazol-1-yl)acetate

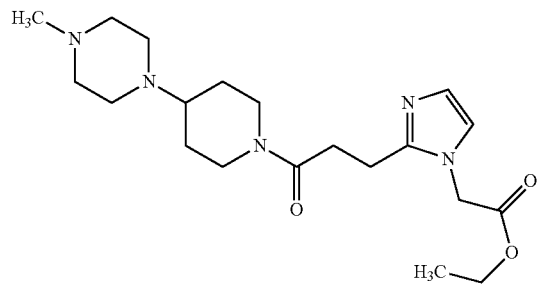 [SMILES: CCOC(=O)Cn1ccnc1CCC(=O)N1CCC(N2CCN(C)CC2)CC1]

Diisopropylethylamine (0.171 g, 1.33 mmol), HBTU (0.402 g, 1.06 mmol), and 4-(1-methylpiperazin-4-yl)piperidine (0.162 g, 0.884 mmol) were added to a solution of crude 3-(1-(2-ethoxy-2-oxoethyl)-1H-imidazol-2-yl)propanoic acid (0.200 g, 0.884 mmol) in dichloromethane (10.0 mL) at room temperature, and the reaction liquid was stirred at the same temperature for 12 hours. The reaction liquid was concentrated under reduced pressure. The residue was purified by flash chromatography (NH silica gel, hexane/ethyl acetate and chloroform/methanol) to obtain ethyl 2-(2-(3-(4-(1-methylpiperazin-4-yl)piperidin-1-yl)-3-oxopropyl)-1H-imidazol-1-yl)acetate (0.280 g, 0.715 mmol, 81%) (hereinafter referred to as a "compound of Example 28") as a pale yellow oil.

$^1$H-NMR (400 MHz, CDCl$_3$) δ: 1.29 (3H, t, J=7.6 Hz), 1.32-1.46 (2H, m), 1.81-1.91 (2H, m), 2.28 (3H, s), 2.36-2.64 (10H, m), 2.91 (4H, s), 2.95-3.03 (1H, m), 3.97-4.04 (1H, m), 4.23 (2H, q, J=7.6 Hz), 4.54-4.62 (1H, m), 4.75 (2H, s), 6.82 (1H, d, J=1.2 Hz), 6.96 (1H, d, J=1.2 Hz).

ESI-MS: m/z=392 (M+H)$^+$.

Example 29

Synthesis of 2-(2-(3-(4-(1-methylpiperazin-4-yl)piperidin-1-yl)-3-oxopropyl)-1H-imidazol-1-yl)acetic acid hydrochloride

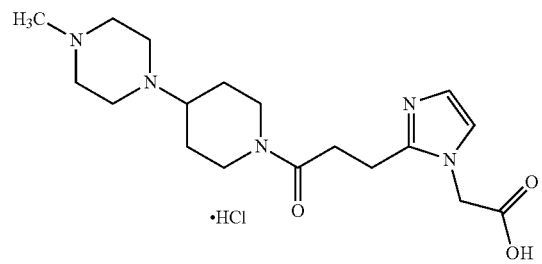 [SMILES: CN1CCN(C2CCN(C(=O)CCc3nccn3CC(=O)O)CC2)CC1 ; Cl]

An aqueous solution of sodium hydroxide (1.0 N, 0.605 mL, 0.605 mmol) was added to a solution of ethyl 2-(2-(3-(4-(1-methylpiperazin-4-yl)piperidin-1-yl)-3-oxopropyl)-1H-imidazol-1-yl)acetate (0.118 g, 0.303 mmol) in water (5.0 mL) at 0° C. The reaction liquid was stirred at the same temperature for 1 hour. Hydrochloric acid (1.0 N, 0.910 mL, 0.910 mmol) was added thereto, and then the resulting mixture was concentrated and exsiccated. The obtained solid was washed with ethanol and filtered, and then the filtrate was concentrated and exsiccated. Again, the obtained solid was washed with ethanol and filtered, and then the filtrate was concentrated and exsiccated. The obtained residue was dried under reduced pressure to obtain 2-(2-(3-(4-(1-methylpiperazin-4-yl)piperidin-1-yl)-3-oxopropyl)-1H-imidazol-1-yl)acetic acid hydrochloride (0.0850 g, 0.213 mmol, 70%) (hereinafter referred to as a "compound of Example 29") as a white solid.

$^1$H-NMR (400 MHz, D$_2$O) δ: 1.26 (1H, ddd, J=24.4, 12.4, 4.0 Hz), 1.36 (1H, ddd, J=24.4, 12.4, 4.0 Hz), 1.91 (2H, t, J=13.2 Hz), 2.55 (1H, t, 12.4 Hz), 2.60-3.30 (9H, m), 2.70 (1H, s), 2.83 (2H, t, J=6.8 Hz), 3.04 (2H, t, J=6.8 Hz), 3.82-3.89 (1H, m), 4.27-4.36 (1H, s), 4.66 (2H, s), 7.19 (1H, d, J=1.6 Hz), 7.21 (1H, d, J=1.6 Hz).

ESI-MS: as 2-(2-(3-(4-(1-methylpiperazin-4-yl)piperidin-1-yl)-3-oxopropyl)-1H-imidazol-1-yl)acetic acid: 364 (M+H)$^+$.

Example 30

Synthesis of ethyl 2-(2-(3-((R)-3-dimethylaminopiperidin-1-yl)-3-oxopropyl)-1H-imidazol-1-yl)acetate

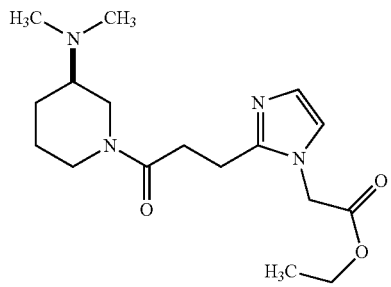 [SMILES: CCOC(=O)Cn1ccnc1CCC(=O)N1CCC[C@@H](N(C)C)C1]

Diisopropylethylamine (0.257 g, 1.99 mmol), HBTU (0.603 g, 1.59 mmol), and (R)-3-dimethylaminopiperidine (0.149 g, 0.880 mmol) were added to a solution of crude 3-(1-(2-ethoxy-2-oxoethyl)-1H-imidazol-2-yl)propanoic acid (0.300 g, 1.33 mmol) in dichloromethane (15.0 mL) at room temperature, and the reaction liquid was stirred at the same temperature for 12 hours. The reaction liquid was concentrated under reduced pressure. The residue was purified by flash chromatography (NH silica gel, hexane/ethyl acetate and chloroform/methanol) to obtain ethyl 2-(2-(3-((R)-3-dimethylaminopiperidin-1-yl)-3-oxopropyl)-1H-imidazol-1-yl)acetate (0.325 g, 0.966 mmol, 73%) (hereinafter referred to as a "compound of Example 30") as a yellow oil.

$^1$H-NMR (400 MHz, CDCl$_3$) δ: 1.29 (3H, t, J=7.2 Hz), 1.36-1.48 (2H, m), 1.95-2.00 (2H, m), 2.32 (6H, s), 2.40-2.55 (1H, m), 2.78-3.00 (6H, m), 3.80-4.05 (1H, m), 4.23 (2H, q, J=7.2), 4.45-4.67 (1H, m), 4.71-4.80 (2H, m), 6.80-6.85 (1H, m), 6.97 (1H, d, J=1.2 Hz).

ESI-MS: m/z=337 (M+H)$^+$.

Example 31

Synthesis of 2-(2-(3-((R)-3-dimethylaminopiperidin-1-yl)-3-oxopropyl)-1H-imidazol-1-yl)acetic acid hydrochloride

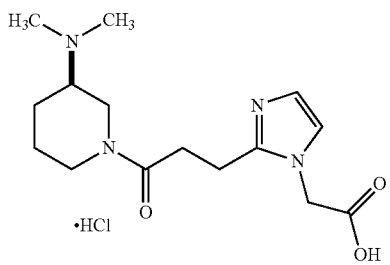 [SMILES: CN(C)[C@@H]1CCCN(C(=O)CCc2nccn2CC(=O)O)C1 ; Cl]

An aqueous solution of sodium hydroxide (1.0 N, 0.329 mL, 0.329 mmol) was added to a solution of ethyl 2-(2-(3-((R)-3-dimethylaminopiperidin-1-yl)-3-oxopropyl)-1H-imidazol-1-yl)acetate (0.0550 g, 0.165 mmol) in water (5.0 mL) at 0° C. The reaction liquid was stirred at the same temperature for 1 hour. Hydrochloric acid (1.0 N, 0.494 mL, 0.494 mmol) was added thereto, and then the resulting mixture was concentrated and exsiccated. The obtained solid was washed with ethanol and filtered, and then the filtrate was concentrated and exsiccated. Again, the obtained solid was washed with ethanol and filtered, and then the filtrate was concentrated and exsiccated. The obtained residue was dried under reduced pressure to obtain 2-(2-(3-((R)-3-dimethylaminopiperidin-1-yl)-3-oxopropyl)-1H-imidazol-1-yl) acetic acid hydrochloride (0.0400 g, 0.116 mmol, 70%) (hereinafter referred to as a "compound of Example 31") as a white solid.

$^1$H-NMR (400 MHz, D$_2$O) δ: 1.02-1.87 (3H, m), 2.00-2.15 (1H, m), 2.55-2.95 (7H, m), 3.05-3.30 (5H, m), 3.47-3.62 (1H, m), 3.95-4.20 (1H, m), 4.99 (2H, s), 7.26 (2H, s).

ESI-MS: as 2-(2-(3-((R)-3-dimethylaminopiperidin-1-yl)-3-oxopropyl)-1H-imidazol-1-yl)acetic acid: 309 (M+H)$^+$.

Example 32

Synthesis of ethyl (S)-2-(2-(3-(3-(dimethylamino)pyrrolidin-1-yl)-3-oxopropyl)-1H-imidazol-1-yl)acetate

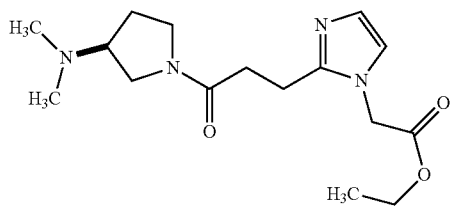 [SMILES: CCOC(=O)Cn1ccnc1CCC(=O)N1CC[C@H](N(C)C)C1]

Diisopropylethylamine (0.174 mL, 0.995 mmol), HBTU (0.302 g, 0.796 mmol), and (S)-3-(dimethylamino)pyrrolidine (0.0840 mL, 0.663 mmol) were added to a solution of crude 3-(1-(2-ethoxy-2-oxoethyl)-1H-imidazol-2-yl)propanoic acid (0.150 g, 0.663 mmol) in dichloromethane (3.0 mL) at room temperature, and the reaction liquid was stirred at the same temperature for 3 hours. The reaction liquid was concentrated under reduced pressure. The residue was purified by flash chromatography (NH silica gel, chloroform/methanol) to obtain ethyl (S)-2-(2-(3-(3-(dimethylamino)pyrrolidin-1-yl)-3-oxopropyl)-1H-imidazol-1-yl)acetate (0.200 g, 0.620 mmol, 93%) (hereinafter referred to as a "compound of Example 32") as a yellow oil.

$^1$H-NMR (400 MHz, CDCl$_3$) δ: 1.30 (3H, t, J=7.3 Hz), 1.71-1.84 (1H, m), 2.09-2.28 (7H, m), 2.61-2.96 (5H, m), 3.02-3.46 (2H, m), 3.64-3.82 (2H, m), 4.23 (2H, q, J=7.3 Hz), 4.72-4.77 (2H, m), 6.81-6.82 (1H, m), 6.95-6.98 (1H, m).

ESI-MS: m/z=323 (M+H)$^+$.

Example 33

Synthesis of (S)-2-(2-(3-(3-(dimethylamino)pyrrolidin-1-yl)-3-oxopropyl)-1H-imidazol-1-yl)acetic acid hydrochloride

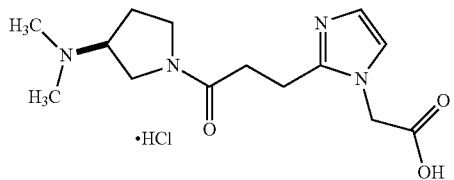 [SMILES: CN(C)[C@H]1CCN(C(=O)CCc2nccn2CC(=O)O)C1 ; Cl]

An aqueous solution of sodium hydroxide (1.0 N, 0.744 mL, 0.744 mmol) was added to ethyl (S)-2-(2-(3-(3-(dimethylamino)pyrrolidin-1-yl)-3-oxopropyl)-1H-imidazol-1-yl)acetate (0.160 g, 0.496 mmol) at room temperature, and the reaction liquid was stirred at room temperature for 4 hours. Hydrochloric acid (1.0 N, 0.744 mL, 0.744 mmol) was added to the reaction liquid at room temperature, and the reaction liquid was stirred at the same temperature for 5 minutes. The reaction liquid was concentrated under reduced pressure. The obtained residue was washed with ethanol (5.0 mL). The resulting mixture was filtered, and then the filtrate was concentrated under reduced pressure. The obtained residue was washed with ethanol (5.0 mL) again. The resulting mixture was filtered, and then the filtrate was concentrated under reduced pressure. Hydrochloric acid (1.0 N, 0.595 mL, 0.595 mmol) was added to the obtained residue at room temperature, and the reaction liquid was stirred at the same temperature for 1 hour. The reaction liquid was concentrated under reduced pressure and dried at room temperature to obtain (S)-2-(2-(3-(3-(dimethylamino) pyrrolidin-1-yl)-3-oxopropyl)-1H-imidazol-1-yl)acetic acid hydrochloride (0.120 g, 0.363 mmol, 73%) (hereinafter referred to as a "compound of Example 33") as a red solid.

$^1$H-NMR (400 MHz, D$_2$O) δ: 1.95-2.18 (1H, m), 2.34-2.44 (1H, m), 2.67-2.90 (8H, m), 3.05-3.11 (2H, m), 3.29-3.67 (3H, m), 3.78-3.93 (2H, m), 4.80 (2H, s), 7.22-7.26 (2H, m).

Example 34

Synthesis of tert-butyl 2-(2-(3-(4-(dimethylamino) piperidin-1-yl)-3-oxopropyl)-1H-imidazol-1-yl)] acetate hydrochloride

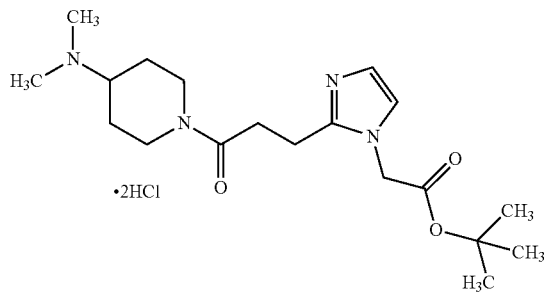 [SMILES: CN(C)C1CCN(C(=O)CCc2nccn2CC(=O)OC(C)(C)C)CC1]

A solution of hydrogen chloride in diethyl ether (2.0 N, 0.302 mL, 0.604 mmol) was added to a solution of tert-butyl 2-(2-(3-(4-(dimethylamino)piperidin-1-yl)-3-oxopropyl)-1H-imidazol-1-yl)acetate (0.100 g, 0.274 mmol) in diethyl ether (5.4 mL) at 0° C., and the reaction liquid was stirred at the same temperature for 30 minutes. The precipitated white solid was filtered and collected, and washed with diethyl ether (20.0 mL), and dried at room temperature for 36 hours to obtain tert-butyl 2-(2-(3-(4-(dimethylamino) piperidin-1-yl)-3-oxopropyl)-1H-imidazol-1-yl)acetate hydrochloride (0.111 g, 0.254 mmol, 93%) (hereinafter referred to as a "compound of Example 34") as a white solid.

$^1$H-NMR (400 MHz, D$_2$O) δ: 1.48-1.72 (11H, m), 2.10-2.17 (2H, m), 2.66-2.74 (1H, m), 2.84 (6H, s), 2.90-3.25 (5H, m), 3.45-3.55 (1H, m), 4.00-4.10 (1H, m), 4.45-4.55 (1H, m), 5.08 (2H, s), 7.37-7.39 (2H, m).

ESI-MS: as tert-butyl 2-(2-(3-(4-(dimethylamino)piperidin-1-yl)-3-oxopropyl)-1H-imidazol-1-yl)acetate: m/z=365 (M+H)$^+$ Example 35

Synthesis of methyl 2-(2-(3-(4-(dimethylamino) piperidin-1-yl)-3-oxopropyl)-1H-imidazol-1-yl)acetate

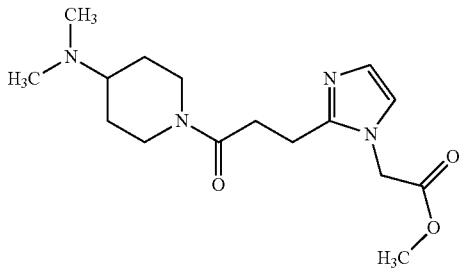 [SMILES: COC(=O)Cn1ccnc1CCC(=O)N1CCC(N(C)C)CC1]

A solution of hydrogen chloride in 1,4-dioxane (4.0 N, 0.718 mL, 2.87 mmol) was added to a solution of tert-butyl 2-(2-(3-(4-(dimethylamino)piperidin-1-yl)-3-oxopropyl)-1H-imidazol-1-yl)acetate (105 mg, 0.287 mmol) in 1,4-dioxane (3.0 mL)-methanol (3.0 mL) at room temperature, and the resulting mixture was stirred at the same temperature for 12 hours. The temperature of the reaction liquid was raised to 60° C., and the reaction liquid was stirred for 1 hour. A saturated aqueous solution of potassium carbonate was added to the reaction liquid, and the resulting mixture was extracted with chloroform. The organic layer was dried over anhydrous sodium sulfate, and then filtered, and the filtrate was concentrated under reduced pressure. The residue was purified by flash chromatography (NH silica gel, chloroform/methanol) to obtain methyl 2-(2-(3-(4-(dimethylamino)piperidin-1-yl)-3-oxopropyl)-1H-imidazol-1-yl)acetate (0.0370 g, 0.113 mmol, 39%) (hereinafter referred to as a "compound of Example 35") as a white solid.

$^1$H-NMR (400 MHz, CDCl$_3$) δ: 1.29-1.42 (2H, m), 1.81-1.86 (2H, m), 2.27 (6H, s), 2.33 (1H, tt, J=11.1, 3.5 Hz), 2.55-2.62 (1H, m), 2.92 (4H, s), 2.96-3.03 (1H, m), 3.78 (3H, s), 3.97-4.01 (1H, m), 4.56-4.59 (1H, m), 4.78 (2H, s), 6.82 (1H, d, J=0.7 Hz), 6.97 (1H, d, J=0.7 Hz).

ESI-MS: m/z=323 (M+H)$^+$.

Example 36

Synthesis of methyl 2-(2-(3-(4-(dimethylamino) piperidin-1-yl)-3-oxopropyl)-1H-imidazol-1-yl)acetate hydrochloride

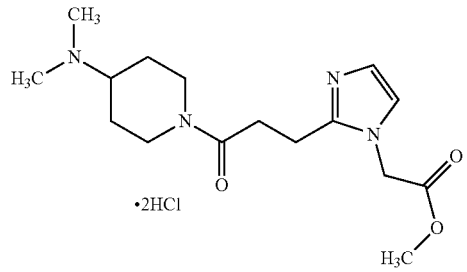 [SMILES: COC(=O)Cn1ccnc1CCC(=O)N1CCC(N(C)C)CC1]

A solution of hydrogen chloride in diethyl ether (2.0 N, 0.140 mL, 0.279 mmol) was added to a solution of methyl 2-(2-(3-(4-(dimethylamino)piperidin-1-yl)-3-oxopropyl)-1H-imidazol-1-yl)acetate (36.0 mg, 0.112 mmol) in diethyl ether (2.2 mL) at 0° C., and the reaction liquid was stirred at the same temperature for 1 hour. The temperature of the reaction liquid was raised to room temperature, and the reaction liquid was stirred for 1 hour. The precipitated white solid was filtered and collected, and washed with diethyl ether, and dried at room temperature to obtain methyl 2-(2-(3-(4-(dimethylamino)piperidin-1-yl)-3-oxopropyl)-1H-imidazol-1-yl)acetate hydrochloride (34.7 mg, 0.0880 mmol, 78%) (hereinafter referred to as a "compound of Example 36") as a white solid.

$^1$H-NMR (400 MHz, D$_2$O) δ: 1.54-1.77 (2H, m), 2.13-2.20 (2H, m), 2.69-2.76 (1H, m), 2.87 (6H, s), 3.04 (2H, t, J=6.6 Hz), 3.16-3.25 (3H, m), 3.52 (1H, tt, J=12.1, 3.7 Hz), 3.85 (3H, s), 4.08-4.11 (1H, m), 4.52-4.55 (1H, m), 5.22 (2H, s), 7.41-7.42 (2H, m).

ESI-MS: as methyl 2-(2-(3-(4-(dimethylamino)piperidin-1-yl)-3-oxopropyl)-1H-imidazol-1-yl)acetate: m/z=323 (M+H)$^+$.

Example 37

Synthesis of ethyl 2-(2-(3-(4-(dimethylamino)piperidin-1-yl)-3-oxopropyl)-1H-imidazol-1-yl)acetate

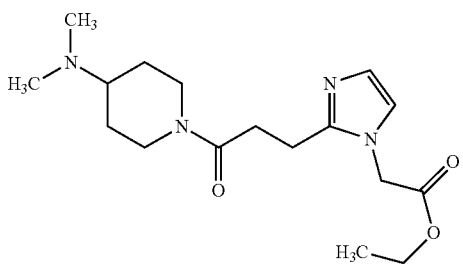 [SMILES: CCOC(=O)Cn1ccnc1CCC(=O)N1CCC(N(C)C)CC1]

Diisopropylethylamine (1.39 mL, 7.96 mmol), HBTU (2.41 g, 6.37 mmol), and 4-dimethylaminopiperidine (0.624 mL, 5.30 mmol) were added to a solution of crude 3-(1-(2-ethoxy-2-oxoethyl)-1H-imidazol-2-yl)propanoic acid (1.20 g, 5.30 mmol) in chloroform (24.0 mL) at room temperature, and the reaction liquid was stirred at the same temperature for 16 hours. The reaction liquid was concentrated under reduced pressure. The residue was purified by flash chromatography (NH silica gel, chloroform/methanol) to obtain ethyl 2-(2-(3-(4-(dimethylamino)piperidin-1-yl)-3-oxopropyl)-1H-imidazol-1-yl)acetate (0.630 g, 1.87 mmol, 35%) (hereinafter referred to as a "compound of Example 37") as a colorless oil.

$^1$H-NMR (400 MHz, CDCl$_3$) δ: 1.22-1.42 (5H, m), 1.77-1.87 (2H, m), 2.24-2.36 (7H, m), 2.54-2.64 (1H, m), 2.89-3.04 (5H, m), 3.95-4.04 (1H, m), 4.22 (2H, q, J=7.2 Hz), 4.53-4.62 (1H, m), 4.74 (2H, s), 6.80-6.82 (1H, m), 6.96-6.97 (1H, m).

ESI-MS: m/z=337 (M+H)$^+$.

Example 38

Synthesis of ethyl 2-(2-(3-(4-(dimethylamino)piperidin-1-yl)-3-oxopropyl)-1H-imidazol-1-yl)acetate hydrochloride

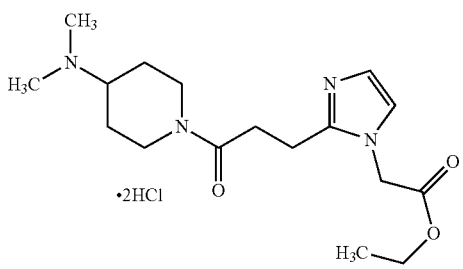 [SMILES: CCOC(=O)Cn1ccnc1CCC(=O)N1CCC(N(C)C)CC1]

A solution of hydrogen chloride in diethyl ether (2.0 N, 0.595 mL, 1.19 mmol) was added to a solution of ethyl 2-(2-(3-(4-(dimethylamino)piperidin-1-yl)-3-oxopropyl)-1H-imidazol-1-yl)acetate (0.182 g, 0.541 mmol) in diethyl ether (10.8 mL) at 0° C., and the reaction liquid was stirred at the same temperature for 30 minutes. The precipitated white solid was filtered and collected, and washed with diethyl ether (40.0 mL), and dried at room temperature for 36 hours to obtain ethyl 2-(2-(3-(4-(dimethylamino)piperidin-1-yl)-3-oxopropyl)-1H-imidazol-1-yl)acetate hydrochloride (0.182 g, 0.445 mmol, 82%) (hereinafter referred to as a "compound of Example 38") as a white solid.

$^1$H-NMR (400 MHz, D$_2$O) δ: 1.27 (3H, t, J=7.2 Hz), 1.50-1.73 (2H, m), 2.09-2.17 (2H, m), 2.66-2.73 (1H, m), 2.84 (6H, s), 2.98-3.05 (5H, m), 3.45-3.55 (1H, m), 4.02-4.09 (1H, m), 4.28 (2H, q, J=7.2 Hz), 4.47-4.53 (1H, m), 5.17 (2H, s), 7.37-7.39 (2H, m).

ESI-MS: as ethyl 2-(2-(3-(4-(dimethylamino)piperidin-1-yl)-3-oxopropyl)-1H-imidazol-1-yl)acetate: m/z=337 (M+H)$^+$.

Example 39

Synthesis of 2-(2-(3-(4-(dimethylamino)piperidin-1-yl)-3-oxopropyl)-1H-imidazol-1-yl)acetic acid

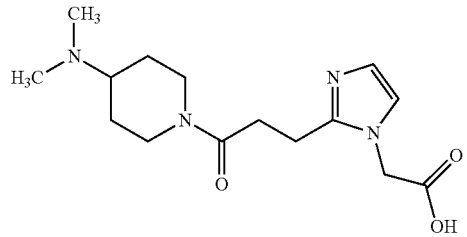 [SMILES: CN(C)C1CCN(C(=O)CCc2nccn2CC(=O)O)CC1]

An aqueous solution of sodium hydroxide (1.0 N, 3.03 mL, 3.03 mmol) was added to a solution of ethyl 2-(2-(3-(4-(dimethylamino)piperidin-1-yl)-3-oxopropyl)-1H-imidazol-1-yl)acetate (0.510 g, 1.52 mmol) in ethanol (3.0 mL) at room temperature, and the reaction liquid was stirred at the same temperature for 3 hours. The reaction liquid was cooled to 0° C., and then hydrochloric acid (1.0 N) was added to the reaction liquid for neutralization, and then the reaction liquid was concentrated under reduced pressure. The residue was subjected to azeotropic distillation with toluene, and ethanol was added. The precipitate was filtered through Celite, and the filtrate was concentrated under reduced pressure to obtain 2-(2-(3-(4-(dimethylamino)piperidin-1-yl)-3-oxopropyl)-1H-imidazol-1-yl)acetic acid (0.430 g, 1.39 mmol, 92%) (hereinafter referred to as a "compound of Example 39") as a white solid.

$^1$H-NMR (400 MHz, CD$_3$OD) δ: 1.40-1.67 (2H, m), 1.95-2.04 (2H, m), 2.50-2.60 (1H, m), 2.73-2.88 (8H, m), 2.95-3.12 (3H, m), 3.20-3.35 (1H, m), 3.93-4.03 (1H, m), 4.54-4.64 (3H, m), 7.12-7.15 (1H, m), 7.18-7.21 (1H, m).

ESI-MS: m/z=307 (M−H)$^-$.

Example 40

Synthesis of propyl 2-(2-(3-(4-(dimethylamino)piperidin-1-yl)-3-oxopropyl)-1H-imidazol-1-yl)acetate

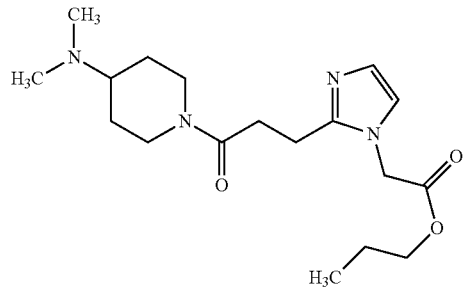 [SMILES: CCCOC(=O)Cn1ccnc1CCC(=O)N1CCC(N(C)C)CC1]

Diisopropylethylamine (0.0710 mL, 0.405 mmol), HBTU (0.0920 g, 0.243 mmol), and propan-1-ol (0.0300 mL, 0.405 mmol) were added to a solution of 2-(2-(3-(4-(dimethylamino)piperidin-1-yl)-3-oxopropyl)-1H-imidazol-1-yl)acetic acid (0.0500 g, 0.162 mmol) in chloroform (3.0 mL) at room temperature, and the reaction liquid was stirred at the same temperature for 16 hours. The reaction liquid was concentrated under reduced pressure. The residue was purified by flash chromatography (NH silica gel, chloroform/methanol) to obtain propyl 2-(2-(3-(4-(dimethylamino)piperidin-1-yl)-3-oxopropyl)-1H-imidazol-1-yl)acetate (0.0499 g, 0.142 mmol, 88%) (hereinafter referred to as a "compound of Example 40") as a colorless oil.

$^{1}$H-NMR (400 MHz, CDCl$_3$) δ: 0.92 (3H, t, J=7.6 Hz), 1.22-1.44 (2H, m), 1.60-1.70 (2H, m), 1.76-1.86 (2H, m), 2.23-2.34 (7H, m), 2.52-2.62 (1H, m), 2.88-3.02 (5H, m), 3.92-4.02 (1H, m), 4.11 (2H, t, J=7.2 Hz), 4.51-4.61 (1H, m), 6.72-6.76 (2H, m), 6.80-6.81 (1H, m), 6.94-6.95 (1H, m).

ESI-MS: m/z=351 (M+H)$^{+}$.

Example 41

Synthesis of propyl 2-(2-(3-(4-(dimethylamino)piperidin-1-yl)-3-oxopropyl)-1H-imidazol-1-yl)acetate hydrochloride

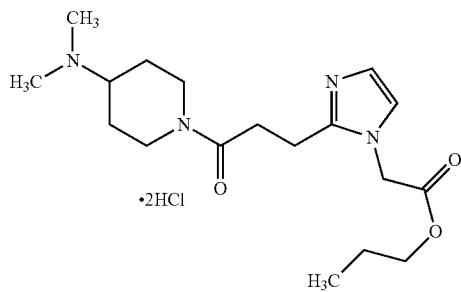 [SMILES: CCCOC(=O)Cn1ccnc1CCC(=O)N1CCC(N(C)C)CC1]

A solution of hydrogen chloride in diethyl ether (2.0 N, 0.157 mL, 0.314 mmol) was added to a solution of propyl 2-(2-(3-(4-(dimethylamino)piperidin-1-yl)-3-oxopropyl)-1H-imidazol-1-yl)acetate (0.0499 g, 0.142 mmol) in diethyl ether (1.0 mL) at 0° C., and the reaction liquid was stirred at the same temperature for 30 minutes. The precipitated white solid was filtered and collected, and washed with diethyl ether (4.0 mL), and dried at room temperature for 36 hours to obtain propyl 2-(2-(3-(4-(dimethylamino)piperidin-1-yl)-3-oxopropyl)-1H-imidazol-1-yl)acetate hydrochloride (0.0552 g, 0.130 mmol, 91%) (hereinafter referred to as a "compound of Example 41") as a white solid.

$^{1}$H-NMR (400 MHz, D$_2$O) δ: 0.91 (3H, t, J=7.2 Hz), 1.52-1.75 (4H, m), 2.08-2.24 (2H, m), 2.68-2.76 (1H, m), 2.86 (6H, s), 2.99-3.06 (2H, m), 3.13-3.26 (3H, m), 3.45-3.60 (1H, m), 4.02-4.12 (1H, m), 4.18-4.24 (2H, m), 4.48-4.58 (1H, m), 5.21 (2H, s), 7.39-7.43 (2H, m).

ESI-MS: as propyl 2-(2-(3-(4-(dimethylamino)piperidin-1-yl)-3-oxopropyl)-1H-imidazol-1-yl)acetate: m/z=351 (M+H)$^{+}$.

Example 42

Synthesis of isopropyl 2-(2-(3-(4-(dimethylamino)piperidin-1-yl)-3-oxopropyl)-1H-imidazol-1-yl)acetate

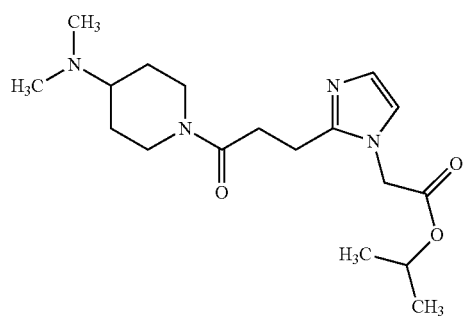 [SMILES: CC(C)OC(=O)Cn1ccnc1CCC(=O)N1CCC(N(C)C)CC1]

Diisopropylethylamine (0.142 mL, 0.811 mmol), HBTU (0.184 g, 0.486 mmol), and propan-2-ol (0.0620 mL, 0.811 mmol) were added to a solution of 2-(2-(3-(4-(dimethylamino)piperidin-1-yl)-3-oxopropyl)-1H-imidazol-1-yl)acetic acid (0.100 g, 0.324 mmol) in chloroform (6.0 mL) at room temperature, and the reaction liquid was stirred at the same temperature for 16 hours. The reaction liquid was concentrated under reduced pressure. The residue was purified by flash chromatography (NH silica gel, chloroform/methanol) to obtain isopropyl 2-(2-(3-(4-(dimethylamino)piperidin-1-yl)-3-oxopropyl)-1H-imidazol-1-yl)acetate (0.0610 g, 0.174 mmol, 54%) (hereinafter referred to as a "compound of Example 42") as a colorless oil.

$^{1}$H-NMR (400 MHz, CDCl$_3$) δ: 1.22-1.38 (8H, m), 1.76-1.88 (2H, m), 2.24-2.38 (7H, m), 2.52-2.62 (1H, m), 2.88-3.02 (5H, m), 3.94-4.04 (1H, m), 4.52-4.62 (1H, m), 4.69 (2H, s), 5.00-5.10 (1H, m), 6.78-6.82 (1H, m), 6.92-6.96 (1H, m).

ESI-MS: m/z=351 (M+H)$^{+}$.

Example 43

Synthesis of isopropyl 2-(2-(3-(4-(dimethylamino)piperidin-1-yl)-3-oxopropyl)-1H-imidazol-1-yl)acetate hydrochloride

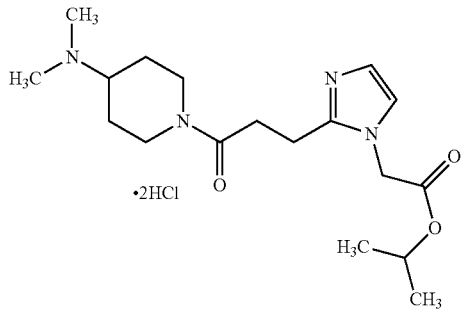 [SMILES: CC(C)OC(=O)Cn1ccnc1CCC(=O)N1CCC(N(C)C)CC1]

A solution of hydrogen chloride in diethyl ether (2.0 N, 0.188 mL, 0.376 mmol) was added to a solution of isopropyl 2-(2-(3-(4-(dimethylamino)piperidin-1-yl)-3-oxopropyl)-1H-imidazol-1-yl)acetate (0.0600 g, 0.171 mmol) in diethyl ether (1.0 mL) at 0° C., and the reaction liquid was stirred at the same temperature for 30 minutes. The precipitated white solid was filtered and collected, and washed with diethyl ether (4.0 mL), and dried at room temperature for 36 hours to obtain isopropyl 2-(2-(3-(4-(dimethylamino)piperidin-1-yl)-3-oxopropyl)-1H-imidazol-1-yl)acetate hydrochloride (0.0359 g, 0.0928 mmol, 54%) (hereinafter referred to as a "compound of Example 43") as a white solid.

$^1$H-NMR (400 MHz, D$_2$O) δ: 1.30 (6H, d, J=6.4 Hz), 1.52-1.76 (2H, m), 2.10-2.22 (2H, m), 2.68-2.78 (1H, m), 2.87 (6H, s), 2.98-3.05 (2H, m), 3.14-3.24 (3H, m), 3.46-3.56 (1H, m), 4.04-4.14 (1H, m), 4.50-4.57 (1H, m), 5.08-5.18 (3H, m), 7.36-7.42 (2H, m).

ESI-MS: as isopropyl 2-(2-(3-(4-(dimethylamino)piperidin-1-yl)-3-oxopropyl)-1H-imidazol-1-yl)acetate: m/z=351 (M+H)$^+$.

Example 44

Synthesis of cyclopropyl 2-(2-(3-(4-(dimethylamino)piperidin-1-yl)-3-oxopropyl)-1H-imidazol-1-yl)acetate

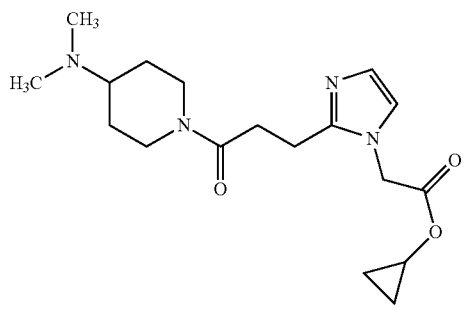 [SMILES: CN(C)C1CCN(C(=O)CCc2nccn2CC(=O)OC2CC2)CC1]

Diisopropylethylamine (0.142 mL, 0.811 mmol), HBTU (0.184 g, 0.486 mmol), and crude cyclopropanol (0.0470 g, 0.811 mmol) were added to a solution of 2-(2-(3-(4-(dimethylamino)piperidin-1-yl)-3-oxopropyl)-1H-imidazol-1-yl)acetic acid (0.100 g, 0.324 mmol) in chloroform (6.0 mL) at room temperature, and the reaction liquid was stirred at the same temperature for 16 hours. Hydrochloric acid (1.0 N) was added to the reaction liquid, and then the reaction liquid was back-extracted. A saturated aqueous solution of sodium hydrogencarbonate was added to the obtained aqueous layer for neutralization, and then the resulting mixture was extracted with chloroform. The organic layer was washed with a 10% aqueous solution of sodium chloride, and then dried over anhydrous sodium sulfate and filtered, and the filtrate was concentrated under reduced pressure to obtain cyclopropyl 2-(2-(3-(4-(dimethylamino)piperidin-1-yl)-3-oxopropyl)-1H-imidazol-1-yl)acetate (0.0610 g, 0.175 mmol, 54%) (hereinafter referred to as a "compound of Example 44") as a colorless oil.

$^1$H-NMR (400 MHz, CDCl$_3$) δ: 0.70-0.78 (4H, m), 1.25-1.45 (2H, m), 1.78-1.87 (2H, m), 2.25-2.38 (7H, m), 2.52-2.62 (1H, m), 2.88-3.05 (5H, m), 3.94-4.04 (1H, m), 4.18-4.26 (1H, m), 4.54-4.62 (1H, m), 4.73 (2H, s), 6.80 (1H, brs), 6.96 (1H, brs).

ESI-MS: m/z=349 (M+H)$^+$.

Example 45

Synthesis of cyclopropyl 2-(2-(3-(4-(dimethylamino)piperidin-1-yl)-3-oxopropyl)-1H-imidazol-1-yl)acetate hydrochloride

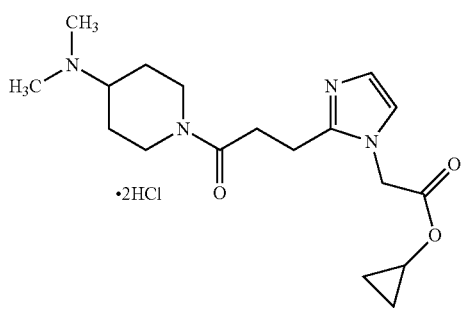 [SMILES: CN(C)C1CCN(C(=O)CCc2nccn2CC(=O)OC2CC2)CC1]

A solution of hydrogen chloride in diethyl ether (2.0 N, 0.189 mL, 0.378 mmol) was added to a solution of cyclopropyl 2-(2-(3-(4-(dimethylamino)piperidin-1-yl)-3-oxopropyl)-1H-imidazol-1-yl)acetate (0.0610 g, 0.175 mmol) in diethyl ether (1.0 mL) at 0° C., and the reaction liquid was stirred at the same temperature for 30 minutes. The precipitated white solid was filtered and collected, and washed with diethyl ether (4.0 mL), and dried at room temperature for 36 hours to obtain cyclopropyl 2-(2-(3-(4-(dimethylamino)piperidin-1-yl)-3-oxopropyl)-1H-imidazol-1-yl)acetate hydrochloride (0.0540 g, 0.128 mmol, 73%) (hereinafter referred to as a "compound of Example 45") as a white solid.

$^1$H-NMR (400 MHz, D$_2$O) δ: 0.78-0.85 (4H, m), 1.53-1.80 (2H, m), 2.10-2.24 (2H, m), 2.68-2.90 (7H, m), 2.99-3.06 (2H, m), 3.13-3.27 (3H, m), 3.45-3.60 (1H, m), 4.04-4.14 (1H, m), 4.22-4.28 (1H, m), 4.50-4.58 (1H, m), 5.19 (2H, s), 7.38-7.45 (2H, m).

ESI-MS: as cyclopropyl 2-(2-(3-(4-(dimethylamino)piperidin-1-yl)-3-oxopropyl)-1H-imidazol-1-yl)acetate: m/z=349 (M+H)$^+$.

Example 46

Synthesis of butyl 2-(2-(3-(4-(dimethylamino)piperidin-1-yl)-3-oxopropyl)-1H-imidazol-1-yl)acetate

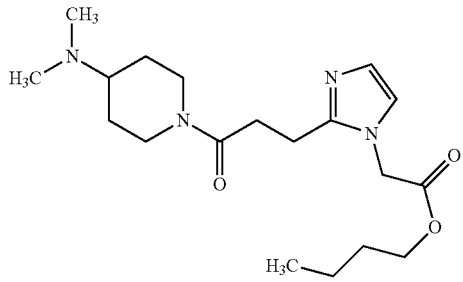 [SMILES: CCCCOC(=O)Cn1ccnc1CCC(=O)N1CCC(N(C)C)CC1]

Diisopropylethylamine (0.0710 mL, 0.405 mmol), HBTU (0.0920 g, 0.243 mmol), and butan-1-ol (0.0370 mL, 0.405 mmol) were added to a solution of 2-(2-(3-(4-(dimethylamino)piperidin-1-yl)-3-oxopropyl)-1H-imidazol-1-yl)acetic acid (0.0500 g, 0.162 mmol) in chloroform (3.0 mL) at room temperature, and the reaction liquid was stirred at the same temperature for 16 hours. The reaction liquid was concentrated under reduced pressure. The residue was purified by flash chromatography (NH silica gel, chloroform/methanol) to obtain butyl 2-(2-(3-(4-(dimethylamino)piperidin-1-yl)-3-oxopropyl)-1H-imidazol-1-yl)acetate (0.0314 g, 0.0861 mmol, 53%) (hereinafter referred to as a "compound of Example 46") as a colorless oil.

$^1$H-NMR (400 MHz, CDCl$_3$) δ: 0.92 (3H, t, J=7.2 Hz), 1.27-1.42 (4H, m), 1.57-1.65 (2H, m), 1.76-1.86 (2H, m), 2.22-2.34 (7H, m), 2.53-2.62 (1H, m), 2.88-3.03 (5H, m), 3.93-4.02 (1H, m), 4.15 (2H, t, J=6.4 Hz), 4.52-4.60 (1H, m), 4.74 (2H, s), 6.76-6.80 (1H, m), 6.95-6.96 (1H, m).

ESI-MS: m/z=365 (M+H)$^+$.

Example 47

Synthesis of butyl 2-(2-(3-(4-(dimethylamino)piperidin-1-yl)-3-oxopropyl)-1H-imidazol-1-yl)acetate hydrochloride

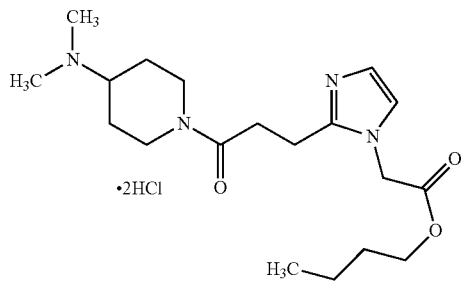 [SMILES: CCCCOC(=O)Cn1ccnc1CCC(=O)N1CCC(N(C)C)CC1]

A solution of hydrogen chloride in diethyl ether (2.0 N, 0.182 mL, 0.364 mmol) was added to a solution of butyl 2-(2-(3-(4-(dimethylamino)piperidin-1-yl)-3-oxopropyl)-1H-imidazol-1-yl)acetate (0.0600 g, 0.165 mmol) in diethyl ether (2.0 mL) at 0° C., and the reaction liquid was stirred at the same temperature for 30 minutes. The precipitated white solid was filtered and collected, and washed with diethyl ether (8.0 mL), and dried at room temperature for 36 hours to obtain butyl 2-(2-(3-(4-(dimethylamino)piperidin-1-yl)-3-oxopropyl)-1H-imidazol-1-yl)acetate hydrochloride (0.0554 g, 0.127 mmol, 77%) (hereinafter referred to as a "compound of Example 47") as a white solid.

$^1$H-NMR (400 MHz, D$_2$O) δ: 0.89 (3H, t, J=7.2 Hz), 1.28-1.40 (2H, m), 1.52-1.75 (4H, m), 2.10-2.20 (2H, m), 2.66-2.76 (1H, m), 2.86 (6H, s), 2.96-3.04 (2H, m), 3.11-3.22 (3H, m), 3.45-3.56 (1H, m), 4.34-4.43 (1H, m), 4.26 (2H, t, J=6.0 Hz), 4.49-4.58 (1H, m), 5.15 (2H, s), 7.26-7.38 (2H, m).

ESI-MS: as butyl 2-(2-(3-(4-(dimethylamino)piperidin-1-yl)-3-oxopropyl)-1H-imidazol-1-yl)acetate: m/z=365 (M+H)$^+$.

Example 48

Synthesis of isobutyl 2-(2-(3-(4-(dimethylamino)piperidin-1-yl)-3-oxopropyl)-1H-imidazol-1-yl)acetate

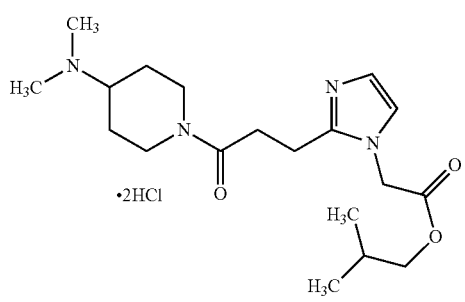 [SMILES: CC(C)COC(=O)Cn1ccnc1CCC(=O)N1CCC(N(C)C)CC1]

Diisopropylethylamine (0.142 mL, 0.811 mmol), HBTU (0.184 g, 0.486 mmol), and 2-methylpropan-1-ol (0.0760 mL, 0.811 mmol) were added to a solution of 2-(2-(3-(4-(dimethylamino)piperidin-1-yl)-3-oxopropyl)-1H-imidazol-1-yl)acetic acid (0.100 g, 0.324 mmol) in chloroform (6.0 mL) at room temperature, and the reaction liquid was stirred at the same temperature for 16 hours. The reaction liquid was concentrated under reduced pressure. The residue was purified by flash chromatography (NH silica gel, chloroform/methanol) to obtain isobutyl 2-(2-(3-(4-(dimethylamino)piperidin-1-yl)-3-oxopropyl)-1H-imidazol-1-yl)acetate (0.101 g, 0.277 mmol, 86%) (hereinafter referred to as a "compound of Example 48") as a colorless oil.

$^1$H-NMR (400 MHz, CDCl$_3$) δ: 0.85-0.89 (6H, m), 1.20-1.36 (2H, m), 1.74-1.95 (3H, m), 2.22-2.34 (7H, m), 2.48-2.58 (1H, m), 2.86-3.00 (5H, m), 3.88-3.98 (3H, m), 4.50-4.57 (1H, m), 4.73 (2H, s), 6.76-6.80 (1H, m), 6.90-6.94 (1H, m).

ESI-MS: m/z=365 (M+H)$^+$.

Example 49

Synthesis of isobutyl 2-(2-(3-(4-(dimethylamino)piperidin-1-yl)-3-oxopropyl)-1H-imidazol-1-yl)acetate hydrochloride

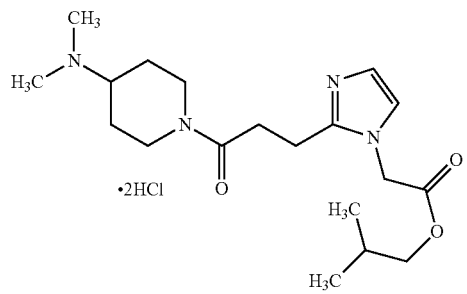 [SMILES: CC(C)COC(=O)Cn1ccnc1CCC(=O)N1CCC(N(C)C)CC1]

A solution of hydrogen chloride in diethyl ether (2.0 N, 0.302 mL, 0.604 mmol) was added to a solution of isobutyl 2-(2-(3-(4-(dimethylamino)piperidin-1-yl)-3-oxopropyl)-1H-imidazol-1-yl)acetate (0.100 g, 0.274 mmol) in diethyl ether (1.0 mL) at 0° C., and the reaction liquid was stirred at the same temperature for 30 minutes. The precipitated white solid was filtered and collected, and washed with diethyl ether (4.0 mL), and dried at room temperature for hours to obtain isobutyl 2-(2-(3-(4-(dimethylamino)piperidin-1-yl)-3-oxopropyl)-1H-imidazol-1-yl)acetate hydrochloride (0.0709 g, 0.177 mmol, 65%) (hereinafter referred to as a "compound of Example 49") as a white solid.

$^1$H-NMR (400 MHz, D$_2$O) δ: 0.88-0.94 (6H, m), 1.52-1.77 (2H, m), 1.92-2.02 (1H, m), 2.12-2.22 (2H, m), 2.68-2.78 (1H, m), 2.86 (6H, s), 2.98-3.05 (2H, m), 3.12-3.28 (3H, m), 3.46-3.56 (1H, m), 4.32-4.42 (3H, m), 4.48-4.58 (1H, m), 5.23 (2H, s), 7.40-7.44 (2H, m).

ESI-MS: as isobutyl 2-(2-(3-(4-(dimethylamino)piperidin-1-yl)-3-oxopropyl)-1H-imidazol-1-yl)acetate: m/z=365 (M+H)$^+$.

Example 50

Synthesis of cyclopropylmethyl 2-(2-(3-(4-(dimethylamino)piperidin-1-yl)-3-oxopropyl)-1H-imidazol-1-yl)acetate

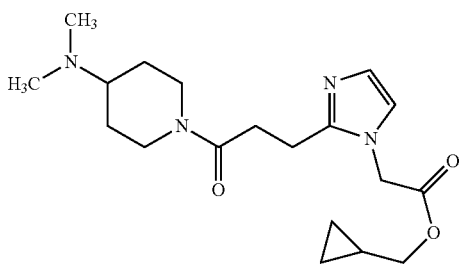 [SMILES: CN(C)C1CCN(C(=O)CCc2nccn2CC(=O)OCC2CC2)CC1]

Diisopropylethylamine (0.142 mL, 0.811 mmol), HBTU (0.184 g, 0.486 mmol), and cyclopropyl methanol (0.0580 g, 0.811 mmol) were added to a solution of 2-(2-(3-(4-(dimethylamino)piperidin-1-yl)-3-oxopropyl)-1H-imidazol-1-yl)acetic acid (0.100 g, 0.324 mmol) in chloroform (6.0 mL) at room temperature, and the reaction liquid was stirred at the same temperature for 16 hours. The reaction liquid was concentrated under reduced pressure. The residue was purified by flash chromatography (NH silica gel, chloroform/methanol) to obtain cyclopropylmethyl 2-(2-(3-(4-(dimethylamino)piperidin-1-yl)-3-oxopropyl)-1H-imidazol-1-yl)acetate (0.0720 g, 0.199 mmol, 61%) (hereinafter referred to as a "compound of Example 50") as a colorless oil.

$^1$H-NMR (400 MHz, CDCl$_3$) δ: 0.23-0.29 (2H, m), 0.53-0.60 (2H, m), 1.05-1.16 (1H, m), 1.20-1.40 (2H, m), 1.74-1.85 (2H, m), 2.20-2.34 (7H, m), 2.50-2.60 (1H, m), 2.87-3.02 (5H, m), 3.93-4.00 (3H, m), 4.52-4.60 (1H, m), 4.75 (2H, s), 6.78-6.82 (1H, m), 6.92-6.96 (1H, m).

ESI-MS: m/z=363 (M+H)$^+$.

Example 51

Synthesis of cyclopropylmethyl 2-(2-(3-(4-(dimethylamino)piperidin-1-yl)-3-oxopropyl)-1H-imidazol-1-yl)acetate hydrochloride

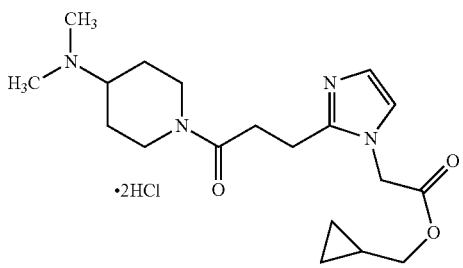 [SMILES: CN(C)C1CCN(C(=O)CCc2nccn2CC(=O)OCC2CC2)CC1]

A solution of hydrogen chloride in diethyl ether (2.0 N, 0.218 mL, 0.436 mmol) was added to a solution of cyclopropylmethyl 2-(2-(3-(4-(dimethylamino)piperidin-1-yl)-3-oxopropyl)-1H-imidazol-1-yl)acetate (0.0720 g, 0.199 mmol) in diethyl ether (1.0 mL) at 0° C., and the reaction liquid was stirred at the same temperature for 30 minutes. The precipitated white solid was filtered and collected, and washed with diethyl ether (4.0 mL), and dried at room temperature for 36 hours to obtain cyclopropylmethyl 2-(2-(3-(4-(dimethylamino)piperidin-1-yl)-3-oxopropyl)-1H-imidazol-1-yl)acetate hydrochloride (0.0652 g, 0.180 mmol, 90%) (hereinafter referred to as a "compound of Example 51") as a white solid.

$^1$H-NMR (400 MHz, D$_2$O) δ: 0.30-0.35 (2H, m), 0.58-0.65 (2H, m), 1.15-1.25 (1H, m), 1.52-1.75 (2H, m), 2.10-2.20 (2H, m), 2.67-2.76 (1H, m), 2.86 (6H, s), 2.99-3.06 (2H, m), 3.13-3.25 (3H, m), 3.44-3.56 (1H, m), 4.05-4.12 (3H, m), 4.49-4.57 (1H, m), 5.20 (2H, s), 7.39-7.41 (2H, m).

ESI-MS: as cyclopropylmethyl 2-(2-(3-(4-(dimethylamino)piperidin-1-yl)-3-oxopropyl)-1H-imidazol-1-yl)acetate: m/z=363 (M+H)$^+$.

Example 52

Synthesis of sec-butyl 2-(2-(3-(4-(dimethylamino)piperidin-1-yl)-3-oxopropyl)-1H-imidazol-1-yl)acetate

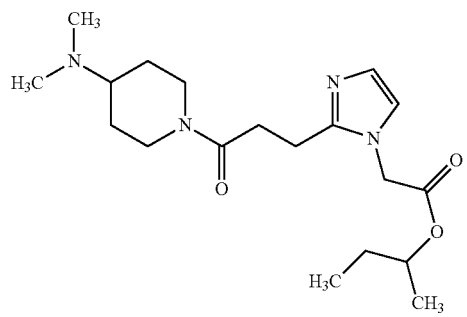 [SMILES: CCC(C)OC(=O)Cn1ccnc1CCC(=O)N1CCC(N(C)C)CC1]

Diisopropylethylamine (0.142 mL, 0.811 mmol), HBTU (0.184 g, 0.486 mmol), and butan-2-ol (0.0740 mL, 0.811 mmol) were added to a solution of 2-(2-(3-(4-(dimethylamino)piperidin-1-yl)-3-oxopropyl)-1H-imidazol-1-yl)acetic acid (0.100 g, 0.324 mmol) in chloroform (6.0 mL) at room temperature, and the reaction liquid was stirred at the same temperature for 60 hours. The reaction liquid was concentrated under reduced pressure. The residue was purified by flash chromatography (NH silica gel, chloroform/methanol) to obtain sec-butyl 2-(2-(3-(4-(dimethylamino)piperidin-1-yl)-3-oxopropyl)-1H-imidazol-1-yl)acetate (0.0700 g, 0.192 mmol, 59%) (hereinafter referred to as a "compound of Example 52") as a colorless oil.

$^1$H-NMR (400 MHz, CDCl$_3$) δ: 0.87 (3H, t, J=7.6 Hz), 1.20-1.40 (5H, m), 1.50-1.65 (2H, m), 1.78-1.86 (2H, m), 2.23-2.35 (7H, m), 2.54-2.62 (1H, m), 2.88-3.04 (5H, m), 3.95-4.02 (1H, m), 4.54-4.60 (1H, m), 4.72 (2H, s), 4.85-4.95 (1H, m), 6.81 (1H, brs), 6.96 (1H, brs).

ESI-MS: m/z=365 (M+H)$^+$.

Example 53

Synthesis of sec-butyl 2-(2-(3-(4-(dimethylamino) piperidin-1-yl)-3-oxopropyl)-1H-imidazol-1-yl)acetate hydrochloride

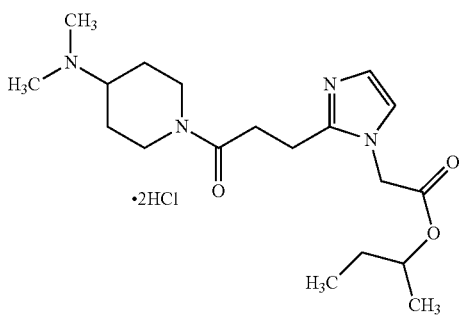 [SMILES: CCC(C)OC(=O)Cn1ccnc1CCC(=O)N1CCC(N(C)C)CC1]

A solution of hydrogen chloride in diethyl ether (2.0 N, 0.211 mL, 0.423 mmol) was added to a solution of sec-butyl 2-(2-(3-(4-(dimethylamino)piperidin-1-yl)-3-oxopropyl)-1H-imidazol-1-yl)acetate (0.0700 g, 0.192 mmol) in diethyl ether (1.0 mL) at 0° C., and the reaction liquid was stirred at the same temperature for 30 minutes. The precipitated white solid was filtered and collected, and washed with diethyl ether (4.0 mL), and dried at room temperature for 36 hours to obtain sec-butyl 2-(2-(3-(4-(dimethylamino)piperidin-1-yl)-3-oxopropyl)-1H-imidazol-1-yl)acetate hydrochloride (0.0582 g, 0.133 mmol, 69%) (hereinafter referred to as a "compound of Example 53") as a white solid.

$^1$H-NMR (400 MHz, D$_2$O) δ: 0.87 (3H, t, J=7.6 Hz), 1.27 (3H, d, J=6.0 Hz). 1.50-1.76 (4H, m), 2.66-2.75 (2H, m), 2.80-2.90 (7H, m), 2.98-3.05 (2H, m), 3.13-3.25 (3H, m), 3.45-3.57 (1H, m), 4.03-4.12 (1H, m), 4.48-4.58 (1H, m), 4.93-5.00 (1H, m), 5.19 (2H, s), 7.37-7.42 (2H, m).

ESI-MS: as sec-butyl 2-(2-(3-(4-(dimethylamino)piperidin-1-yl)-3-oxopropyl)-1H-imidazol-1-yl)acetate: m/z=365 (M+H)$^+$.

Example 54

Synthesis of octyl 2-(2-(3-(4-(dimethylamino)piperidin-1-yl)-3-oxopropyl)-1H-imidazol-1-yl)acetate

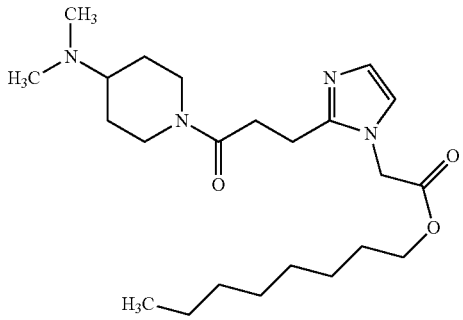 [SMILES: CCCCCCCCOC(=O)Cn1ccnc1CCC(=O)N1CCC(N(C)C)CC1]

Diisopropylethylamine (0.113 mL, 0.649 mmol), HBTU (0.184 g, 0.486 mmol), and octan-1-ol (0.103 mL, 0.649 mmol) were added to a solution of 2-(2-(3-(4-(dimethylamino)piperidin-1-yl)-3-oxopropyl)-1H-imidazol-1-yl)acetic acid (0.100 g, 0.324 mmol) in chloroform (3.0 mL) at room temperature, and the reaction liquid was stirred at the same temperature for 16 hours. The reaction liquid was concentrated under reduced pressure. The residue was purified by flash chromatography (NH silica gel, chloroform/methanol) to obtain octyl 2-(2-(3-(4-(dimethylamino)piperidin-1-yl)-3-oxopropyl)-1H-imidazol-1-yl)acetate (0.0602 g, 0.143 mmol, 44%) (hereinafter referred to as a "compound of Example 54") as a colorless oil.

$^1$H-NMR (400 MHz, CDCl$_3$) δ: 0.85-0.93 (3H, m), 1.23-1.43 (12H, m), 1.58-1.68 (2H, m), 1.77-1.87 (2H, m), 2.25-2.40 (7H, m), 2.54-2.64 (1H, m), 2.88-3.04 (5H, m), 3.94-4.04 (1H, m), 4.12-4.17 (2H, m), 4.53-4.65 (1H, m), 4.74 (2H, s), 6.80-6.83 (1H, m), 6.94-6.98 (1H, m).

ESI-MS: m/z=421 (M+H)$^+$.

Example 55

Synthesis of octyl 2-(2-(3-(4-(dimethylamino)piperidin-1-yl)-3-oxopropyl)-1H-imidazol-1-yl)acetate hydrochloride

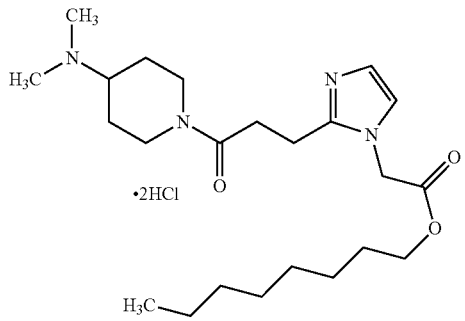 [SMILES: CCCCCCCCOC(=O)Cn1ccnc1CCC(=O)N1CCC(N(C)C)CC1]

A solution of hydrogen chloride in diethyl ether (2.0 N, 0.105 mL, 0.209 mmol) was added to a solution of octyl 2-(2-(3-(4-(dimethylamino)piperidin-1-yl)-3-oxopropyl)-1H-imidazol-1-yl)acetate (0.0400 g, 0.0950 mmol) in diethyl ether (2.0 mL) at 0° C., and the reaction liquid was stirred at the same temperature for 30 minutes. The precipitated white solid was filtered and collected, and washed with diethyl ether (8.0 mL), and dried at room temperature for 36 hours to obtain octyl 2-(2-(3-(4-(dimethylamino)piperidin-1-yl)-3-oxopropyl)-1H-imidazol-1-yl)acetate hydrochloride (0.0109 g, 0.0221 mmol, 23%) (hereinafter referred to as a "compound of Example 55") as a white solid.

$^1$H-NMR (400 MHz, D$_2$O) δ: 0.84-0.89 (3H, m), 1.14-1.37 (10H, m), 1.54-1.76 (4H, m), 2.10-2.22 (2H, m), 2.65-2.77 (1H, m), 2.87 (6H, s), 3.00-3.05 (2H, m), 3.13-3.28 (3H, m), 3.46-3.58 (1H, m), 4.03-4.11 (1H, m), 4.26 (2H, t, J=6.8 Hz), 4.49-4.57 (1H, m), 5.21 (2H, s), 7.40-7.44 (2H, m).

ESI-MS: as octyl 2-(2-(3-(4-(dimethylamino)piperidin-1-yl)-3-oxopropyl)-1H-imidazol-1-yl)acetate: m/z=421 (M+H)$^+$.

Example 56

Synthesis of 2,3-dihydro-1H-inden-5-yl 2-(2-(3-(4-(dimethylamino)piperidin-1-yl)-3-oxopropyl)-1H-imidazol-1-yl)acetate

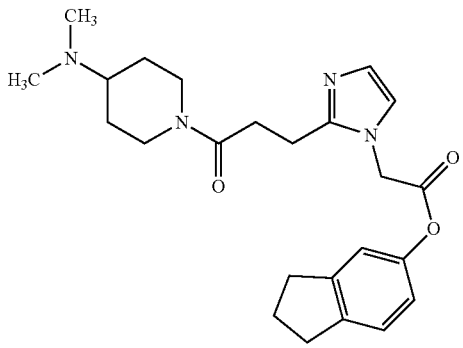 [SMILES: CN(C)C1CCN(C(=O)CCc2nccn2CC(=O)Oc2ccc3c(c2)CCC3)CC1]

Diisopropylethylamine (0.113 mL, 0.649 mmol), HBTU (0.184 g, 0.486 mmol), and 2,3-dihydro-1H-inden-5-ol (0.0870 g, 0.649 mmol) were added to a solution of 2-(2-(3-(4-(dimethylamino)piperidin-1-yl)-3-oxopropyl)-1H-imidazol-1-yl)acetic acid (0.100 g, 0.324 mmol) in chloroform (3.0 mL) at room temperature, and the reaction liquid was stirred at the same temperature for 16 hours. Hydrochloric acid (1.0 N) was added to the reaction liquid, and then the reaction liquid was back-extracted. A saturated aqueous solution of sodium hydrogencarbonate was added to the obtained aqueous layer for neutralization, and then the resulting mixture was extracted with chloroform. The organic layer was washed with a 10% aqueous solution of sodium chloride, and then dried over anhydrous sodium sulfate and filtered, and the filtrate was concentrated under reduced pressure to obtain 2,3-dihydro-1H-inden-5-yl 2-(2-(3-(4-(dimethylamino)piperidin-1-yl)-3-oxopropyl)-1H-imidazol-1-yl)acetate (0.0644 g, 0.152 mmol, 47%) (hereinafter referred to as a "compound of Example 56") as a colorless oil.

$^1$H-NMR (400 MHz, CDCl$_3$) δ: 1.19-1.42 (2H, m), 1.76-1.87 (2H, m), 2.02-2.14 (2H, m), 2.24-2.40 (7H, m), 2.50-2.64 (1H, m), 2.83-3.03 (9H, m), 3.93-4.03 (1H, m), 4.53-4.62 (1H, m), 4.98-5.03 (2H, m), 6.82-7.02 (4H, m), 7.18 (1H, d, J=8.0 Hz).

ESI-MS: m/z=425 (M+H)$^+$.

Example 57

Synthesis of 2,3-dihydro-1H-inden-5-yl 2-(2-(3-(4-(dimethylamino)piperidin-1-yl)-3-oxopropyl)-1H-imidazol-1-yl)acetate hydrochloride

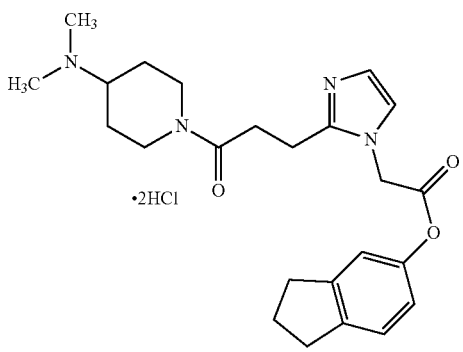 [SMILES: CN(C)C1CCN(C(=O)CCc2nccn2CC(=O)Oc2ccc3c(c2)CCC3)CC1]

A solution of hydrogen chloride in diethyl ether (2.0 N, 0.130 mL, 0.259 mmol) was added to a solution of 2,3-dihydro-1H-inden-5-yl 2-(2-(3-(4-(dimethylamino)piperidin-1-yl)-3-oxopropyl)-1H-imidazol-1-yl)acetate (0.0500 g, 0.118 mmol) in diethyl ether (2.0 mL) at 0° C., and the reaction liquid was stirred at the same temperature for 30 minutes. The precipitated white solid was filtered and collected, and washed with diethyl ether (8.0 mL), and dried at room temperature for 36 hours to obtain 2,3-dihydro-1H-inden-5-yl 2-(2-(3-(4-(dimethylamino)piperidin-1-yl)-3-oxopropyl)-1H-imidazol-1-yl)acetate hydrochloride (0.0475 g, 0.0955 mmol, 81%) (hereinafter referred to as a "compound of Example 57") as a white solid.

$^1$H-NMR (400 MHz, D$_2$O) δ: 1.30-1.62 (2H, m), 1.94-2.16 (4H, m), 2.58-2.78 (7H, m), 2.87-3.15 (7H, m), 3.25-3.50 (3H, m), 3.97-4.05 (1H, m), 4.43-4.50 (1H, m), 5.50 (2H, s), 6.97-7.02 (1H, m), 7.11-7.14 (1H, m), 7.33-7.37 (1H, m), 7.43-7.51 (2H, m).

ESI-MS: as 2,3-dihydro-1H-inden-5-yl 2-(2-(3-(4-(dimethylamino)piperidin-1-yl)-3-oxopropyl)-1H-imidazol-1-yl)acetate: m/z=425 (M+H)$^+$.

Example 58

Synthesis of (2-(2-(3-(4-(dimethylamino)piperidin-1-yl)-3-oxopropyl)-1H-imidazol-1-yl)acetoxy)methyl pivalate

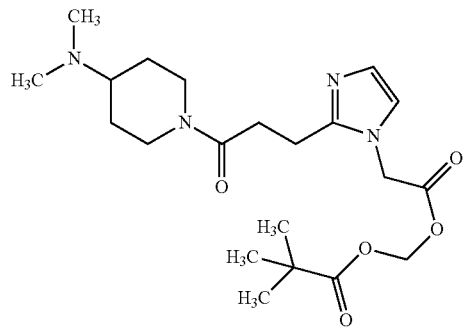 [SMILES: CN(C)C1CCN(C(=O)CCc2nccn2CC(=O)OCOC(=O)C(C)(C)C)CC1]

Potassium carbonate (0.0760 g, 0.553 mmol), chloromethyl pivalate (0.0400 mL, 0.276 mmol), and sodium iodide (0.0414 g, 0.276 mmol) were added to a solution of 2-(2-(3-(4-(dimethylamino)piperidin-1-yl)-3-oxopropyl)-1H-imidazol-1-yl)acetic acid (0.0980 g, 0.276 mmol) in DMF (2.0 mL) at room temperature, and the reaction liquid was stirred at the same temperature for 12 hours. Ethyl acetate was added to the reaction liquid, and the precipitate was filtered through Celite, and the filtrate was concentrated under reduced pressure. Ethyl acetate was added to the residue, and the precipitate was filtered through Celite, and the filtrate was concentrated under reduced pressure. Chloroform was added to the residue, and the precipitate was filtered through Celite, and the filtrate was concentrated under reduced pressure to obtain (2-(2-(3-(4-(dimethylamino)piperidin-1-yl)-3-oxopropyl)-1H-imidazol-1-yl)acetoxy)methyl pivalate (0.0300 g, 0.0710 mmol, 26%) (hereinafter referred to as a "compound of Example 58") as a colorless oil.

$^1$H-NMR (400 MHz, CDCl$_3$) δ: 1.19-1.45 (11H, m), 1.75-1.90 (2H, m), 2.22-2.40 (7H, m), 2.53-2.63 (1H, m), 2.88-3.02 (5H, m), 3.92-4.02 (1H, m), 4.52-4.62 (1H, m), 4.84 (2H, s), 5.81 (2H, s), 6.81 (1H, brs), 6.97 (1H, brs).

ESI-MS: m/z=423 (M+H)$^+$.

Example 59

Synthesis of (5-methyl-2-oxo-1,3-dioxol-4-yl)methyl 2-(2-(3-(4-(dimethylamino)piperidin-1-yl)-3-oxopropyl)-1H-imidazol-1-yl)acetate

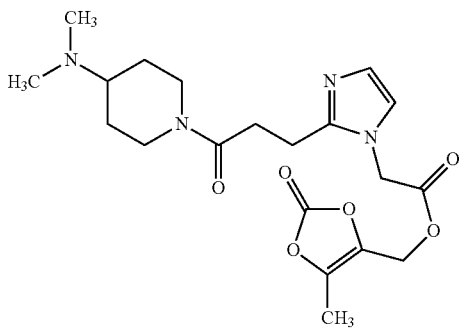 [SMILES: Cc1oc(=O)oc1COC(=O)Cn1ccnc1CCC(=O)N1CCC(N(C)C)CC1]

Diisopropylethylamine (0.113 mL, 0.649 mmol), HBTU (0.184 g, 0.486 mmol), and crude 4-(hydroxymethyl)-5-methyl-1,3-dioxol-2-one (0.0840 g, 0.649 mmol) were added to a solution of 2-(2-(3-(4-(dimethylamino)piperidin-1-yl)-3-oxopropyl)-1H-imidazol-1-yl)acetic acid (0.100 g, 0.324 mmol) in chloroform (3.0 mL) at room temperature, and the reaction liquid was stirred at the same temperature for 16 hours. Hydrochloric acid (1.0 N) was added to the reaction liquid, and then the reaction liquid was back-extracted. A saturated aqueous solution of sodium hydrogencarbonate was added to the obtained aqueous layer for neutralization, and then the resulting mixture was extracted with chloroform. The organic layer was washed with a 10% aqueous solution of sodium chloride, and then dried over anhydrous sodium sulfate and filtered, and the filtrate was concentrated under reduced pressure to obtain (5-methyl-2-oxo-1,3-dioxol-4-yl)methyl 2-(2-(3-(4-(dimethylamino)piperidin-1-yl)-3-oxopropyl)-1H-imidazol-1-yl)acetate (0.0501 g, 0.119 mmol, 37%) (hereinafter referred to as a "compound of Example 59") as a colorless oil.

$^1$H-NMR (400 MHz, CDCl$_3$) δ: 1.16-1.44 (2H, m), 1.77-1.90 (2H, m), 2.16 (3H, s), 2.20-2.42 (7H, m), 2.52-2.62 (1H, m), 2.86-3.04 (5H, m), 3.92-4.04 (1H, m), 4.50-4.62 (1H, m), 4.84 (2H, s), 4.92 (2H, s), 6.78-6.83 (1H, m), 6.95-6.98 (1H, m).

ESI-MS: m/z=421 (M+H)$^+$.

Example 60

Synthesis of 2-(dimethylamino)-2-oxoethyl 2-(2-(3-(4-(dimethylamino)piperidin-1-yl)-3-oxopropyl)-1H-imidazol-1-yl)acetate

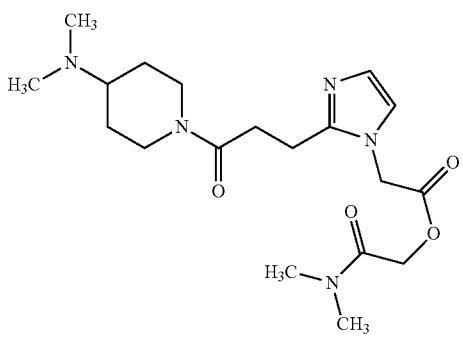 [SMILES: CN(C)C(=O)COC(=O)Cn1ccnc1CCC(=O)N1CCC(N(C)C)CC1]

Diisopropylethylamine (0.142 mL, 0.811 mmol), HBTU (0.184 g, 0.486 mmol), and crude 2-hydroxy-N,N-dimethylacetamide (0.0500 g, 0.486 mmol) were added to a solution of 2-(2-(3-(4-(dimethylamino)piperidin-1-yl)-3-oxopropyl)-1H-imidazol-1-yl)acetic acid (0.100 g, 0.324 mmol) in chloroform (6.0 mL) at room temperature, and the reaction liquid was stirred at the same temperature for 16 hours. Hydrochloric acid (1.0 N) was added to the reaction liquid, and then the reaction liquid was back-extracted. A saturated aqueous solution of sodium hydrogencarbonate was added to the obtained aqueous layer for neutralization, and then the resulting mixture was extracted with chloroform. The organic layer was washed with a 10% aqueous solution of sodium chloride, and then dried over anhydrous sodium sulfate and filtered, and the filtrate was concentrated under reduced pressure to obtain 2-(dimethylamino)-2-oxoethyl 2-(2-(3-(4-(dimethylamino)piperidin-1-yl)-3-oxopropyl)-1H-imidazol-1-yl)acetate (0.100 g, 0.254 mmol, 78%) (hereinafter referred to as a "compound of Example 60") as a colorless oil.

$^1$H-NMR (400 MHz, CDCl$_3$) δ: 1.24-1.44 (2H, m), 1.78-1.86 (2H, m), 2.25-2.40 (7H, m), 2.52-2.62 (1H, m), 2.78-3.05 (12H, m), 3.95-4.05 (1H, m), 4.79 (2H, m), 4.90-4.94 (2H, m), 6.86-6.88 (1H, m), 6.94-6.96 (1H, m).

ESI-MS: m/z=394 (M+H)$^+$.

Example 61

Synthesis of 2-(dimethylamino)-2-oxoethyl 2-(2-(3-(4-(dimethylamino)piperidin-1-yl)-3-oxopropyl)-1H-imidazol-1-yl)acetate hydrochloride

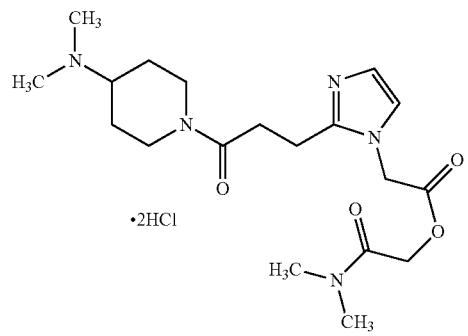 [SMILES: CN(C)C(=O)COC(=O)Cn1ccnc1CCC(=O)N1CCC(N(C)C)CC1]

A solution of hydrogen chloride in diethyl ether (2.0 N, 0.188 mL, 0.376 mmol) was added to a solution of 2-(dimethylamino)-2-oxoethyl 2-(2-(3-(4-(dimethylamino)piperidin-1-yl)-3-oxopropyl)-1H-imidazol-1-yl)acetate (0.100 g, 0.254 mmol) in diethyl ether (1.0 mL) at 0° C., and the reaction liquid was stirred at the same temperature for 30 minutes. The precipitated white solid was filtered and collected, and washed with diethyl ether (4.0 mL), and dried at room temperature for 36 hours to obtain 2-(dimethylamino)-2-oxoethyl 2-(2-(3-(4-(dimethylamino)piperidin-1-yl)-3-oxopropyl)-1H-imidazol-1-yl)acetate hydrochloride (0.0455 g, 0.0976 mmol, 38%) (hereinafter referred to as a "compound of Example 61") as a white solid.

$^1$H-NMR (400 MHz, D$_2$O) δ: 1.54-1.78 (2H, m), 2.10-2.23 (2H, m), 2.67-2.80 (1H, m), 2.85-3.05 (14H, m), 3.13-3.28 (3H, m), 3.47-3.57 (1H, m), 4.05-4.15 (1H, m), 4.50-4.60 (1H, m), 5.05 (2H, s), 5.36 (2H, m), 7.40-7.46 (2H, m).

ESI-MS: as 2-(dimethylamino)-2-oxoethyl 2-(2-(3-(4-(dimethylamino)piperidin-1-yl)-3-oxopropyl)-1H-imidazol-1-yl)acetate: m/z=394 (M+H)$^+$.

Example 62

Synthesis of 3-oxo-2,3-dihydroisobenzofuran-2-yl 2-(2-(3-(4-(dimethylamino)piperidin-1-yl)-3-oxopropyl)-1H-imidazol-1-yl)acetate

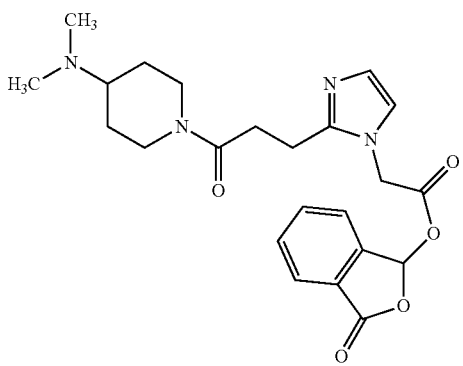 [SMILES: CN(C)C1CCN(C(=O)CCc2nccn2CC(=O)OC2OC(=O)c3ccccc32)CC1]

Potassium carbonate (0.0900 g, 0.649 mmol), 3-bromophthalide (0.0691 g, 0.324 mmol), and sodium iodide (0.0486 g, 0.324 mmol) were added to a solution of 2-(2-(3-(4-(dimethylamino)piperidin-1-yl)-3-oxopropyl)-1H-imidazol-1-yl)acetic acid (0.100 g, 0.324 mmol) in DMF (3.2 mL) at room temperature, and the reaction liquid was stirred at the same temperature for 14 hours. Ethyl acetate was added to the reaction liquid, and the precipitate was filtered through Celite, and the filtrate was concentrated under reduced pressure. Ethyl acetate was added to the residue, and the precipitated was filtered and collected to obtain 3-oxo-2,3-dihydroisobenzofuran-2-yl 2-(2-(3-(4-(dimethylamino)piperidin-1-yl)-3-oxopropyl)-1H-imidazol-1-yl)acetate (0.0320 g, 0.0726 mmol, 22%) (hereinafter referred to as a "compound of Example 62") as a brown solid.

$^1$H-NMR (400 MHz, DMSO-d$_6$) δ: 1.10-1.38 (2H, m), 1.65-1.80 (2H, m), 2.15 (6H, s), 2.22-2.36 (1H, m), 2.45-2.81 (5H, m), 2.90-3.03 (1H, m), 3.85-3.93 (1H, m), 4.15 (2H, s), 4.30-4.40 (1H, m), 6.62 (1H, s), 6.85 (1H, s), 7.36 (1H, t, J=7.2 Hz), 7.45-7.55 (2H, m), 7.71 (1H, d, J=7.2 Hz), 10.64 (1H, s).

Example 63

Synthesis of ethyl 3-(2-(3-(4-(dimethylamino)piperidin-1-yl)-3-oxopropyl)-1H-imidazol-1-yl)propanoate

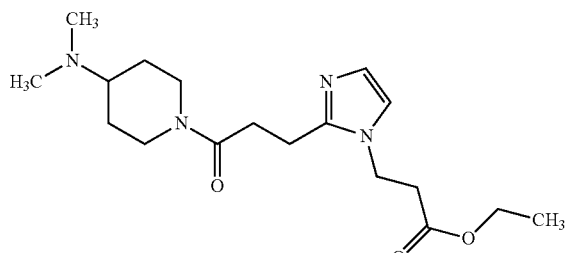

Diisopropylethylamine (0.651 mL, 3.73 mmol), HBTU (0.883 g, 2.33 mmol), and 4-dimethylaminopiperidine (0.208 mL, 1.77 mmol) were added to a solution of crude 3-(1-(3-ethoxy-3-oxopropyl)-1H-imidazol-2-yl)propanoic acid (0.330 g, 0.931 mmol) in chloroform (10.0 mL) at room temperature, and the reaction liquid was stirred at the same temperature for 16 hours. The reaction liquid was concentrated under reduced pressure. The residue was purified by flash chromatography (NH silica gel, chloroform/methanol) to obtain ethyl 3-(2-(3-(4-(dimethylamino)piperidin-1-yl)-3-oxopropyl)-1H-imidazol-1-yl)propanoate (0.172 g, 0.491 mmol, 53%) (hereinafter referred to as a "compound of Example 63") as a colorless oil.

$^1$H-NMR (400 MHz, CDCl$_3$) δ: 1.21-1.45 (5H, m), 1.78-1.88 (2H, m), 2.25-2.38 (7H, m), 2.55-2.64 (1H, m), 2.74 (2H, t, J=7.2 Hz), 2.90-3.05 (5H, m), 3.98-4.18 (3H, m), 4.24 (2H, t, J=7.2 Hz), 4.56-4.65 (1H, m), 6.84-6.86 (1H, m), 6.90-6.92 (1H, m).

ESI-MS: m/z=351 (M+H)$^+$.

Example 64

Synthesis of ethyl 3-(2-(3-(4-(dimethylamino)piperidin-1-yl)-3-oxopropyl)-1H-imidazol-1-yl)propanoate hydrochloride

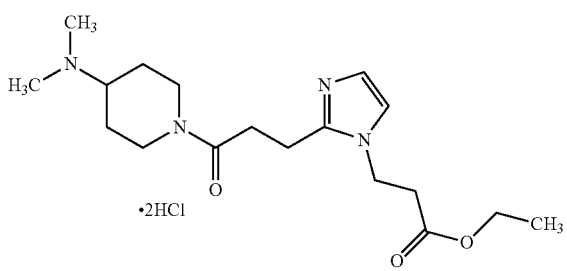 [SMILES: CCOC(=O)CCn1ccnc1CCC(=O)N1CCC(N(C)C)CC1]

A solution of hydrogen chloride in diethyl ether (2.0 N, 0.214 mL, 0.428 mmol) was added to a solution of ethyl 3-(2-(3-(4-(dimethylamino)piperidin-1-yl)-3-oxopropyl)-1H-imidazol-1-yl)propanoate (0.0500 g, 0.143 mmol) in diethyl ether (1.0 mL) at 0° C., and the reaction liquid was stirred at the same temperature for 30 minutes. The precipitated white solid was filtered and collected, and washed with diethyl ether (4.0 mL), and dried at room temperature for 36 hours to obtain ethyl 3-(2-(3-(4-(dimethylamino)piperidin-1-yl)-3-oxopropyl)-1H-imidazol-1-yl)propanoate hydrochloride (0.0541 g, 0.128 mmol, 89%) (hereinafter referred to as a "compound of Example 64") as a white solid.

$^1$H-NMR (400 MHz, D$_2$O) δ: 1.19-1.25 (3H, m), 1.53-1.80 (2H, m), 2.10-2.23 (2H, m), 2.67-2.78 (1H, m), 2.87 (6H, s), 3.00-3.10 (4H, m), 3.15-3.34 (3H, m), 3.47-3.57 (1H, m), 4.07-4.20 (3H, m), 4.45-4.58 (3H, m), 7.32-7.36 (1H, m), 7.42-7.45 (1H, m).

ESI-MS: as ethyl 3-(2-(3-(4-(dimethylamino)piperidin-1-yl)-3-oxopropyl)-1H-imidazol-1-yl) propanoate: m/z=351 (M+H)$^+$.

Example 65

Synthesis of 3-(2-(3-(4-(dimethylamino)piperidin-1-yl)-3-oxopropyl)-1H-imidazol-1-yl)propanoic acid

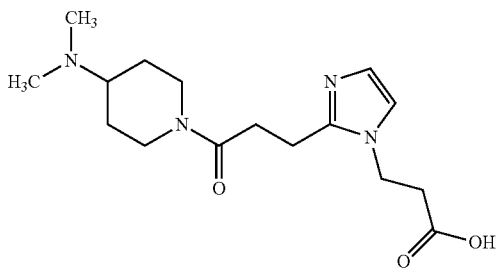 [SMILES: CN(C)C1CCN(C(=O)CCc2nccn2CCC(=O)O)CC1]

An aqueous solution of sodium hydroxide (1.0 N, 0.377 mL, 0.377 mmol) was added to a solution of ethyl 3-(2-(3-(4-(dimethylamino)piperidin-1-yl)-3-oxopropyl)-1H-imidazol-1-yl)propanoate (0.120 g, 0.342 mmol) in ethanol (3.0 mL) at room temperature, and the reaction liquid was stirred at the same temperature for 4 hours. The reaction liquid was cooled to 0° C., and hydrochloric acid (1.0 N) was added to the reaction liquid for neutralization, and then the reaction liquid was concentrated under reduced pressure. The residue was subjected to azeotropic distillation with toluene, and ethanol was added. The precipitate was filtered through Celite, and the filtrate was concentrated under reduced pressure to obtain 3-(2-(3-(4-(dimethylamino)piperidin-1-yl)-3-oxopropyl)-1H-imidazol-1-yl)propanoic acid (0.105 g, 0.326 mmol, 95%) (hereinafter referred to as a "compound of Example 65") as a white solid.

$^1$H-NMR (400 MHz, DMSO-$d_6$) δ: 1.34-1.47 (1H, m), 1.54-1.69 (1H, m), 1.95-2.08 (2H, m), 2.60-2.68 (8H, m), 2.75-3.05 (7H, m), 3.96-4.06 (1H, m), 4.21 (2H, t, J=6.8 Hz), 4.42-4.51 (1H, m), 7.13 (1H, brs), 7.33 (1H, brs).

ESI-MS: m/z=323 (M+H)$^+$.

Example 66

Synthesis of 3-(2-(3-(4-(dimethylamino)piperidin-1-yl)-3-oxopropyl)-1H-imidazol-1-yl)propanoic acid hydrochloride

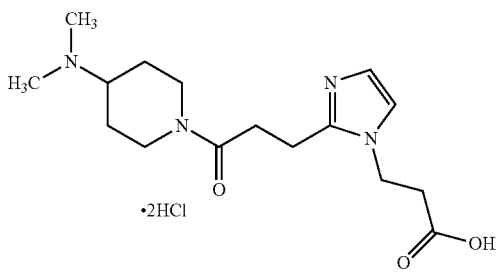 [SMILES: CN(C)C1CCN(C(=O)CCc2nccn2CCC(=O)O)CC1]

Hydrochloric acid (1.0 N, 1.02 mL, 1.02 mmol) was added to a solution of 3-(2-(3-(4-(dimethylamino)piperidin-1-yl)-3-oxopropyl)-1H-imidazol-1-yl)propanoic acid (0.105 g, 0.326 mmol) in water (1.0 mL) at 0° C., and the reaction liquid was stirred at the same temperature for 2 hours. The reaction liquid was concentrated under reduced pressure and the precipitated white solid was filtered and collected to obtain 3-(2-(3-(4-(dimethylamino)piperidin-1-yl)-3-oxopropyl)-1H-imidazol-1-yl)propanoic acid hydrochloride (0.0418 g, 0.116 mmol, 36%) (hereinafter referred to as a "compound of Example 66") as a white solid.

$^1$H-NMR (400 MHz, D$_2$O) δ: 1.53-1.80 (2H, m), 2.12-2.24 (2H, m), 2.68-2.78 (1H, m), 2.87 (6H, s), 2.98-3.34 (7H, m), 3.45-3.58 (1H, m), 4.07-4.17 (1H, m), 4.43-4.58 (3H, m), 7.34 (1H, brs), 7.43 (1H, brs).

ESI-MS: as 3-(2-(3-(4-(dimethylamino)piperidin-1-yl)-3-oxopropyl)-1H-imidazol-1-yl) propanoic acid: m/z=323 (M+H)$^+$.

Example 67

Synthesis of ethyl 3-(2-(3-((S)-3-dimethylaminopiperidin-1-yl)-3-oxopropyl)-1H-imidazol-1-yl)propanoate

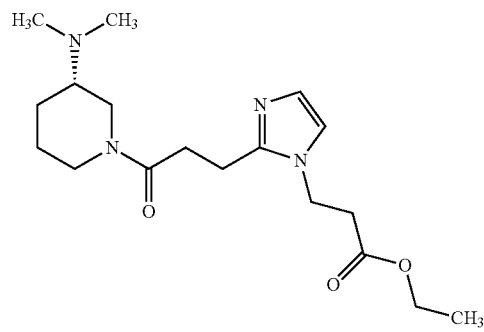 [SMILES: CCOC(=O)CCn1ccnc1CCC(=O)N1CCC[C@H](N(C)C)C1]

Diisopropylethylamine (0.0810 g, 0.620 mmol), HBTU (0.189 g, 0.500 mmol), and (S)-3-dimethylaminopiperidine (0.0530 g, 0.420 mmol) were added to a solution of crude 3-(1-(3-ethoxy-3-oxopropyl)-1H-imidazol-2-yl)propanoic acid (0.100 g, 0.420 mmol) in dichloromethane (10.0 mL) at room temperature, and the reaction liquid was stirred at the same temperature for 12 hours. The reaction liquid was concentrated under reduced pressure. The residue was purified by flash chromatography (NH silica gel, hexane/ethyl acetate and chloroform/methanol) to obtain ethyl 3-(2-(3-((S)-3-dimethylaminopiperidin-1-yl)-3-oxopropyl)-1H-imidazol-1-yl)propanoate (0.120 g, 0.340 mmol, 82%) (hereinafter referred to as a "compound of Example 67") as a yellow oil.

$^1$H-NMR (400 MHz, CDCl$_3$) δ: 1.24 (3H, t, J=7.2 Hz), 1.36-1.50 (2H, m), 1.70-1.85 (1H, m), 1.95-2.05 (1H, m), 2.07-2.23 (2H, m), 2.32 (6H, s), 2.43-2.60 (1H, m), 2.73-2.78 (2H, m), 2.81-3.03 (5H, m), 3.83-4.06 (1H, m), 4.14 (2H, q, J=7.2 Hz), 4.22-4.28 (2H, m), 4.47-4.68 (1H, m), 6.84-6.88 (1H, m), 6.91 (1H, d, J=1.2 Hz).

ESI-MS: m/z=351 (M+H)$^+$.

Example 68

Synthesis of 3-(2-(3-((S)-3-dimethylaminopiperidin-1-yl)-3-oxopropyl)-1H-imidazol-1-yl)propanoic acid hydrochloride

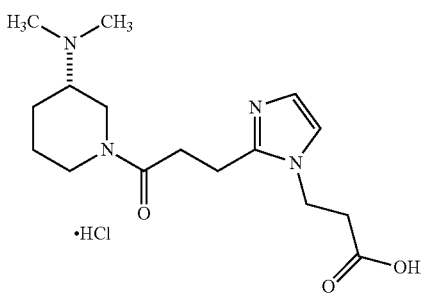 [SMILES: CN(C)[C@H]1CCCN(C(=O)CCc2nccn2CCC(=O)O)C1 ; Cl]

An aqueous solution of sodium hydroxide (1.0 N, 0.351 mL, 0.351 mmol) was added to a solution of ethyl 3-(2-(3-((S)-3-dimethylaminopiperidin-1-yl)-3-oxopropyl)-1H-imidazol-1-yl)propanoate (0.062 g, 0.175 mmol) in water (5.0 mL) at 0° C. The reaction liquid was stirred at the same temperature for 2 hours. Hydrochloric acid (1.0 N, 0.526 mL, 0.526 mmol) was added thereto, and then the resulting mixture was concentrated and exsiccated. The obtained solid was washed with ethanol and filtered, and then the filtrate was concentrated and exsiccated. Again, the obtained solid was washed with ethanol and filtered, and then the filtrate was concentrated and exsiccated. The residue was dried under reduced pressure to obtain 3-(2-(3-((S)-3-dimethylaminopiperidin-1-yl)-3-oxopropyl)-1H-imidazol-1-yl)propanoic acid hydrochloride (0.0430 g, 0.120 mmol, 68%) (hereinafter referred to as a "compound of Example 68") as a white solid.

$^1$H-NMR (400 MHz, D$_2$O) δ: 1.02-1.87 (3H, m), 2.00-2.15 (1H, m), 2.55-2.95 (7H, m), 3.05-3.30 (7H, m), 3.47-3.62 (1H, m), 3.95-4.20 (1H, m), 4.99 (2H, s), 7.26 (2H, s).

ESI-MS: as 3-(2-(3-((S)-3-dimethylaminopiperidin-1-yl)-3-oxopropyl)-1H-imidazol-1-yl)propanoic acid: 323 (M+H)$^+$.

Example 69

Synthesis of ethyl (S)-3-(2-(3-(3-(dimethylamino)pyrrolidin-1-yl)-3-oxopropyl)-1H-imidazol-1-yl)propanoate

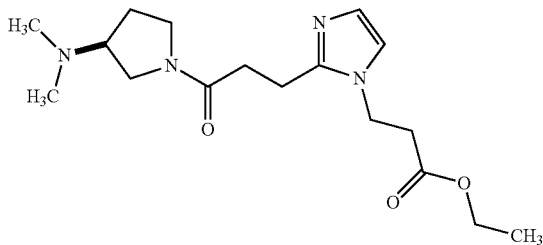 [SMILES: CCOC(=O)CCn1ccnc1CCC(=O)N1CC[C@H](N(C)C)C1]

Diisopropylethylamine (0.0870 mL, 0.499 mmol), HBTU (0.152 g, 0.400 mmol), and (S)-3-(dimethylamino)pyrrolidine (0.0420 mL, 0.333 mmol) were added to a solution of crude 3-(1-(3-ethoxy-3-oxopropyl)-1H-imidazol-2-yl)pro- panoic acid (0.0800 g, 0.333 mmol) in dichloromethane (1.6 mL) at room temperature, and the reaction liquid was stirred at the same temperature for 5 hours. The reaction liquid was concentrated under reduced pressure. The residue was purified by flash chromatography (NH silica gel, chloroform/methanol) to obtain ethyl (S)-3-(2-(3-(3-(dimethylamino)pyrrolidin-1-yl)-3-oxopropyl)-1H-imidazol-1-yl)propanoate (0.103 g, 0.306 mmol, 92%) (hereinafter referred to as a "compound of Example 69") as a reddish brown oil.

$^1$H-NMR (400 MHz, CDCl$_3$) δ: 1.23-1.27 (3H, m), 1.67-1.91 (1H, m), 2.06-2.26 (7H, m), 2.58-3.36 (9H, m), 3.43-3.83 (2H, m), 4.12-4.28 (4H, m), 6.85-6.93 (2H, m).

ESI-MS: m/z=337 (M+H)$^+$.

Example 70

Synthesis of (S)-3-(2-(3-(3-(dimethylamino)pyrrolidin-1-yl)-3-oxopropyl)-1H-imidazol-1-yl)propanoic acid hydrochloride

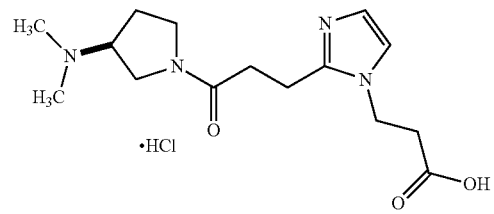 [SMILES: CN(C)[C@H]1CCN(C(=O)CCc2nccn2CCC(=O)O)C1 ; Cl]

An aqueous solution of sodium hydroxide (1.0 N, 0.446 mL, 0.446 mmol) was added to ethyl (S)-3-(2-(3-(3-(dimethylamino)pyrrolidin-1-yl)-3-oxopropyl)-1H-imidazol-1-yl)propanoate (0.100 g, 0.297 mmol) at room temperature, and the reaction liquid was stirred at the same temperature for 4 hours. Hydrochloric acid (1.0 N, 0.446 mL, 0.446 mmol) was added to the reaction liquid at room temperature, and the reaction liquid was stirred at the same temperature for 5 minutes. The reaction liquid was concentrated under reduced pressure. The obtained residue was washed with ethanol (5.0 mL). The resulting mixture was filtered, and then the filtrate was concentrated under reduced pressure. The obtained residue was washed with ethanol (5.0 mL) again. The resulting mixture was filtered, and then the filtrate was concentrated under reduced pressure. Hydrochloric acid (1.0 N, 0.358 mL, 0.358 mmol) was added to the obtained residue at room temperature, and the reaction liquid was stirred at the same temperature for 1 hour. The reaction liquid was concentrated under reduced pressure and dried at room temperature to obtain (S)-2-(2-(3-(3-(dimethylamino)pyrrolidin-1-yl)-3-oxopropyl)-1H-imidazol-1-yl)propane hydrochloride (0.0900 g, 0.259 mmol, 87%) (hereinafter referred to as a "compound of Example 70") as a brown solid.

$^1$H-NMR (400 MHz, D$_2$O) δ: 1.95-2.21 (1H, m), 2.35-2.49 (1H, m), 2.64-2.94 (10H, m), 3.15-3.19 (2H, m), 3.29-4.08 (5H, m), 4.30-4.33 (2H, m), 7.23 (1H, s), 7.31 (1H, s).

Example 71

Effect on Mouse Partial Sciatic Nerve Ligation Model

Using a partial sciatic nerve ligation model (Seltzer model) in mice by which neuropathic pain can be evaluated, the analgesic action of a cyclic amine derivative (I) or a prodrug thereof or a pharmacologically acceptable salt thereof was investigated.

As the cyclic amine derivative (I) or a pharmacologically acceptable salt thereof, the compounds of Example 2, 4, 6, 8, 10, 12, 13, 15, 18, 22, 25, 27, 29, 31, 33, 66, 68 or 70 was used for evaluation. As the prodrug of the cyclic amine derivative (I) or a pharmacologically acceptable salt thereof, the compound of Example 38 was used for evaluation. The compound of Example 38 is a hydrochloride of a prodrug obtained by esterifying the carboxyl group of the compound of Example 39 with an ethyl group.

1. Experimental Method

The mouse partial sciatic nerve ligation model was prepared in accordance with the method of Seltzer et al. (Malmberg et al., Pain, vol. 76, p. 215-222, 1998).

Slc: ICR mice (5 weeks old, male; from Japan SLC, Inc.) or Crl: CD1 (ICR) mice (5 weeks old, male; from CHARLES RIVER LABORATORIES JAPAN, INC.) were anesthetized with sodium pentobarbital (70 mg/kg, intraperitoneal administration). The sciatic nerve at the femoral region of the right hind paw of each mouse was exposed and triply ligated tightly with silk suture of 8-0 (from NATSUME SEISAKUSHO CO., LTD.) under a stereomicroscope so that only half thickness of the nerve was trapped in the ligature. A group of mice thus treated was designated as a partial sciatic nerve ligation group. A group of mice whose sciatic nerve was just exposed and not ligated was designated as a sham surgery group.

Evaluation of neuropathic pain (hereinafter referred to as von Frey test) was performed as follows. Mice were conditioned for at least two hours in an acrylic cage for measurement (from NATSUME SEISAKUSHO CO. LTD.) placed on a wire net. Thereafter, using a filament (from North Coast Medical or neuroscience) which exerted a pressure of 0.16 g, the mice were subjected to mechanical tactile stimulus by applying the filament to the plantar surface of the right hind paw 3 times, each for 3 seconds, with an interval of 3 seconds. The withdrawal response observed during each mechanical tactile stimulus was scored (0, no response; 1, showed slow and/or slight withdrawal response in response to the stimulation; 2, showed quick withdrawal response without flinching (shaking paws quickly and continuously) nor licking (licking paws) in response to the stimulation; 3, showed quick withdrawal response with flinching and/or licking), and the sum of the scores obtained in the triplicate trials (hereinafter referred to as the total score) were used as a pain index.

(1) Oral Administration

Day 7 after the sciatic nerve ligation surgery, the compound of Example 8 (the compound of Example 8: 10 mg/kg) or pregabalin (10 mg/kg; Bosche Scientific) serving as a positive control was dissolved in distilled water and then orally administered to the mice of the partial sciatic nerve ligation group. A group wherein the compound of Example 8 was administered to the mice of the partial sciatic nerve ligation group was designated as a "partial sciatic nerve ligation+the compound of Example 8" group. A group wherein pregabalin was administered to the mice of the partial sciatic nerve ligation group was designated as a "partial sciatic nerve ligation+pregabalin" group. A group wherein distilled water was orally administered to the mice of the partial sciatic nerve ligation group was designated as a "partial sciatic nerve ligation+distilled water" group. A group wherein distilled water was orally administered to the mice of the sham surgery group was designated as a "sham surgery+distilled water" group.

Day 8 after the sciatic nerve ligation surgery, the compound of Example 38 (the compound of Example 38: 0.1 to 10 mg/kg) or pregabalin (10 mg/kg; from KEMPROTEC) serving as a positive control was dissolved in distilled water and then orally administered to the mice of the partial sciatic nerve ligation group. A group wherein the compound of Example 38 was administered to the mice of the partial sciatic nerve ligation group was designated as a "partial sciatic nerve ligation+the compound of Example 38" group. A group wherein pregabalin was administered to the mice of the partial sciatic nerve ligation group was designated as a "partial sciatic nerve ligation+pregabalin" group. A group wherein distilled water was orally administered to the mice of the partial sciatic nerve ligation group was designated as a "partial sciatic nerve ligation+distilled water" group. A group wherein distilled water was orally administered to the mice of sham surgery group was designated as a "sham surgery+distilled water" group.

The von Frey test was carried out before oral administration of a test compound (pre-value), one hour, two hours, and 3 hours after the oral administration of a test compound.

(2) Intravenous Administration

Day 7 after the sciatic nerve ligation surgery, compounds of Example 2, 4, 13, 18, 22, 25, 27, 29, 31, 33, 66, 68 or 70 (each of the compounds of Example 2 and 4: 0.1 to 10 mg/kg, the compound of Example 13: 0.01 to 1 mg/kg, each of the compounds of Example 18 and 22: 0.1 and 1 mg/kg, each of the compounds of Example 25, 27, 29, 31, 33, 66, 68 and 70: 0.1 mg/kg) or pregabalin serving as a positive control (1 mg/kg; from Bosche Scientific or 3 mg/kg; from KEMPROTEC) was dissolved in physiological saline and then administered to the mice of the partial sciatic nerve ligation group through the tail vein. A group wherein the compounds of Example 2, 4, 13, 18, 22, 25, 27, 29, 31, 33, 66, 68 or 70 was administered to the mice of the partial sciatic nerve ligation group, was designated as a "partial sciatic nerve ligation+the compound of Example 2" group, a "partial sciatic nerve ligation+the compound of Example 4" group, a "partial sciatic nerve ligation+the compound of Example 13" group, a "partial sciatic nerve ligation+the compound of Example 18" group, a "partial sciatic nerve ligation+the compound of Example 22" group, a "partial sciatic nerve ligation+the compound of Example 25" group, a "partial sciatic nerve ligation+the compound of Example 27" group, a "partial sciatic nerve ligation+the compound of Example 29" group, a "partial sciatic nerve ligation+the compound of Example 31" group, a "partial sciatic nerve ligation+the compound of Example 33" group, a "partial sciatic nerve ligation+the compound of Example 66" group, a "partial sciatic nerve ligation+the compound of Example 68" group, or a "partial sciatic nerve ligation+the compound of Example 70" group, respectively. A group wherein pregabalin was administered to the mice of the partial sciatic nerve ligation group was designated as a "partial sciatic nerve ligation+pregabalin" group. A group wherein physiological saline was intravenously administered to the mice of the partial sciatic nerve ligation group was designated as a "partial sciatic nerve ligation+physiological saline" group. A group wherein physiological saline was intravenously administered to the mice of the sham surgery group was designated as a "sham surgery+physiological saline" group.

The von Frey test for the compounds of Example 2 or 4 was carried out before intravenous administration of a test compound (pre-value), 30 minutes and 60 minutes after the intravenous administration of a test compound. The von Frey test for the compounds of Example 13, 18, 22, 25, 27, 29, 31, 33, 66, 68 or 70, was carried out before intravenous administration of a test compound (pre-value), 30 minutes and 2 hours after the intravenous administration of a test compound.

(3) Intraventricular Administration

Day 7 after the sciatic nerve ligation surgery, the compounds of Example 2, 4, 6, 10, 12, 13 or 15 (10 μg/site) was dissolved in physiological saline and then intraventricularly administered to the mice of the partial sciatic nerve ligation group. A group wherein the compounds of Example 2, 4, 6, 10, 12, 13 or 15 was administered to the mice of the partial sciatic nerve ligation group was designated as a "partial sciatic nerve ligation+the compound of Example 2" group, a "partial sciatic nerve ligation+the compound of Example 4" group, a "partial sciatic nerve ligation+the compound of Example 6" group, a "partial sciatic nerve ligation+the compound of Example 10" group, a "partial sciatic nerve ligation+the compound of Example 12" group, a "partial sciatic nerve ligation+the compound of Example 13" group or a "partial sciatic nerve ligation+the compound of Example 15" group, respectively. A group wherein physiological saline was intraventricularly administered to the mice of the partial sciatic nerve ligation group was designated as a "partial sciatic nerve ligation+physiological saline" group. A group wherein physiological saline was intraventricularly administered to the mice of the sham surgery group was designated as a "sham surgery+physiological saline" group.

The von Frey test was carried out before intraventricular administration of a test compound (pre-value), 15 minutes, 30 minutes and 60 minutes after the intraventricular administration of a test compound.

2. Results (1) Oral Administration

Figure 11:
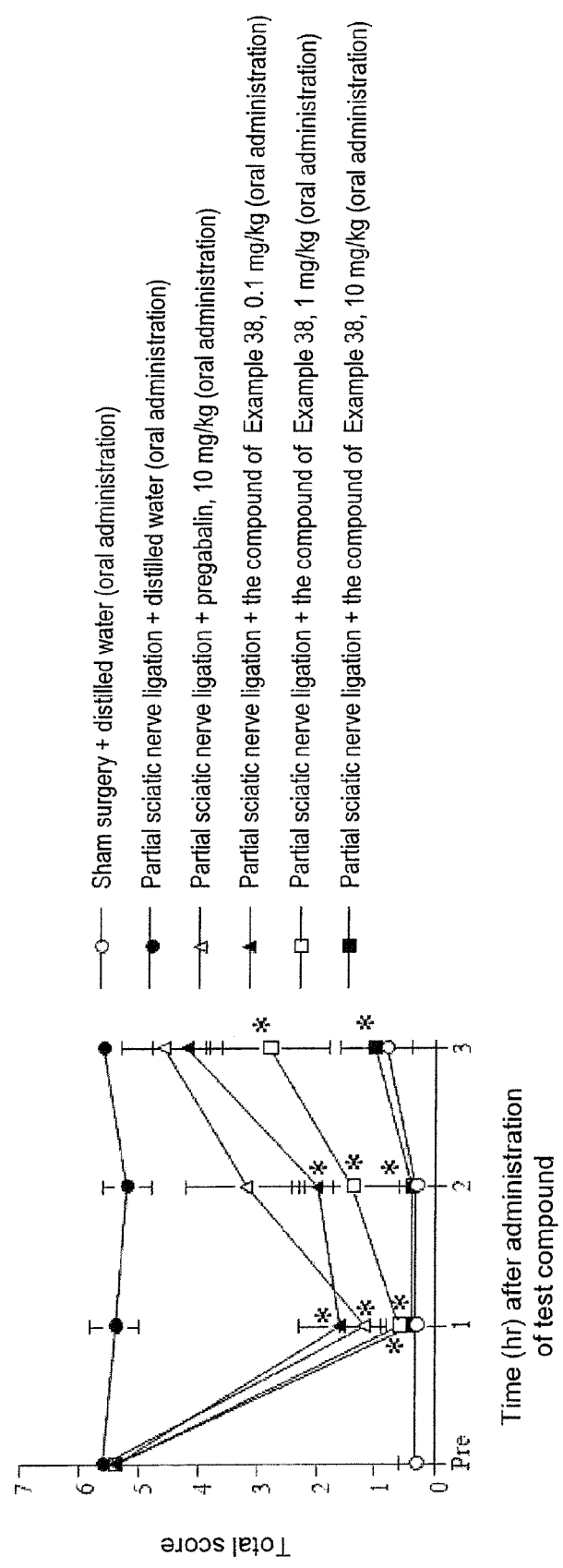
FIG. 11 is a graph showing the effect of the compound of Example 38 on mouse partial sciatic nerve ligation models (oral administration).
Figure 12:
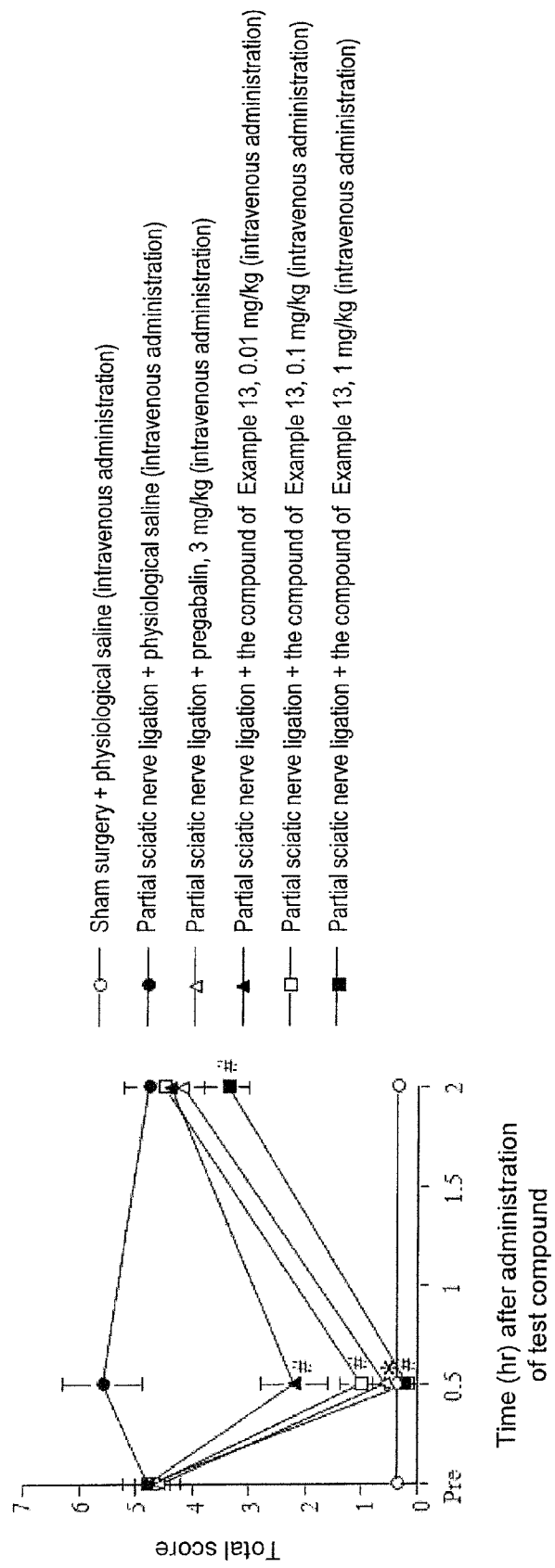
FIG. 12 is a graph showing the effect of the compound of Example 13 on mouse partial sciatic nerve ligation models (intravenous administration).
Figure 13:
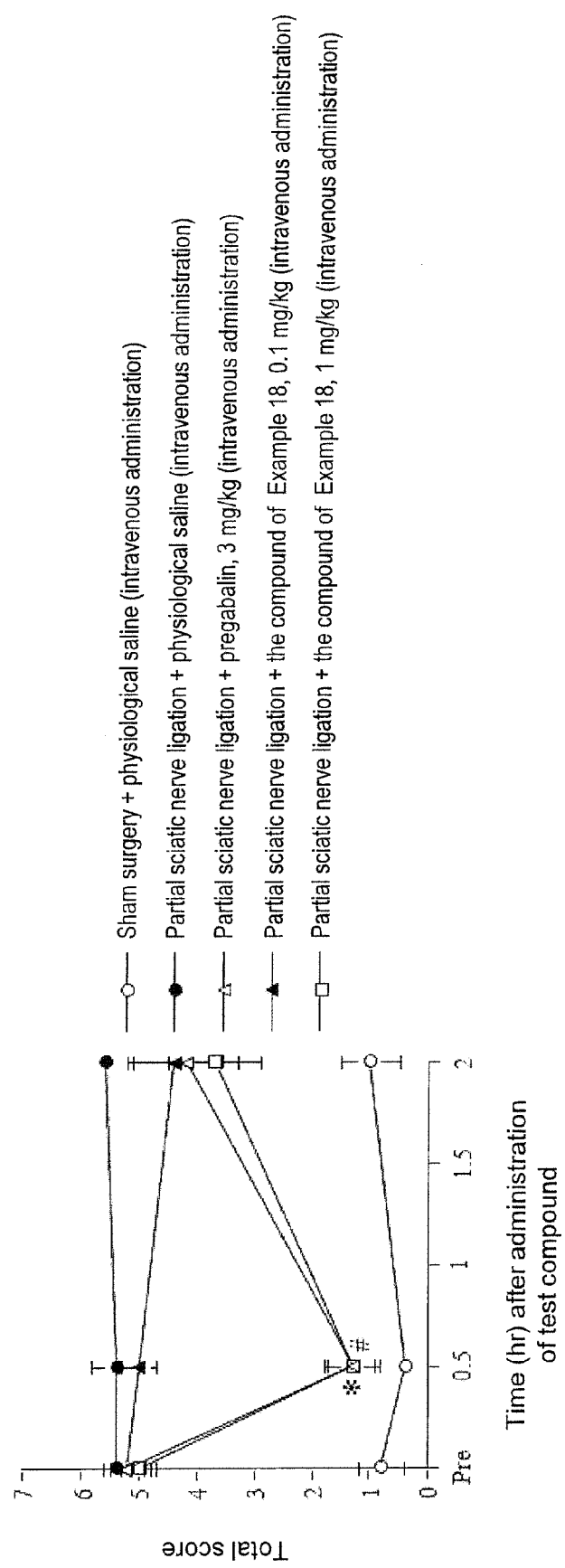
FIG. 13 is a graph showing the effect of the compound of Example 18 on mouse partial sciatic nerve ligation models (intravenous administration).
Figure 14:
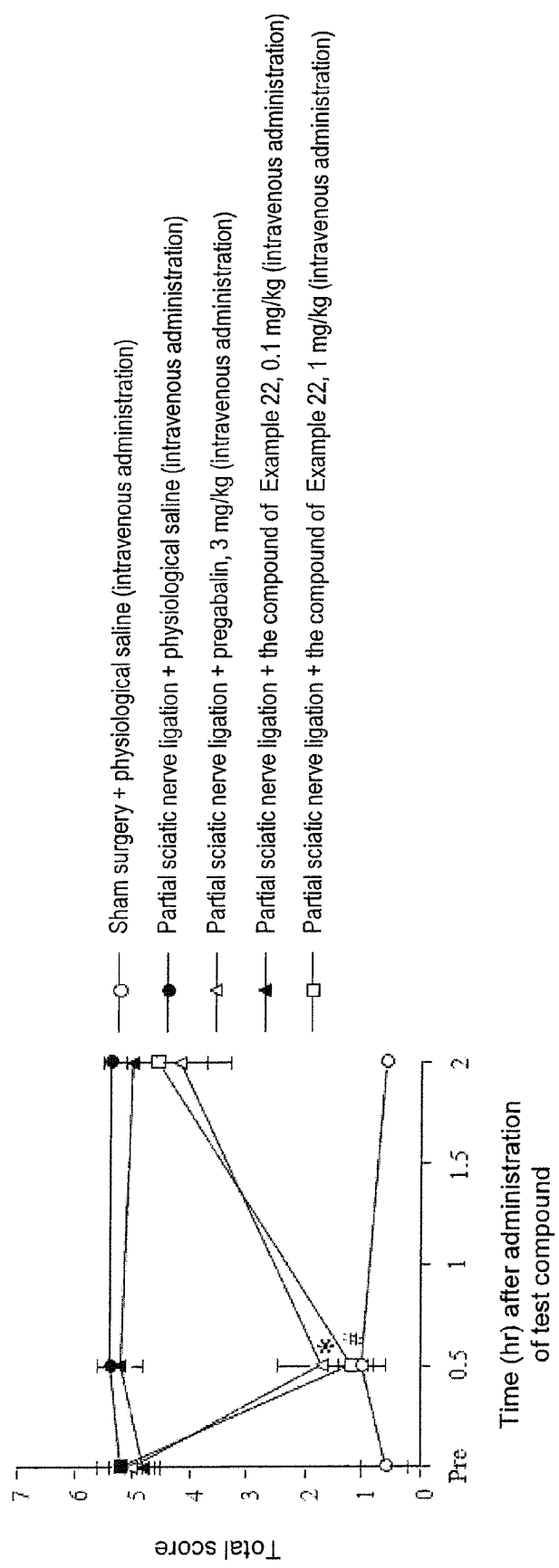
FIG. 14 is a graph showing the effect of the compound of Example 22 on mouse partial sciatic nerve ligation models (intravenous administration).
Figure 15:
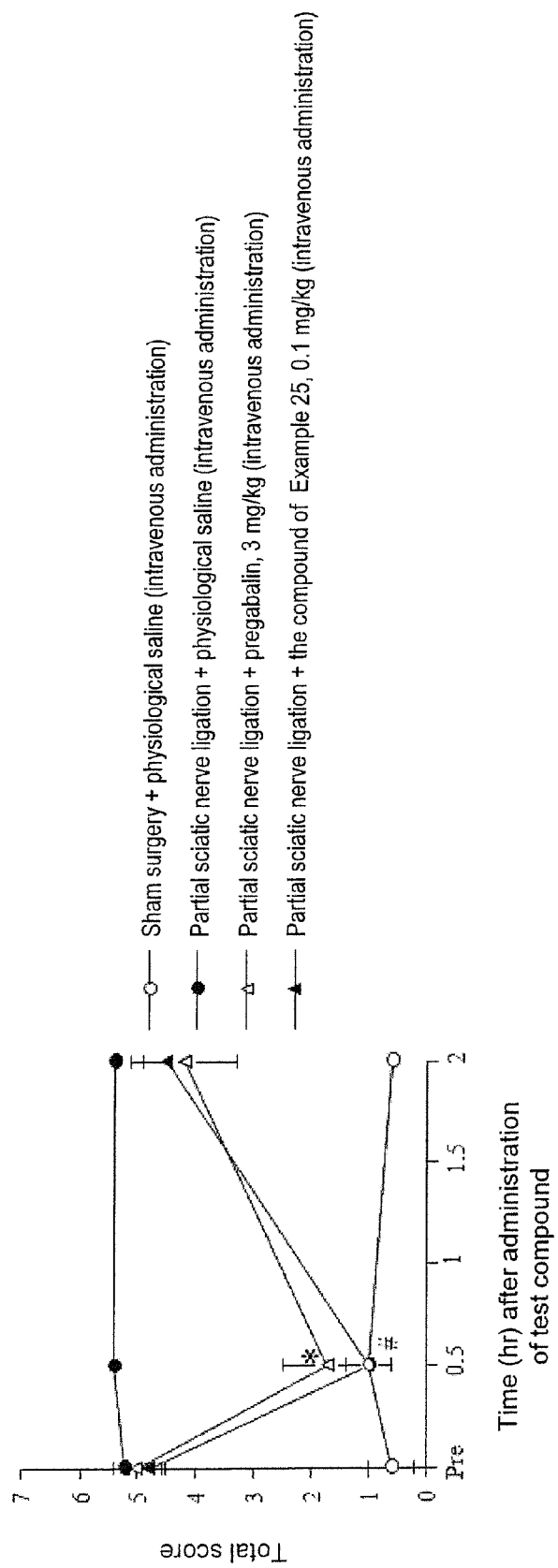
FIG. 15 is a graph showing the effect of the compound of Example 25 on mouse partial sciatic nerve ligation models (intravenous administration).
Figure 16:
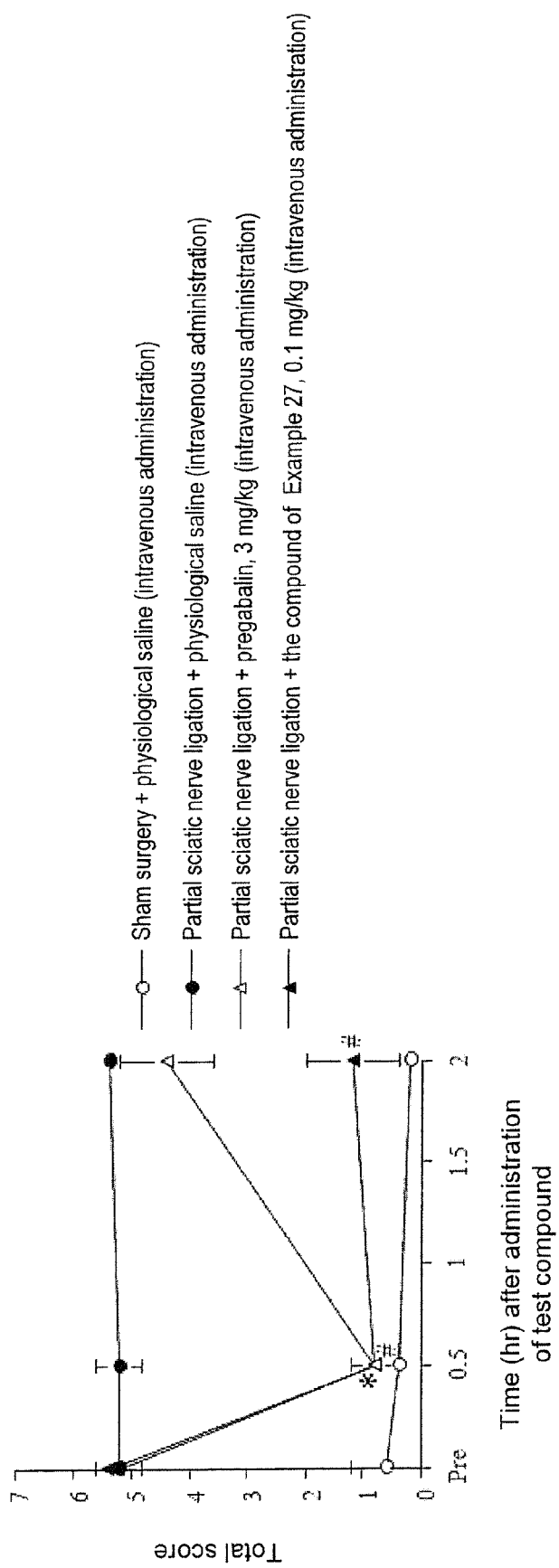
FIG. 16 is a graph showing the effect of the compound of Example 27 on mouse partial sciatic nerve ligation models (intravenous administration).
Figure 17:
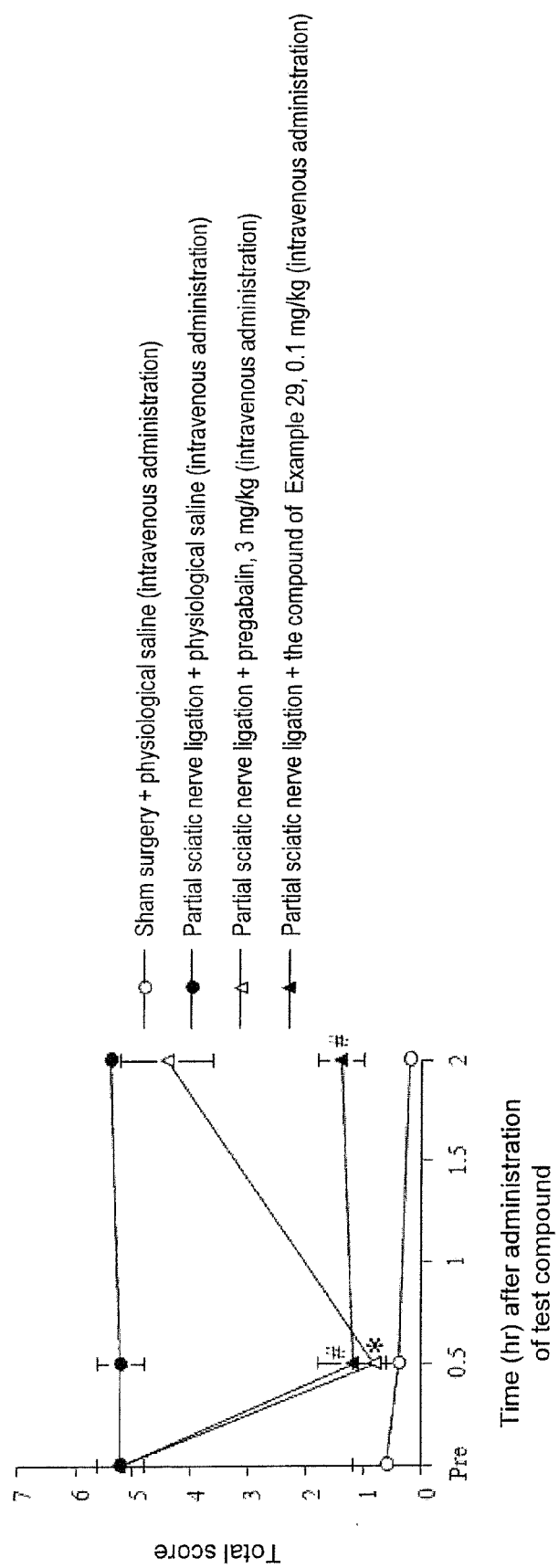
FIG. 17 is a graph showing the effect of the compound of Example 29 on mouse partial sciatic nerve ligation models (intravenous administration).
Figure 18:
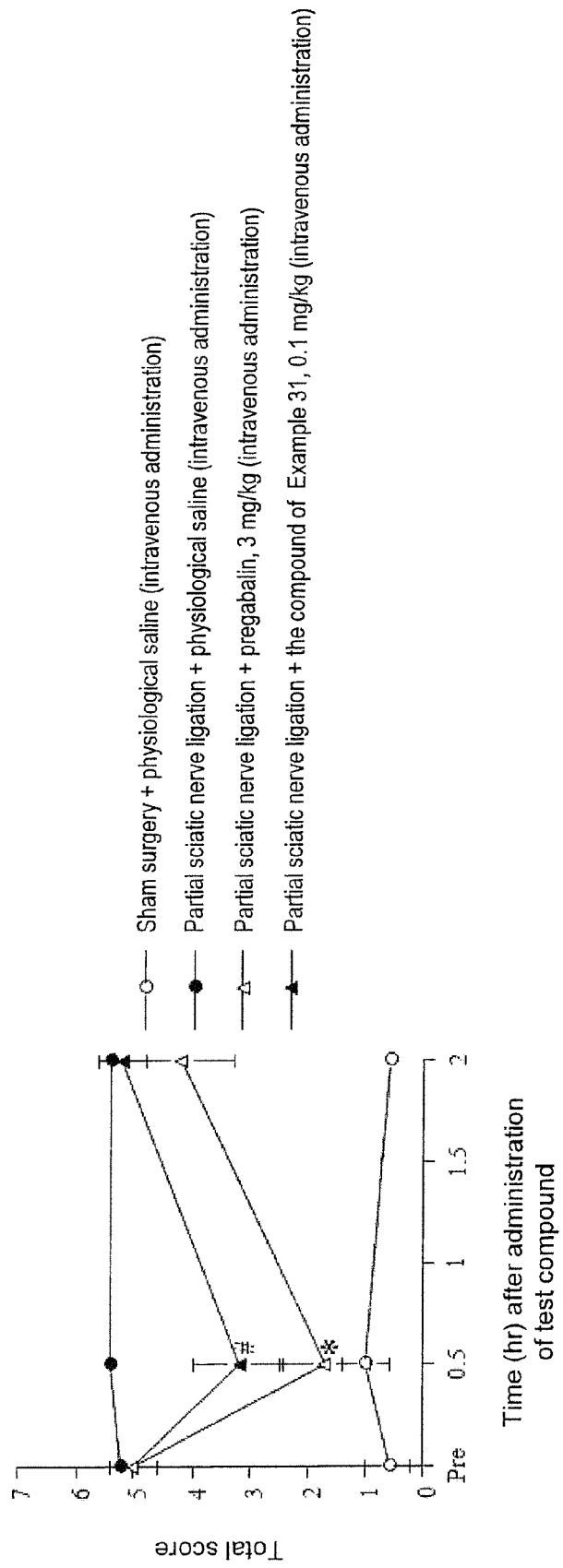
FIG. 18 is a graph showing the effect of the compound of Example 31 on mouse partial sciatic nerve ligation models (intravenous administration).
Figure 19:
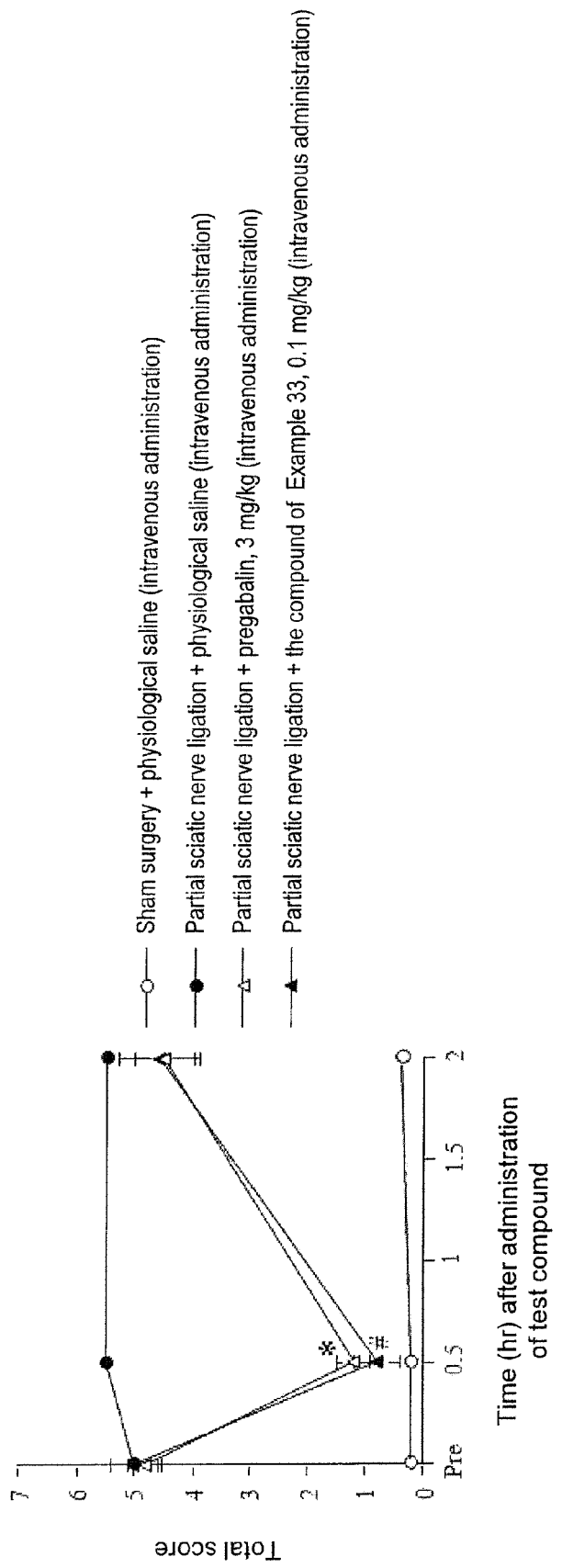
FIG. 19 is a graph showing the effect of the compound of Example 33 on mouse partial sciatic nerve ligation models (intravenous administration).
Figure 20:
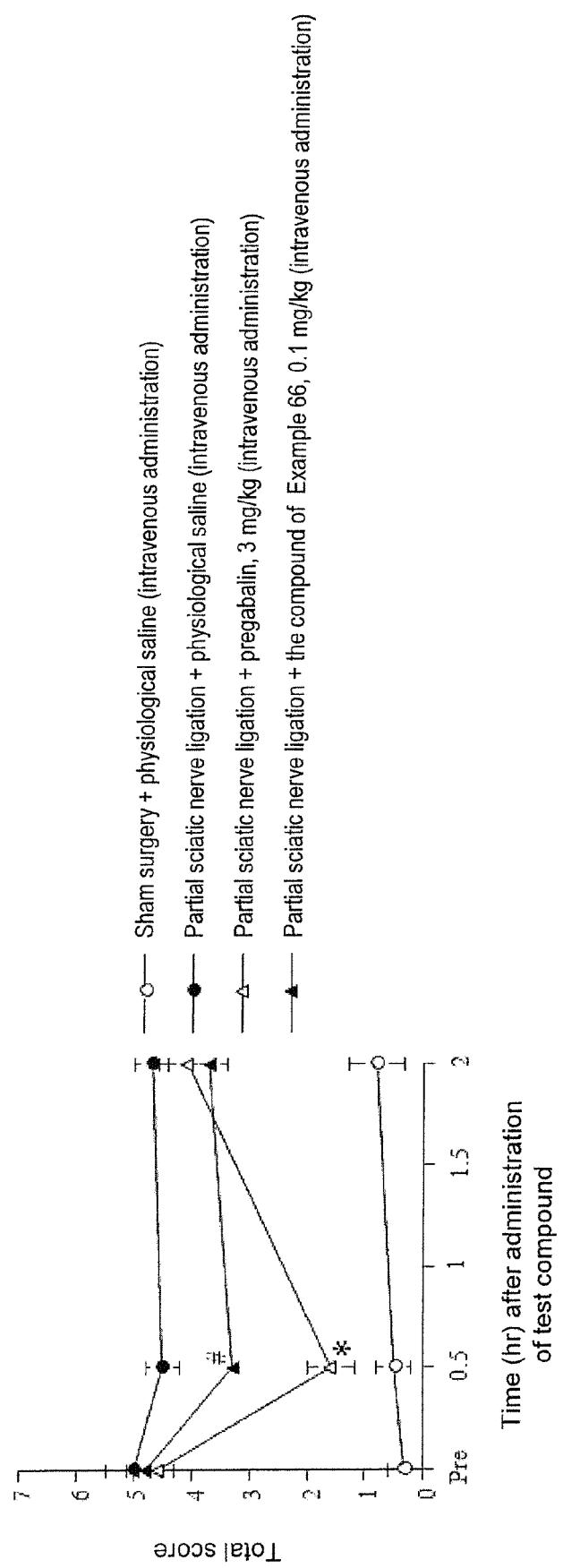
FIG. 20 is a graph showing the effect of the compound of Example 66 on mouse partial sciatic nerve ligation models (intravenous administration).
Figure 21:
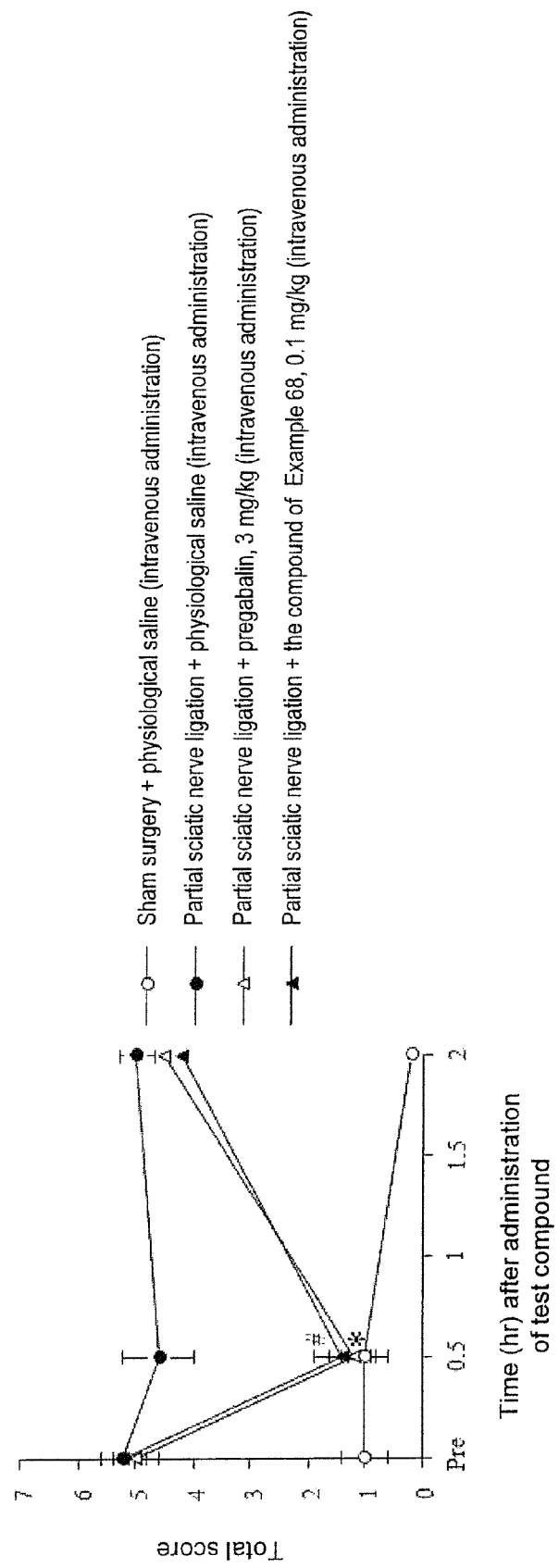
FIG. 21 is a graph showing the effect of the compound of Example 68 on mouse partial sciatic nerve ligation models (intravenous administration).
Figure 22:
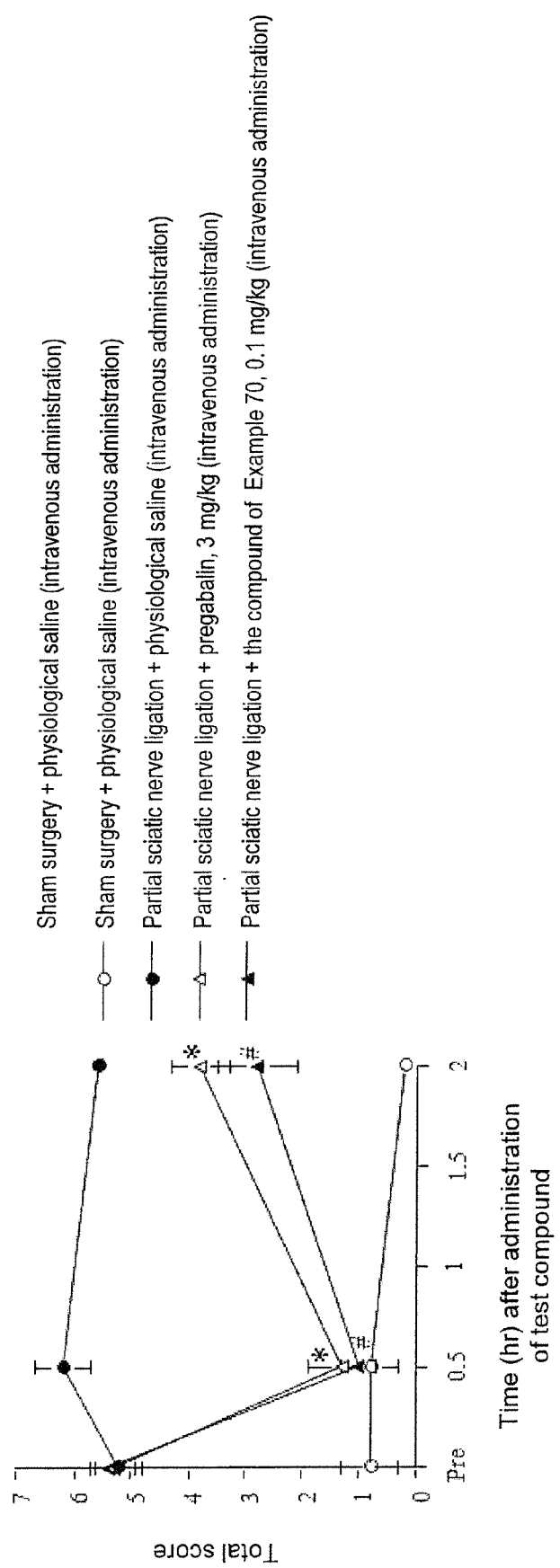
FIG. 22 is a graph showing the effect of the compound of Example 70 on mouse partial sciatic nerve ligation models (intravenous administration).

The results are shown in FIGS. 1 and 11. In the figures, the vertical axis represents the total score (mean value±standard error; n=5 in FIG. 1, n=4 to 5 in FIG. 11) in the von Frey test. The higher numerical value indicates that pain is stronger. The horizontal axis represents time (hr) after administration of a test compound. Efficacy was statistically evaluated by a two-sample unpaired t-test or Welch test (FIG. 1) or a multi-sample unpaired t-test (corrected by Dunnett) (FIG. 11) using the "partial sciatic nerve ligation+distilled water" group ("partial sciatic nerve ligation+distilled water" in the figure) of every measurement time as a control. In the figures, mark "*" indicates that the value is statistically significant ($p<0.05$) compared to the "partial sciatic nerve ligation+distilled water" group.

According to the results of the von Frey test, oral administration of the compounds of Example 8 or 38 ("partial sciatic nerve ligation+the compound of Example 8" or "partial sciatic nerve ligation+the compound of Example 38" in the figures) showed a statistically significant analgesic action similarly to the positive control, pregabalin ("partial sciatic nerve ligation+pregabalin" in the figures).

(2) Intravenous Administration

Figure 2:
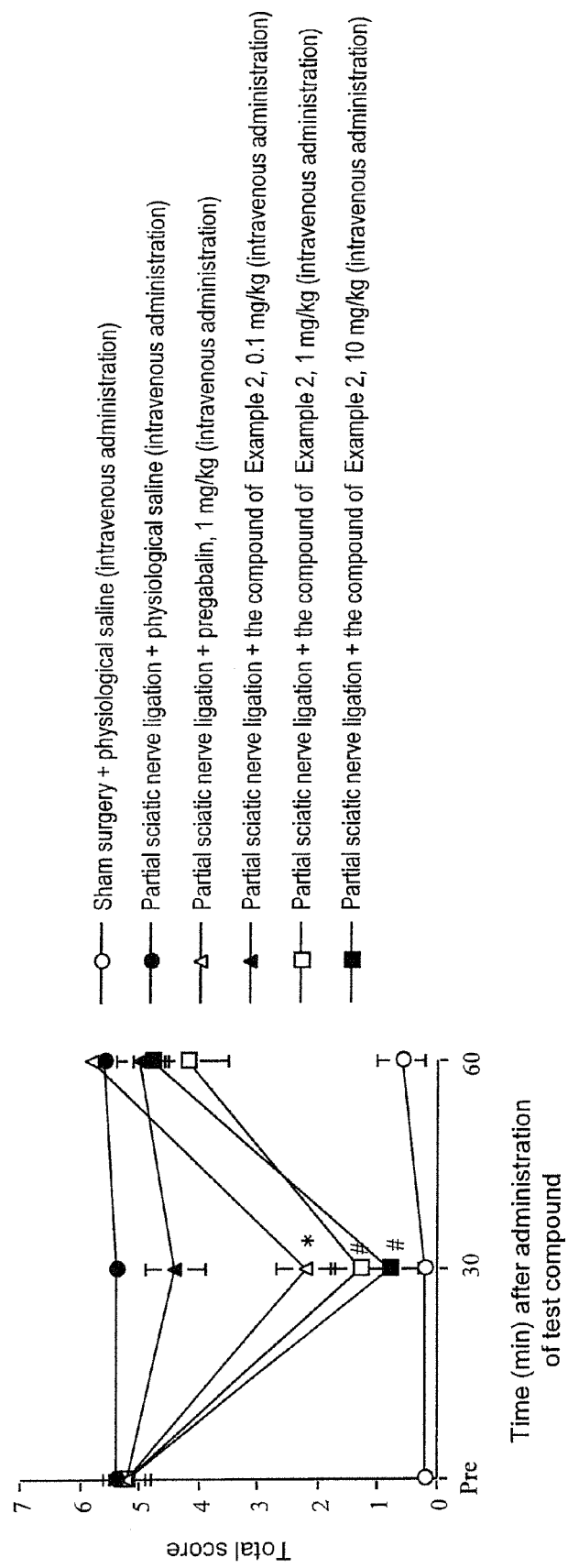
FIG. 2 is a graph showing the effect of the compound of Example 2 on mouse partial sciatic nerve ligation models (intravenous administration).
Figure 3:
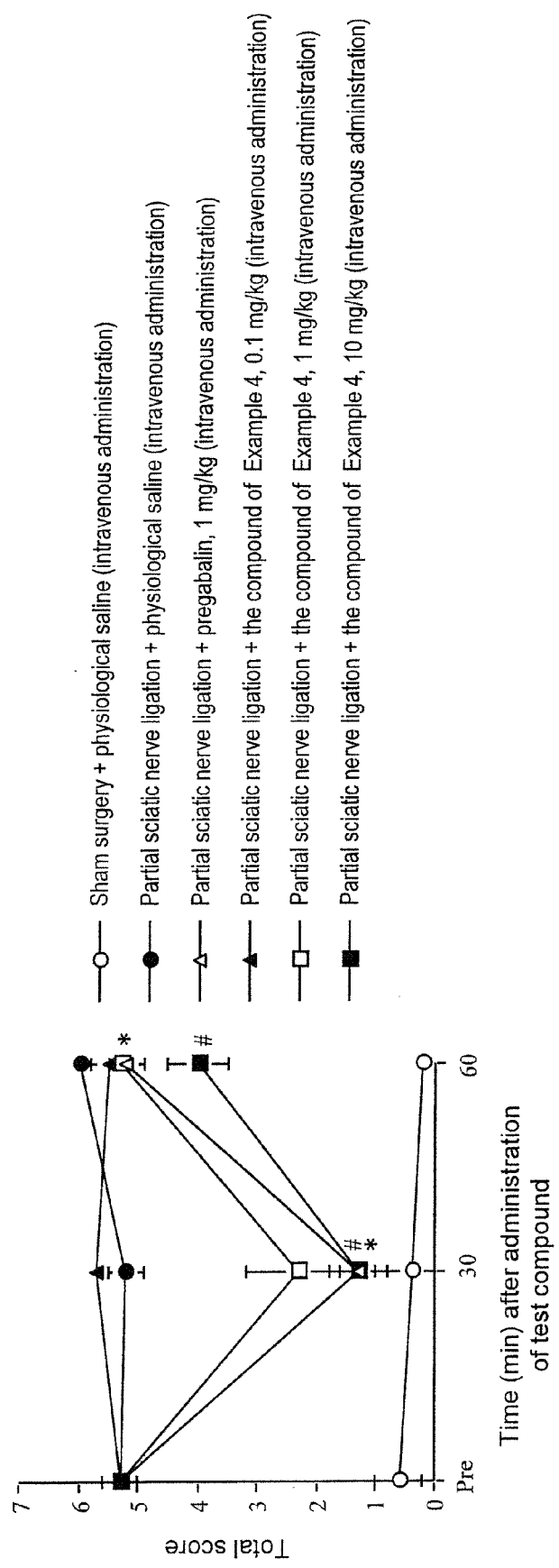
FIG. 3 is a graph showing the effect of the compound of Example 4 on mouse partial sciatic nerve ligation models (intravenous administration).
Figure 4:
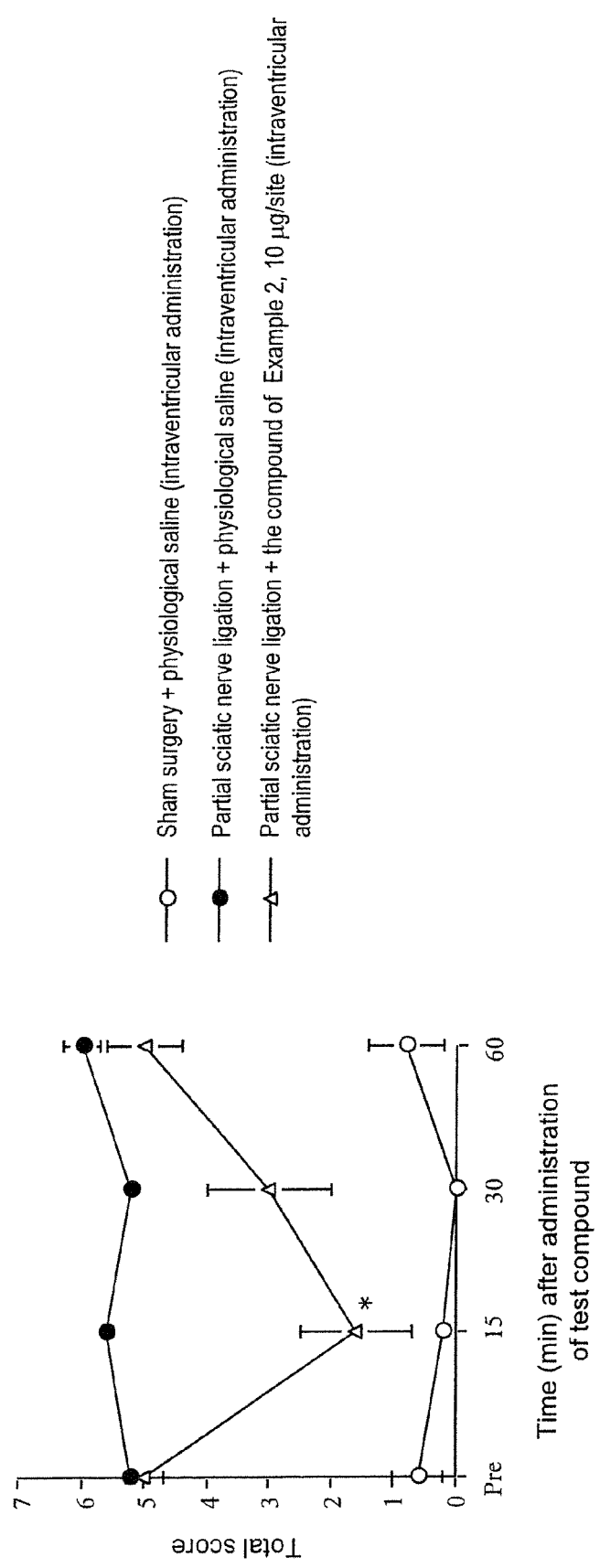
FIG. 4 is a graph showing the effect of the compound of Example 2 on mouse partial sciatic nerve ligation models (intraventricular administration).
Figure 5:
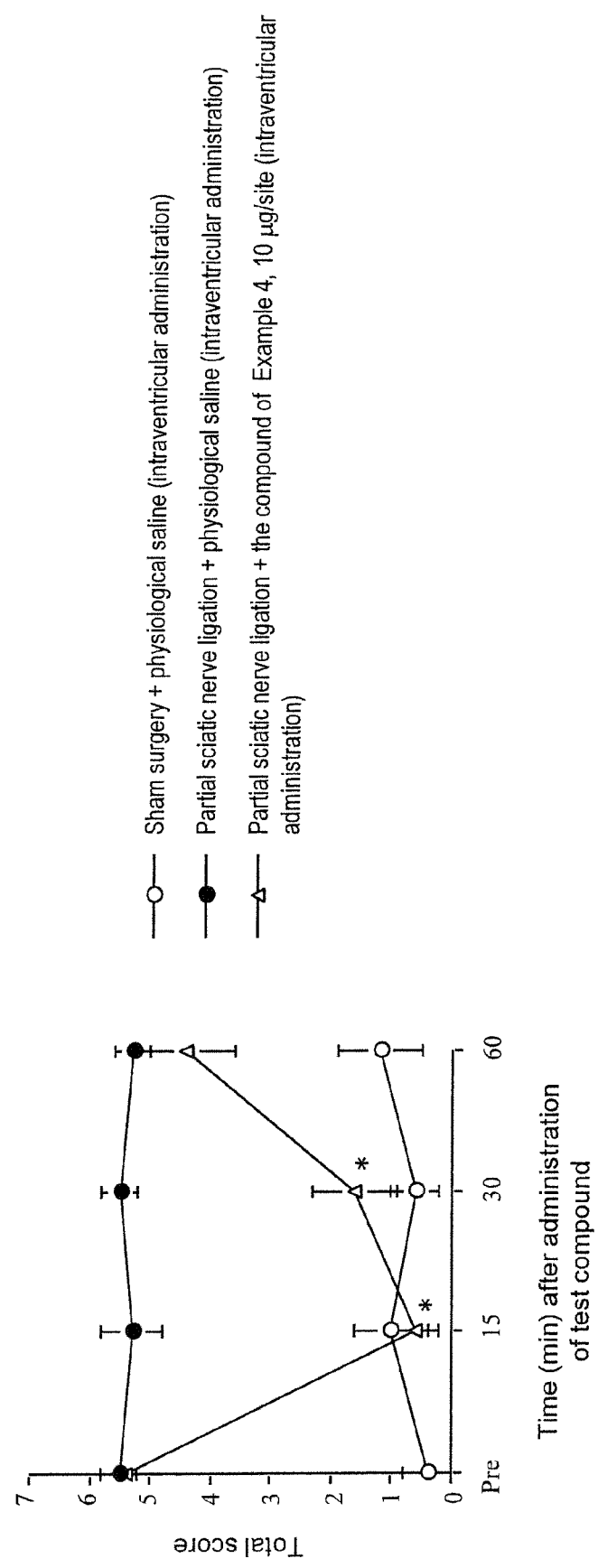
FIG. 5 is a graph showing the effect of the compound of Example 4 on mouse partial sciatic nerve ligation models (intraventricular administration).
Figure 6:
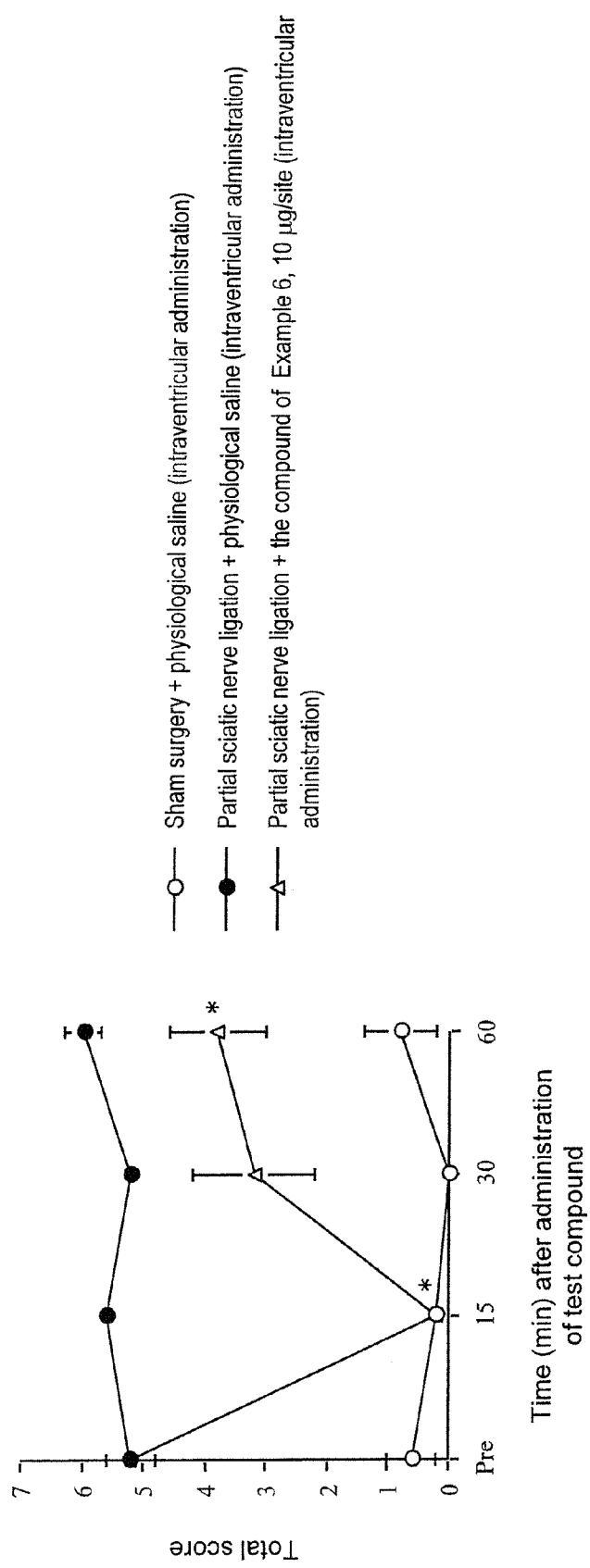
FIG. 6 is a graph showing the effect of the compound of Example 6 on mouse partial sciatic nerve ligation models (intraventricular administration).
Figure 7:
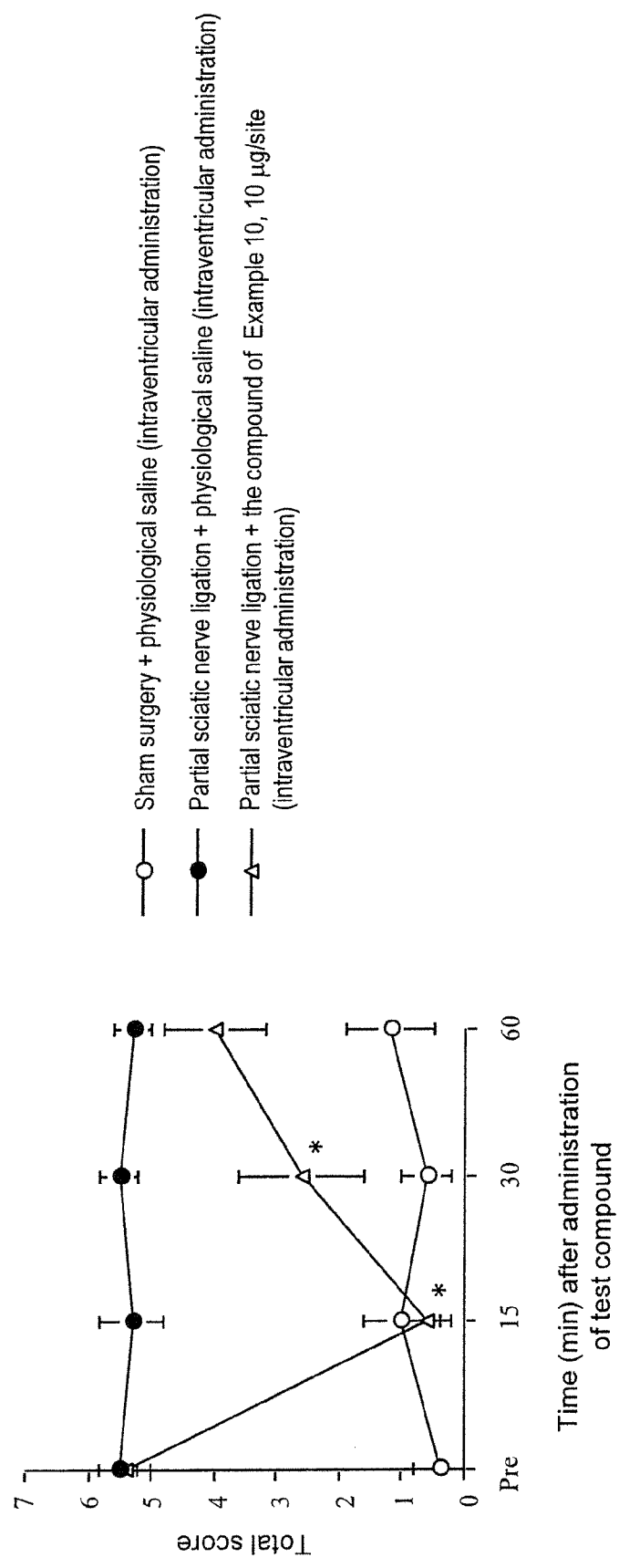
FIG. 7 is a graph showing the effect of the compound of Example 10 on mouse partial sciatic nerve ligation models (intraventricular administration).
Figure 8:
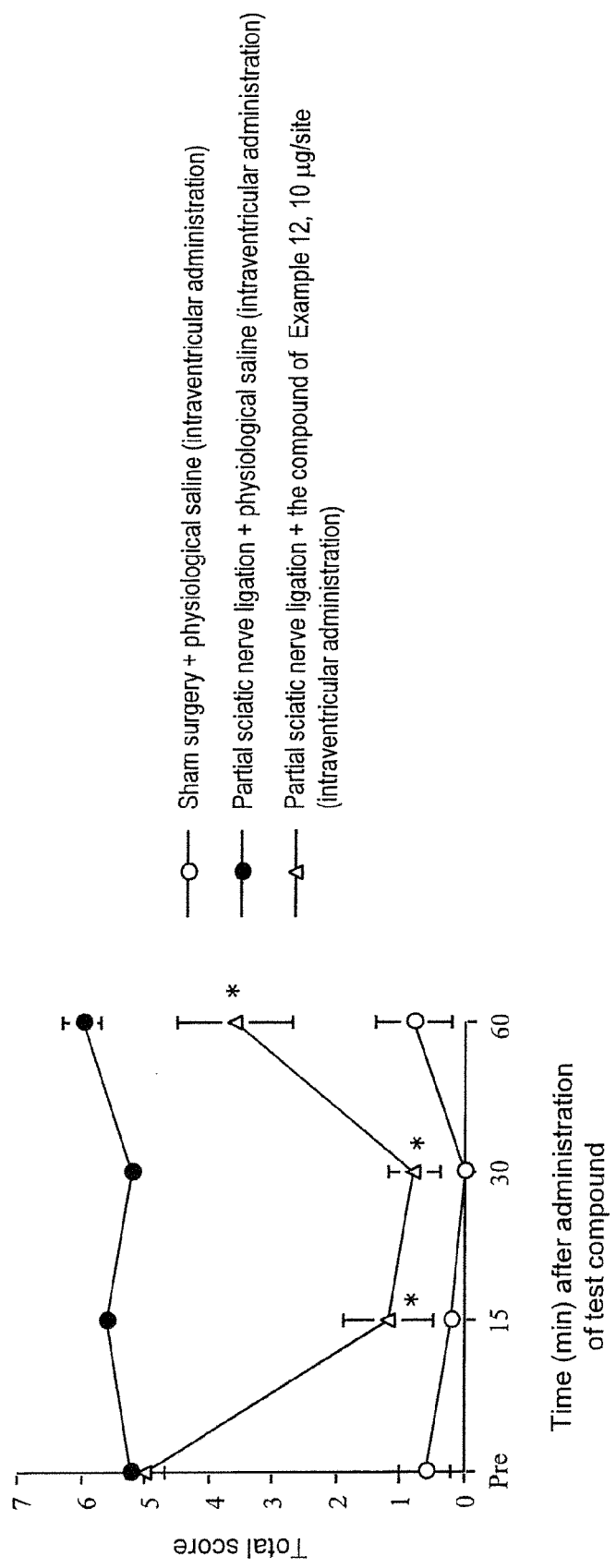
FIG. 8 is a graph showing the effect of the compound of Example 12 on mouse partial sciatic nerve ligation models (intraventricular administration).
Figure 9:
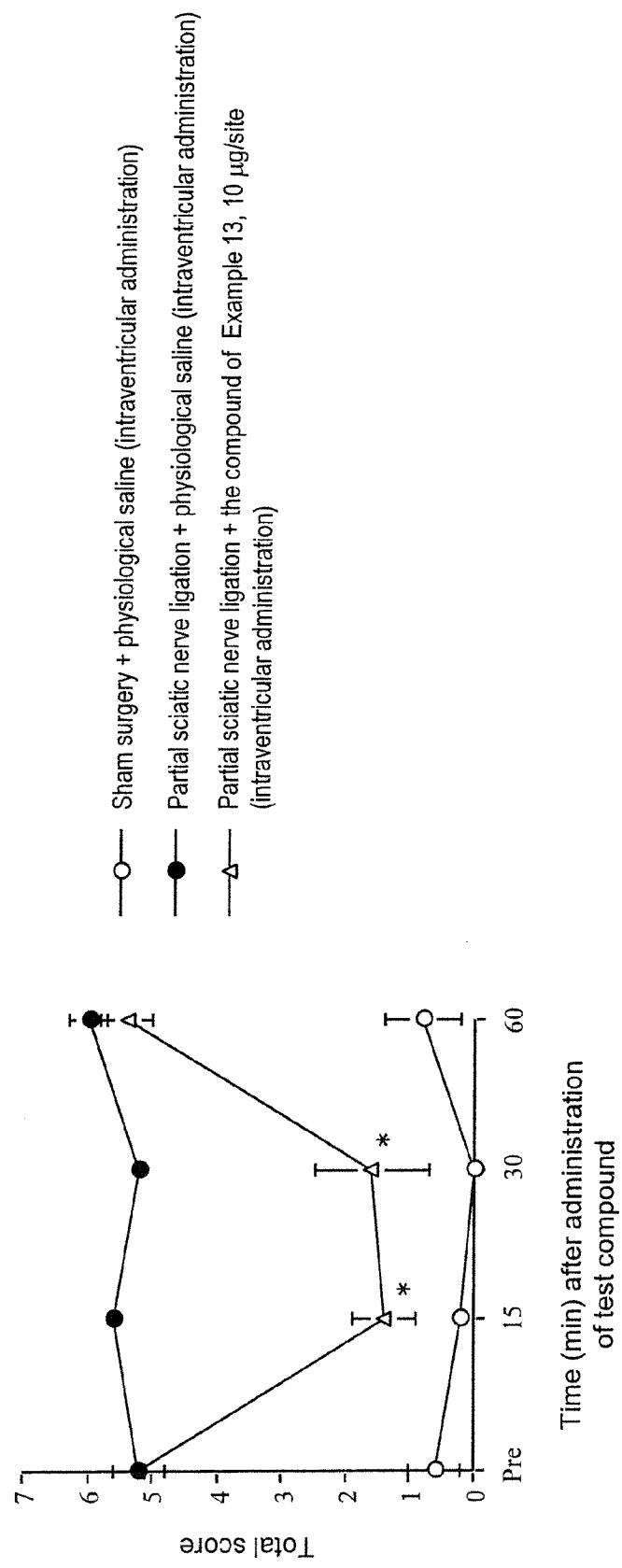
FIG. 9 is a graph showing the effect of the compound of Example 13 on mouse partial sciatic nerve ligation models (intraventricular administration).
Figure 10:
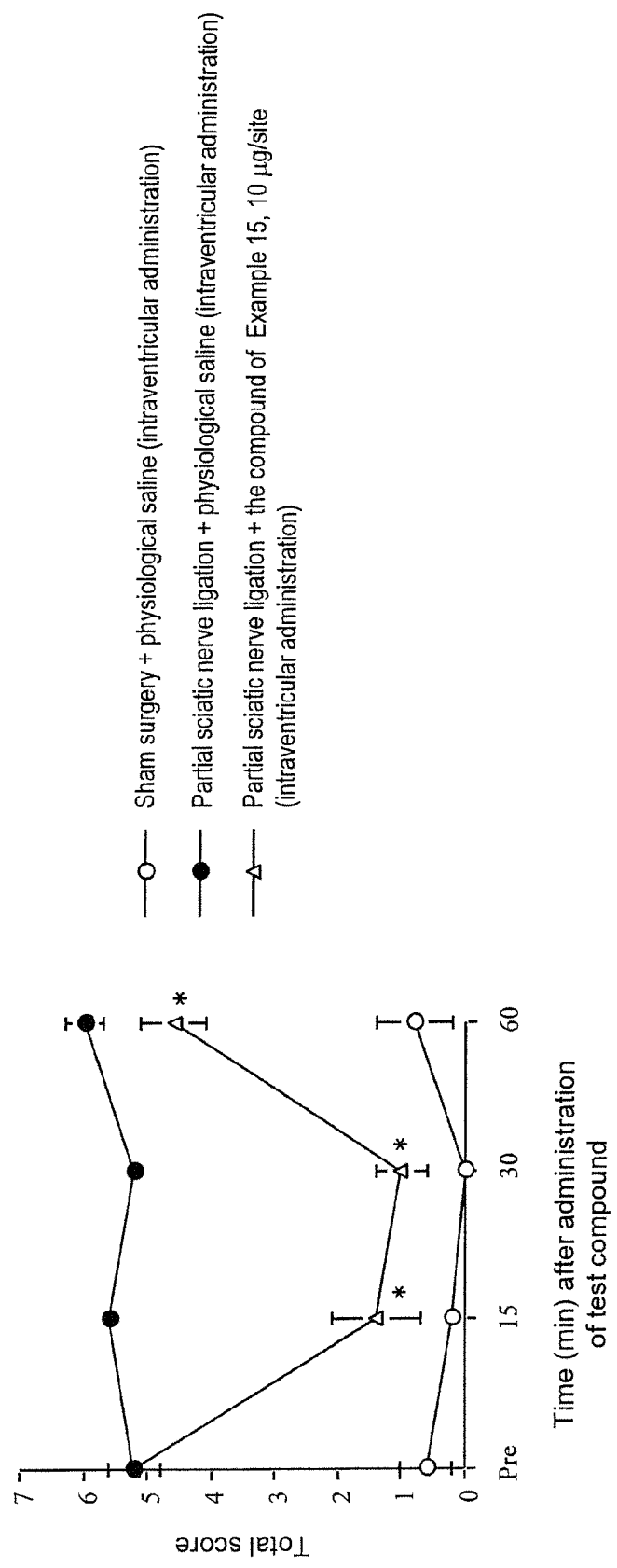
FIG. 10 is a graph showing the effect of the compound of Example 15 on mouse partial sciatic nerve ligation models (intraventricular administration).

The results are shown in FIGS. 2, 3 and 12 to 22. In the figures, the vertical axis represents the total score (mean value±standard error; n=5 to 6 in FIGS. 2 and 3, n=4 to 7 in FIGS. 12 to 22) in the von Frey test. The higher numerical value indicates that pain is stronger. The horizontal axis represents time (min or hr) after administration of a test compound. Efficacy in the group receiving pregabalin ("partial sciatic nerve ligation+pregabalin" in the figure) was statistically evaluated by a two-sample unpaired t-test or Welch test using the "partial sciatic nerve ligation+physiological saline" group ("partial sciatic nerve ligation+physiological saline" in the figure) of every measurement time as a control. Efficacy in the group receiving the compound of Example 2 or 4 ("partial sciatic nerve ligation+the compound of Example 2" or "partial sciatic nerve ligation+the compound of Example 4" in the figures) was statistically evaluated by Williams test or Shirley-Williams test using the "partial sciatic nerve ligation+physiological saline" group ("partial sciatic nerve ligation+physiological saline" in the figures) of every measurement time as a control. The group receiving the compounds of Example 13, 18, 22, 25, 27, 29, 31, 33, 66, 68 or 70 ("partial sciatic nerve ligation+the compound of Example 13, 18, 22, 25, 27, 29, 31, 33, 66, 68 or 70" in the figures) was statistically evaluated by Shirley-Williams test or Welch test using the "partial sciatic nerve ligation+physiological saline" group ("partial sciatic nerve ligation+physiological saline" in the figures) of every measurement time as a control. In the figures, mark "*" indicates that the value is statistically significant ($p<0.05$) compared to the "partial sciatic nerve ligation+physiological saline" group (two-group unpaired t-test or Welch test). In the figures, mark "#" indicates that the value is statistically significant compared to the "partial sciatic nerve ligation+physiological saline" group (Williams test or Shirley-Williams test ($p<0.025$), or Welch test ($p<0.05$)).

According to the von Frey test, intravenous administration of the compounds of Example 2, 4, 13, 18, 22, 25, 27, 29, 31, 33, 66, 68 or 70 ("partial sciatic nerve ligation+the compounds of Example 2, 4, 13, 18, 22, 25, 27, 29, 31, 33, 66, 68 or 70" in the figures) showed a statistically significant analgesic action similarly to the positive control, pregabalin ("partial sciatic nerve ligation+pregabalin" in the figure).

(3) Intraventricular Administration

The results are shown in FIGS. 4 to 10. In the figures, the vertical axis represents the total score (mean value±standard error; n=4 to 5 in FIGS. 4 to 10) in the von Frey test. The higher numerical value indicates that pain is stronger. The horizontal axis represents the time (min) after administration of a test compound. Efficacy was statistically evaluated by a two-sample unpaired t-test or Welch test using the "partial sciatic nerve ligation+physiological saline" group ("partial sciatic nerve ligation+physiological saline" in the figures) of every measurement time as a control. In the figures, mark "*" indicates that the value is statistically significant ($p<0.05$) compared to the "partial sciatic nerve ligation+physiological saline" group.

According to the results of the von Frey test, oral administration of the compounds of Example 2, 4, 6, 10, 12, 13 or 15 ("partial sciatic nerve ligation+the compound of Example 2, 4, 6, 10, 12, 13 or 15" in the figures) showed a statistically significant analgesic action.

From these results, it was clearly demonstrated that a cyclic amine derivative (I) or a prodrug thereof or a pharmacologically acceptable salt thereof has a strong analgesic effect against neuropathic pain.

Example 72

Effect on Fibromyalgia Syndrome Model in Rats

Using a fibromyalgia syndrome model in rats by which fibromyalgia syndrome can be evaluated, the analgesic action of a cyclic amine derivative (I) or a prodrug thereof or a pharmacologically acceptable salt thereof was investigated.

As the cyclic amine derivative (I) or a pharmacologically acceptable salt thereof, the compound of Example 13 was used for evaluation. As the prodrug of a cyclic amine derivative (I) or a pharmacologically acceptable salt thereof, the compound of Example 38 was used for evaluation. The compound of Example 38 is a hydrochloride of a prodrug obtained by esterifying the carboxyl group of the compound of Example 39 with an ethyl group.

1. Experimental Method

To prepare a fibromyalgia syndrome model rat (Sluka et al., Journal of Pharmacology and Experimental Therapeutics, vol. 302, p. 1146-50, 2002; Nagakura et al., Pain, vol. 146, p. 26-33, 2009; Sluka et al., Pain, vol. 146, p. 3-4, 2009), which is generally employed widely in basic research for fibromyalgia syndrome, acidic saline (100 µL) adjusted to pH4.0 was intramuscularly injected to the gastrocnemius muscle of the right hind paw of Crl: CD(SD) rat (6 to 7 weeks old, male; from CHARLES RIVER LABORATORIES JAPAN, INC.) under continuous inhalation anesthesia with isoflurane, twice (once in each day of Day 1 and Day 6, wherein Day 1 was the date on which the acidic saline was initially administrated). The rats thus prepared were raised in a breeding room controlled at an indoor temperature of 21 to 25° C. and an indoor humidity of 40 to 70% under the conditions of voluntary intake of food and water. In the same manner, rats to which physiological saline in place of acidic saline was intramuscularly injected were raised. The rats thus raised and not afflicted with fibromyalgia syndrome ("physiological saline-vehicle" group in FIGS. 23 and 24) were also used in the experiment.

Day 7 after the initial administration of acidic saline, allodynia in each rat was measured. The rats, which exhibited a 50% response threshold (mean value of the right hind paw and the left hind paw) of 2 g or more to 6 g or less, were selected as fibromyalgia syndrome model rats with the onset of fibromyalgia syndrome and subjected to the following administration experiment. Note that, measurement of allodynia was performed by use of a von Frey filament (from North Coast Medical) in accordance with the method described in a known literature (Chaplan et al., Journal of Neuroscience Methods, vol. 53, p. 55-63, 1994).

The fibromyalgia syndrome model rats thus obtained are divided into groups such that the 50% response threshold (mean value of the right hind paw and the left hind paw) of the individual groups became equal, and a test compound was administered to the fibromyalgia syndrome model rats on Day 7 after the initial administration of acidic saline.

Figure 23:
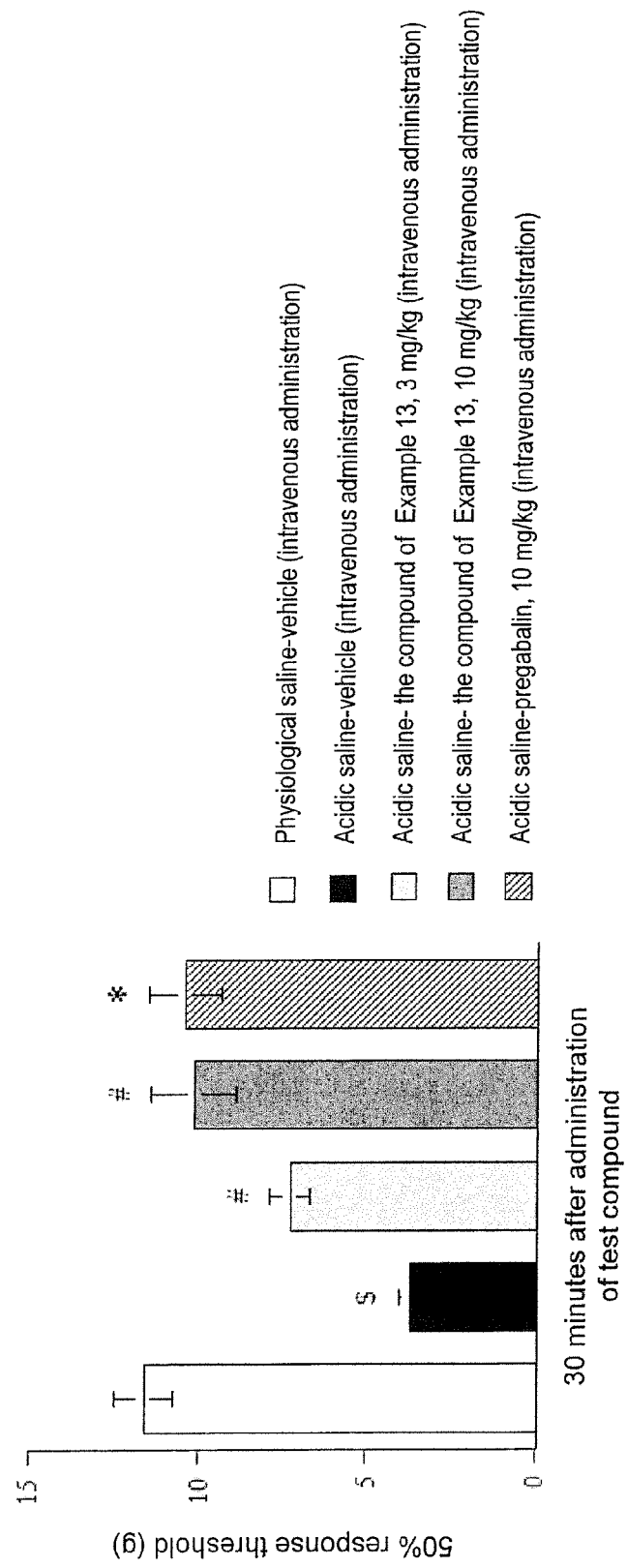
FIG. 23 is a graph showing the effect of the compound of Example 13 on rat fibromyalgia syndrome models (intravenous administration).

The compound of Example 13 (3 and 10 mg/kg) was dissolved in physiological saline and then administered (intravenous administration) to fibromyalgia syndrome model rats through the tail vein ("acidic saline—the compound of Example 13" in FIG. 23). Pregabalin serving as a positive control (10 mg/kg; from KEMPROTEC) was dissolved in physiological saline and then intravenously administered ("acidic saline-pregabalin" in FIG. 23). As a control, physiological saline was intravenously administered to fibromyalgia syndrome model rats ("acidic saline-vehicle" in FIG. 23). Furthermore, physiological saline was intravenously administered to rats not afflicted with fibromyalgia syndrome ("physiological saline-vehicle" in FIG. 23). In thirty minutes after the intravenous administration, allodynia in individual rats was measured to evaluate an analgesic action.

Figure 24:
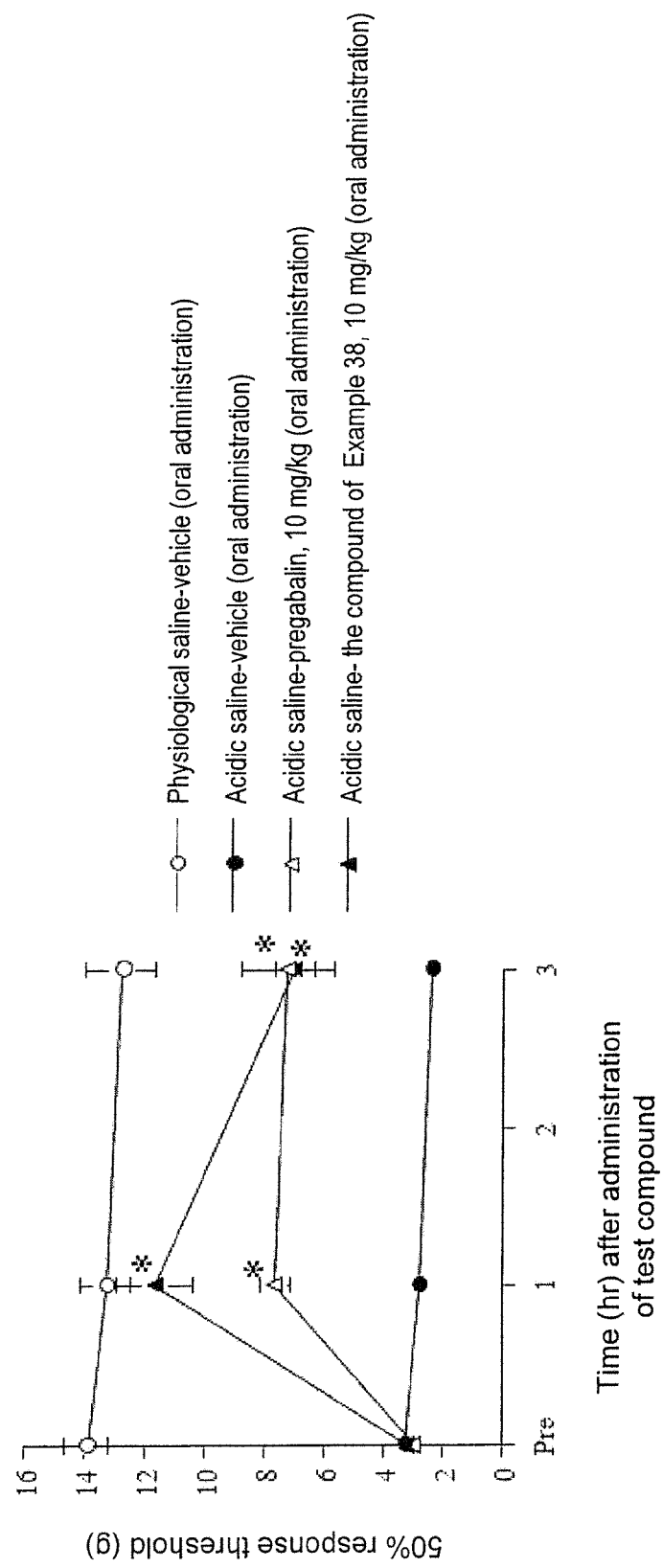
FIG. 24 is a graph showing the effect of the compound of Example 38 on rat fibromyalgia syndrome models (oral administration).

The compound of Example 38 (10 mg/kg) was dissolved in distilled water and then orally administered to fibromyalgia syndrome model rats ("acidic saline—the compound of Example 38" in FIG. 24). Pregabalin serving as a positive control (10 mg/kg; from KEMPROTEC) was dissolved in distilled water and then orally administered ("acidic saline-pregabalin" in FIG. 24). As a control, distilled water was orally administered to fibromyalgia syndrome model rats ("acidic saline-vehicle" in FIG. 24). Furthermore, distilled water was orally administered to rats not afflicted with fibromyalgia syndrome ("physiological saline-vehicle" in FIG. 24). In one hour and three hours after the oral administration, allodynia in individual rats was measured to evaluate an analgesic action. At this time, the 50% response threshold value in the measurement of allodynia before oral administration of the test compound on Day 7 after initial administration of acidic saline was defined as the pre-value.

2. Results

The results are shown in FIGS. 23 and 24. In the figures, the vertical axis represents 50% response threshold (mean value of the right hind paw and the left hind paw) (g) (mean value±standard error, n=5 to 6). The higher numerical value indicates that allodynia is improved in the fibromyalgia syndrome model rats.

FIG. 23 shows the results of 30 minutes after intravenous administration of the compound of Example 13. In the figure, the mark "$" indicates that the value is statistically significant ($: $p<0.05$) as the result of two-sample unpaired t-test using the "physiological saline-vehicle" group ("physiological saline-vehicle" in the figure) as a control. In the figure, mark "#" indicates that the value is statistically significant (#: $p<0.025$) as the results of Shirley-Williams test using the "acidic saline-vehicle" group ("acidic saline-vehicle" in the figure) as a control. In the figure, mark "*" indicates that the value is statistically significant (*: $p<0.05$) as a result of Welch test using "acidic saline-vehicle" group ("acidic saline-vehicle" in the figure) as a control.

FIG. 24 shows the results of oral administration of the compound of Example 38. In the figure, the horizontal axis represents the time before oral administration of the compound of Example 38 (pre-value) and the time (hr) from the oral administration. In the figure, mark "*" indicates that the value is statistically significant (*: $p<0.05$) as the result of multi-group unpaired t-test (corrected by Dunnett) using the "acidic saline-vehicle" group ("acidic saline-vehicle" in the figure) of every measuring time as a control.

In the group to which the compound of Example 13 was intravenously administered ("acidic saline—the compound of Example 13" in FIG. 23), and the group to which the compound of Example 38 was orally administered ("acidic saline—the compound of Example 38" in FIG. 24), the allodynia observed in the fibromyalgia syndrome model rats was statistically significantly improved compared to the "acidic saline-vehicle" group, similarly to a positive control, i.e., the group to which pregabalin was intravenously or orally administered ("acidic saline-pregabalin" in FIGS. 23 and 24).

From these results, it was clearly demonstrated that a cyclic amine derivative (I) or a prodrug thereof or a pharmacologically acceptable salt thereof is effective to fibromyalgia syndrome.

Example 73

Pharmacokinetics of Prodrug of Cyclic Amine Derivative (I) or Pharmacologically Acceptable Salt Thereof in Rats A pharmacologically acceptable salt of a prodrug obtained by esterifying the carboxyl group of a cyclic amine derivative (I), i.e., the compound of Example 38, was orally administered to rats and the plasma was analyzed by LC/MS/MS analysis. As a result, it was confirmed that the compound of Example 38 is converted into a cyclic amine derivative (I), i.e., the compound of Example 39, in-vivo in the rats.

INDUSTRIAL APPLICABILITY

The cyclic amine derivative or a pharmacologically acceptable salt thereof can be used as medicines for pain symptoms since it can exhibit an analgesic action against pain, in particular, neuropathic pain or fibromyalgia syndrome.

The invention claimed is:

1. A cyclic amine derivative represented by Formula (I), a prodrug of the derivative, or a pharmacologically acceptable salt thereof:

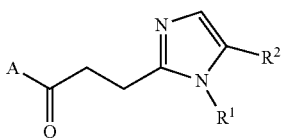
(I)

wherein A represents a group represented by Formula (IIa), (IIb) or (IIc):

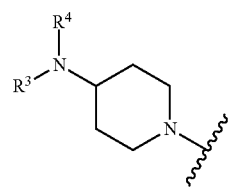
(IIa)

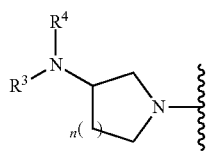
(IIb)

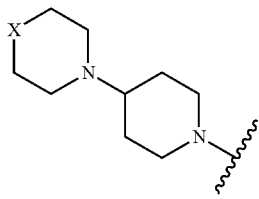
(IIc)

wherein
when A represents a group represented by Formula (IIa) or (IIb), $R^1$ represents an alkyl group having 1 to 6 carbon atoms and optionally substituted with a halogen atom, a hydroxyl group, an amino group or a carboxyl group, $R^2$ represents a hydrogen atom or a halogen atom, $R^3$ represents a hydrogen atom or an alkyl group having 1 to 6 carbon atoms, $R^4$ represents a hydrogen atom or an alkylcarbonyl group having 2 to 6 carbon atoms or an alkyl group having 1 to 6 carbon atoms and optionally substituted with an alkylcarbonylamino group having 2 to 6 carbon atoms and n represents 1 or 2, in which when $R^3$ and $R^4$ each independently represent an alkyl group having 1 to 6 carbon atoms, $R^1$ represents an alkyl group having 1 to 6 carbon atoms and substituted with a hydroxyl group, an amino group or a carboxyl group; and when A represents a group represented by Formula (IIc), $R^1$ represents an alkyl group having 1 to 6 carbon atoms and substituted with a carboxyl group, $R^2$ represents a hydrogen atom or a halogen atom, X represents $CH_2$, O or $—NR^5$ and $R^5$ represents an alkyl group having 1 to 6 carbon atoms.

2. The derivative, the prodrug of the derivative, or the salt thereof according to claim 1, wherein A is Formula (IIa) or (IIb).

3. The derivative, the prodrug of the derivative, or the salt thereof according to claim 2, wherein $R^3$ is a hydrogen atom, a methyl group or an ethyl group.

4. The derivative, the prodrug of the derivative, or the salt thereof according to claim 2, wherein
$R^2$ is a hydrogen atom or a chlorine atom,
$R^3$ is a hydrogen atom or a methyl group, and
$R^4$ is a hydrogen atom or a methylcarbonyl group or an alkyl group having 1 to 6 carbon atoms and optionally substituted with a methylcarbonylamino group.

5. The derivative, the prodrug of the derivative, or the salt thereof according to claim 1, wherein A is Formula (IIc).

6. The derivative, the prodrug of the derivative, or the salt thereof according to claim 5, wherein
$R^2$ is a hydrogen atom or a chlorine atom, and
$R^5$ is a methyl group.

7. The prodrug of the derivative, or the salt thereof according to claim 1, wherein the prodrug is obtained by esterifying a carboxyl group of the derivative.

8. A medicine comprising the derivative, the prodrug of the derivative, or the salt thereof according to claim 1 as an active ingredient.

9. An analgesic agent comprising the derivative, the prodrug of the derivative, or the salt thereof according to claim 1 as an active ingredient.

10. A therapeutic agent for neuropathic pain comprising the derivative, the prodrug of the derivative, or the salt thereof according to claim 1 as an active ingredient.

11. A therapeutic agent for fibromyalgia syndrome comprising the derivative, the prodrug of the derivative, or the salt thereof according to claim 1 as an active ingredient.

12. A method of treating pain comprising administering an effective amount of the derivative, the prodrug of the derivative, or the salt thereof according to claim 1.

13. A method of treating neuropathic pain comprising administering an effective amount of the derivative, the prodrug of the derivative, or the salt thereof according to claim 1.

14. A method of treating fibromyalgia syndrome comprising administering an effective amount of the derivative, the prodrug of the derivative, or the salt thereof according to claim 1.

* * * * *